US011793507B2

(12) United States Patent
Stewart et al.

(10) Patent No.: US 11,793,507 B2
(45) Date of Patent: Oct. 24, 2023

(54) METHOD AND APPARATUS FOR PASSING SUTURE THROUGH TISSUE

(71) Applicant: Stryker Corporation, Kalamazoo, MI (US)

(72) Inventors: Daren Stewart, Belmont, CA (US); James Flom, San Carlos, CA (US)

(73) Assignee: Stryker Corporation, Kalamazoo, MI (US)

( * ) Notice: Subject to any disclaimer, the term of this patent is extended or adjusted under 35 U.S.C. 154(b) by 333 days.

(21) Appl. No.: 17/093,447

(22) Filed: Nov. 9, 2020

(65) Prior Publication Data

US 2021/0052269 A1     Feb. 25, 2021

Related U.S. Application Data

(60) Division of application No. 15/692,839, filed on Aug. 31, 2017, now Pat. No. 10,828,023, which is a
(Continued)

(51) Int. Cl.
*A61B 17/04*       (2006.01)
*A61B 17/00*       (2006.01)
(Continued)

(52) U.S. Cl.
CPC ...... *A61B 17/0469* (2013.01); *A61B 17/0483* (2013.01); *A61B 17/0485* (2013.01);
(Continued)

(58) Field of Classification Search
CPC ............ A61B 17/0469; A61B 17/0483; A61B 17/0485; A61B 2017/00862;
(Continued)

(56) References Cited

U.S. PATENT DOCUMENTS

| 292,195 A | 1/1884 | Austin |
| 1,545,682 A | 7/1925 | Nelson |

(Continued)

FOREIGN PATENT DOCUMENTS

| DE | 2532242 A1 | 2/1977 |
| EP | 0769272 A1 | 4/1997 |

(Continued)

OTHER PUBLICATIONS

Acufex Microsurgical Product Catalog, 1995.
(Continued)

*Primary Examiner* — Thomas McEvoy
(74) *Attorney, Agent, or Firm* — MORRISON & FOERSTER LLP

(57) ABSTRACT

A method for passing a suture includes extending a distal end of a suture manipulator of a suture passer from a distal portion of a hollow tube of the suture passer, locating a portion of a suture adjacent to a catching portion of the suture manipulator, retracting the distal end of the suture manipulator into the hollow tube and pulling the portion of the suture into the hollow tube so that a loop of the suture is located in the lumen and the portion of the suture is compressed by an inner surface of the hollow tube and a side surface of the catching portion, and sliding the suture manipulator distally relative to the hollow tube and pushing the portion of the suture with a pushing portion of the suture manipulator that is located proximally of the catching portion to expel the suture from the hollow tube.

20 Claims, 116 Drawing Sheets

Related U.S. Application Data division of application No. 14/531,531, filed on Nov. 3, 2014, now Pat. No. 10,405,850, which is a continuation-in-part of application No. PCT/US2013/060167, filed on Sep. 17, 2013, which is a continuation-in-part of application No. 13/230,652, filed on Sep. 12, 2011, now Pat. No. 10,123,794, and a continuation-in-part of application No. 13/791,395, filed on Mar. 8, 2013, now Pat. No. 10,098,631, and a continuation-in-part of application No. 13/230,652, filed on Sep. 12, 2011, now Pat. No. 10,123,794, said application No. 14/531,531 is a continuation-in-part of application No. 13/230,652, filed on Sep. 12, 2011, now Pat. No. 10,123,794, said application No. 14/531,531 is a continuation-in-part of application No. 13/791,395, filed on Mar. 8, 2013, now Pat. No. 10,098,631, and a continuation-in-part of application No. 13/230,652, filed on Sep. 12, 2011, now Pat. No. 10,123,794.

(60) Provisional application No. 61/701,920, filed on Sep. 17, 2012, provisional application No. 61/384,423, filed on Sep. 20, 2010, provisional application No. 61/473,219, filed on Apr. 8, 2011, provisional application No. 61/495,441, filed on Jun. 10, 2011, provisional application No. 61/381,787, filed on Sep. 10, 2010, provisional application No. 61/898,729, filed on Nov. 1, 2013, provisional application No. 61/947,870, filed on Mar. 4, 2014.

(51) Int. Cl.
*A61B 17/06* (2006.01)
*A61B 17/30* (2006.01)

(52) U.S. Cl.
CPC .............. *A61B 2017/00862* (2013.01); *A61B 2017/00867* (2013.01); *A61B 2017/061* (2013.01); *A61B 2017/06009* (2013.01); *A61B 2017/06014* (2013.01); *A61B 2017/06042* (2013.01); *A61B 2017/306* (2013.01)

(58) Field of Classification Search
CPC ........... A61B 2017/06009; A61B 2017/06042; A61B 2017/061
See application file for complete search history.

(56) References Cited

U.S. PATENT DOCUMENTS

| | | |
|---|---|---|
| 1,583,271 A | 5/1926 | Biro |
| 2,363,334 A | 11/1944 | Jones |
| 2,496,111 A | 1/1950 | Turkel |
| 2,738,790 A | 3/1956 | Todt, Sr. et al. |
| 2,959,172 A | 11/1960 | Held |
| 3,630,192 A | 12/1971 | Jamshidi |
| 3,877,434 A | 4/1975 | Ferguson et al. |
| 3,929,123 A | 12/1975 | Jamshidi |
| 4,174,715 A | 11/1979 | Hasson |
| 4,372,302 A | 2/1983 | Akerlund |
| 4,427,014 A | 1/1984 | Bel et al. |
| 4,602,635 A | 7/1986 | Mulhollan et al. |
| 4,641,652 A | 2/1987 | Hutterer et al. |
| 4,712,545 A | 12/1987 | Honkanen |
| 4,779,616 A | 10/1988 | Johnson |
| 4,781,190 A | 11/1988 | Lee |
| 4,784,139 A | 11/1988 | Demos |
| 4,923,461 A | 5/1990 | Caspari et al. |
| 4,957,498 A | 9/1990 | Caspari et al. |
| 4,976,269 A | 12/1990 | Mehl |
| 4,986,279 A | 1/1991 | O'Neill |
| 5,015,250 A | 5/1991 | Foster |
| 5,036,860 A | 8/1991 | Leigh et al. |
| 5,059,201 A | 10/1991 | Asnis |
| 5,090,419 A | 2/1992 | Palestrant |
| 5,149,329 A | 9/1992 | Richardson |
| 5,176,700 A | 1/1993 | Brown et al. |
| 5,181,919 A | 1/1993 | Bergman et al. |
| 5,201,741 A | 4/1993 | Dulebohn |
| 5,222,508 A | 6/1993 | Contarini |
| 5,222,977 A | 6/1993 | Esser |
| 5,250,054 A | 10/1993 | Li |
| 5,250,055 A | 10/1993 | Moore et al. |
| 5,281,237 A | 1/1994 | Gimpelson |
| 5,304,203 A | 4/1994 | El-Mallawany et al. |
| 5,312,422 A | 5/1994 | Trott |
| 5,364,410 A | 11/1994 | Failla et al. |
| 5,376,096 A | 12/1994 | Foster |
| 5,387,227 A | 2/1995 | Grice |
| 5,405,354 A | 4/1995 | Sarrett |
| 5,411,519 A | 5/1995 | Tovey et al. |
| 5,437,681 A | 8/1995 | Meade et al. |
| 5,439,467 A | 8/1995 | Benderev et al. |
| 5,447,512 A | 9/1995 | Wilson et al. |
| 5,499,991 A | 3/1996 | Garman et al. |
| 5,514,148 A | 5/1996 | Smith, III |
| 5,520,703 A | 5/1996 | Essig et al. |
| 5,522,830 A | 6/1996 | Aranyi |
| 5,569,269 A | 10/1996 | Hart et al. |
| 5,571,119 A | 11/1996 | Atala |
| 5,573,542 A | 11/1996 | Stevens |
| 5,618,290 A | 4/1997 | Toy et al. |
| 5,626,597 A | 5/1997 | Urban et al. |
| 5,628,757 A | 5/1997 | Hasson |
| 5,643,292 A | 7/1997 | Hart |
| 5,649,939 A | 7/1997 | Reddick |
| 5,653,716 A | 8/1997 | Malo et al. |
| 5,658,299 A | 8/1997 | Hart |
| 5,716,367 A | 2/1998 | Koike et al. |
| 5,722,981 A | 3/1998 | Stevens |
| 5,741,278 A | 4/1998 | Stevens |
| 5,746,759 A | 5/1998 | Meade et al. |
| 5,772,672 A | 6/1998 | Toy et al. |
| 5,797,928 A | 8/1998 | Kogasaka |
| 5,810,865 A | 9/1998 | Koscher et al. |
| 5,817,111 A | 10/1998 | Riza |
| 5,827,299 A | 10/1998 | Thomason et al. |
| 5,830,220 A | 11/1998 | Wan et al. |
| 5,893,873 A | 4/1999 | Rader et al. |
| 5,899,911 A | 5/1999 | Carter |
| 5,904,692 A | 5/1999 | Steckel et al. |
| 5,910,148 A | 6/1999 | Reimels et al. |
| 5,919,202 A | 7/1999 | Yoon |
| 5,922,001 A | 7/1999 | Yoon |
| 5,922,002 A | 7/1999 | Yoon |
| 5,928,255 A | 7/1999 | Meade et al. |
| 5,951,575 A | 9/1999 | Bolduc et al. |
| 5,954,734 A | 9/1999 | Thomason et al. |
| 5,976,161 A | 11/1999 | Kirsch et al. |
| 5,984,932 A | 11/1999 | Yoon |
| 5,984,938 A | 11/1999 | Yoon |
| 5,984,939 A | 11/1999 | Yoon |
| 5,993,466 A | 11/1999 | Yoon |
| 6,022,360 A | 2/2000 | Reimels et al. |
| 6,074,403 A | 6/2000 | Nord |
| 6,080,180 A | 6/2000 | Yoon et al. |
| 6,270,508 B1 | 8/2001 | Klieman et al. |
| 6,322,578 B1 | 11/2001 | Houle et al. |
| 6,383,199 B2 | 5/2002 | Carter et al. |
| 6,503,264 B1 | 1/2003 | Birk |
| 6,517,552 B1 | 2/2003 | Nord et al. |
| 6,554,829 B2 | 4/2003 | Schulze et al. |
| 6,616,683 B1 | 9/2003 | Toth et al. |
| 6,629,984 B1 | 10/2003 | Chan |
| 6,676,673 B2 | 1/2004 | Chang |
| 6,716,224 B2 | 4/2004 | Singhatat |
| 6,723,107 B1 | 4/2004 | Skiba et al. |
| 6,770,084 B1 | 8/2004 | Bain et al. |
| 6,840,900 B2 | 1/2005 | Smith |
| 6,921,408 B2 | 7/2005 | Sauer |
| 6,936,054 B2 | 8/2005 | Chu |

(56) References Cited

U.S. PATENT DOCUMENTS

| | | |
|---|---|---|
| 6,945,984 B2 | 9/2005 | Arumi et al. |
| 6,991,636 B2 | 1/2006 | Rose |
| 7,033,315 B2 | 4/2006 | Smith |
| 7,063,699 B2 | 6/2006 | Hess et al. |
| 7,105,000 B2 | 9/2006 | McBrayer |
| 7,105,004 B2 | 9/2006 | Dicesare et al. |
| 7,131,978 B2 | 11/2006 | Sancoff et al. |
| 7,137,988 B2 | 11/2006 | Frye |
| 7,147,650 B2 | 12/2006 | Lee |
| 7,169,156 B2 | 1/2007 | Hart |
| 7,261,725 B2 | 8/2007 | Binmoeller |
| 7,338,513 B2 | 3/2008 | Lee et al. |
| 7,364,582 B2 | 4/2008 | Lee |
| 7,736,372 B2 | 6/2010 | Reydel et al. |
| 7,766,937 B2 | 8/2010 | Ravikumar |
| 7,815,654 B2 | 10/2010 | Chu |
| 7,842,050 B2 | 11/2010 | Diduch et al. |
| 7,879,048 B2 | 2/2011 | Bain et al. |
| 7,883,519 B2 | 2/2011 | Oren et al. |
| 8,066,718 B2 | 11/2011 | Weisel et al. |
| 8,105,350 B2 | 1/2012 | Lee et al. |
| 8,133,255 B2 | 3/2012 | Ravikumar |
| 8,157,817 B2 | 4/2012 | Bonadio et al. |
| 8,230,863 B2 | 7/2012 | Ravikumar et al. |
| 8,308,725 B2 | 11/2012 | Bell et al. |
| 8,313,507 B2 | 11/2012 | Ravikumar |
| 8,328,824 B2 | 12/2012 | Hart |
| 8,361,089 B2 | 1/2013 | Chu |
| 8,469,992 B2 | 6/2013 | Roy et al. |
| 8,545,521 B2 | 10/2013 | McClurg et al. |
| 8,556,916 B2 | 10/2013 | Torrie |
| 8,585,714 B2 | 11/2013 | Weisel et al. |
| 8,679,135 B2 | 3/2014 | Stone et al. |
| 8,758,368 B2 | 6/2014 | Weisel et al. |
| 8,758,405 B2 | 6/2014 | Zeiner et al. |
| 8,764,771 B2 | 7/2014 | Chu |
| 8,870,897 B2 | 10/2014 | Torrie |
| 8,906,041 B2 | 12/2014 | Chu |
| 9,066,717 B2 | 6/2015 | Sherts et al. |
| 9,089,323 B2 | 7/2015 | Bonutti et al. |
| 9,931,114 B2 | 4/2018 | Stewart et al. |
| 10,123,794 B2 | 11/2018 | Flom et al. |
| 10,828,023 B2 | 11/2020 | Stewart et al. |
| 2001/0056283 A1 | 12/2001 | Carter et al. |
| 2002/0147456 A1 | 10/2002 | Diduch et al. |
| 2003/0171760 A1 | 9/2003 | Gambale |
| 2004/0092953 A1 | 5/2004 | Salameh et al. |
| 2004/0236353 A1 | 11/2004 | Bain et al. |
| 2004/0249393 A1 | 12/2004 | Weisel et al. |
| 2006/0069399 A1 | 3/2006 | Weisel et al. |
| 2006/0069699 A1 | 3/2006 | Smadja et al. |
| 2007/0093859 A1 | 4/2007 | Phillips |
| 2007/0118153 A1 | 5/2007 | Funamura et al. |
| 2007/0185505 A1 | 8/2007 | Hart |
| 2007/0213766 A1 | 9/2007 | Ravikumar |
| 2007/0250112 A1 | 10/2007 | Ravikumar et al. |
| 2008/0154286 A1 | 6/2008 | Abbott et al. |
| 2009/0012538 A1 | 1/2009 | Saliman |
| 2009/0036905 A1* | 2/2009 | Schmieding ....... A61B 17/0401 606/232 |
| 2009/0062743 A1 | 3/2009 | Rotella et al. |
| 2009/0131956 A1 | 5/2009 | Dewey et al. |
| 2010/0016884 A1 | 1/2010 | Ravikumar |
| 2010/0198235 A1 | 8/2010 | Pierce et al. |
| 2010/0292724 A1 | 11/2010 | Ravikumar et al. |
| 2011/0066165 A1 | 3/2011 | Skinlo et al. |
| 2011/0071550 A1 | 3/2011 | Diduch et al. |
| 2011/0106124 A1 | 5/2011 | Beauchamp |
| 2011/0270280 A1 | 11/2011 | Saliman |
| 2012/0123448 A1 | 5/2012 | Flom et al. |
| 2012/0172897 A1 | 7/2012 | McClurg et al. |
| 2013/0116709 A1 | 5/2013 | Ziniti et al. |
| 2013/0211415 A1 | 8/2013 | Zerfas et al. |
| 2013/0218173 A1 | 8/2013 | Weisel et al. |
| 2013/0218175 A1 | 8/2013 | Auerbach et al. |
| 2013/0226200 A1 | 8/2013 | Kappel et al. |
| 2013/0253542 A1 | 9/2013 | Ostrovsky et al. |
| 2013/0253543 A1 | 9/2013 | Heneveld |
| 2014/0012292 A1 | 1/2014 | Stewart et al. |
| 2014/0039529 A1 | 2/2014 | Torrie |
| 2014/0039530 A1 | 2/2014 | Torrie |
| 2014/0188138 A1 | 7/2014 | Melsheimer et al. |
| 2014/0207158 A1 | 7/2014 | Stone et al. |
| 2014/0222033 A1 | 8/2014 | Foerster et al. |
| 2014/0228865 A1 | 8/2014 | Weisel et al. |
| 2014/0303653 A1 | 10/2014 | Weisel et al. |
| 2015/0018854 A1 | 1/2015 | Haines et al. |
| 2015/0025550 A1 | 1/2015 | Heneveld |
| 2015/0051622 A1 | 2/2015 | Domingo |
| 2015/0088167 A1 | 3/2015 | Chin et al. |
| 2015/0094739 A1 | 4/2015 | Norton et al. |
| 2015/0100073 A1 | 4/2015 | Chu |
| 2015/0112368 A1 | 4/2015 | Stewart et al. |
| 2015/0157317 A1 | 6/2015 | Bagaoisan et al. |
| 2015/0282804 A1 | 10/2015 | Bonutti et al. |
| 2015/0320417 A1 | 11/2015 | Stewart et al. |
| 2017/0325809 A1 | 11/2017 | Stewart et al. |
| 2017/0360434 A1 | 12/2017 | Stewart et al. |
| 2019/0110790 A1 | 4/2019 | Stewart et al. |

FOREIGN PATENT DOCUMENTS

| | | |
|---|---|---|
| WO | 97/03615 A1 | 2/1997 |
| WO | 2012/034131 A2 | 3/2012 |
| WO | 2012/093094 A1 | 7/2012 |

OTHER PUBLICATIONS

Caborn, D. et al., "Arthroscopic Repair of a Bankhart Lesion Using Tag Suture Anchors", Andover, MA, Smith & Nephew Endoscopy, 1996.

Decision to Grant dated Mar. 8, 2018, directed to EP Application No. 11 824 246.0; 2 pages.

Examination Report No. 1 dated Jun. 27, 2018, directed to AU Application No. 2014341911; 4 pages.

Examination Report No. 2 dated Mar. 5, 2019, directed to AU Application No. 2014341911; 3 pages.

Extended European Search Report dated Nov. 24, 2015, directed to EP Application No. 11 824 246.0; 10 pages.

Extended European Search Report dated Nov. 24, 2016, directed to EP Application No. 13837709.8; 8 pages.

Flom et al., U.S. Office Action dated Feb. 25, 2016, directed to U.S. Appl. No. 13/230,652; 10 pages.

Flom et al., U.S. Office Action dated Feb. 6, 2018, directed to U.S. Appl. No. 13/230,652; 8 pages.

Flom et al., U.S. Office Action dated Jul. 28, 2015, directed to U.S. Appl. No. 13/230,652; 8 pages.

Flom et al., U.S. Office Action dated Jun. 27, 2017, directed to U.S. Appl. No. 13/230,652; 11 pages.

Flom et al., U.S. Office Action dated Nov. 1, 2016, directed to U.S. Appl. No. 13/230,652; 11 pages.

Flom et al., U.S. Office Action dated Oct. 10, 2014, directed to U.S. Appl. No. 13/230,652; 7 pages.

Flom et al., U.S. Notice of Allowance and Fee(s) Due dated Jul. 9, 2018, directed to U.S. Appl. No. 13/230,652; 10 pages.

Flom et al., U.S. Restriction Requirement dated Apr. 29, 2014, directed to U.S. Appl. No. 13/230,652; 9 pages.

Intention to Grant dated Nov. 2, 2017, directed to EP Application No. 11 824 246.0; 5 pages.

International Preliminary Report on Patentability dated Mar. 12, 2013, directed to International Application No. PCT/US2011/051257; 10 pages.

International Preliminary Report on Patentability dated Mar. 17, 2015, directed to International Application No. PCT/US2013/060167; 9 pages.

International Preliminary Report on Patentability dated May 12, 2016, directed to International Application No. PCT/US2014/063703; 5 pages.

(56) References Cited

OTHER PUBLICATIONS

International Search Report and Written Opinion dated Feb. 12, 2015, directed to International Application No. PCT/US2014/063703; 10 pages.

International Search Report and Written Opinion dated Mar. 26, 2012, directed to International Application No. PCT/US2011/51257; 15 pages.

International Search Report and Written Opinion dated Jan. 10, 2014, directed to International Application No. PCT/US2013/060167; 11 pages.

Invitation to Pay Additional Fees, and, where Applicable, Protest Fee mailed Jan. 10, 2012, directed to International Application No. PCT/US2011/051257; 2 pages.

Notice of Acceptance dated May 18, 2015, directed to AU Application No. 2011298986; 2 pages.

Notice of Acceptance dated Apr. 2, 2019, directed to AU Application No. 2014341911; 3 pages.

Notice of Allowance dated Feb. 8, 2019, directed to CA Application No. 2,813,597; 1 page.

Office Action dated Jan. 2, 2017, directed to EP Application No. 11 824 246.0; 7 pages.

Office Action dated Jan. 22, 2020, directed to EP Application No. 14 858 480.8; 6 pages.

Office Action dated Jul. 16, 2018, directed to CA Application No. 2,813,597; 4 pages.

Office Action dated Jul. 4, 2017, directed to CA Application No. 2,813,597; 4 pages.

Office Action dated Sep. 26, 2019, directed to EP Application No. 13 837 709.8; 3 pages.

Patent Examination Report No. 1 dated May 9, 2014, directed to AU Application No. 2011298986; 4 pages.

Stewart et al., U.S. Office Action dated Apr. 16, 2020, directed to U.S. Appl. No. 15/666,994; 8 pages.

Stewart et al., U.S. Office Action dated Feb. 6, 2020, directed to U.S. Appl. No. 15/692,839; 13 pages.

Stewart et al., U.S. Office Action dated Sep. 6, 2019, directed to U.S. Appl. No. 15/666,994; 6 pages.

Stewart et al., U.S. Office Action dated Apr. 19, 2017, directed to U.S. Appl. No. 13/791,395; 14 pages.

Stewart et al., U.S. Office Action dated Feb. 21, 2018, directed to U.S. Appl. No. 14/531,531; 14 pages.

Stewart et al., U.S. Office Action dated Jun. 14, 2017, directed to U.S. Appl. No. 14/531,531; 10 pages.

Stewart et al., U.S. Office Action dated Jun. 23, 2016, directed to U.S. Appl. No. 13/791,395; 10 pages.

Stewart et al., U.S. Office Action dated Mar. 10, 2015, directed to U.S. Appl. No. 13/791,395; 7 pages.

Stewart et al., U.S. Office Action dated Nov. 19, 2015, directed to U.S. Appl. No. 13/791,395; 12 pages.

Stewart et al., U.S. Office Action dated Oct. 3, 2017, directed to U.S. Appl. No. 13/791,395; 10 pages.

Stewart et al., U.S. Office Action dated Oct. 3, 2018, directed to U.S. Appl. No. 14/531,531; 7 pages.

Stewart et al., U.S. Notice of Allowance and Fee(s) due dated Jun. 30, 2020, directed to U.S. Appl. No. 15/692,839; 9 pages.

Stewart et al., U.S. Office Action dated Oct. 29, 2020, directed to U.S. Appl. No. 15/666,994; 10 pages.

Stewart et al., U.S. Office Action dated Sep. 17, 2020, directed to U.S. Appl. No. 16/161,770; 13 pages.

Stewart et al., U.S. Restriction Requirement dated Jan. 12, 2017, directed to U.S. Appl. No. 14/428,856; 9 pages.

Stewart et al., U.S. Restriction Requirement dated May 30, 2019, directed to U.S. Appl. No. 15/666,994; 5 pages.

Stewart et al., U.S. Restriction Requirement dated Sep. 19, 2019, directed to U.S. Appl. No. 15/692,839; 5 pages.

Stewart, U.S. Office Action dated Jun. 20, 2017, directed to U.S. Appl. No. 14/428,856; 8 pages.

Stewart et al., U.S. Notice of Allowance and Fee(s) due dated Nov. 20, 2017, directed to U.S. Appl. No. 14/428,856; 9 pages.

Extended European Search Report dated May 30, 2017, directed to EP Application No. 14 858 480.8; 11 pages.

Office Action dated Jan. 29, 2021, directed to CA Application No. 2,915,912; 5 pages.

Office Action dated Nov. 20, 2020, directed to EP Application No. 13837709.8; 3 pages.

Stewart et al., U.S. Advisory Action dated Aug. 25, 2020, directed to U.S. Appl. No. 15/666,994; 6 pages.

Stewart et al., U.S. Office Action dated Apr. 15, 2021, directed to U.S. Appl. No. 16/161,770; 9 pages.

Stewart et al., U.S. Office Action dated May 11, 2021, directed to U.S. Appl. No. 15/666,994; 9 pages.

* cited by examiner

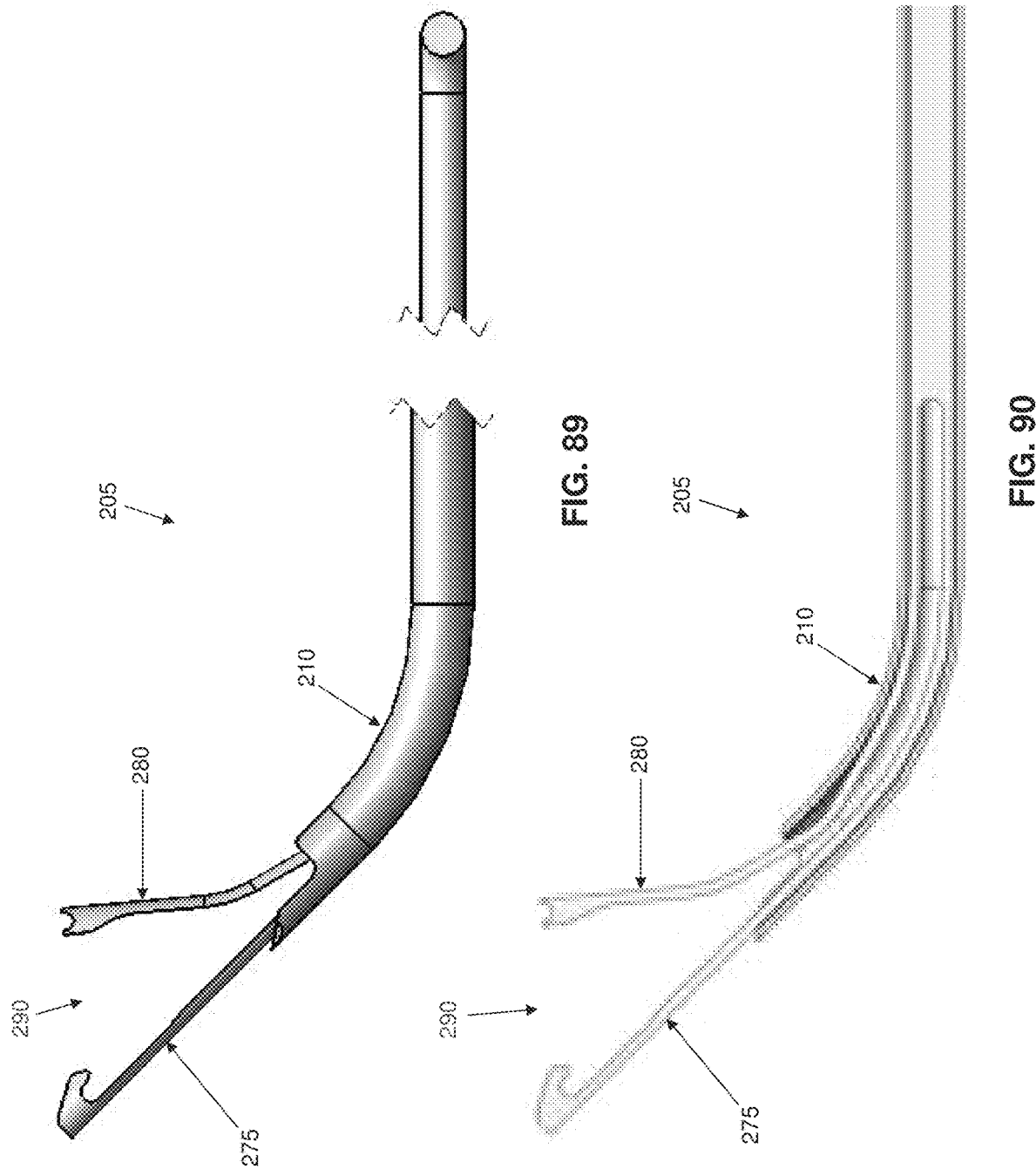

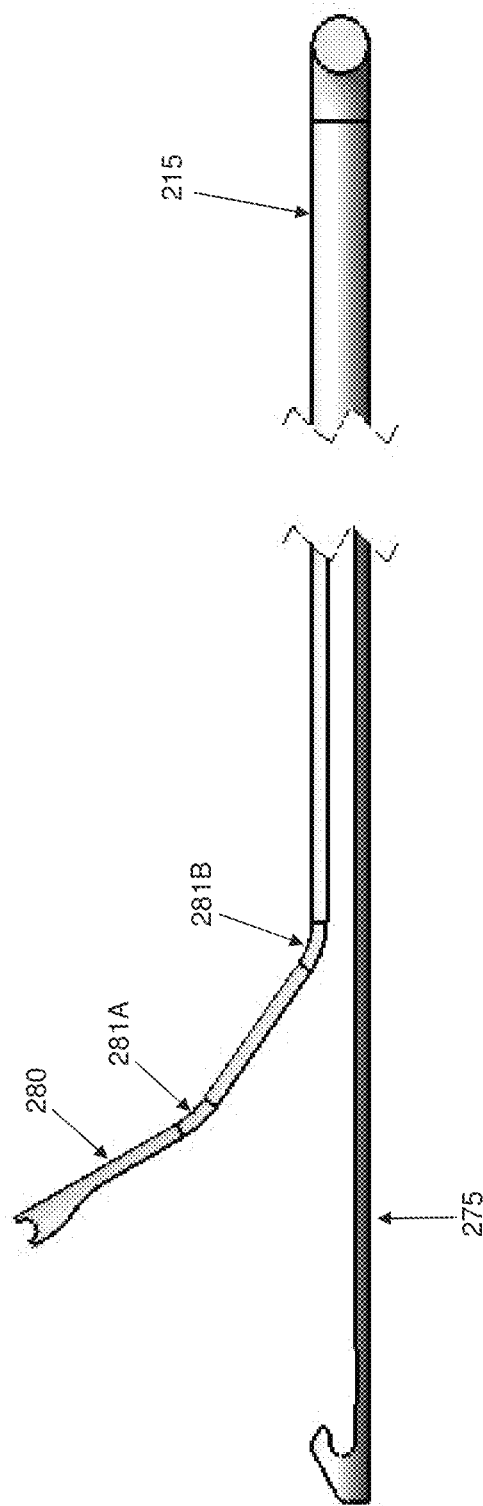

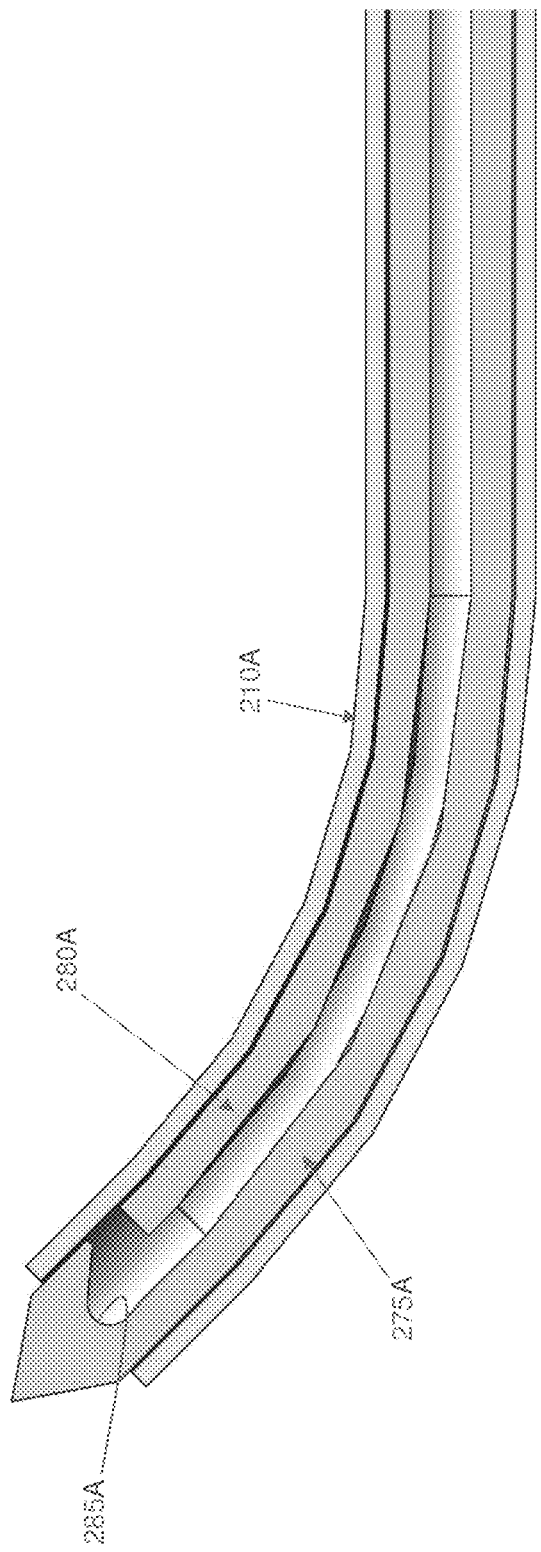

METHOD AND APPARATUS FOR PASSING SUTURE THROUGH TISSUE

CROSS-REFERENCE TO RELATED APPLICATIONS

This application is a divisional of U.S. patent application Ser. No. 15/692,839, filed Aug. 31, 2017, which is a divisional of U.S. patent application Ser. No. 14/531,531, filed Nov. 3, 2014, now U.S. Pat. No. 10,405,850, which in turn:

(1) is a continuation-in-part of International Application No. PCT/US2013/060167, filed Sep. 17, 2013, which patent application:
- (A) is a continuation-in-part of U.S. patent application Ser. No. 13/230,652, filed Sep. 12, 2011, now U.S. Pat. No. 10,123,794, which claims benefit of:
  - (i) U.S. Provisional Application No. 61/384,423, filed Sep. 20, 2010;
  - (ii) U.S. Provisional Application No. 61/473,219, filed Apr. 8, 2011;
  - (iii) U.S. Provisional Application No. 61/495,441, filed Jun. 10, 2011; and
  - (iv) U.S. Provisional Application No. 61/381,787, filed Sep. 10, 2010;
- (B) claims benefit of U.S. Provisional Application No. 61/701,920, filed Sep. 17, 2012; and
- (C) is a continuation-in-part of U.S. patent application Ser. No. 13/791,395, filed Mar. 8, 2013, now U.S. Pat. No. 10,098,631, which patent application:
  - (i) claims benefit of U.S. Provisional Application No. 61/701,920, filed Sep. 17, 2012; and
  - (ii) is a continuation-in-part of U.S. patent application Ser. No. 13/230,652, filed Sep. 12, 2011, now U.S. Pat. No. 10,123,794, which patent application in turn claims benefit of:
    - (a) U.S. Provisional Patent Application No. 61/384,423, filed Sep. 20, 2010;
    - (b) U.S. Provisional Application No. 61/473,219, filed Apr. 8, 2011;
    - (c) U.S. Provisional Application No. 61/495,441, filed Jun. 10, 2011; and (2) is a continuation-in-part of U.S. patent application Ser. No. 13/230,652, filed Sep. 12, 2011, now U.S. Pat. No. 10,123,794, which patent application in turn claims benefit of:
- (A) U.S. Provisional Application No. 61/384,423, filed Sep. 20, 2010;
- (B) U.S. Provisional Application No. 61/473,219, filed Apr. 8, 2011;
- (C) U.S. Provisional Application No. 61/495,441, filed Jun. 10, 2011; and
- (D) U.S. Provisional Application No. 61/381,787, filed Sep. 10, 2010;

(3) is a continuation-in-part of U.S. patent application Ser. No. 13/791,395, filed Mar. 8, 2013, now U.S. Pat. No. 10,098,631, which patent application:
- (A) claims benefit of U.S. Provisional Application No. 61/701,920, filed Sep. 17, 2012; and
- (B) is a continuation-in-part of U.S. patent application Ser. No. 13/230,652, filed Sep. 12, 2011, now U.S. Pat. No. 10,123,794, which patent application in turn claims benefit of:
  - (i) U.S. Provisional Application No. 61/384,423, filed Sep. 20, 2010;
  - (ii) U.S. Provisional Application No. 61/473,219, filed Apr. 8, 2011;
  - (iii) U.S. Provisional Application No. 61/495,441, filed Jun. 10, 2011; and
  - (iv) U.S. Provisional Application No. 61/381,787, filed Sep. 10, 2010;

(4) claims benefit of U.S. Provisional Application No. 61/898,729, filed Nov. 1, 2013; and (5) claims benefit of U.S. Provisional Application No. 61/947,870, filed Mar. 4, 2014.

The above-identified patent applications are each hereby incorporated herein by reference in their entirety.

FIELD OF THE INVENTION

This invention relates to surgical apparatus and procedures in general, and more particularly to surgical apparatus and procedures for passing suture through tissue.

BACKGROUND OF THE INVENTION

In many situations suture must be passed through tissue. In open surgical procedures, the suture is typically attached to a needle and the needle is then used to draw the suture through the tissue. However, in closed surgical procedures (e.g., so-called "keyhole" surgeries, where an interior surgical site is accessed through a narrow cannula), it can be difficult to advance a needle (and particularly a curved needle) to the interior surgical site, and it can be even more difficult to maneuver the needle about the interior surgical site. Furthermore, in closed surgical procedures, it is frequently necessary to advance the suture through tissue, and then to retrieve the suture on the far side of the tissue, so that the suture can thereafter be drawn back through the tissue, e.g., at a second point of penetration. Conventional needles are typically inadequate for these situations.

On account of the foregoing, in closed surgical procedures, it is common to use a suture passer to pass suture through tissue, e.g., at a remote surgical site. Such suture passers are dedicated suture passing instruments generally comprising a shaft, a tissue-penetrating and suture-carrying working tip set at the distal end of the shaft, and a handle set at the proximal end of the shaft. However, such suture passers all tend to suffer from one or more deficiencies, including but not limited to: (i) size; (ii) a need to place the suture adjacent to an edge of the tissue; (iii) difficulty in picking up suture on the far side of the tissue; (iv) complexity of operation; (v) cost of manufacture, etc.

Thus there is a need for a new and improved method and apparatus for passing suture through tissue which does not suffer from one or more of the disadvantages associated with the prior art.

SUMMARY OF THE INVENTION

The present invention provides a new and improved method and apparatus for passing suture through tissue.

In one form of the present invention, there is provided a suture passer comprising:

a hollow tube, the hollow tube comprising a distal end, a proximal end, a lumen extending from the distal end to the proximal end, and a window formed in the sidewall of the hollow tube, the window communicating with the lumen; and a clamping rod slidably received in the lumen of the hollow tube, the clamping rod comprising a distal end and a proximal end, the distal end being bifurcated into a first arm and a second arm, one of the first and second arms extending distally of the other of the first and second arms and including a clamping surface, and at least one of the first and second arms being outwardly biased such that when the clamping rod is moved distally so that the distal end of the at least one outwardly biased arm is adjacent to the window, the distal end of the at least one outwardly biased arm extends outwardly through the window.

In another form of the present invention, there is provided a method for passing suture through an object, the method comprising:

providing a suture passer comprising:
a hollow tube, the hollow tube comprising a distal end, a proximal end, a lumen extending from the distal end to the proximal end, and a window formed in the sidewall of the hollow tube, the window communicating with the lumen; and
a clamping rod slidably received in the lumen of the hollow tube, the clamping rod comprising a distal end and a proximal end, the distal end being bifurcated into a first arm and a second arm, one of the first and second arms extending distally of the other of the first and second arms and including a clamping surface, and at least one of the first and second arms being outwardly biased such that when the clamping rod is moved distally so that the distal end of the at least one outwardly biased arm is adjacent to the window, the distal end of the at least one outwardly biased arm extends outwardly through the window;
positioning the clamping rod so that the at least one outwardly biased arm extends out of the window;
positioning at least one of the suture passer and the suture so that the suture is disposed in the window;
moving the clamping rod proximally so that the clamping surface clamps the suture to the hollow tube; and
moving the suture passer so that the suture is passed through the object.

In another form of the present invention, there is provided a suture passer comprising:
a hollow tube, the hollow tube comprising a pointed distal end, a proximal end and a lumen extending from the distal end to the proximal end; and
a clamping rod slidably received in the lumen of the hollow tube, the clamping rod comprising a distal end and a proximal end, the distal end being bifurcated into a first arm and a second arm, the first arm extending distally of the second arm and including a clamping surface, and the second arm being outwardly biased such that when the clamping rod is moved distally so that the distal end of the second arm extends out of the distal end of the hollow tube, the distal end of the second arm extends laterally of the hollow tube.

In another form of the present invention, there is provided a method for passing suture through an object, the method comprising:

providing a suture passer comprising:
a hollow tube, the hollow tube comprising a pointed distal end, a proximal end and a lumen extending from the distal end to the proximal end; and
a clamping rod slidably received in the lumen of the hollow tube, the clamping rod comprising a distal end and a proximal end, the distal end being bifurcated into a first arm and a second arm, the first arm extending distally of the second arm and including a clamping surface, and the second arm being outwardly biased such that when the clamping rod is moved distally so that the distal end of the second arm extends out of the distal end of the hollow tube, the distal end of the second arm extends laterally of the hollow tube;
positioning the clamping rod so that the second arm extends out of the distal end of the hollow tube;
positioning at least one of the suture passer and the suture so that the suture is disposed between the clamping surface and the distal end of the hollow tube;
moving the clamping rod proximally so that the clamping surface clamps the suture to the hollow tube; and
moving the suture passer so that the suture is passed through the object.

In another form of the present invention, there is provided a suture passer comprising:
a shaft comprising a distal end, a proximal end, a lumen extending from the proximal end toward the distal end, and a window formed in the sidewall of the shaft, the window communicating with the lumen; and
a suture spear movable within the lumen of the shaft, the suture spear comprising a distal end and a proximal end, the distal end being pointed to pierce a suture located in the window.

In another form of the present invention, there is provided a method for passing suture through an object, the method comprising:

providing a suture passer comprising:
a shaft comprising a distal end, a proximal end, a lumen extending from the proximal end toward the distal end, and a window formed in the sidewall of the shaft, the window communicating with the lumen; and
a suture spear movable within the lumen of the shaft, the suture spear comprising a distal end and a proximal end, the distal end being pointed to pierce a suture located in the window.
positioning the suture spear so that it is disposed proximal to the window;
positioning at least one of the suture passer and the suture so that the suture is disposed in the window;
moving the suture spear distally so that the suture spear extends into the suture disposed in the window; and
moving the suture passer so that the suture is passed through the object.

In another form of the present invention, there is provided a suture passer comprising:
a hollow tube, the hollow tube comprising a distal end, a proximal end, a lumen extending from the distal end to the proximal end, and a window formed in the sidewall of the hollow tube, the window communicating with the lumen; and
a clamping rod slidably received in the lumen of the hollow tube, the clamping rod comprising a distal end and a proximal end, the distal end including a clamping surface, and the distal end being outwardly biased such that when the clamping rod is moved distally so that the distal end of the clamping rod is adjacent to the window, the distal end of the clamping rod extends outwardly through the window.

In another form of the present invention, there is provided a method for passing suture through an object, the method comprising:

providing a suture passer comprising:
a hollow tube, the hollow tube comprising a distal end, a proximal end, a lumen extending from the distal end to the proximal end, and a window formed in the sidewall of the hollow tube, the window communicating with the lumen; and
a clamping rod slidably received in the lumen of the hollow tube, the clamping rod comprising a distal end and a proximal end, the distal end including a clamping surface, and the distal end being outwardly biased such that when the clamping rod is moved distally so that the distal end of the clamping rod is adjacent to the window, the distal end of the clamping rod extends outwardly through the window;

positioning the clamping rod so that the distal end of the clamping rod extends out of the window;

positioning at least one of the suture passer and the suture so that the suture is disposed in the window;

moving the clamping rod proximally so that the clamping surface clamps the suture to the hollow tube; and moving the suture passer so that the suture is passed through the object.

In another form of the present invention, there is provided a suture passer comprising:

a hollow tube, the hollow tube comprising a distal end, a proximal end, and a lumen extending from the distal end to the proximal end; and a clamping rod slidably received in the lumen of the hollow tube, the clamping rod comprising a distal end and a proximal end, the distal end being bifurcated into a first arm and a second arm, one of the first and second arms extending distally of the other of the first and second arms and including a clamping surface;

wherein at least one of the first arm and the second arm comprises a friction-enhancing surface for facilitating manipulation of a suture via engagement of the suture with the friction-enhancing surface.

In another form of the present invention, there is provided a method for passing suture through an object, the method comprising:

providing a suture passer comprising:
a hollow tube, the hollow tube comprising a distal end, a proximal end, and a lumen extending from the distal end to the proximal end; and
a clamping rod slidably received in the lumen of the hollow tube, the clamping rod comprising a distal end and a proximal end, the distal end being bifurcated into a first arm and a second arm, one of the first and second arms extending distally of the other of the first and second arms and including a clamping surface;
wherein at least one of the first arm and the second arm comprises a friction-enhancing surface for facilitating manipulation of a suture via engagement of the suture with the friction-enhancing surface;

positioning the clamping rod so that at least one of the first arm and the second arm extends out of the hollow tube;

manipulating a suture via engagement of the suture with the friction-enhancing surface on the at least one of the first arm and the second arm;

positioning at least one of the suture passer and the suture so that the suture is disposed between the first arm and the second arm;

moving the clamping rod proximally so that the clamping surface clamps the suture to the hollow tube; and moving the suture passer so that the suture is passed through the object.

In another form of the present invention, there is provided a suture passer comprising:

a hollow tube, the hollow tube comprising a pointed distal end, a proximal end and a lumen extending from the distal end to the proximal end; and a clamping rod slidably received in the lumen of the hollow tube, the clamping rod comprising a distal end and a proximal end, the distal end being bifurcated into a first arm and a second arm, the first arm extending distally of the second arm and including a clamping surface, and the second arm being outwardly biased such that when the clamping rod is moved distally, the distal end of the second arm extends laterally of the hollow tube, and wherein the second arm is configured to releasably hold a suture to the distal end of the second arm.

In another form of the present invention, there is provided a method for passing suture through an object, the method comprising:

providing a suture passer comprising:
a hollow tube, the hollow tube comprising a pointed distal end, a proximal end and a lumen extending from the distal end to the proximal end; and
a clamping rod slidably received in the lumen of the hollow tube, the clamping rod comprising a distal end and a proximal end, the distal end being bifurcated into a first arm and a second arm, the first arm extending distally of the second arm and including a clamping surface, and the second arm being outwardly biased such that when the clamping rod is moved distally so that the distal end of the second arm extends out of the distal end of the hollow tube, the distal end of the second arm extends laterally of the hollow tube, and wherein the second arm is configured to releasably hold a suture to the distal end thereof;

positioning the clamping rod so that the second arm extends out of the distal end of the hollow tube;

positioning at least one of the suture passer and the suture so that the suture is disposed between the clamping surface and the distal end of the hollow tube;

moving the clamping rod proximally so that the clamping surface clamps the suture to the hollow tube;

moving the suture passer so that the suture is passed through the object; and moving the clamping rod distally so that the distal end of the second arm moves the suture away from the hollow tube.

In another form of the present invention, there is provided a suture passer comprising:

a hollow tube, said hollow tube comprising a distal end, a proximal end, and a lumen extending from said distal end to said proximal end; and a suture manipulation rod slidably received in said lumen of said hollow tube and selectively projectable out said distal end of said hollow tube, said suture manipulation rod comprising a distal end and a proximal end, said distal end of said suture manipulation rod being bifurcated into a first arm and a second arm, wherein said first arm includes a hook comprising a proximally oriented hooking surface and a return extending proximally of said hooking surface;

wherein said hollow tube and said suture manipulation rod are sized so that said suture manipulation rod may capture a suture disposed adjacent to said distal end of said hollow tube and draw the suture into said lumen of said hollow tube, and further wherein, after a suture has been drawn into said lumen of said hollow tube, distal movement of said suture manipulation rod causes the suture to be expelled from said hollow tube.

In another form of the present invention, there is provided a method for passing suture through an object, the method comprising:

providing a suture passer comprising:
a hollow tube, said hollow tube comprising a distal end, a proximal end, and a lumen extending from said distal end to said proximal end; and
a suture manipulation rod slidably received in said lumen of said hollow tube and selectively projectable out said distal end of said hollow tube, said suture manipulation rod comprising a distal end and a proximal end, said distal end of said suture manipulation rod being bifurcated into a first arm and a second arm, wherein said first arm includes a hook comprising a proximally oriented hooking surface and a return extending proximally of said hooking surface;

wherein said hollow tube and said suture manipulation rod are sized so that said suture manipulation rod may capture a suture disposed adjacent to said distal end of said hollow tube and draw a suture into said lumen of said hollow tube, and further wherein, after a suture has been drawn into said lumen of said hollow tube, distal movement of said suture manipulation rod causes the suture to be expelled from said hollow tube;

positioning said suture manipulation rod so that said suture manipulation rod extends out of said hollow tube;

positioning at least one of said suture passer and the suture so that the suture is disposed between said first arm and said second arm;

moving said suture manipulation rod proximally so that said suture manipulation rod captures the suture and draws the suture into said lumen of said hollow tube; and moving said suture passer so that the suture is passed through the object.

In another form of the present invention, there is provided a suture passer comprising:

a hollow tube, said hollow tube comprising a distal end, a proximal end, and a lumen extending from said distal end to said proximal end; and a suture manipulation rod slidably received in said lumen of said hollow tube and selectively projectable out said distal end of said hollow tube, said suture manipulation rod comprising a distal end and a proximal end, said distal end of said suture manipulation rod comprising a hook comprising a proximally oriented hooking surface and a return extending proximally of said hooking surface, and a pushing surface disposed proximally of said return of said hook of said suture manipulation rod;

wherein said hollow tube and said suture manipulation rod are sized so that said suture manipulation rod may capture a suture disposed adjacent to said distal end of said hollow tube and draw the suture into said lumen of said hollow tube, and further wherein, after a suture has been drawn into said lumen of said hollow tube, distal movement of said suture manipulation rod causes the suture to be expelled from said hollow tube.

In another form of the present invention, there is provided a method for passing suture through an object, the method comprising:

providing a suture passer comprising:

a hollow tube, said hollow tube comprising a distal end, a proximal end, and a lumen extending from said distal end to said proximal end; and a suture manipulation rod slidably received in said lumen of said hollow tube and selectively projectable out said distal end of said hollow tube, said suture manipulation rod comprising a distal end and a proximal end, said distal end of said suture manipulation rod comprising a hook comprising a proximally oriented hooking surface and a return extending proximally of said hooking surface, and a pushing surface disposed proximally of said return of said hook of said suture manipulation rod;

wherein said hollow tube and said suture manipulation rod are sized so that said suture manipulation rod may capture a suture disposed adjacent to said distal end of said hollow tube and draw the suture into said lumen of said hollow tube, and further wherein, after a suture has been drawn into said lumen of said hollow tube, distal movement of said suture manipulation rod causes the suture to be expelled from said hollow tube;

positioning said suture manipulation rod so that said suture manipulation rod extends out of said hollow tube;

positioning at least one of said suture passer and the suture so that the suture is disposed between said hooking surface and said pushing surface;

moving said suture manipulation rod proximally so that said suture manipulation rod captures the suture and draws the suture into said lumen of said hollow tube; and moving said suture passer so that the suture is passed through the object.

BRIEF DESCRIPTION OF THE DRAWINGS

These and other objects and features of the present invention will be more fully disclosed or rendered obvious by the following detailed description of the preferred embodiments of the invention, which is to be considered together with the accompanying drawings wherein like numbers refer to like parts, and further wherein:

FIGS. 87-91 are schematic views showing yet another novel form of suture passer formed in accordance with the present invention;

FIGS. 114 and 115 are schematic views showing another form of suture passer formed in accordance with the present invention.

DETAILED DESCRIPTION OF THE PREFERRED EMBODIMENTS

Figure 1:
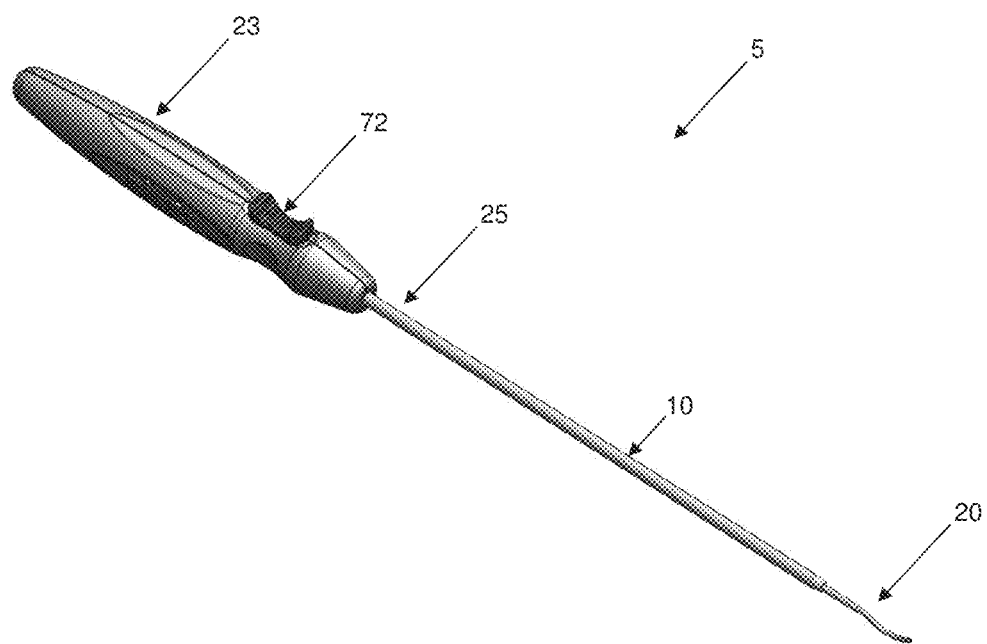
FIGS. 1-11 are schematic views showing a novel suture passer formed in accordance with the present invention.
Figure 2:
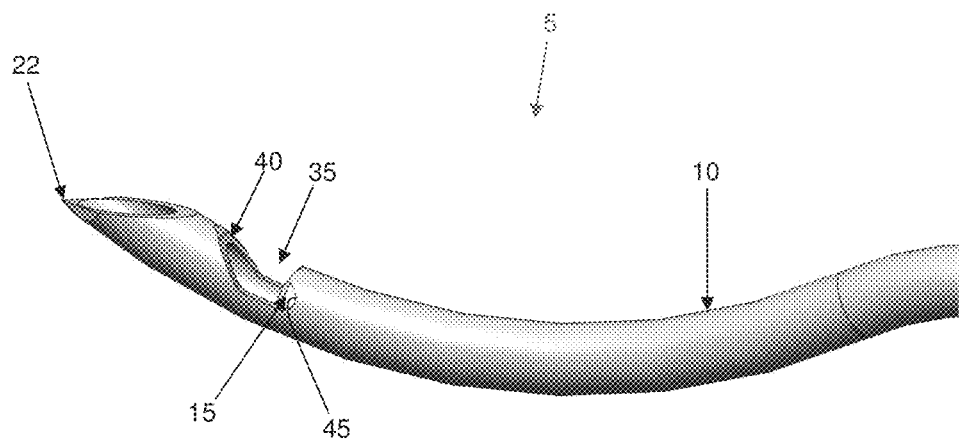
Figure 3:
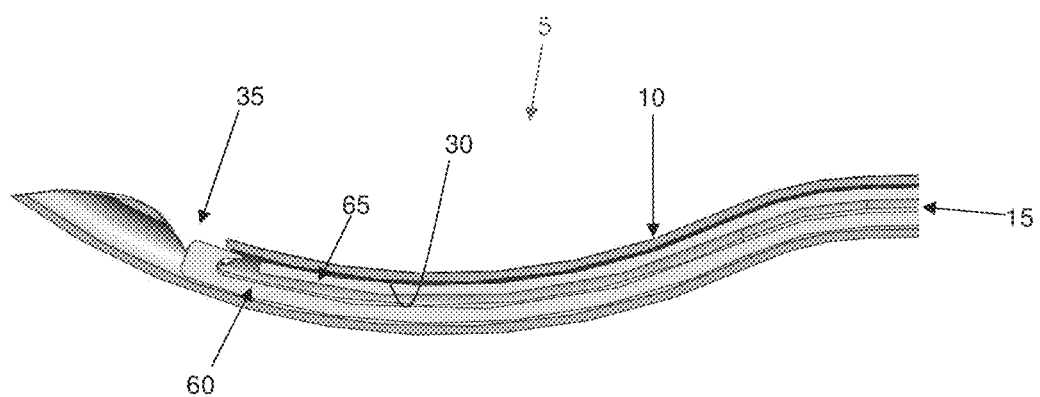
Figure 4:
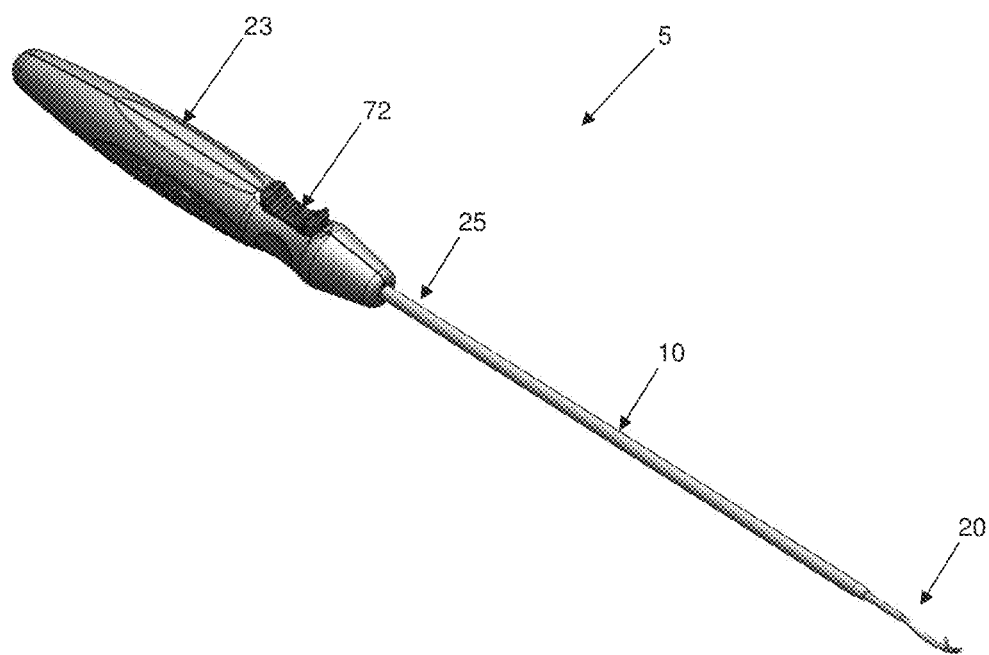

The present invention provides a new and improved method and apparatus for passing suture through tissue.

The Novel Suture Passer

Looking first at FIGS. 1-11, there is shown a novel suture passer 5 formed in accordance with the present invention. Suture passer 5 generally comprises a hollow tube 10 and a clamping rod 15 slidably disposed within the lumen of hollow tube 10, as will hereinafter be discussed in further detail.

More particularly, hollow tube 10 comprises a distal end 20 preferably terminating in a sharp point 22, and a proximal end 25 preferably terminating in a handle 23, with a lumen 30 extending therebetween. It will be appreciated that the pointed hollow tube 10 essentially comprises a hollow needle adapted to pierce tissue.

Hollow tube 10 further comprises a window 35 which extends radially into the hollow tube and communicates with lumen 30. Window 35 is sized so as to selectively receive a suture S therein, as will hereinafter be discussed in further detail. Window 35 preferably comprises an inclined distal surface 40 and an inclined proximal surface 45. Preferably, distal surface 40 and proximal surface 45 are inclined in the same direction, and preferably both surfaces are inclined distally (e.g., in the manner shown in FIGS. 1-11). The forward incline of inclined distal surface 40 allows suture to more easily pass into and out of window 35. The forward incline of inclined proximal surface 45 provides an undercut which helps to trap the suture S between the clamping surface 47 of clamping rod 15 and the inclined proximal surface 45 of window 35, as will hereinafter be discussed in further detail.

Hollow tube 10 is preferably formed out of a substantially rigid material (e.g., stainless steel) so as to maintain rigidity when passing through tissue, particularly relatively tough fibrous tissue (e.g., the labrum of the hip).

In one preferred form of the present invention, the distal end 20 of hollow tube 10 is curved, however, it should be appreciated that hollow tube 10 can be formed in other configurations well known in the art (e.g., straight, etc.).

Figure 9:
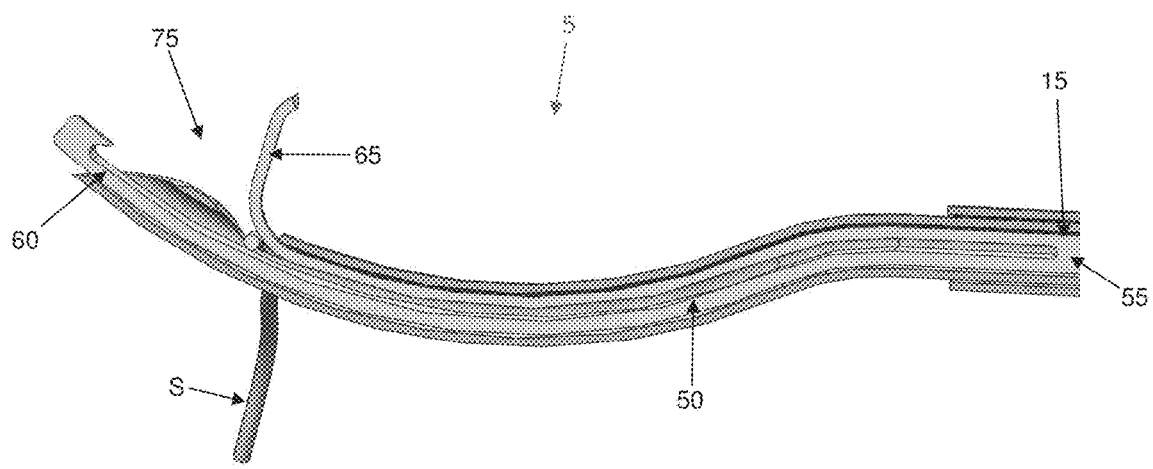

Clamping rod 15 comprises a distal end 50 (FIG. 9) and a proximal end 55 (FIG. 9). Distal end 50 of clamping rod 15 is bifurcated so as to form a first arm 60 and a second arm 65.

First arm 60 comprises the aforementioned clamping surface 47, with clamping surface 47 extending radially from the longitudinal axis of clamping rod 15. Clamping surface 47 may take the form of a hook, as shown in FIGS. 1-11. This hook helps trap the suture S between clamping surface 47 of clamping rod 15 and inclined proximal surface 45 of window 35, in the manner shown in FIGS. 10 and 11.

Second arm 65 extends parallel to first arm 60 when clamping rod 15 is disposed within lumen 30 of hollow tube 10, with second arm 65 terminating proximally of first arm 60, shy of clamping surface 47.

Second arm 65 is outwardly biased so that when second arm 65 advances past window 35, second arm 65 passes radially outwardly through window 35 so as to project at an angle of approximately 10-120 degrees relative to the adjacent longitudinal axis of first arm 60 (FIG. 6) (i.e., the longitudinal axis of first arm 60 at the point adjacent to where second arm 65 advances outwardly through window 35), and more preferably at an angle of approximately 30-90 degrees to the instantaneous longitudinal axis of first arm 60, whereby to create a funnel region 75 (FIG. 7) between hollow tube 10 and second arm 65 when second arm 65 extends out window 35. To this end, second arm 65 is preferably formed out of a material consistent with this spring bias (e.g., a superelastic material such as Nitinol, etc.). In one preferred form of the invention, the entire clamping rod 15 is formed out of a superelastic material such as Nitinol.

The proximal end 55 of clamping rod 15 extends through lumen 30 of hollow tube 10 and is connected to an actuator 72 (FIG. 1) which is movably mounted to handle 23, such that movement of actuator 72 relative to handle 23 will cause movement of clamping rod 15 relative to hollow tube 10.

Figure 5:
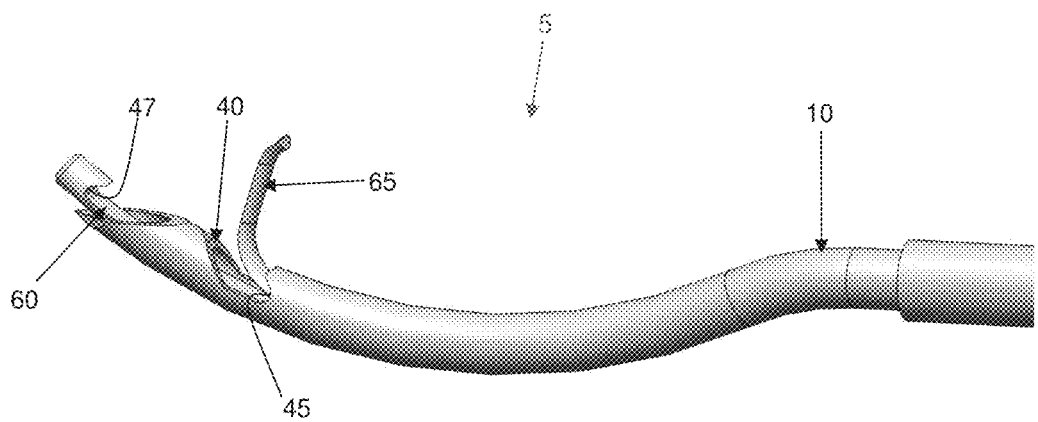
Figure 6:
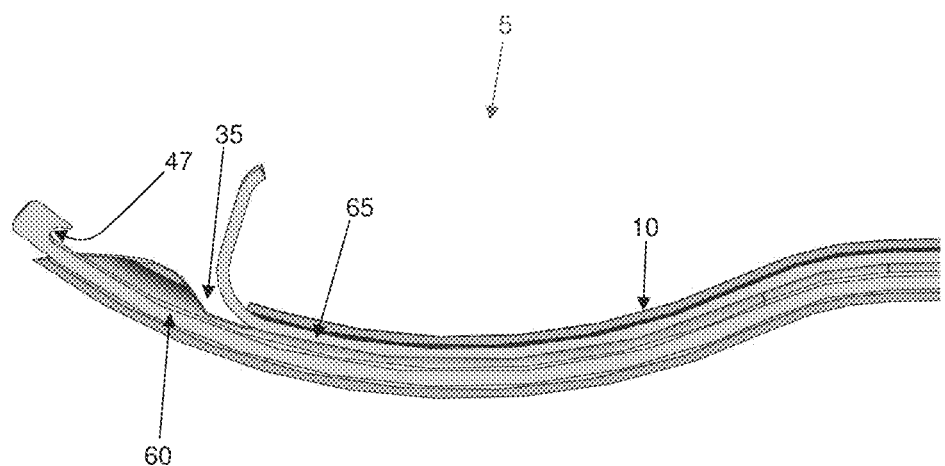
Figure 7:
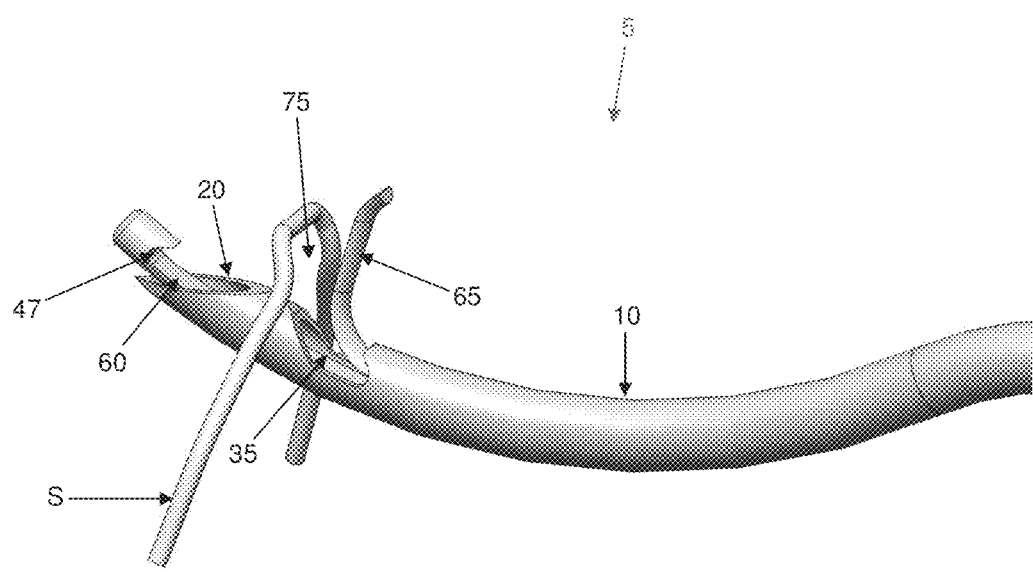
Figure 8:
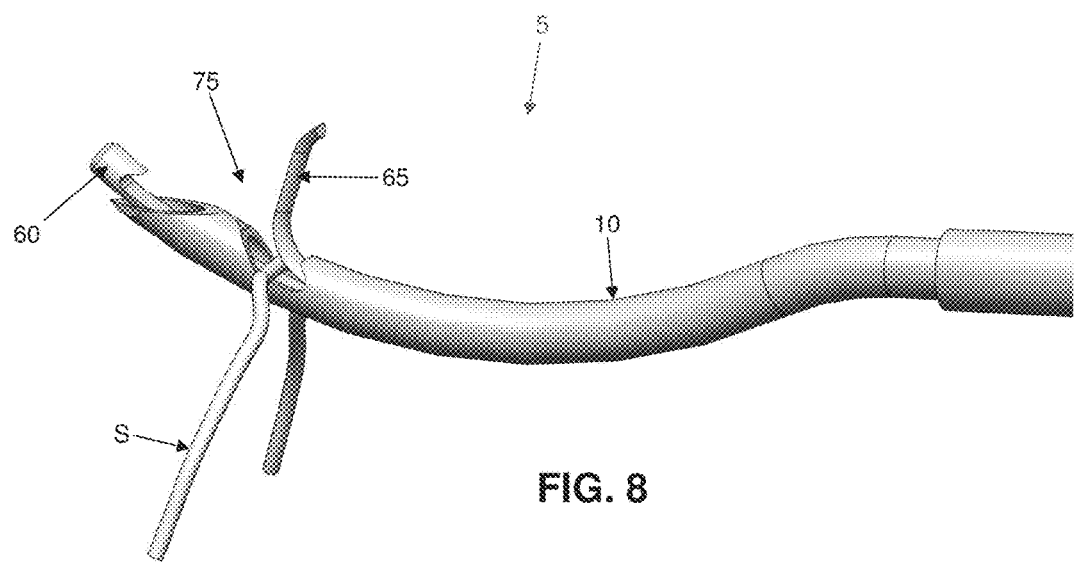
Figure 10:
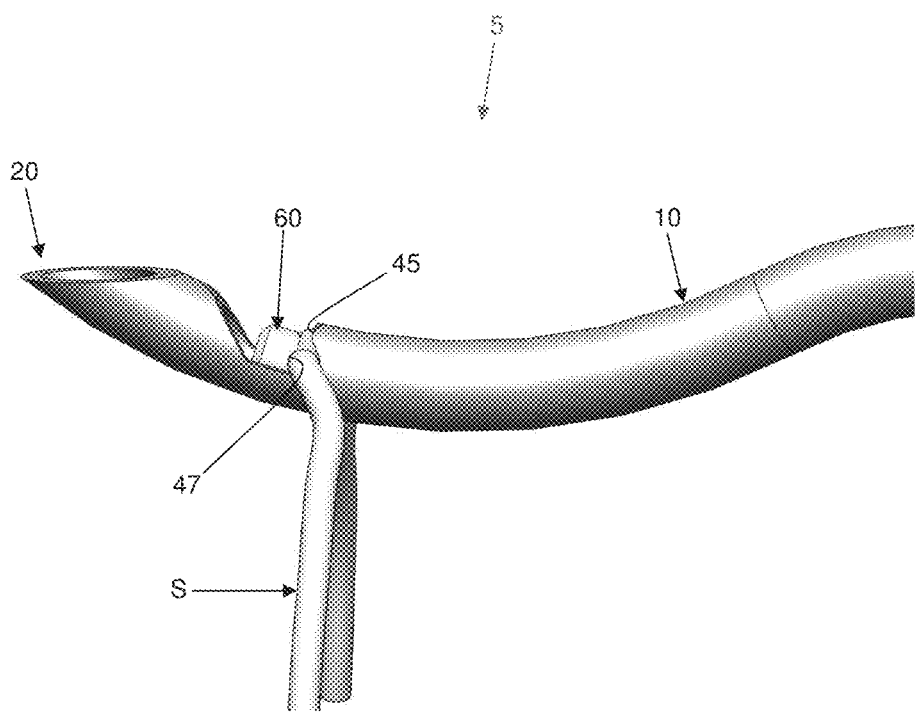
Figure 11:
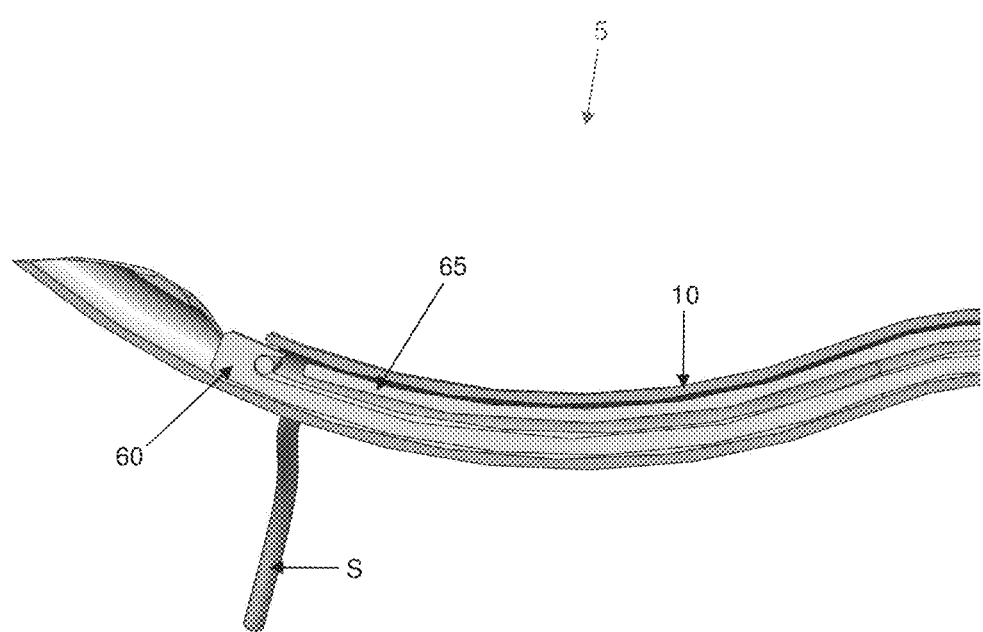

It will be appreciated that, on account of the foregoing construction, a piece of suture S may be clamped to the distal end of suture passer 5 by (i) moving clamping rod 15 to the position shown in FIGS. 5 and 6 (e.g., by moving actuator 72 distally relative to handle 23) so that clamping surface 47 of first arm 60 is distal to window 35, and so that second arm 65 extends out of window 35; (ii) positioning the suture S in window 35 (FIGS. 7-9); and (iii) moving clamping rod 15 proximally (e.g., by moving actuator 72 proximally relative to handle 23) so as to cause clamping surface 47 of first arm 60 to clamp suture S against proximal surface 45 of window 35, as shown in FIGS. 10 and 11. In this respect it will be appreciated that the creation of the funnel region 75 (established between hollow tube 10 and the extended second arm 65) at the mouth of window 35 facilitates guidance of suture S into window 35, as shown in FIGS. 7-9.

It will also be appreciated that, on account of the foregoing construction, a clamped piece of suture may thereafter be released from suture passer 5 by (a) moving clamping rod 15 distally (FIGS. 8 and 9) so as to space clamping surface 47 of first arm 60 away from proximal surface 45 of window 35; and (b) causing suture S to be withdrawn from window 35 (FIG. 7), either by moving suture S relative to suture passer 5 or by moving suture passer 5 relative to suture S or by moving both suture S and suture passer 5 relative to one another.

It should be appreciated that, in one preferred form of the invention, when clamping rod 15 is moved proximally, both first arm 60 and second arm 65 are disposed within lumen 30 of hollow tube 10, so that the distal end of suture passer 5 presents a smooth outer surface, whereby to facilitate passage of the distal end of suture passer 5 through tissue.

Using the Novel Suture Passer to Pass Suture from the Near Side of Tissue to the Far Side of Tissue In one preferred form of the present invention, and looking now at FIGS. 12-18, the novel suture passer 5 can be used to pass suture S from the near side of tissue T to the far side of tissue T (i.e., in an "antegrade" manner).

Figure 12:
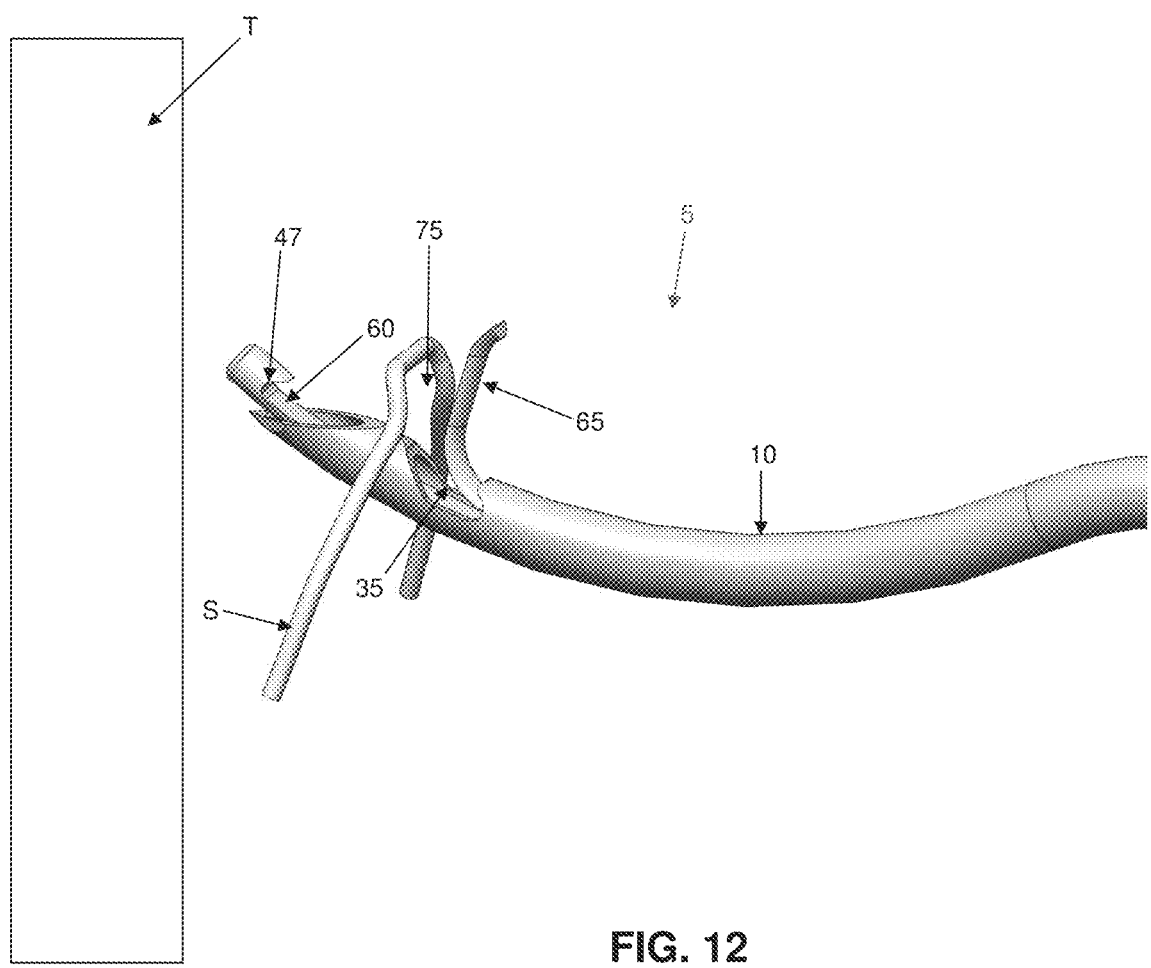
FIGS. 12-25 are schematic views showing an exemplary manner of passing suture through tissue using the novel suture passer of FIGS. 1-11.
Figure 13:
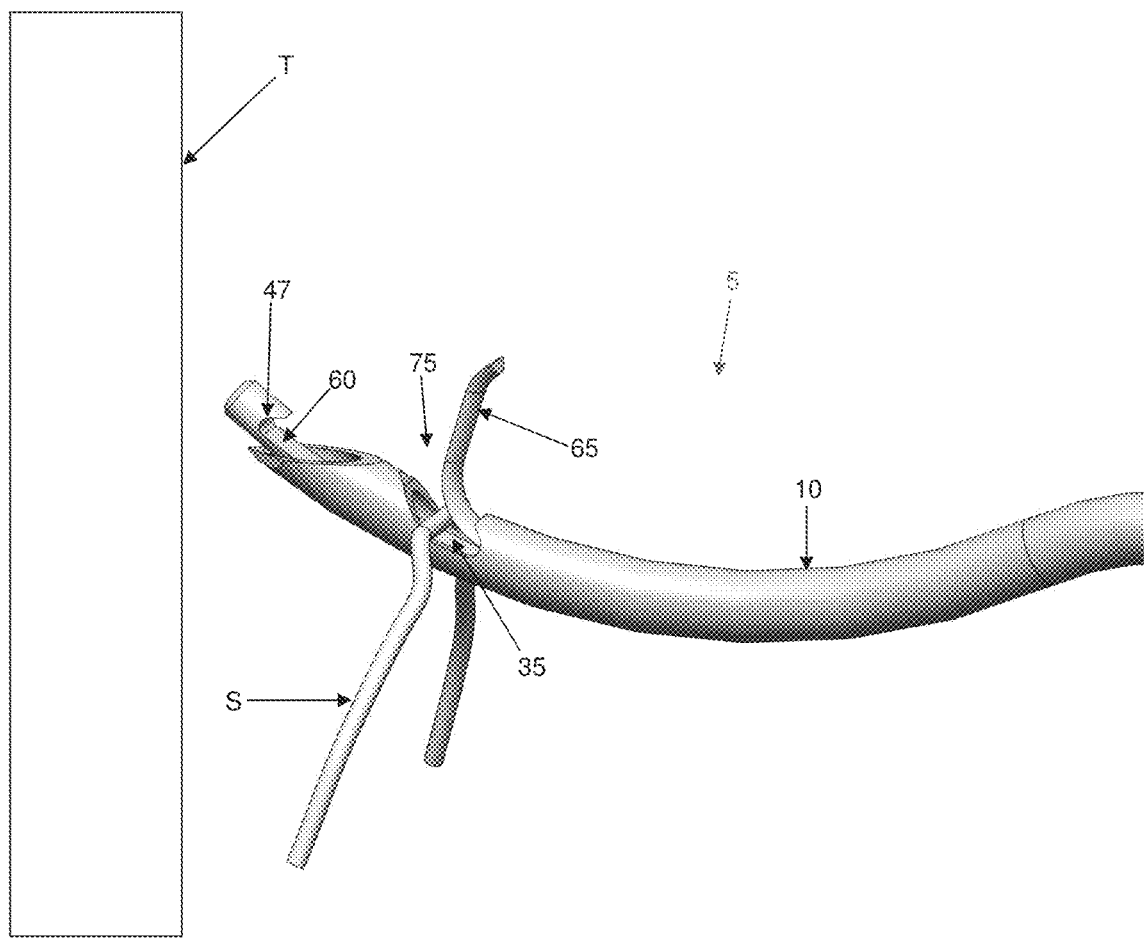
Figure 14:
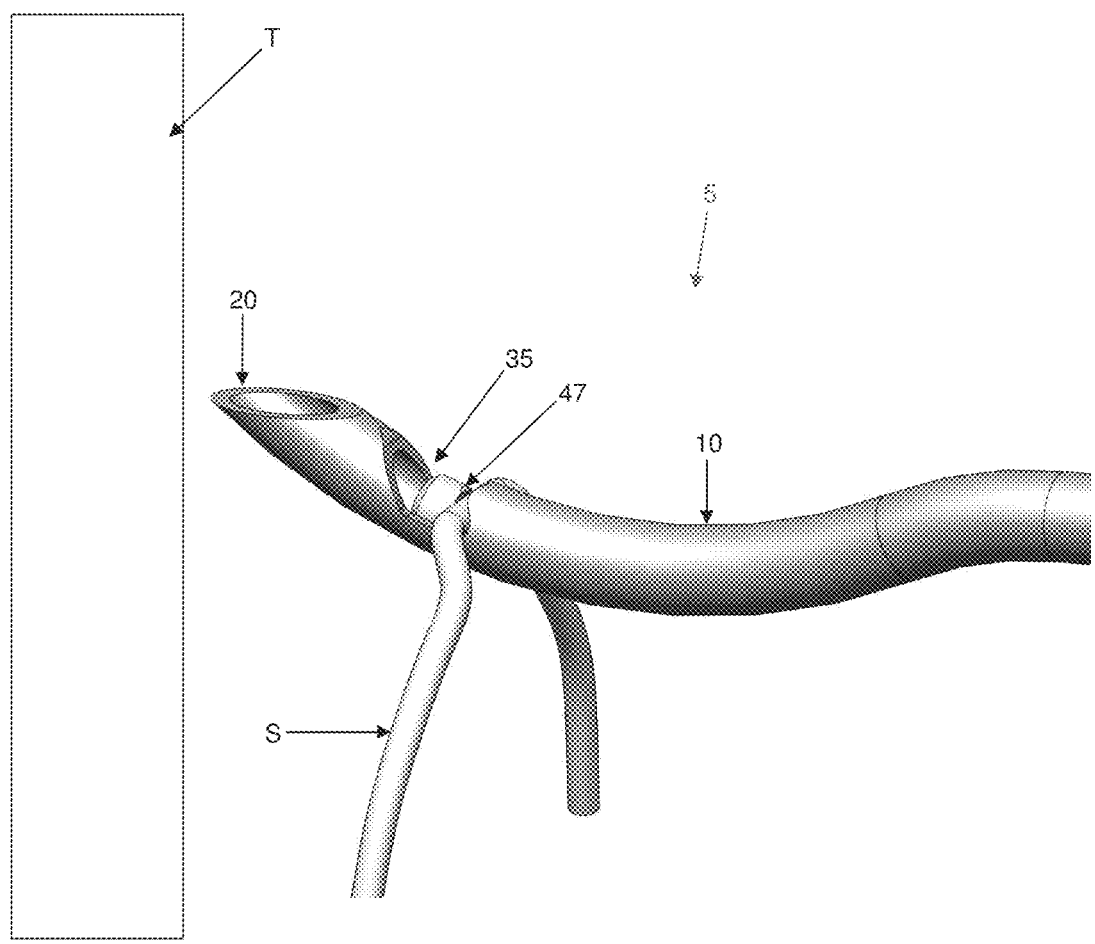

More particularly, the preliminary loading of suture S into suture passer 5 may be performed away from the surgical site (e.g., outside of the patient) or it may be performed adjacent to the near side of the tissue T which is to be sutured (e.g., inside of the patient). As seen in FIG. 12, clamping rod 15 is advanced to its most distal position so that second arm 65 advances out of window 35, whereby to project out of the axis of hollow tube 10 and create the aforementioned funnel region 75. Suture S is then guided into window 35 using this funnel effect, as seen in FIG. 13, either by moving suture S relative to suture passer 5 or by moving suture passer 5 relative to suture S or by moving both suture S and suture passer 5 relative to one another. Clamping rod 15 is then retracted proximally so that clamping surface 47 clamps suture S between clamping surface 47 of first arm 60 and proximal surface 45 of window 35. See FIG. 14.

Figure 15:
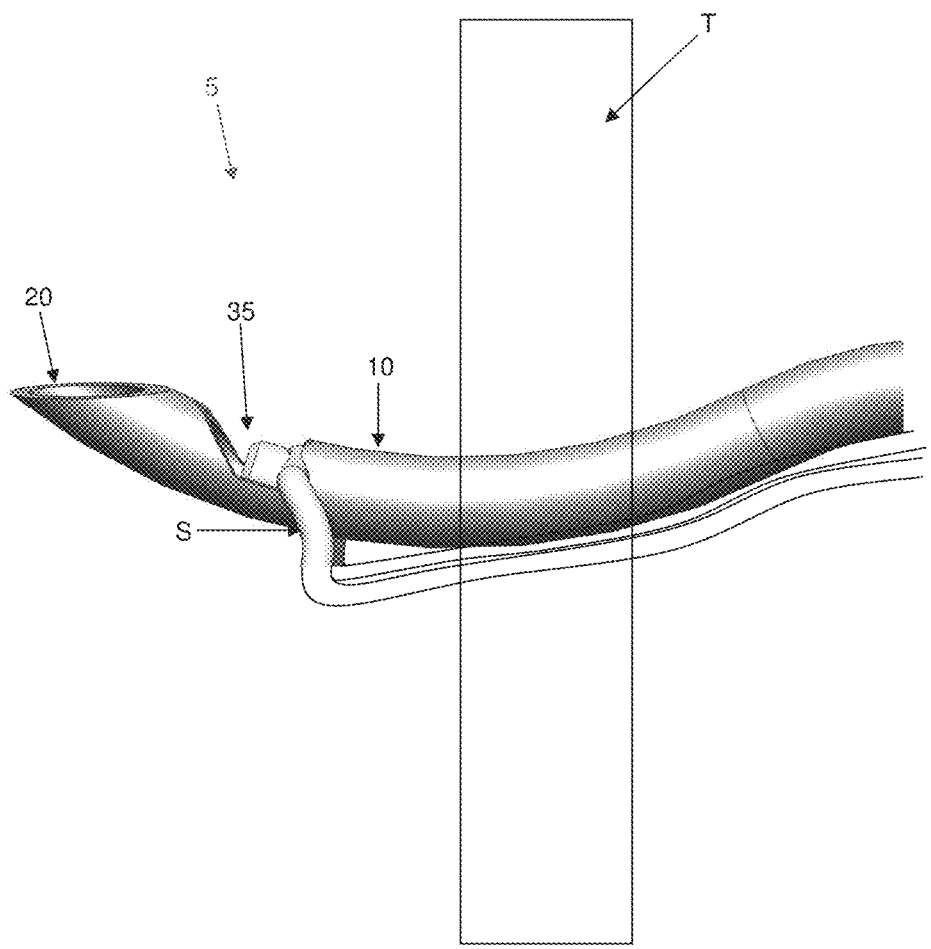
Figure 16:
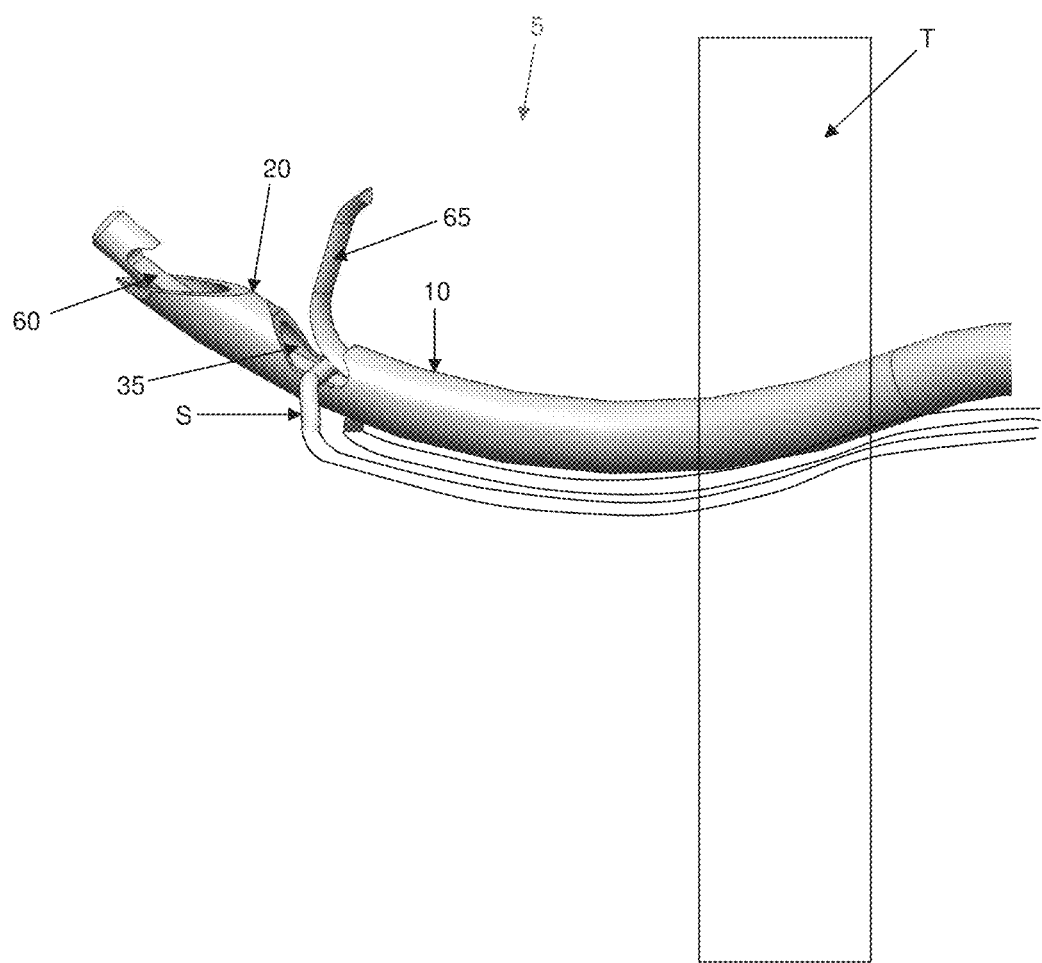
Figure 17:
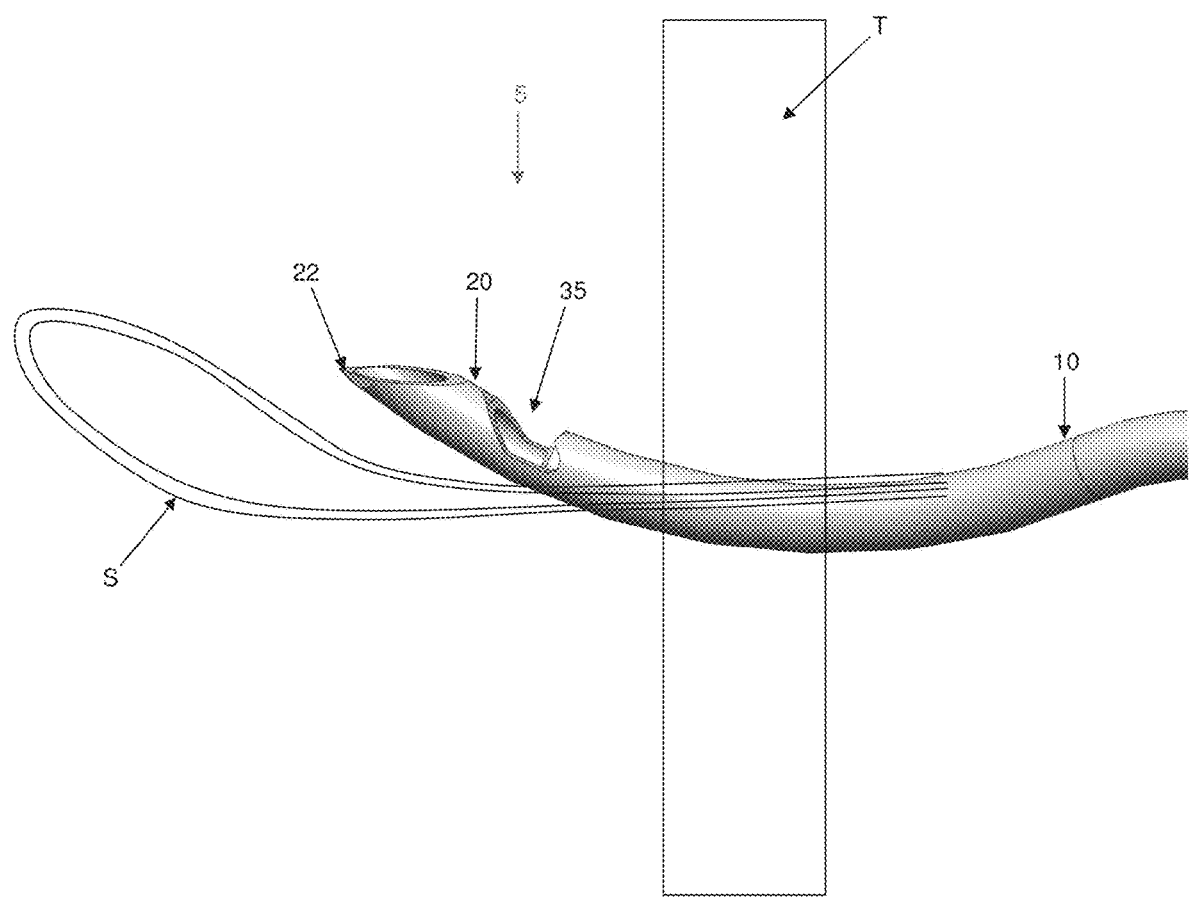
Figure 18:
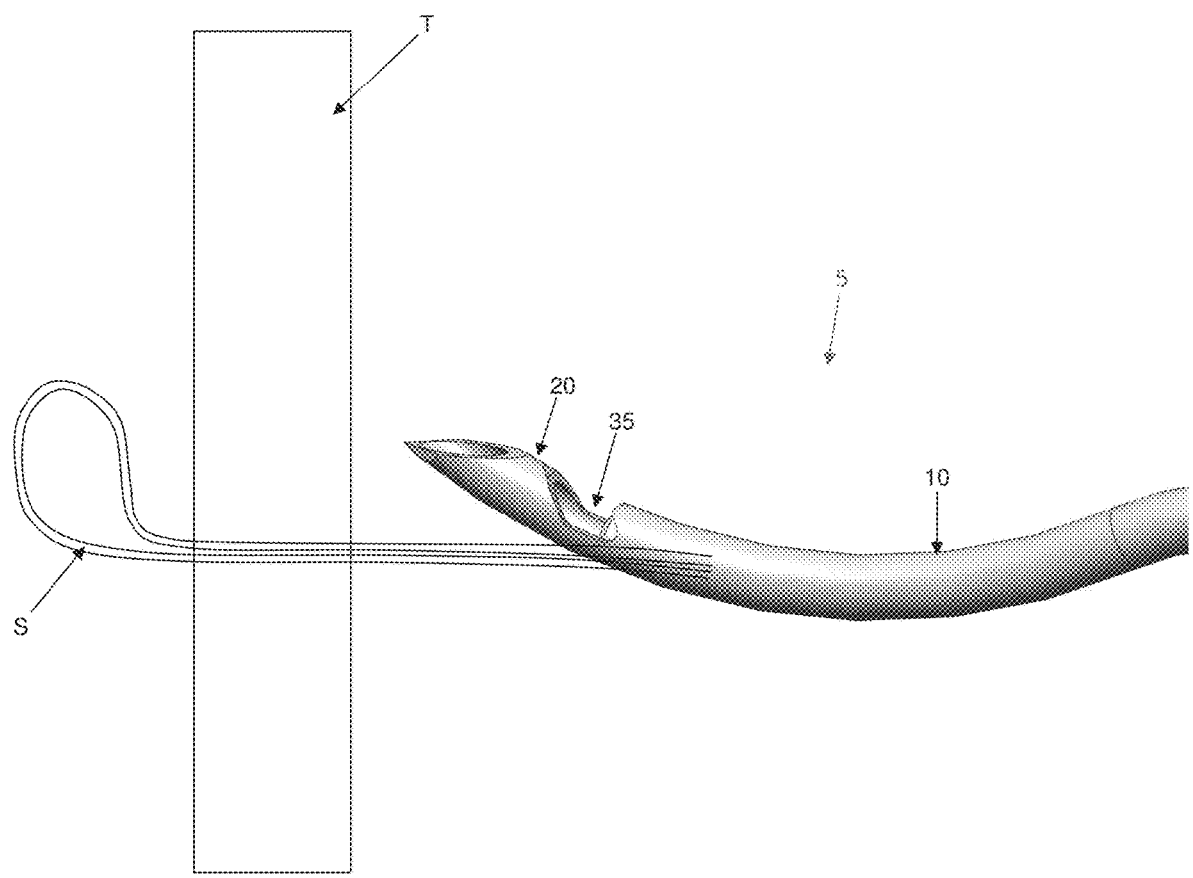

Suture passer 5 is then advanced distally so that window 35 passes through tissue T, whereby to carry suture S through the tissue (FIG. 15). With suture S extending through tissue T, and looking now at FIG. 16, clamping rod 15 is advanced distally so that clamping surface 47 is disposed distal to window 35, thereby releasing suture S from suture passer 5. Suture passer 5 and/or suture S are then manipulated so that suture S is clear of window 35 (FIG. 17). Clamping rod 15 is then moved proximally so as to retract first arm 60 and second arm 65 back into hollow tube 10. Suture passer 5 may then be withdrawn back through tissue T, leaving suture S extending through tissue T, as shown in FIG. 18.

Using the Novel Suture Passer to Draw Suture from the Far Side of Tissue to the Near Side of Tissue In another preferred form of the present invention, and looking now at FIGS. 19-25, the novel suture passer 5 can be used to draw suture S from the far side of tissue T to the near side of tissue T (i.e., in a "retrograde" manner).

Figure 19:
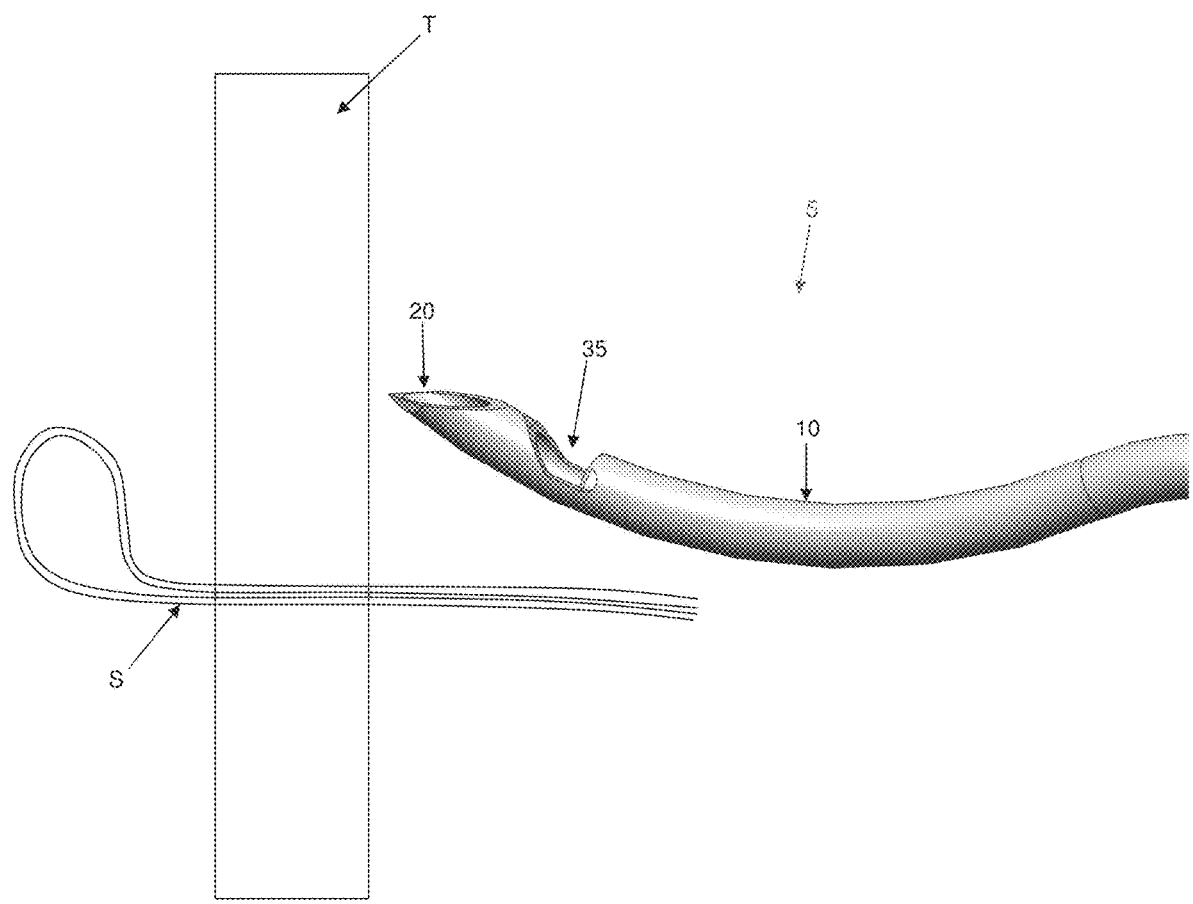
Figure 20:
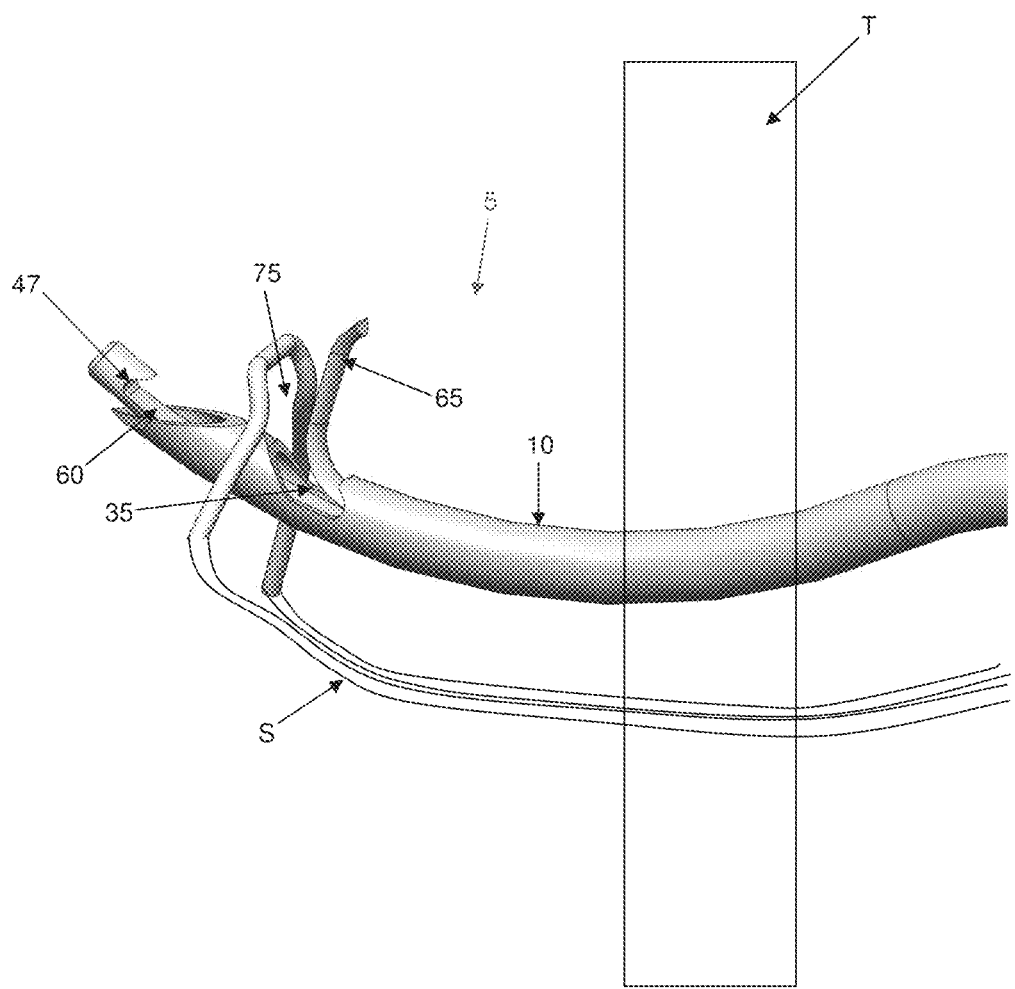
Figure 21:
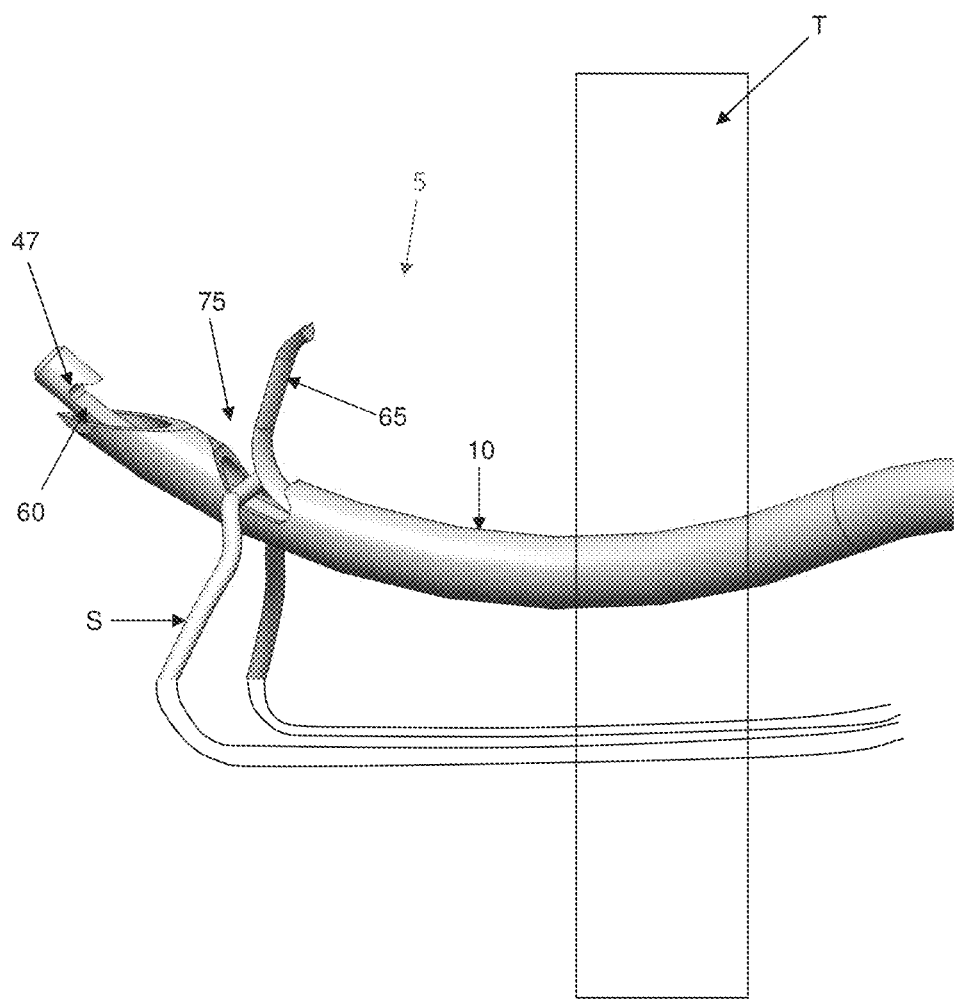

More particularly, in this form of the invention, the suture S is loaded into suture passer 5 on the far side of the tissue T. This is done by first passing suture passer 5 through tissue T so that window 35 resides on the far side of the tissue, and then moving clamping rod 15 distally so that second arm 65 extends out of window 35, substantially perpendicularly to hollow tube 10, whereby to create the aforementioned funnel region 75 (FIGS. 19 and 20). This funnel effect is then used to guide free suture (disposed on the far side of tissue T) into window 35 (see FIG. 21), either by moving suture S relative to suture passer 5 or by moving suture passer 5 relative to suture S or by moving both suture S and suture passer 5 relative to one another. If desired, the suture S may be tensioned so as to help draw it into the window 35.

Figure 22:
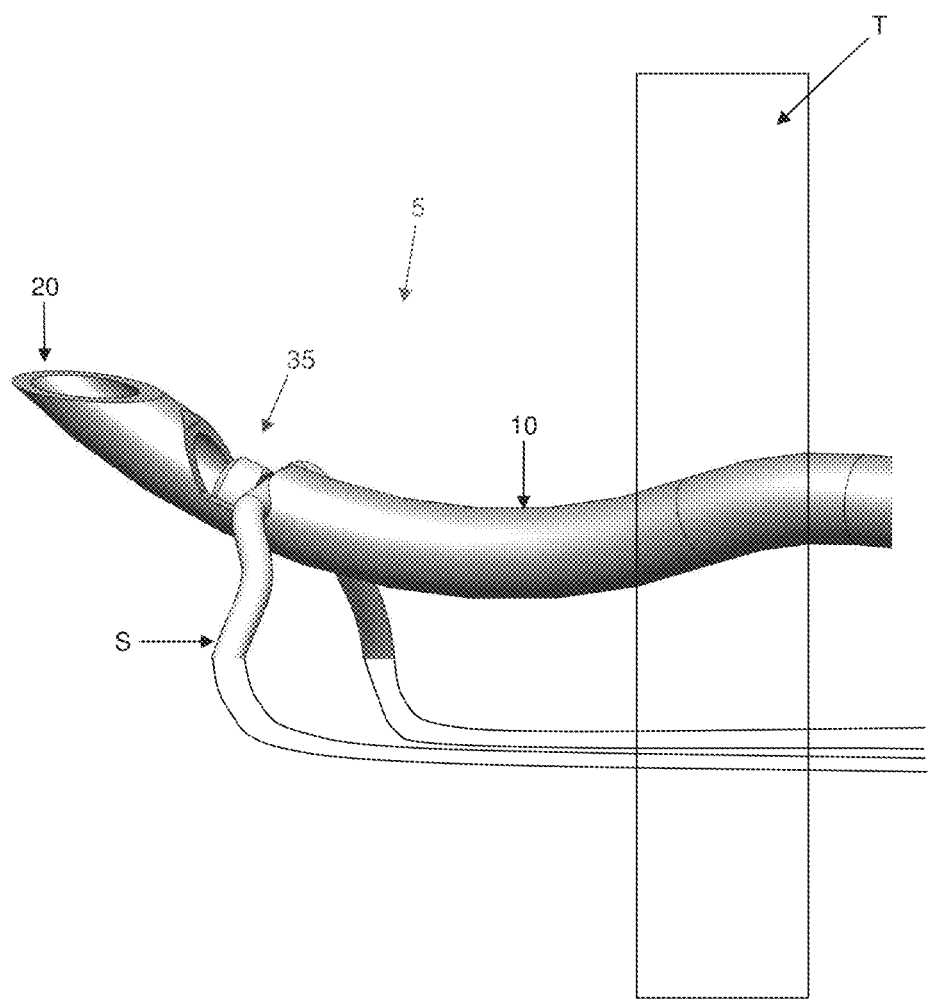
Figure 23:
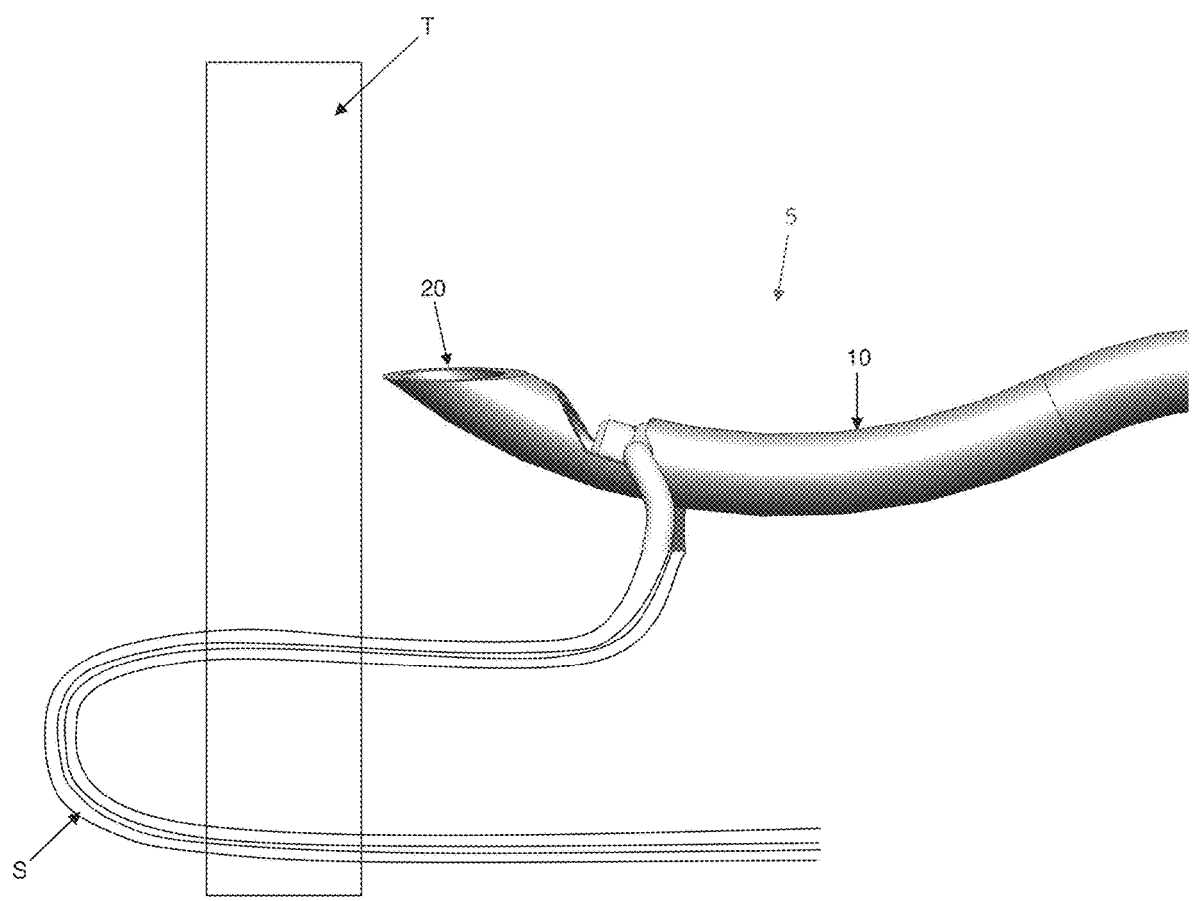
Figure 24:
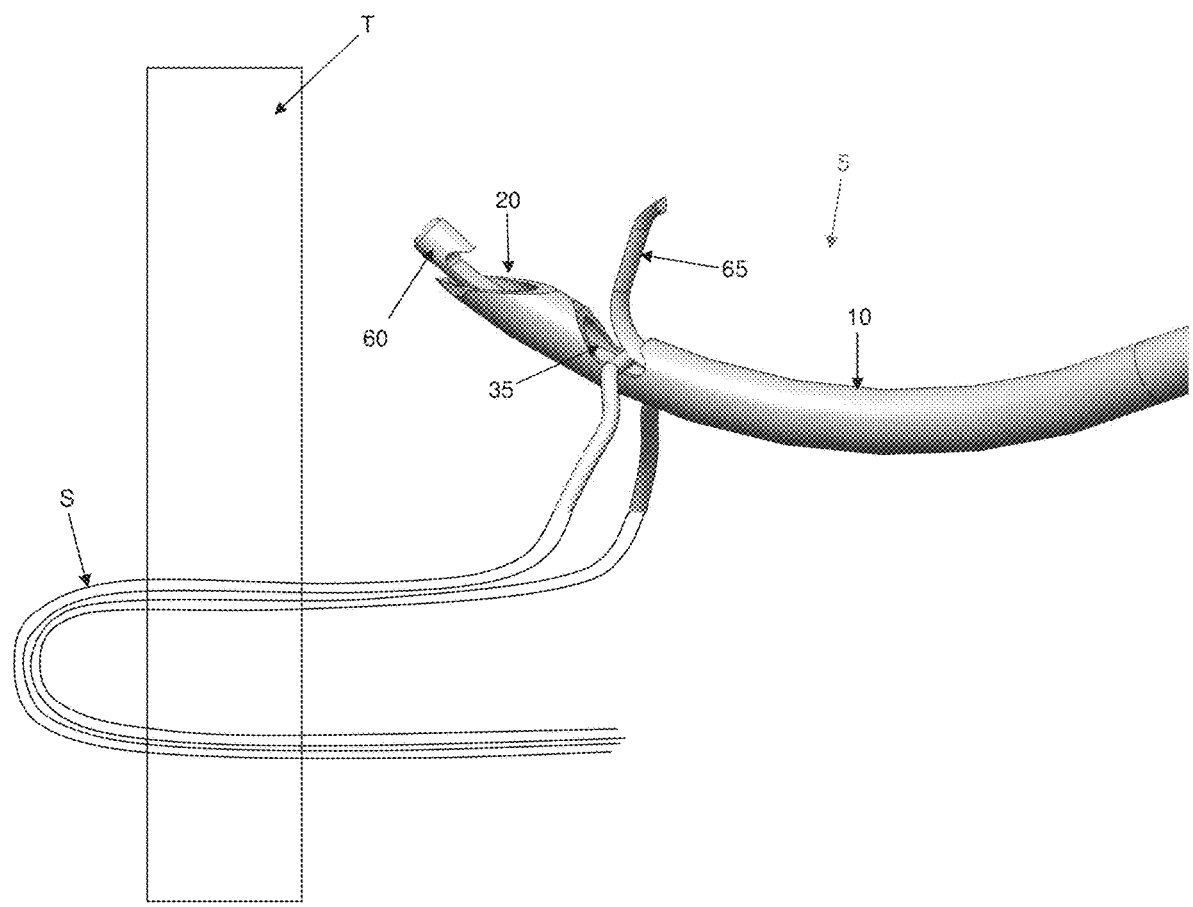

Next, clamping rod 15 is retracted proximally so as to releasably secure suture S between clamping surface 47 and proximal surface 45 of window 35 (FIG. 22). Hollow tube 10 is then retracted proximally through tissue T, carrying suture S therethrough (FIG. 23). If desired, suture S can then be released from suture passer 5 by moving clamping rod 15 distally (FIGS. 24 and 25).

Figure 25:
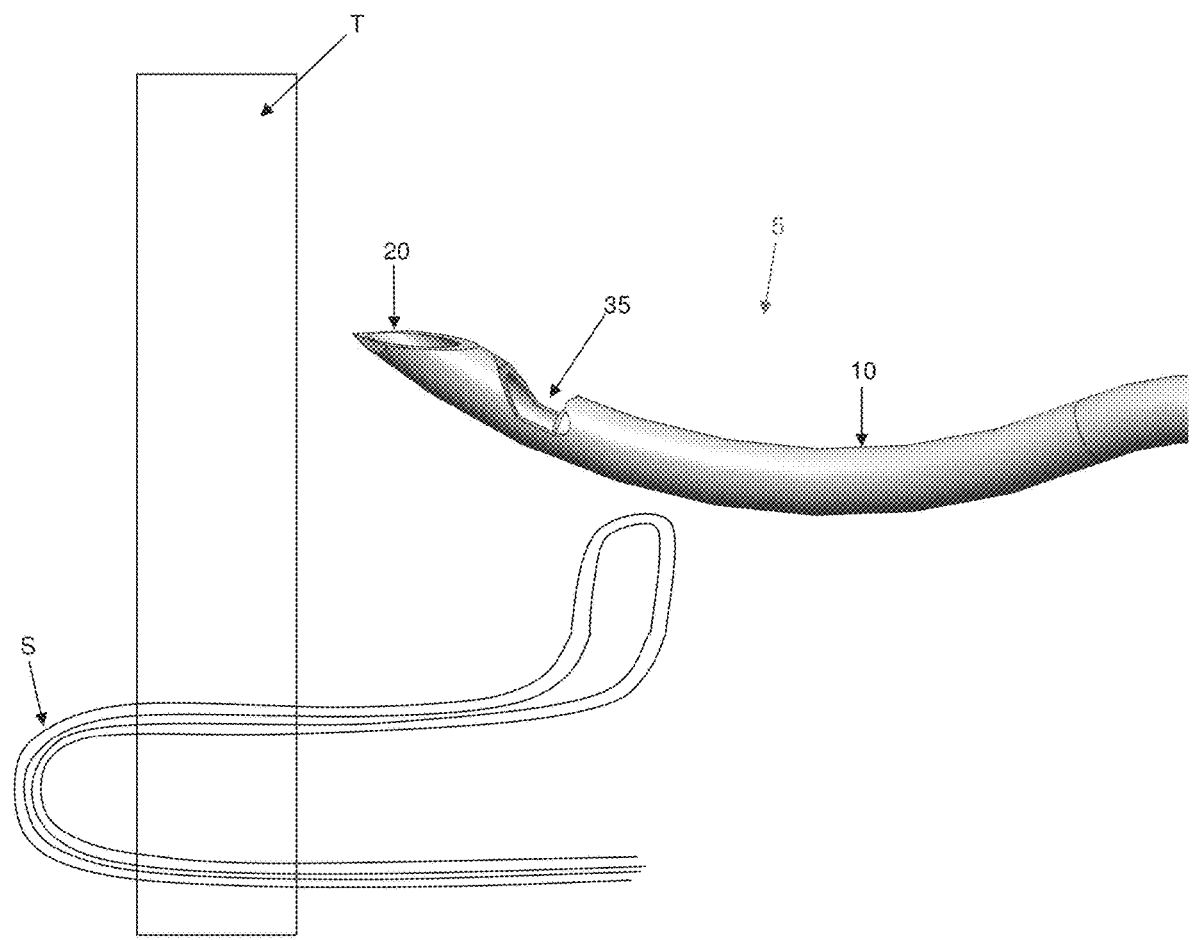

Significantly, by alternating the aforementioned antegrade suture passing procedure (FIGS. 12-18) with the aforementioned retrograde suture passing procedure (FIGS. 19-25), with the needle "plunges" being laterally spaced from one another in the tissue (FIG. 19), a mattress stitch may be placed in the tissue (FIG. 25).

If desired, the novel suture passer 5 may also be used to pass suture S around a side edge of the tissue T, rather than passing the suture S through the tissue. By way of example but not limitation, if the hollow tube 10 is passed around the side edge of the tissue (rather than through it), the suture passer could then be used to retrieve the suture on the far side of the tissue and draw it back around the side edge of the tissue so that the suture is brought to the near side of the tissue.

As described above, the novel suture passer 5 has the ability to both pass (advance) and retrieve (draw) the suture S through and/or around the tissue in a continuous series of steps. This allows the surgeon to complete the desired suture passing without having to remove the suture passer 5 from the portal through which the suture passer 5 is being used. Significantly, this passing/retrieving process can be accomplished with a single instrument, rather than requiring one instrument for passing and a separate instrument for retrieving. This offers significant advantages in convenience and in reducing surgery time.

Alternative Embodiments

Figure 26:
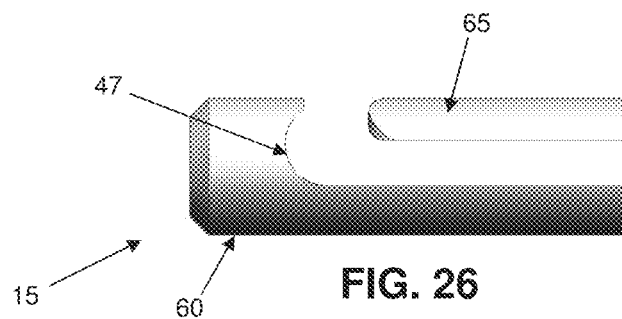
FIGS. 26-29 are schematic views showing various configurations for the clamping surface of the first arm of the clamping rod of the suture passer of FIGS. 1-11.
Figure 27:
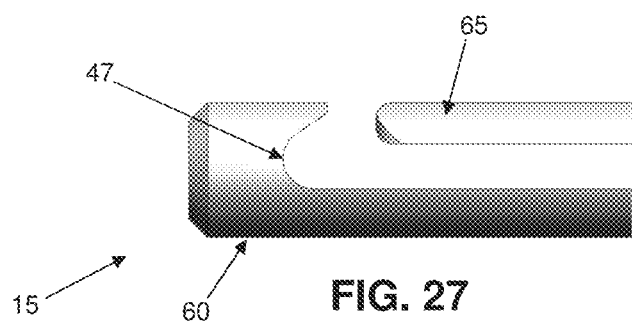
Figure 28:
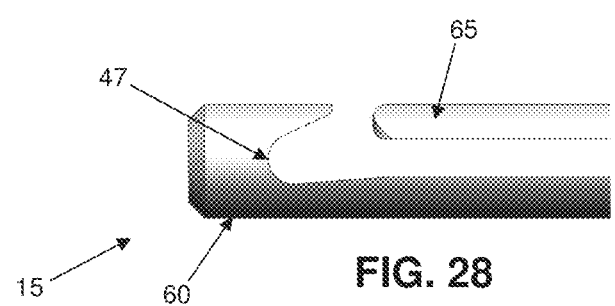
Figure 29:
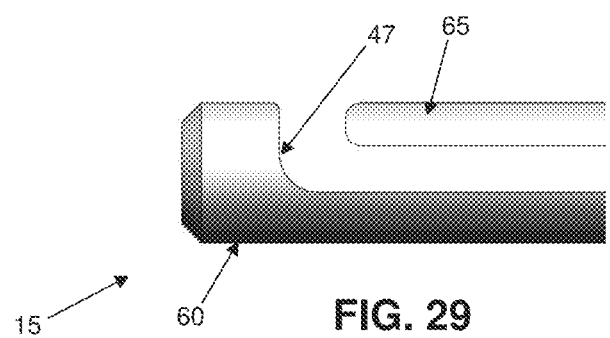

As noted above, clamping surface 47 of clamping rod 15 may take the form of a hook, as shown in FIGS. 1-11. This hook may have various degrees of depth and return, as seen in FIGS. 26-28. Alternatively, clamping surface 47 may be substantially flat, as shown in FIG. 29.

Figure 29A:
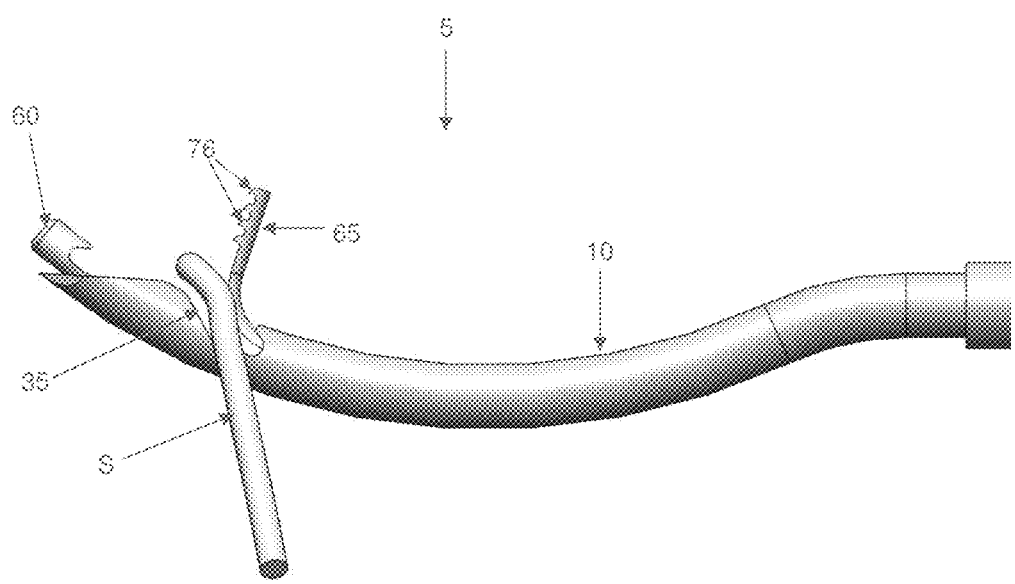
FIGS. 29A and 29B are schematic views showing a modified form of the novel suture passer of FIGS. 1-11, wherein an arm of the suture passer includes a plurality of suture-engaging projections on its distal side.
Figure 29B:
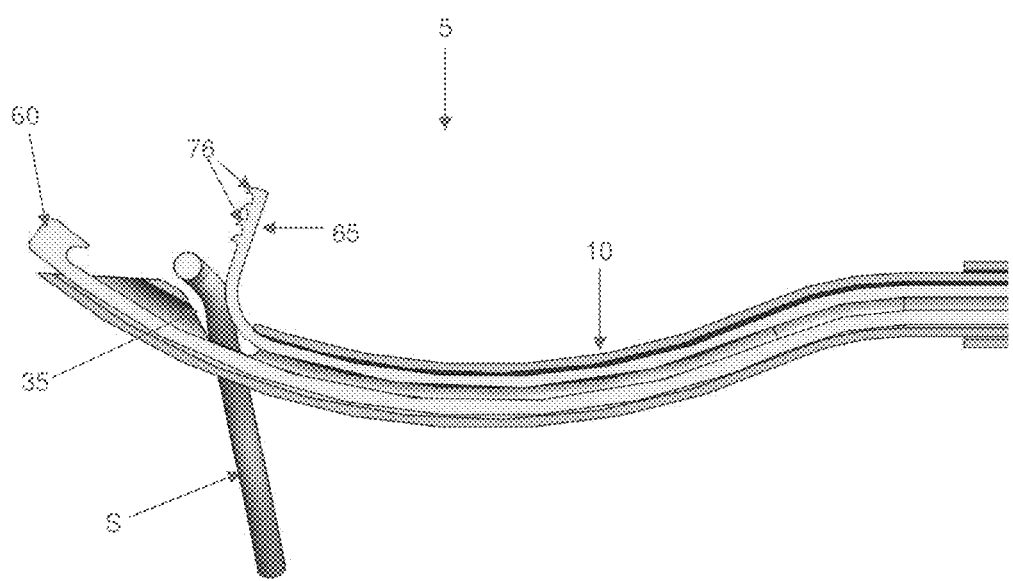

In addition, and looking now at FIGS. 29A and 29B, if desired, second arm 65 of suture passer 5 may include a plurality of suture-engaging projections 76 on its distal side. Suture-engaging projections 76 allow the user to more aggressively engage (e.g., in a contact or frictional sense) suture S with second arm 65, whereby to facilitate manipulation of suture S via engagement with second arm 65. Thus, for example, with the construction shown in FIGS. 29A and 29B, if the user needs to move the suture S about a surgical site, the user can "grip" the suture S with the suture-engaging projections 76 of second arm 65 and "drag" the suture S into a desired position. In another example, the suture-engaging projections 76 of second arm 65 can assist in dragging suture S into window 35. More particularly, as the clamping rod 15 is moved proximally in hollow tube 10, the second arm 65 retracts into the lumen of the hollow tube 10. As it does so, if the suture S is in contact with the suture-engaging projections 76 of second arm 65, suture S will be drawn into window 35. Once in window 35, the suture S is then clamped between clamping surface 47 of clamping rod 15 and inclined proximal surface 45 of window 35 as described above.

Figure 29C:
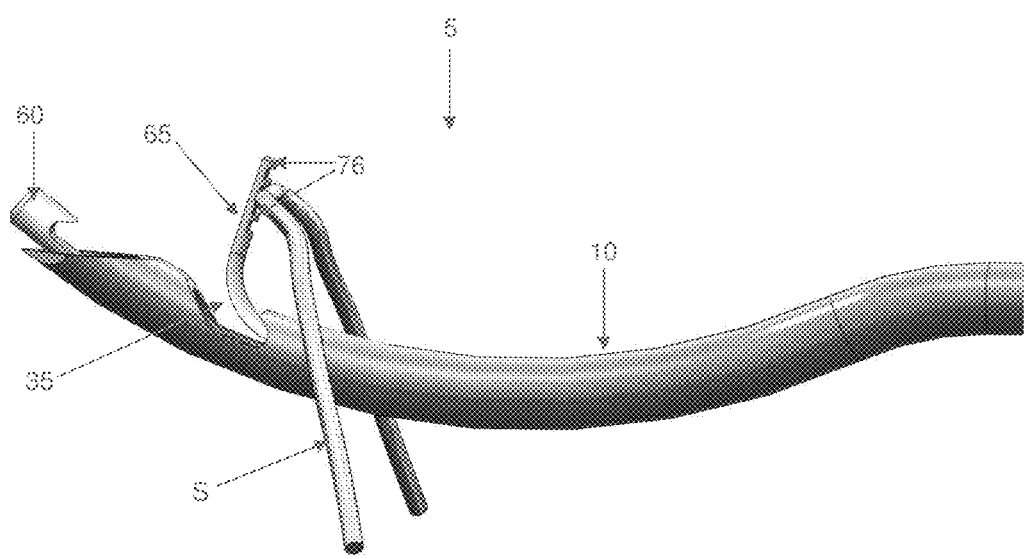
FIGS. 29C and 29D are schematic views showing a modified form of the novel suture passer of FIGS. 1-11, wherein an arm of the suture passer includes a plurality of suture-engaging projections on its proximal side.
Figure 29D:
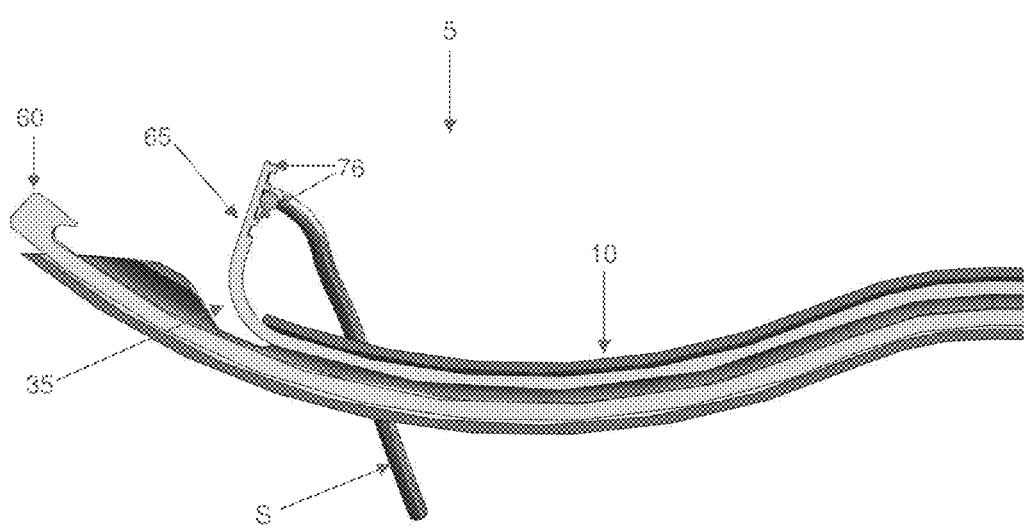

Alternatively, and looking now at FIGS. 29C and 29D, second arm 65 of suture passer 5 may include a plurality of suture-engaging projections 76 on its proximal side. Again, suture-engaging projections 76 allow the user to more aggressively engage (e.g., in a contact or frictional sense) suture S with second arm 65, whereby to facilitate manipulation of suture S via engagement with second arm 65.

If desired, suture-engaging projections 76 may also be provided on both the distal and proximal sides of second arm 65, and/or on one or both of the lateral sides of second arm 65.

It will be appreciated that suture-engaging projections 76 essentially constitute a friction-enhancing surface on second arm 65 so as to allow second arm 65 to engage and "drag" suture S about a surgical site. To this end, it will also be appreciated that the friction-enhancing surface(s) on second arm 65 may be formed with a variety of geometries, e.g., barbs, fingers, ribs, threads or other surface texturing which increases the frictional aspects of second arm 65 at a desired location or locations.

Figure 30:
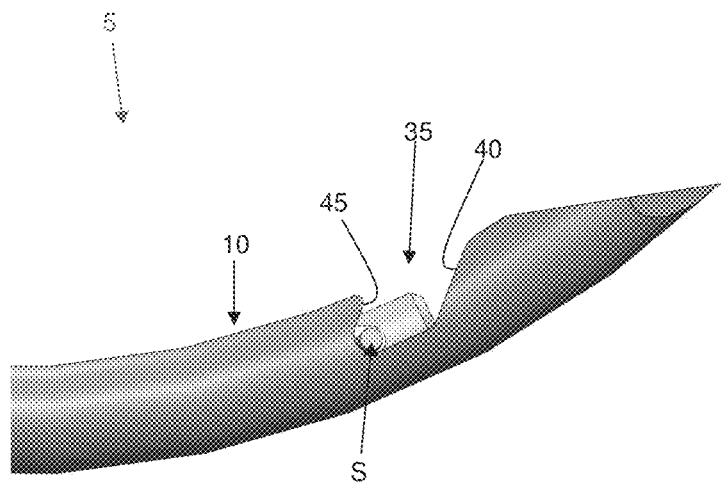
FIGS. 30 and 31 are schematic views showing another configuration for the suture passer of the present invention, wherein the clamping rod and hollow tube are configured so as to allow suture to slide between the clamping rod and the hollow tube.
Figure 31:
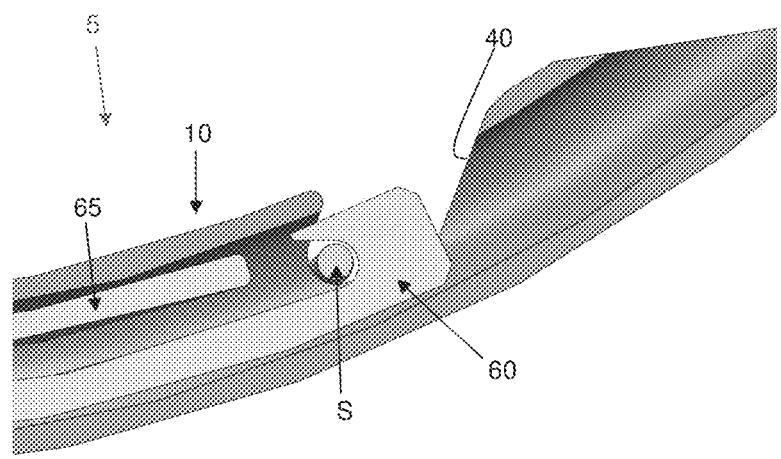

Furthermore, if desired, the suture passer may be constructed so that the suture S is slidably captured—but not clamped—between clamping surface 47 of clamping rod 15 and inclined proximal surface 45 of window 35. In this form of the invention, suture S is slidably captured between the two surfaces (i.e., clamping surface 47 and proximal surface 45), in the manner shown in FIGS. 30 and 31. In this form of the invention, clamping rod 15 may be limited in its proximal travel (e.g., by means of interaction between actuator 72 and handle 23) in order to provide a gap sufficient to slidingly capture, but not bind, suture S. This gap may be equal to, or larger than, the diameter of suture S.

Figure 32:
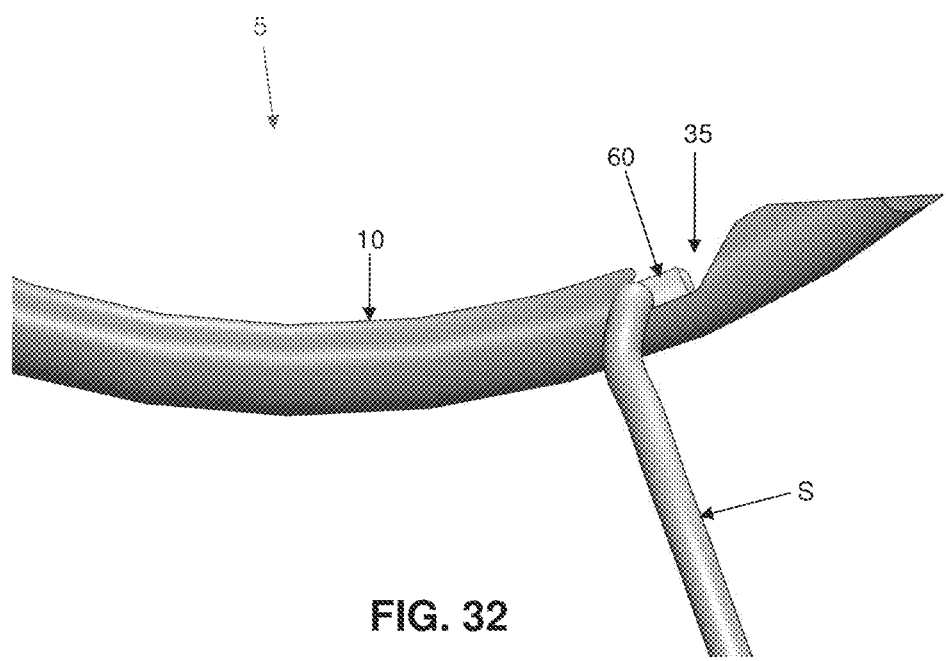
FIGS. 32 and 33 are schematic views showing another configuration for the suture passer of the present invention, wherein the clamping rod is configured to pierce the suture when the clamping rod is moved proximally.
Figure 33:
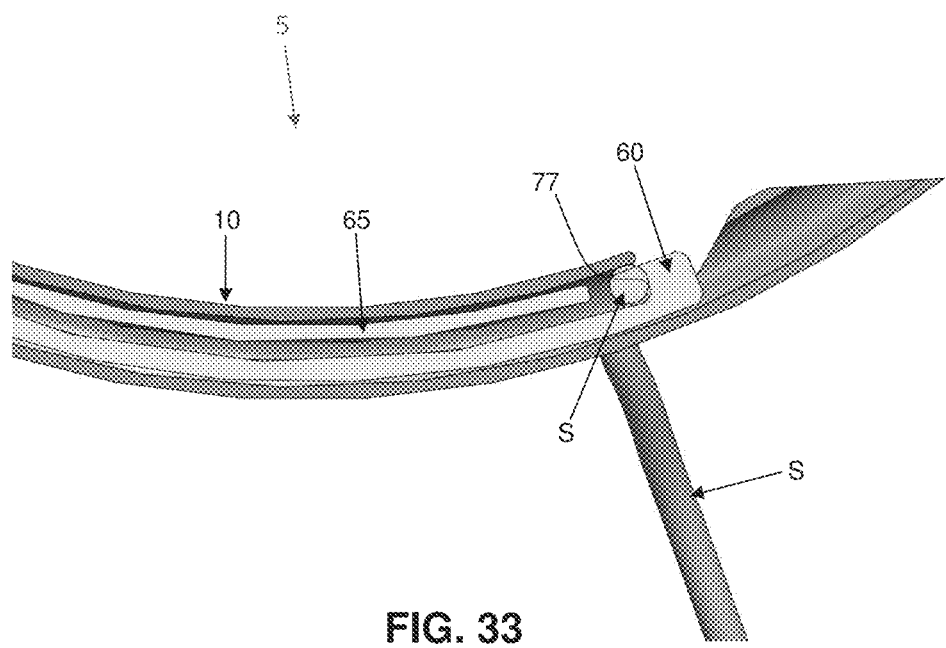

Alternatively, if desired, the clamping rod can be configured to pierce the suture when the clamping rod is moved proximally, as shown in FIGS. 32 and 33. This spearing of the suture can enhance clamping of the suture S to the suture passer 5. By way of example but not limitation, first arm 60 of clamping rod 15 may include a pointed return 77, with pointed return 77 being configured and located such that it will spear suture S when clamping rod 15 is moved proximally.

Figure 34:
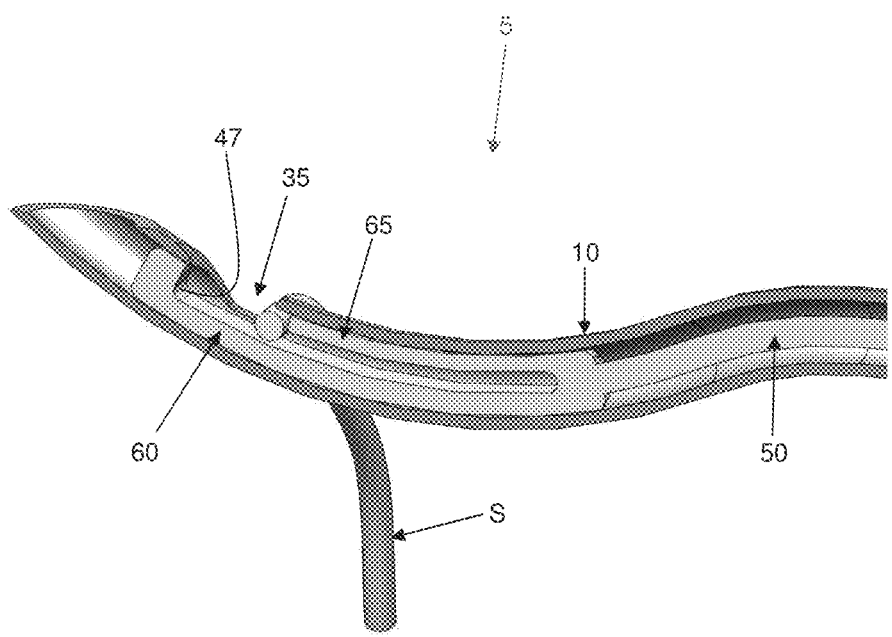
FIGS. 34 and 35 are schematic views illustrating how the lengths of the first and second arms of the bifurcated distal end of the clamping rod can vary from the construction shown in FIGS. 1-11.
Figure 35:
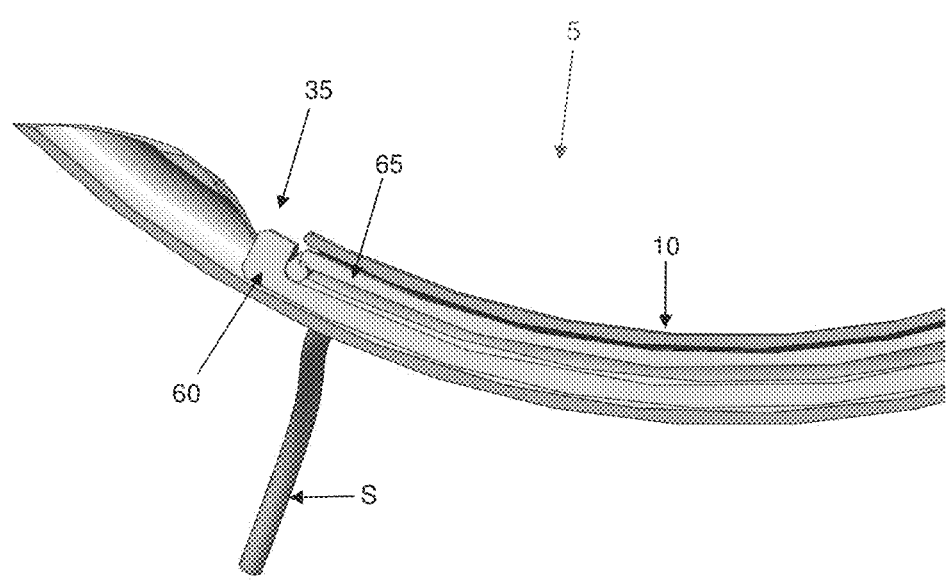

It should be appreciated that the lengths of the first and second arms 60, 65 of clamping rod 15 can vary from the construction shown in FIGS. 1-11. By way of example but not limitation, in one preferred form of the invention, the distance between the distal tip of second arm 65 and clamping surface 47 is approximately the length of window 35, as shown in FIG. 34. In another preferred form of the invention, only a nominal gap is provided between the distal tip of second arm 65 and clamping surface 47 (FIG. 35). This construction can provide for improved capturing of suture S to suture passer 5.

In another form of the present invention, suction may be applied to lumen 30 of hollow tube 10 proximal to window 35. This suction will draw fluid into window 35, and the fluid entering window 35 will assist suture S in seating itself into window 35 as the suture S approaches window 35.

In another form of the present invention, fluid is delivered down lumen 30 of hollow tube 10 so as to assist ejection of suture S from window 35 once the clamping rod 15 has released suture S.

In yet another form of the present invention, hollow tube 10 comprises a second window 35 opposite first window 35, and the distal end of clamping rod 15 is trifurcated so as to form a first arm 60 carrying a pair of clamping surfaces 47 and a pair of second arms 65, with each of the second arms 65 being outboard of first arm 60 and being biased out a window 35. Thus, with this construction, suture can be clamped on either side of hollow tube 10.

In another form of the present invention, the suture passer may further comprise a push rod to assist in ejecting suture S from window 35. The push rod may be a component separate from clamping rod 15 (but slidably movable relative thereto), or it may be integrated with clamping rod 15 (e.g., slidably movable thereon).

Figure 35A:
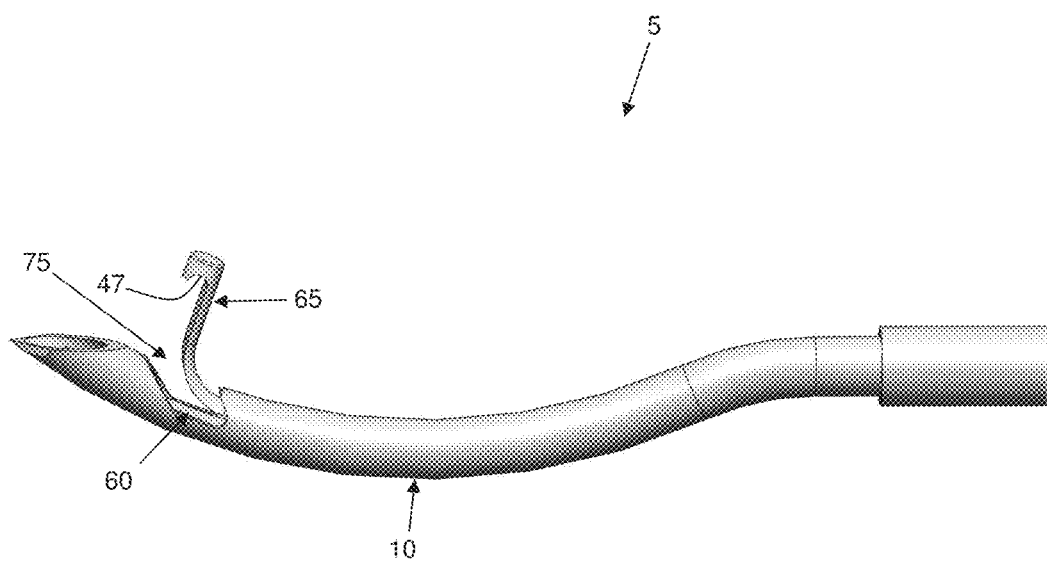
FIGS. 35A-35C are schematic views showing another novel form of suture passer formed in accordance with the present invention.
Figure 35B:
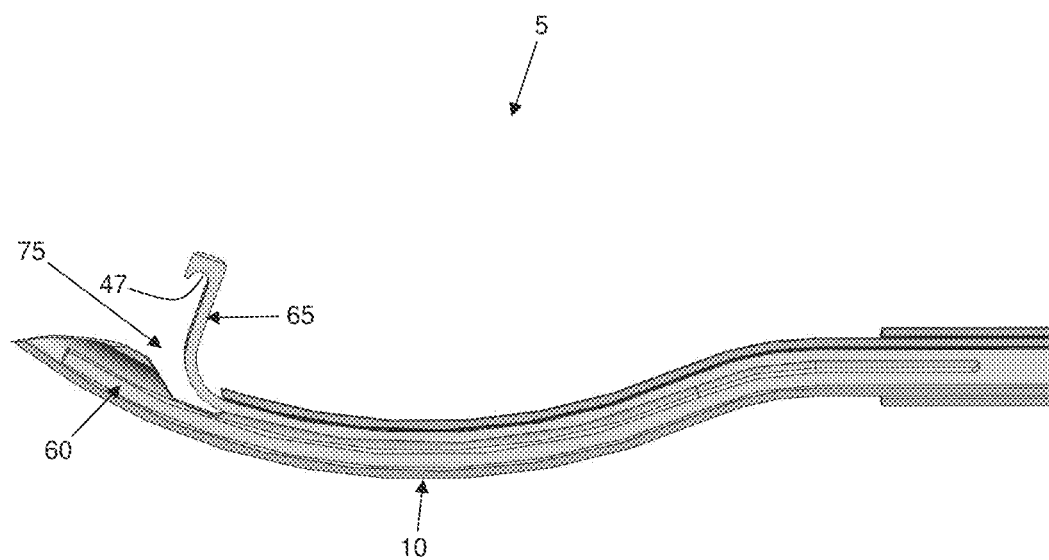
Figure 35C:
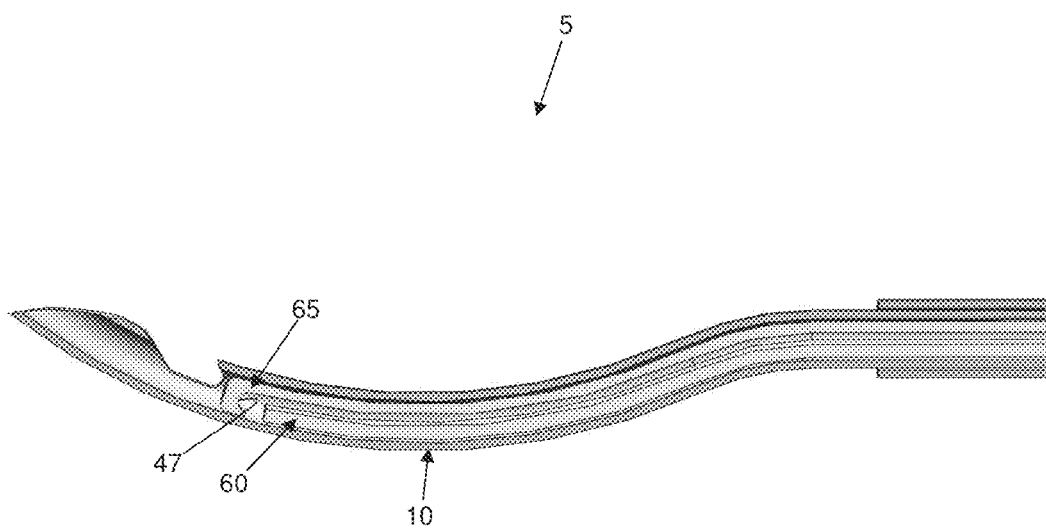
Figure 35D:
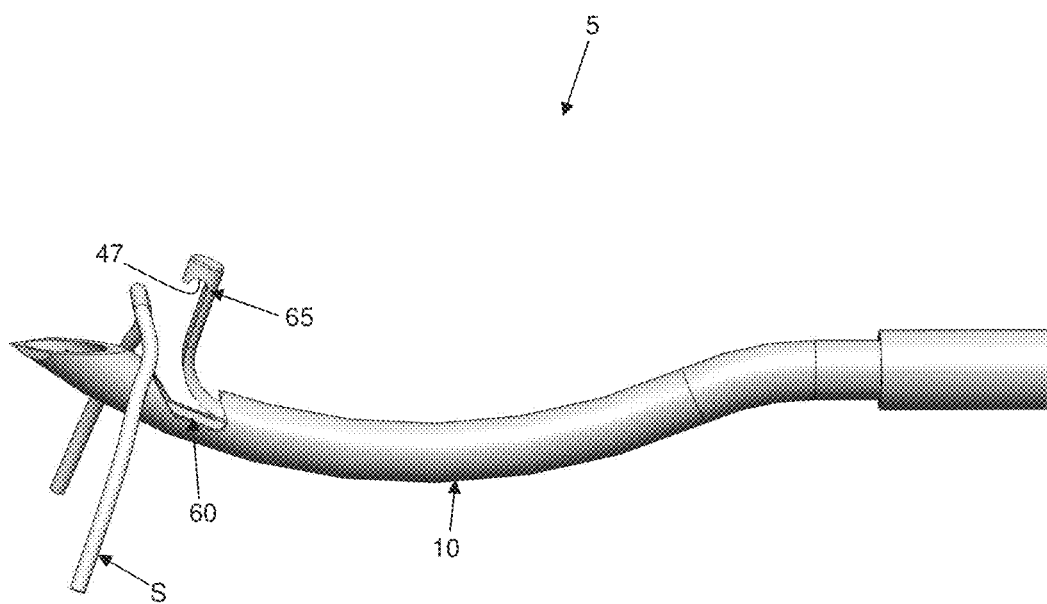
FIGS. 35D-35F are schematic views showing the novel suture passer of FIGS. 35A-35C securing a suture to the distal end of the suture passer.
Figure 35E:
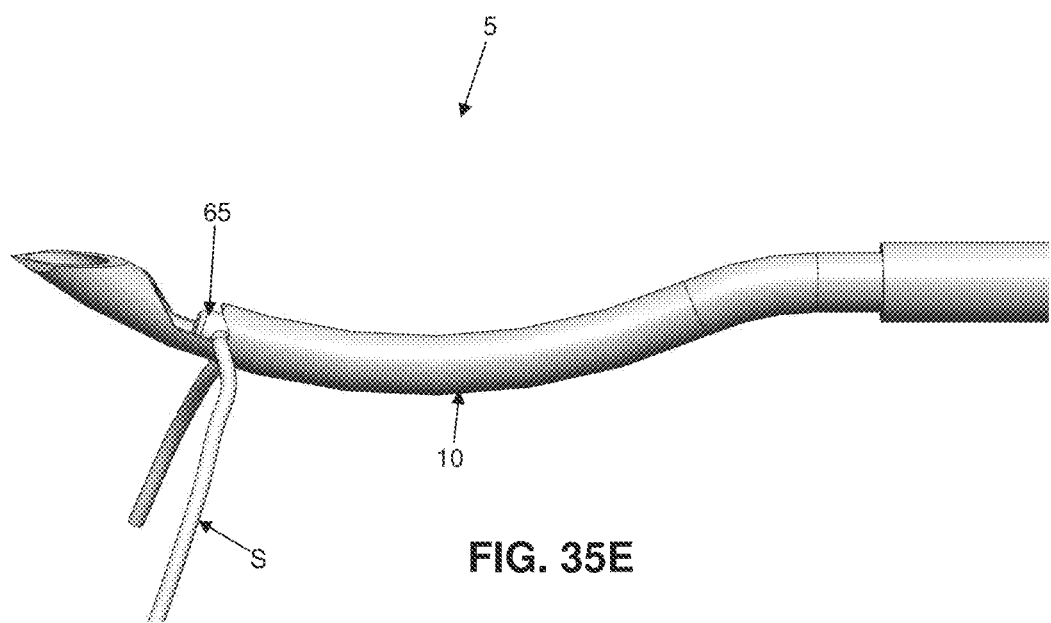
Figure 35F:
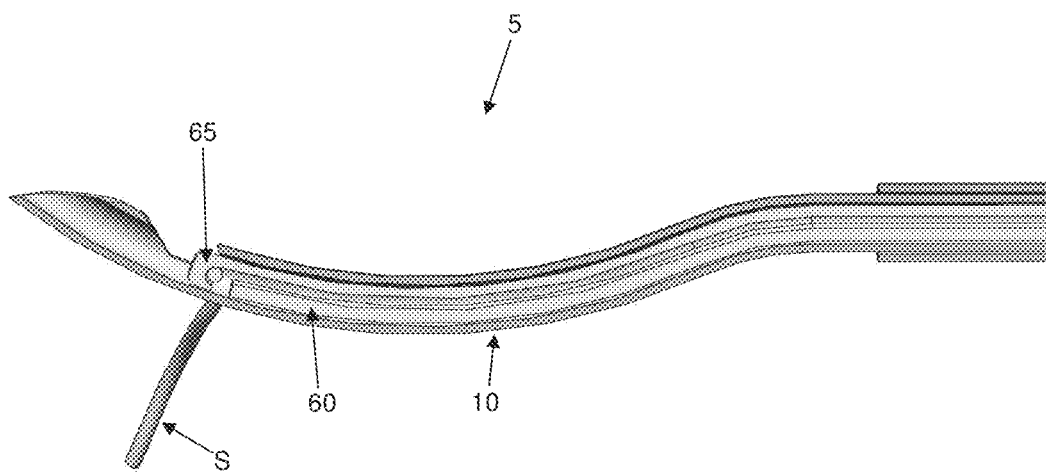

Looking next at FIGS. 35A-35C, it is also possible to form novel suture passer 5 so that (i) first arm 60 is shorter than second arm 65, and (ii) clamping surface 47 is formed on the outwardly biased second arm 65 (rather than on first arm 60). In this form of the invention, funnel region 75 is formed between the distal end of shaft 10 and first arm 60. FIGS. 35D-35F show the novel suture passer of FIGS. 35A-35C securing a suture S to the distal end of the suture passer.

Furthermore, if desired, where clamping surface 47 is formed on the outwardly biased second arm 65 (e.g., in the manner shown in FIGS. 35A-35C and FIGS. 35D-35F), first arm 60 may be omitted entirely, in which case the distal end of clamping rod 15 preferably comprises only outwardly biased second arm 65.

Figure 35G:
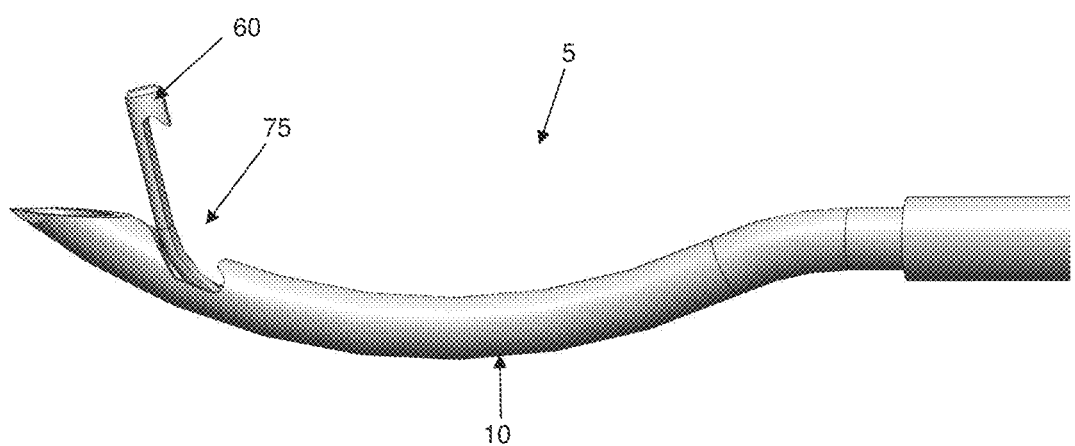
FIGS. 35G-35I are schematic views showing another novel form of suture passer formed in accordance with the present invention.
Figure 35H:
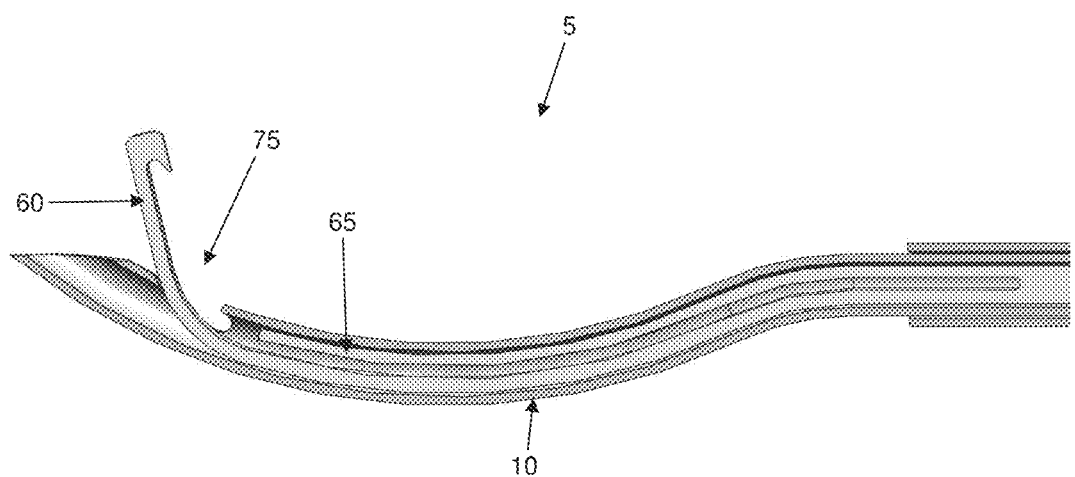
Figure 35I:
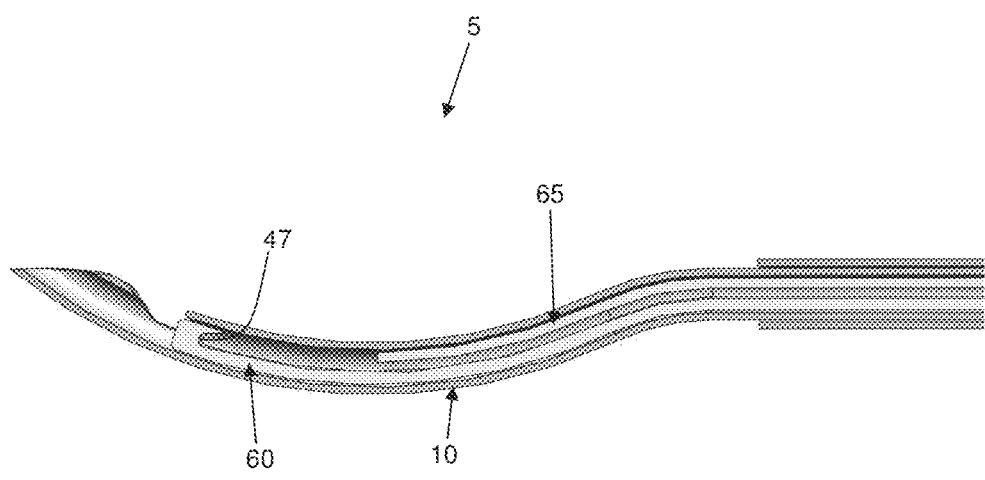
Figure 35J:
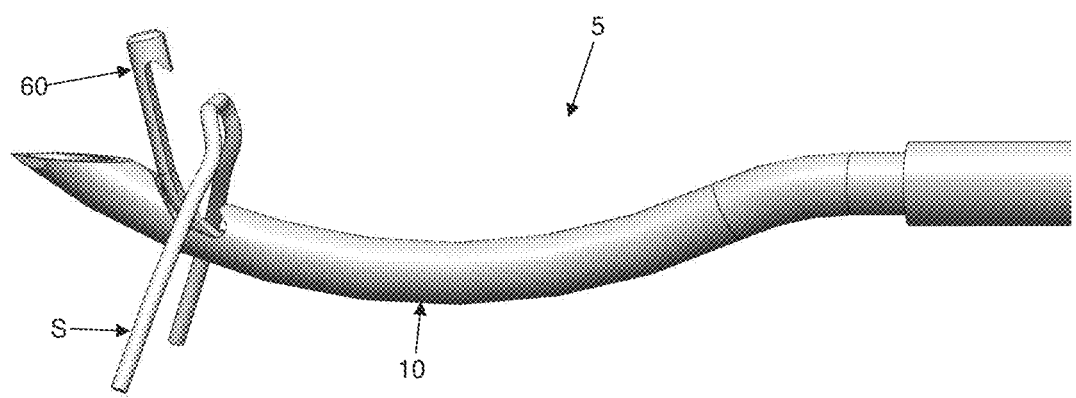
FIGS. 35J-35L are schematic views showing the novel suture passer of FIGS. 35G-35I securing a suture to the distal end of the suture passer.
Figure 35K:
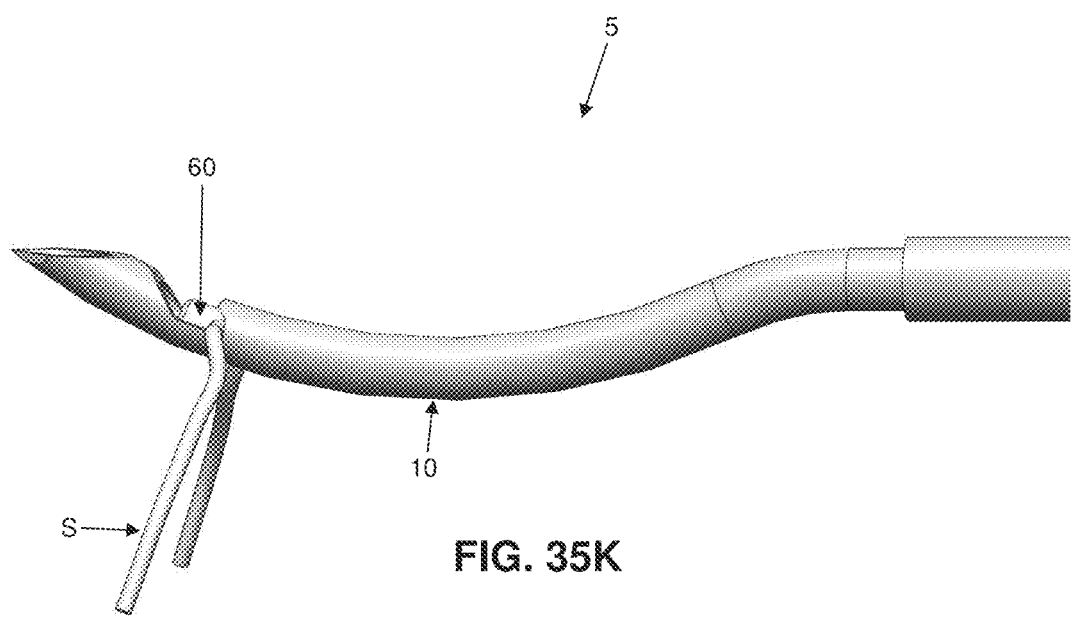
Figure 35L:
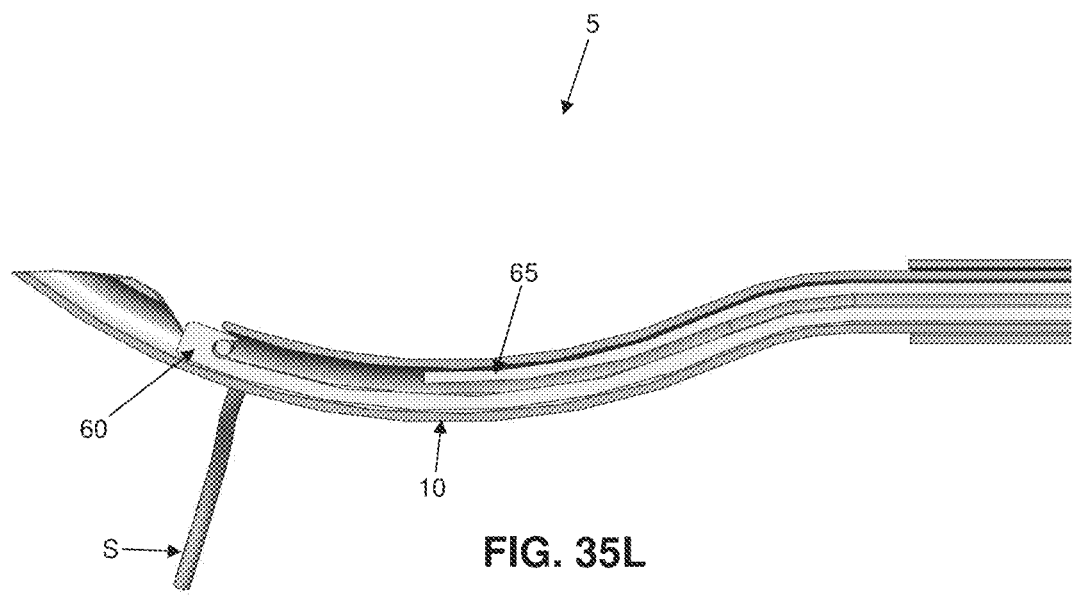

In another form of the present invention, and looking now at FIGS. 35G-35I, novel suture passer 5 may be constructed so that first arm 60 (carrying clamping surface 47) is outwardly biased, so that first arm 60 (and clamping surface 47) extends out window 35 when clamping rod 15 is moved distally. In this form of the invention, the funnel region 75 is formed between the distal end of shaft 10 and first arm 60. FIGS. 35J-35L show the novel suture passer of FIGS. 35G-35I securing a suture S to the distal end of the suture passer.

Furthermore, if desired, where first arm 60 is outwardly biased and carries clamping surface 47 (e.g., in the manner shown in FIGS. 35G-35I and FIGS. 35J-35L), second arm 65 may be omitted entirely, in which case the distal end of clamping rod 15 preferably comprises only outwardly biased first arm 60 (with clamping surface 47).

Figure 35M:
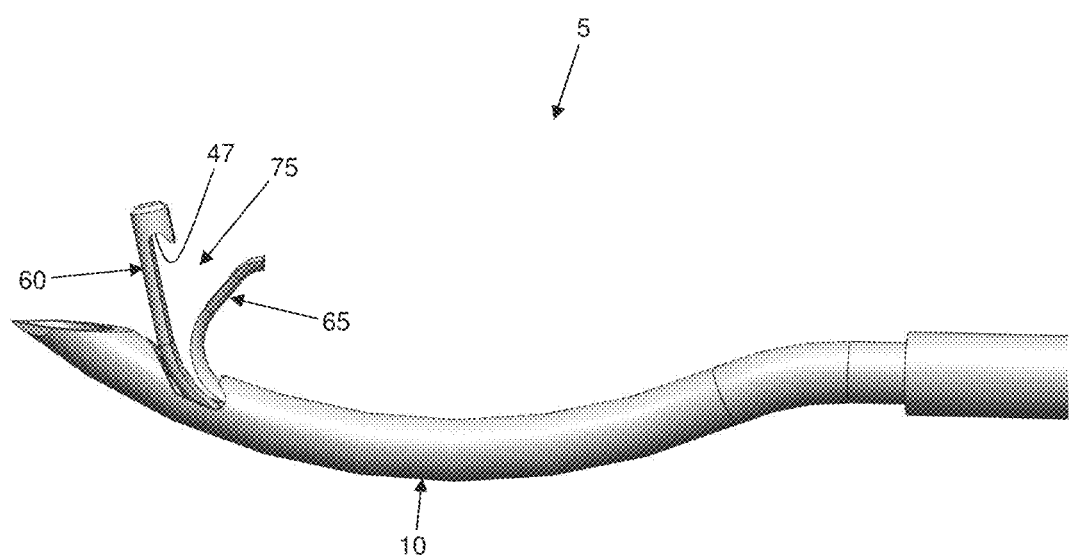
FIGS. 35M-35O are schematic views showing another novel form of suture passer formed in accordance with the present invention.
Figure 35N:
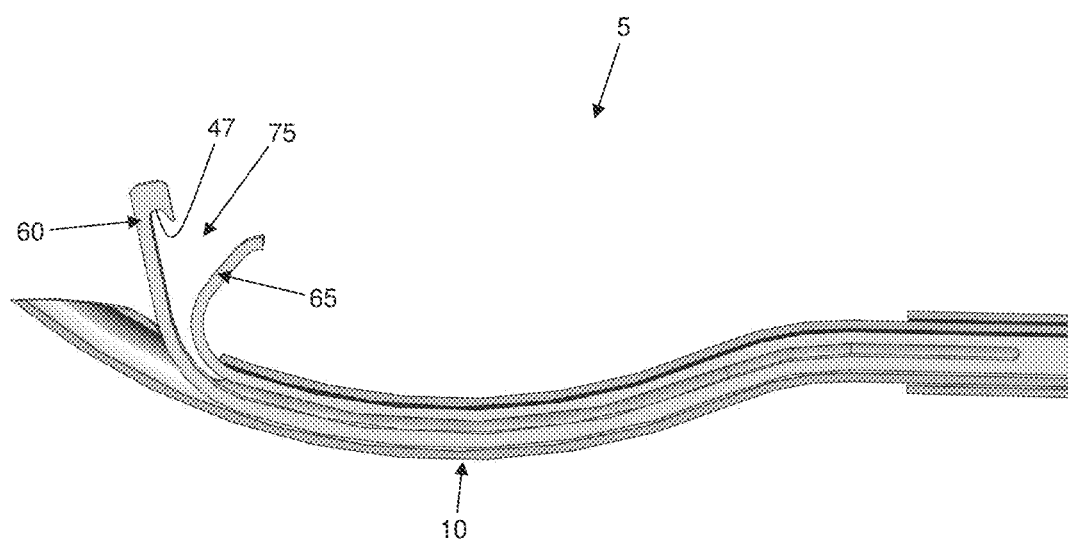
Figure 35O:
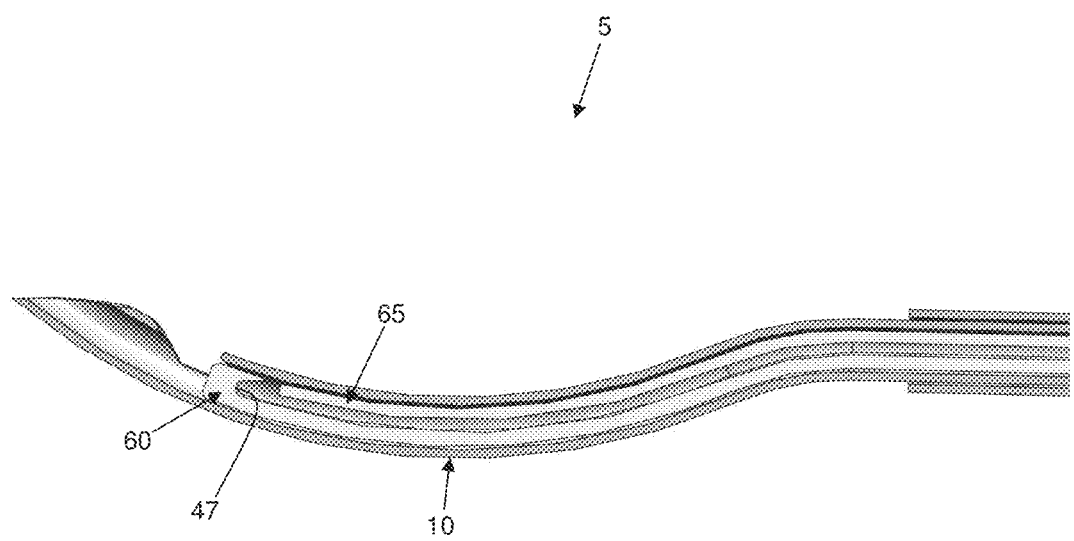
Figure 35P:
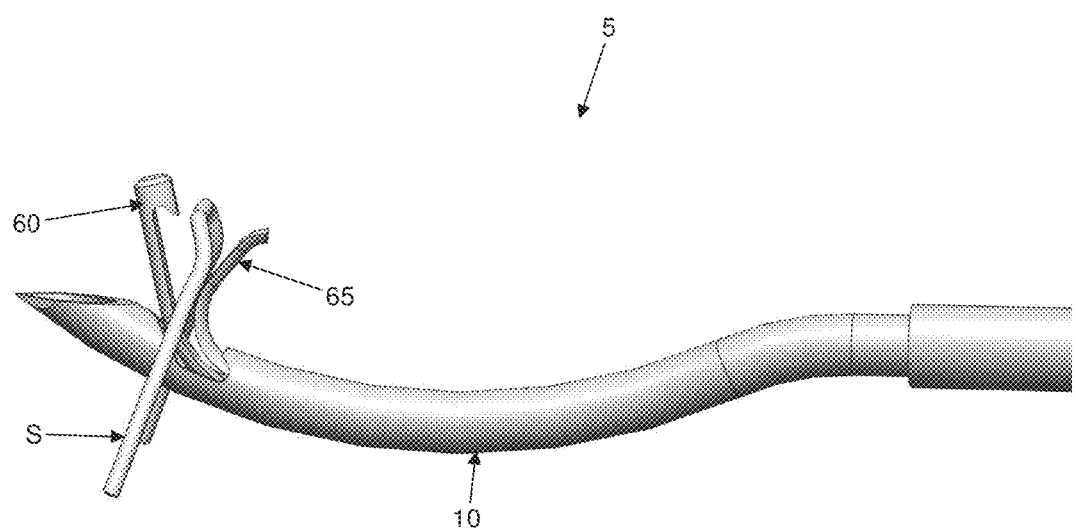
FIGS. 35P-35R are schematic views showing the novel suture passer of FIGS. 35M-35O securing a suture to the distal end of the suture passer.
Figure 35Q:
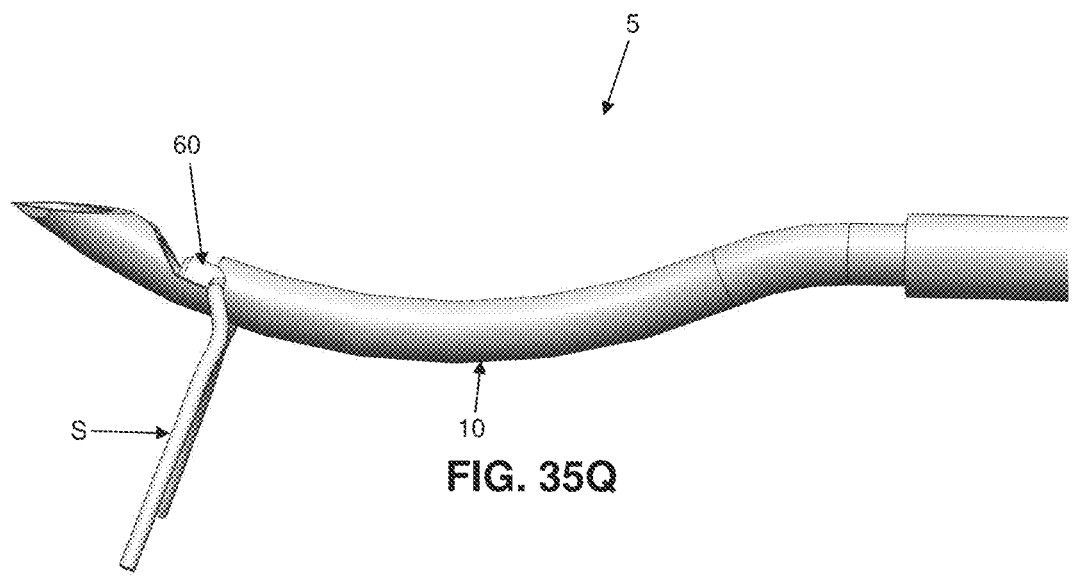
Figure 35R:
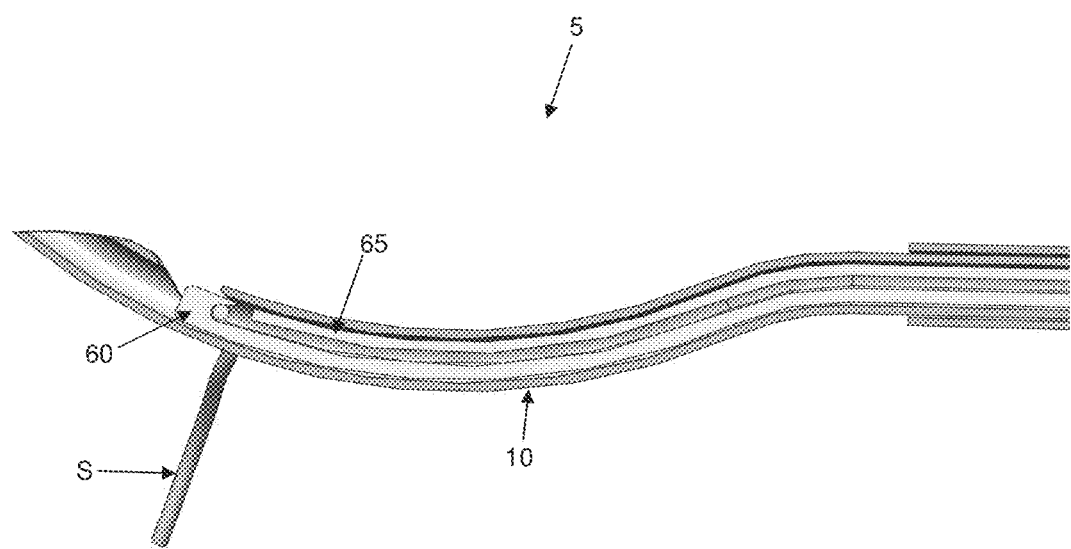
Figure 36:
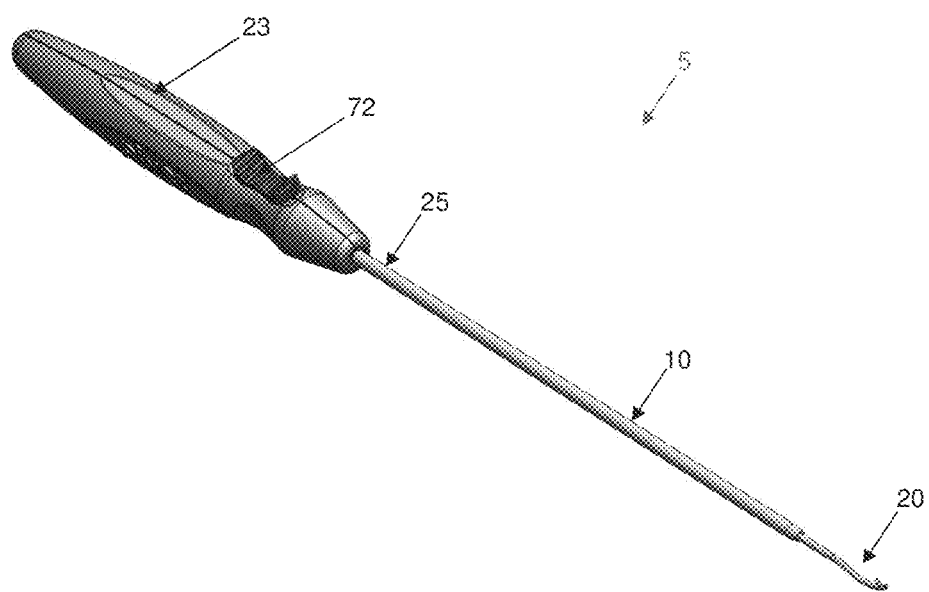
FIGS. 36-40 are schematic views showing another novel form of suture passer formed in accordance with the present invention.
Figure 37:
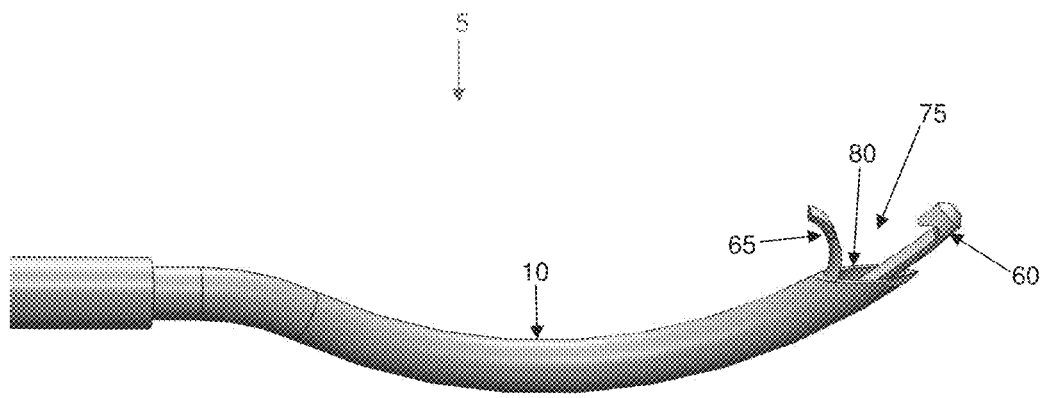
Figure 38:
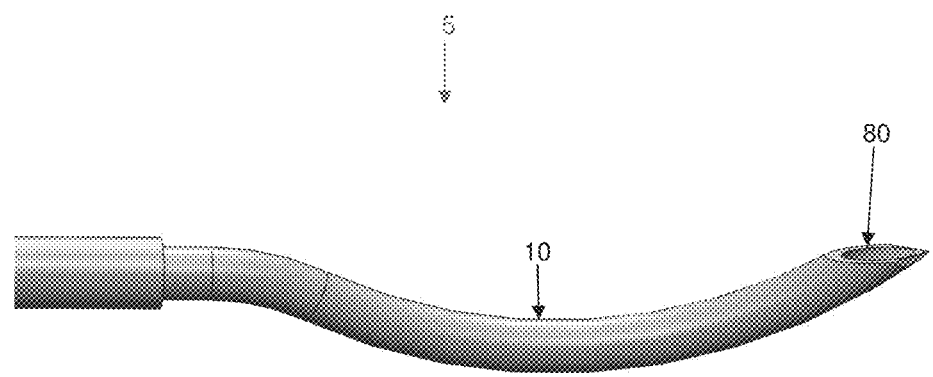
Figure 39:
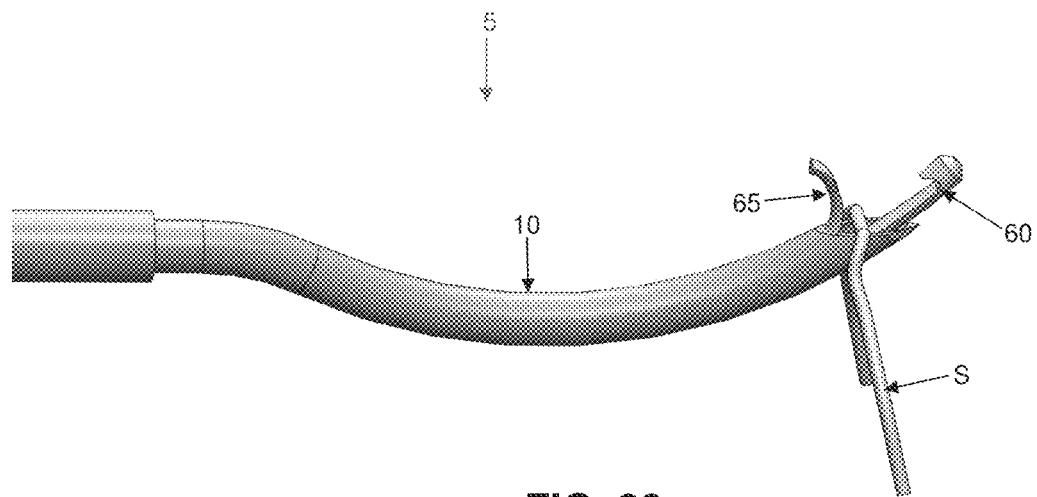

In still another form of the present invention, and looking now at FIGS. 35M-35O, novel suture passer 5 may be constructed so that both first arm 60 (carrying clamping surface 47) and second arm 65 are outwardly biased, so that both first arm 60 (and clamping surface 47) and second arm 65 extend out window 35 when clamping rod 15 is moved distally. In this form of the invention, funnel region 75 is formed between first arm 60 and second arm 65. FIGS. 35P-35R show the novel suture passer of FIGS. 35M-35O securing a suture S to the distal end of the suture passer.

In another form of the present invention, and looking now at FIGS. 36-40, window 35 may be eliminated, and clamping rod 15 may clamp suture S against the distal end surface 80 of hollow tube 10.

Figure 40:
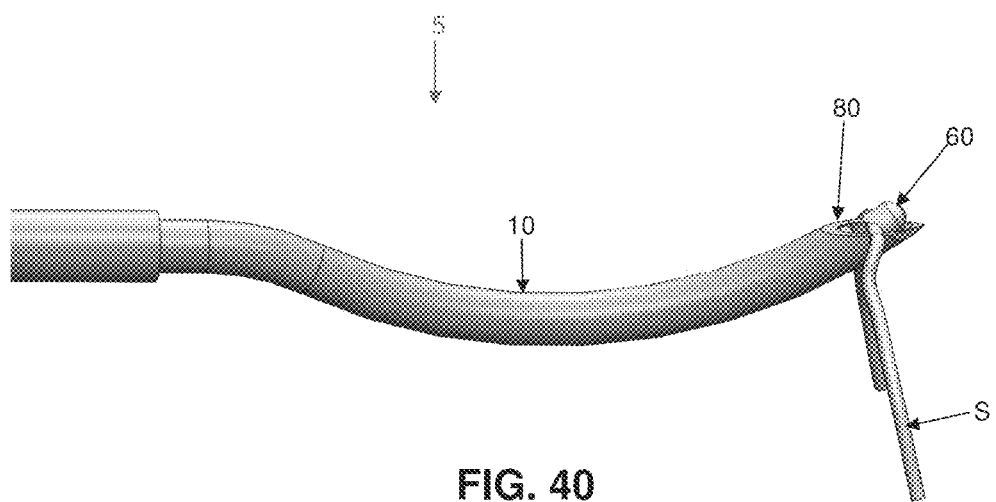
Figure 40A:
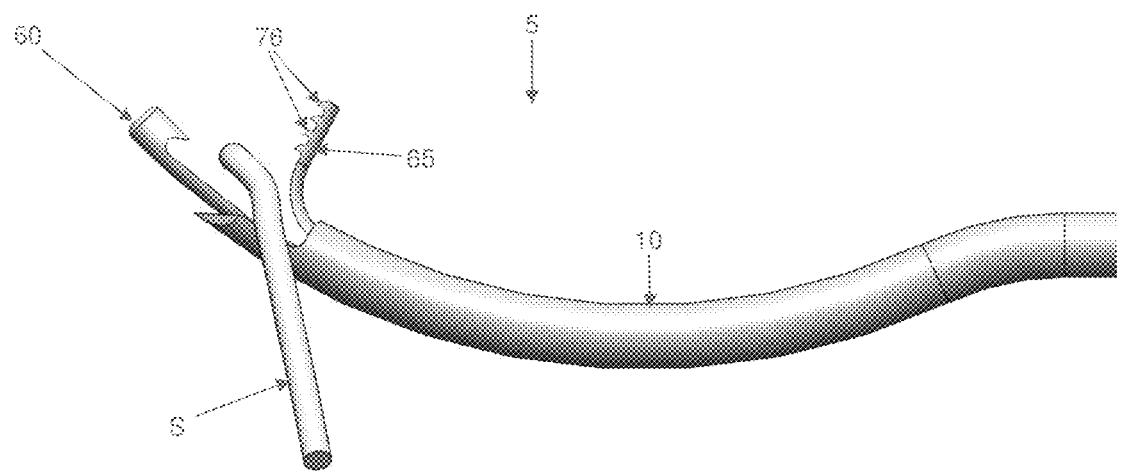
FIGS. 40A and 40B are schematic views showing a modified form of the novel suture passer of FIGS. 36-40, wherein an arm of the suture passer includes a plurality of suture-engaging projections on its distal side.
Figure 40B:
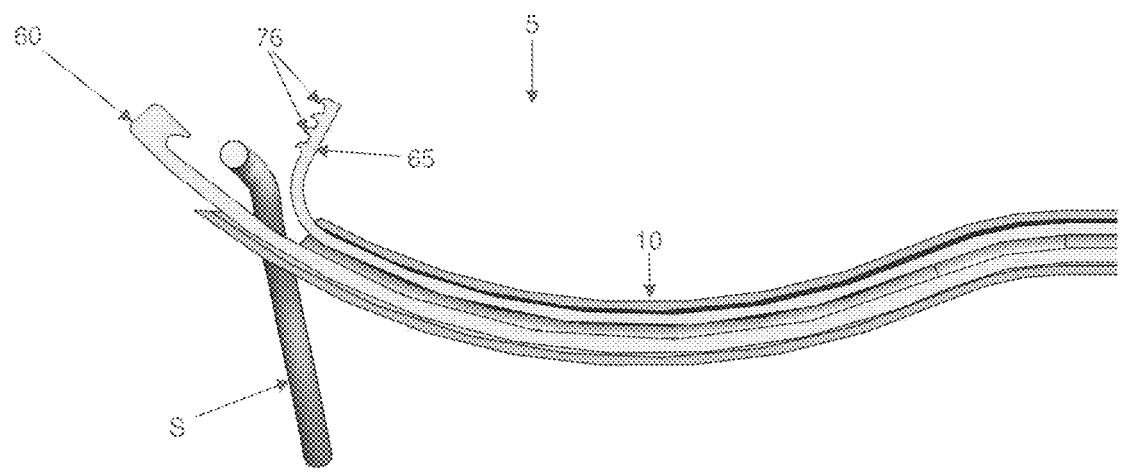
Figure 41:
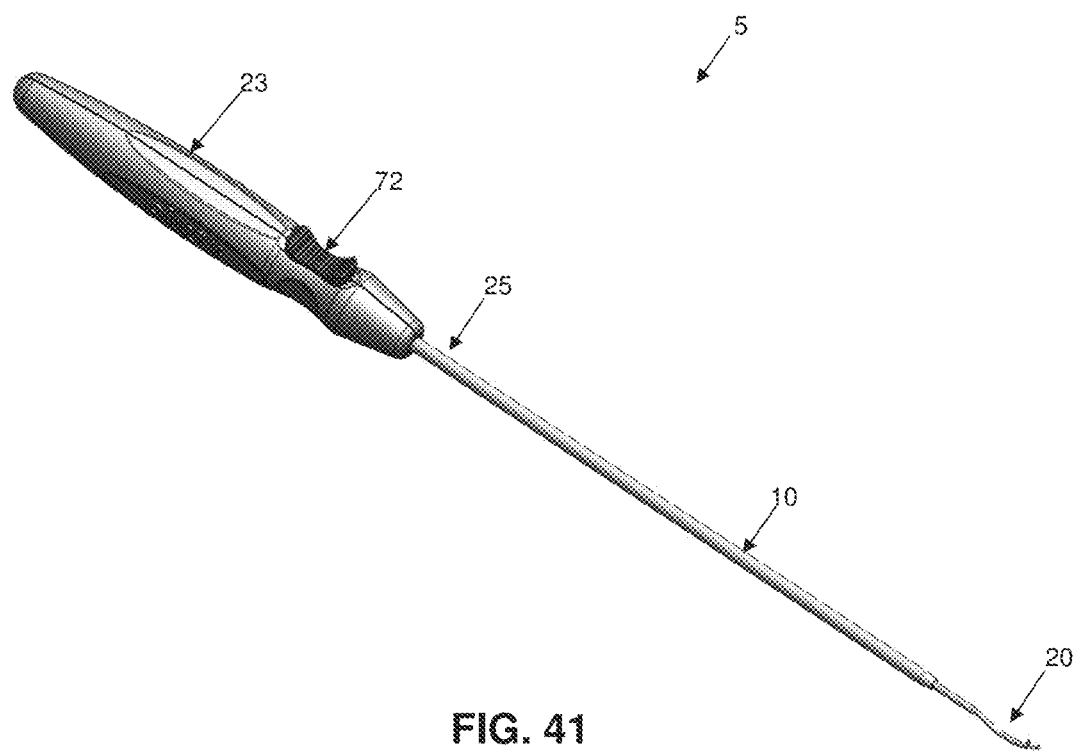
FIGS. 41-47 are schematic views showing still another novel form of suture passer formed in accordance with the present invention.
Figure 42:
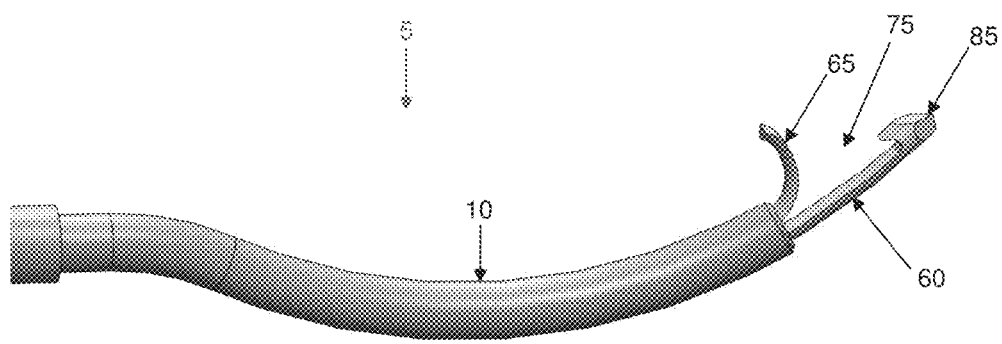
Figure 43:
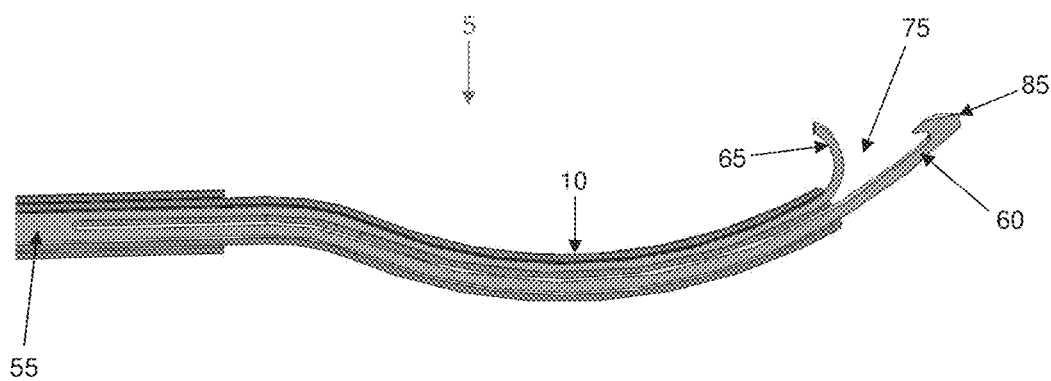
Figure 44:
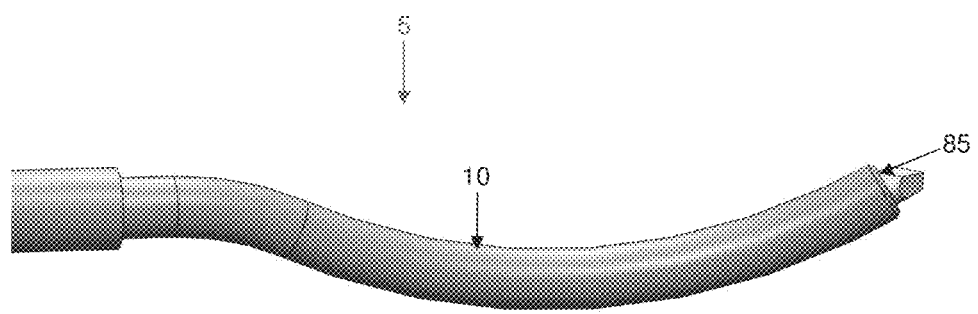
Figure 45:
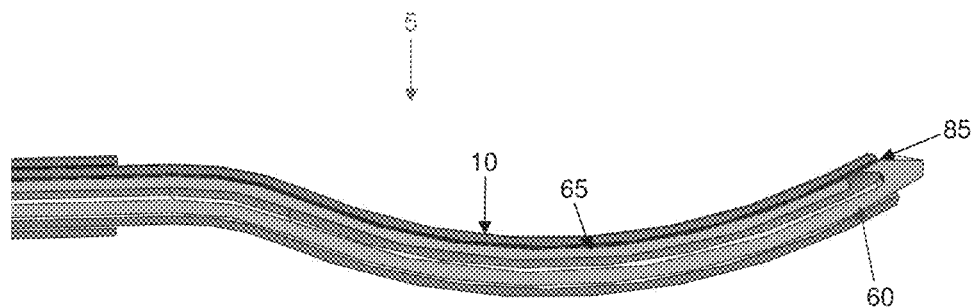
Figure 46:
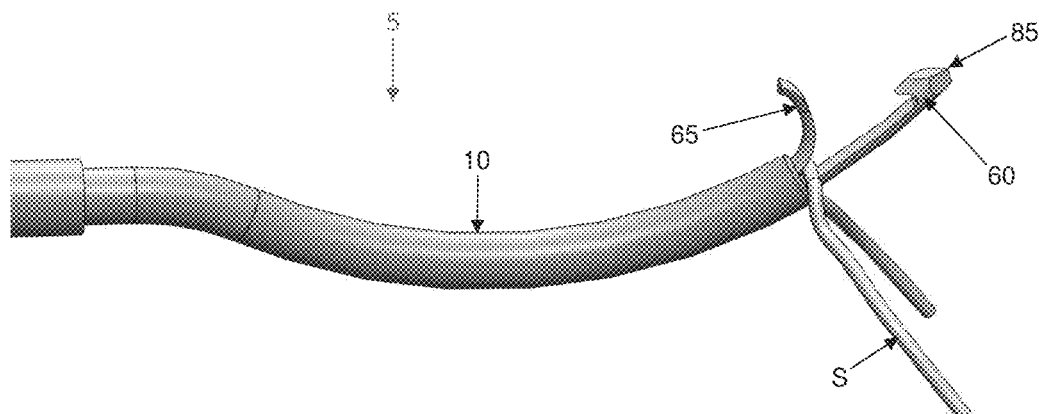
Figure 47:
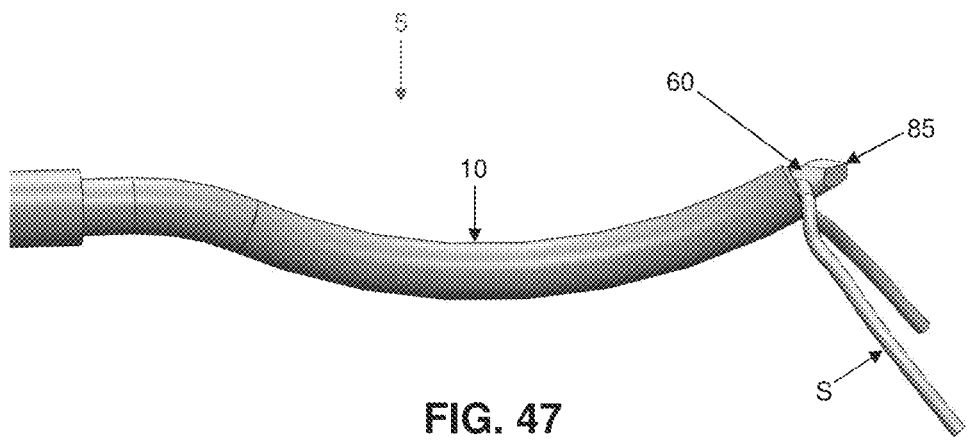
Figure 48:
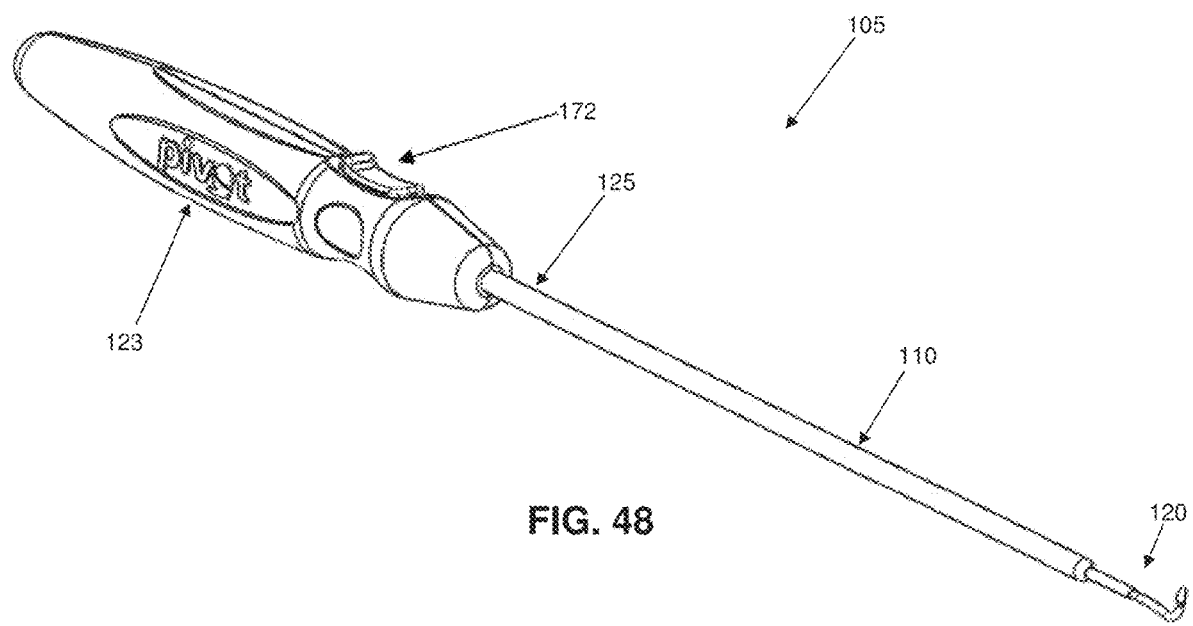
FIGS. 48-60 are schematic views showing yet another novel form of suture passer formed in accordance with the present invention.
Figure 49:
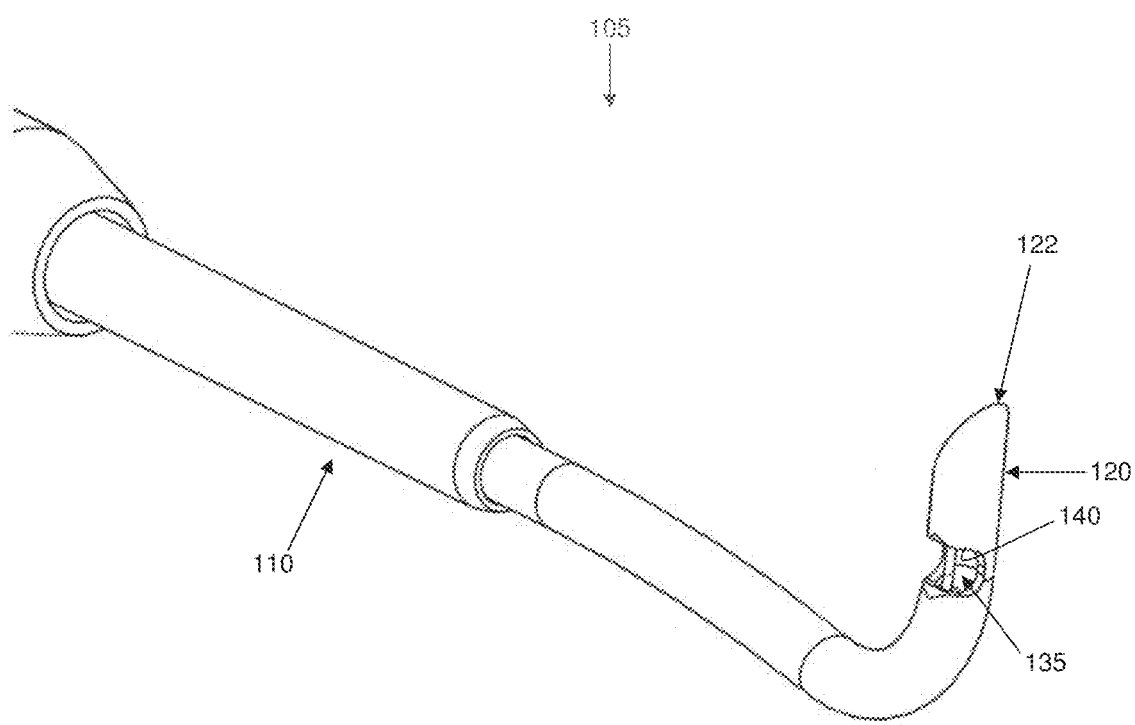

Again, if desired, and looking now at FIGS. 40A and 40B, second arm 65 of suture passer 5 may include a plurality of suture-engaging projections 76 on its distal side. As noted above, suture-engaging projections 76 allow the user to more aggressively engage (e.g., in a contact or frictional sense) suture S with second arm 65, whereby to facilitate manipulation of suture S via engagement with second arm 65. Thus, for example, with the construction shown in FIGS. 40A and 40B, if the user needs to move the suture S about a surgical site, the user can "grip" the suture S with the suture-engaging projections 76 of second arm 65 and "drag" the suture S into a desired position. In another example, the suture-engaging projections 76 of second arm 65 can assist in dragging suture S against the distal end of hollow tube 10. More particularly, as the clamping rod 15 is moved proximally in hollow tube 10, the second arm 65 retracts into the lumen of hollow tube 10. As it does so, if the suture S is in contact with the suture-engaging projections 76 of second arm 65, suture S will be drawn into engagement with the distal end of hollow tube 10 and then clamped in place by first arm 60.

Alternatively, if desired, second arm 65 of suture passer 5 may include a plurality of suture-engaging projections 76 on its proximal side (e.g., in a manner analogous to that shown in FIGS. 29C and 29D). Again, suture-engaging projections 76 allow the user to more aggressively engage (e.g., in a contact or frictional sense) suture S with second arm 65, whereby to facilitate manipulation of suture S via engagement with second arm 65.

Again, it will be appreciated that, if desired, suture-engaging projections 76 may also be provided on both the distal and proximal sides of second arm 65, and/or on one or both lateral sides of second arm 65.

It will be appreciated that suture-engaging projections 76 essentially constitute a suture engaging surface on second arm 65 so as to allow second arm 65 to engage and "drag" suture S about a surgical site. To this end, it will also be appreciated that the suture engaging surface(s) on second arm 65 may be formed with a variety of geometries, e.g., barbs, fingers or other surface texturing which increases the frictional aspects of second arm 65 at a desired location or locations.

Furthermore, if desired, and looking now at FIGS. 41-47, the distal end surface 80 of hollow tube 10 can be disposed substantially perpendicular to the longitudinal axis of hollow tube 10, whereby to enhance clamping of suture S against distal end surface 80 of hollow tube 10. In this construction, it may be desirable to provide a sharp point 85 to the distal end of first arm 60, in order to facilitate passage of the suture passer through tissue.

Handle

As noted above, suture passer 5 preferably comprises a handle 23, and handle 23 preferably comprises an actuator 72 which actuates clamping rod 15 so as to clamp and/or release suture S. If desired, actuator 72 may comprise a lock or detent which maintains the position of clamping rod 15 relative to hollow tube 10. For example, the lock or detent may hold the clamping rod in a distal position and/or in a proximal position (e.g., while it is clamping suture S).

Actuator 72 may also comprise a spring to bias clamping rod 15 proximally or distally. In one preferred form of the invention, this spring biases the clamping rod in a proximal direction (for example, to clamp suture S between clamping surface 47 and inclined proximal surface 45).

Novel "Spear" Suture Passer

Looking next at FIGS. 48-60, there is shown a novel suture passer 105 also formed in accordance with the present invention. Suture passer 105 will sometimes hereinafter be referred to as the "spear" suture passer.

More particularly, the spear suture passer 105 generally comprises an outer shaft tube 110, an inner guide tube 112 fixedly disposed within the interior of outer shaft tube 110, and a suture spear 116 slidably disposed within the lumen of inner guide tube 112, as will hereinafter be discussed in further detail.

More particularly, outer shaft tube 110 comprises a distal end 120 preferably terminating in a sharp point 122, and a proximal end 125 preferably terminating in a handle 123, with a lumen 130 extending therebetween. It will be appreciated that the pointed outer shaft tube 110 essentially comprises a hollow needle adapted to pierce tissue.

Figure 50:
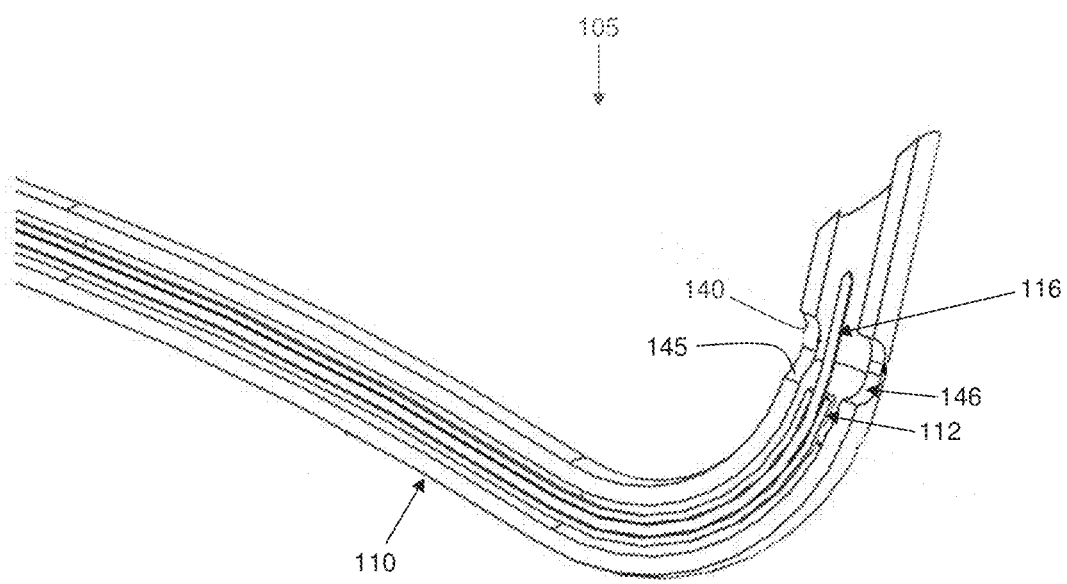
Figure 51:
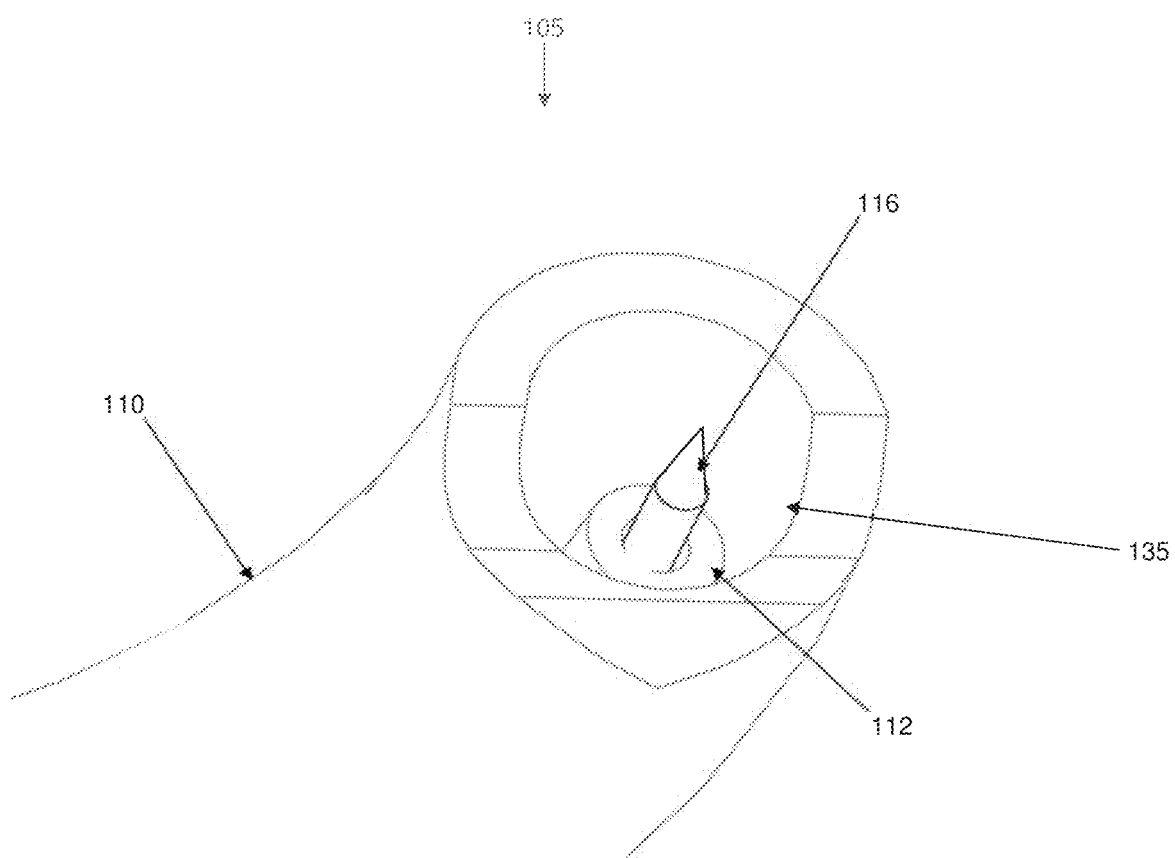
Figure 52:
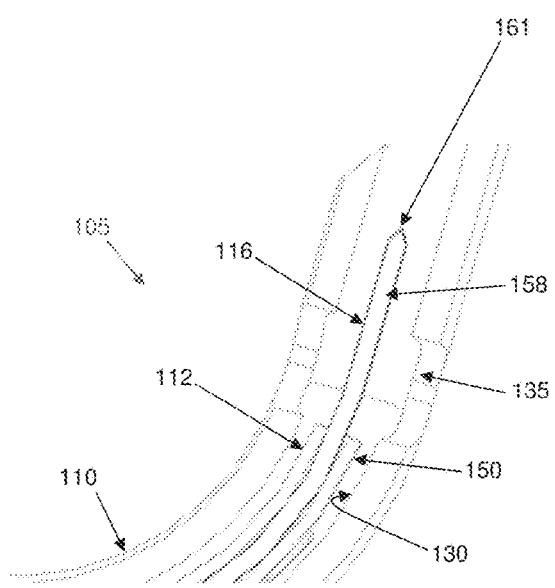

Outer shaft tube 110 further comprises a window 135 which extends radially into the outer shaft tube and communicates with lumen 130. Window 135 is sized so as to selectively receive a suture S therein, as will hereinafter be discussed in further detail. Window 135 comprises a pair of distal surfaces 140, a pair of proximal surfaces 145, and a pair of side surfaces 146. Preferably, distal surfaces 140 and proximal surfaces 145 extend substantially perpendicular to the longitudinal axis of outer shaft tube 110 (FIG. 49), and side surfaces 146 preferably extend substantially parallel to the longitudinal axis of outer shaft tube 110 (FIG. 50). Distal surfaces 140 are preferably spaced from proximal surfaces 145 by a distance which is somewhat larger than the diameter of suture S, so that window 135 provides an adequate seat for suture S, as will hereinafter be discussed in further detail.

Outer shaft tube 110 is preferably formed out of a substantially rigid material (e.g., stainless steel) so as to maintain rigidity when passing through tissue, particularly relatively tough fibrous tissue (e.g., the labrum of the hip).

In one preferred form of the present invention, the distal end 120 of outer shaft tube 110 is curved (see, for example, FIGS. 49, 58 and 59), however, it should also be appreciated that outer shaft tube 110 can be formed in other configurations well known in the art (e.g., straight, etc.).

Inner guide tube 112 comprises a distal end 150 (FIG. 52) and a proximal end 155 (FIG. 60), with a lumen 156 extending therebetween. Inner guide tube 112 is fixedly disposed within outer shaft tube 110 so that the distal end 150 of inner guide tube 112 terminates proximal to window 135 in outer shaft tube 110, with lumen 156 of inner guide tube 112 being substantially aligned with the center of window 135. The distal end 150 of inner guide tube 112 preferably terminates just proximal to window 135 of outer shaft tube 110. See, for example, FIGS. 50, 52 and 53. As will hereinafter be discussed, inner guide tube 112 acts as a guide and stiffening member for suture spear 116, which is selectively extendable out of the inner guide tube (and hence selectively extendable across window 135) and selectively withdrawable back into the inner guide tube (and hence selectively withdrawable out of window 135).

Figure 53:
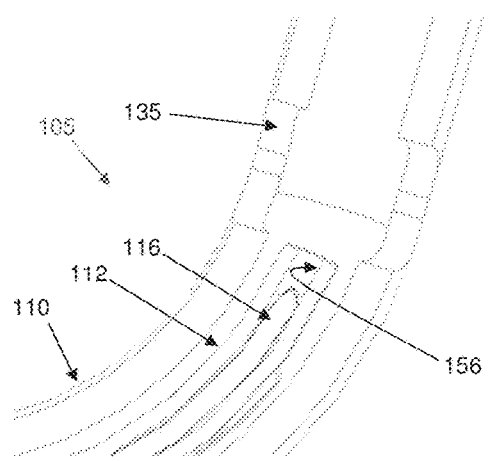
Figure 60:
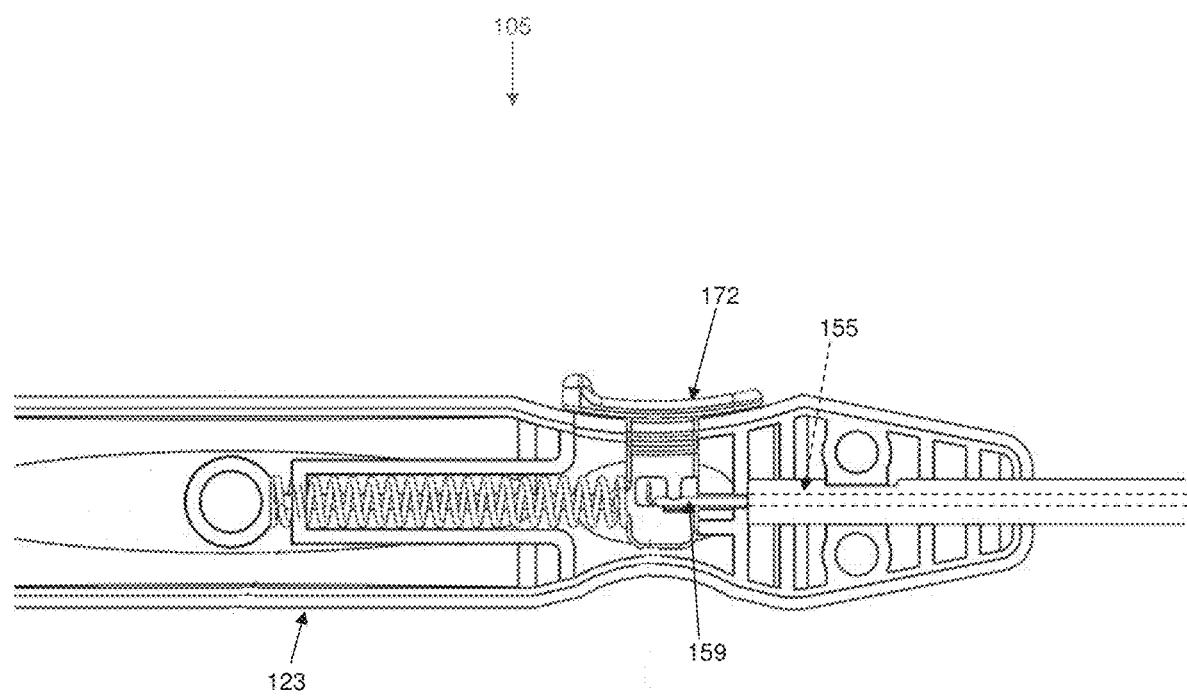
Figure 61:
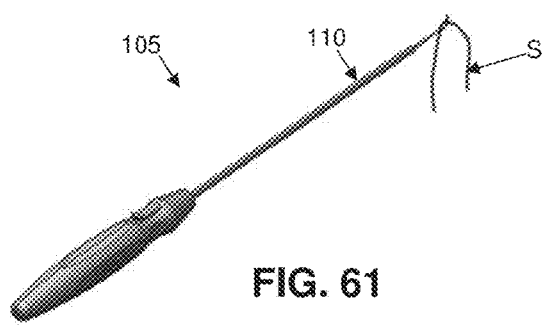
FIGS. 61-64 are schematic views showing an exemplary manner of passing suture using the novel suture passer of FIGS. 48-60.

Suture spear 116 comprises a distal end 158 (FIG. 52) and a proximal end 159 (FIG. 60). Distal end 158 of suture spear 116 terminates in a point 161. It will be appreciated that suture spear 116 essentially comprises a needle which, as will hereinafter be discussed, is adapted to pierce suture. Suture spear 116 is slidably disposed within lumen 156 of inner guide tube 112, such that suture spear 116 can extend across window 135 (FIG. 52) or be withdrawn from window 135 (FIG. 53). Preferably the proximal end 159 of suture spear 116 extends out of the proximal end 155 of inner guide tube 112 and is connected to an actuator 172 (e.g., a thumb slide) which is movably mounted to handle 123, such that movement of actuator 172 relative to handle 123 will cause movement of suture spear 116 relative to inner guide tube 112 (and hence relative to outer shaft tube 110). Specifically, movement of actuator 172 relative to handle 123 will cause the distal end of suture spear 116 to intrude across, or be withdrawn from, window 135 of outer shaft tube 110.

It should be appreciated that the distal end of inner guide tube 112 is positioned within outer shaft tube 110 so that the inner guide tube (and hence the suture spear 116) is aligned with a suture S that is laid in window 135 so as to ensure that suture spear 116 can securely pierce the suture S, as will hereinafter be discussed.

Figure 54:
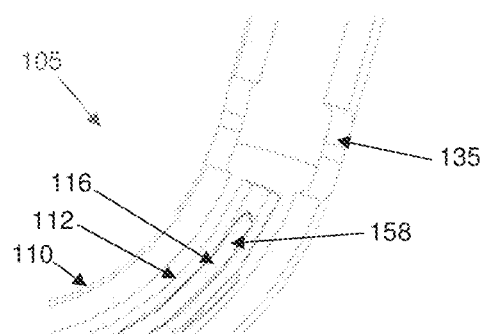
Figure 55:
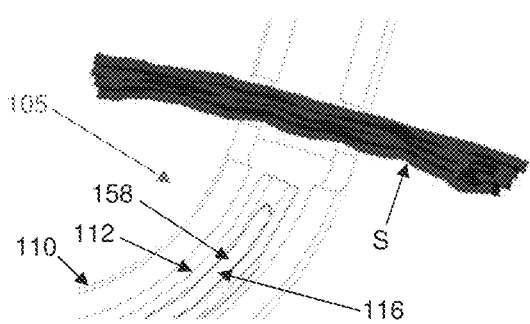
Figure 56:
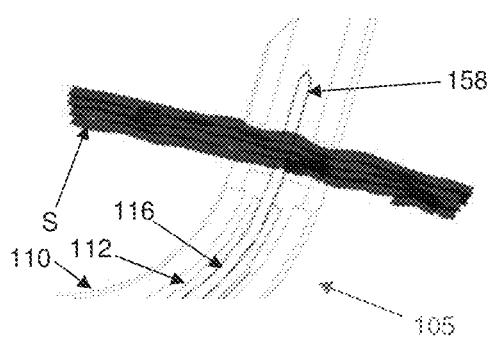
Figure 57:
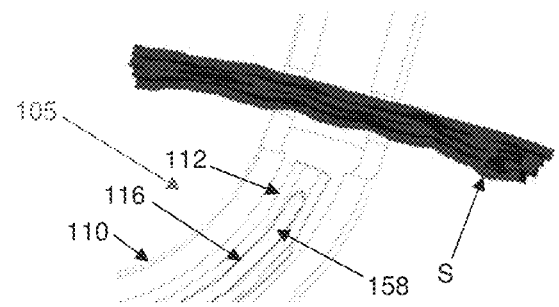
Figure 58:
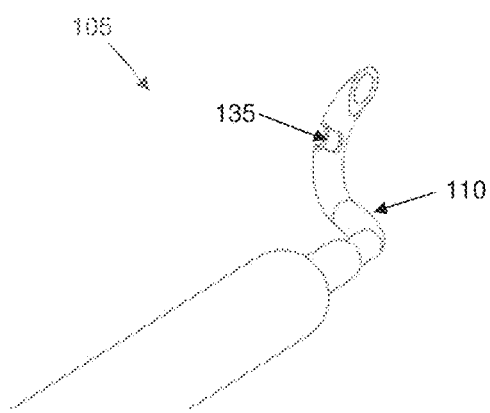
Figure 59:
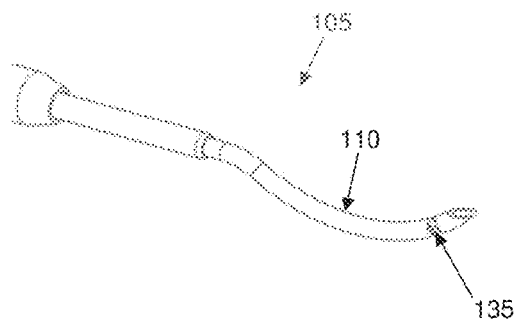

It will be appreciated that, on account of the foregoing construction, a piece of suture S may be clamped to the distal end of suture passer 105 by (i) moving suture spear 116 proximally so that the distal end 158 of suture spear 116 is withdrawn from window 135 of outer shaft tube 110, in the manner shown in FIG. 54 (e.g., by moving actuator 172 proximally relative to handle 123); (ii) positioning the suture S in window 135 (FIG. 55); and (iii) moving suture spear 116 distally (e.g., by moving actuator 172 distally relative to handle 123) so as to cause suture spear 116 to "spear" (e.g., penetrate) suture S, as shown in FIG. 56, whereby to secure suture S to suture passer 105.

It will also be appreciated that, on account of the foregoing construction, a speared piece of suture S (FIG. 56) may thereafter be released from suture passer 105 by (a) moving suture spear 116 proximally (FIG. 57) so as to "unspear" suture S; and (b) causing suture S to be withdrawn from window 135.

Using the Novel "Spear" Suture Passer to Pass Suture from the Near Side of Tissue to the Far Side of Tissue In one preferred form of the present invention, and looking now at FIGS. 61-64, the novel suture passer 105 can be used to pass suture S from the near side of tissue T to the far side of tissue T (i.e., in an "antegrade" manner).

More particularly, the preliminary loading of suture S into suture passer 105 may be performed away from the surgical site (e.g., outside of the patient) or it may be performed adjacent to the near side of the tissue T which is to be sutured (e.g., inside of the patient). As discussed previously, suture S may be loaded into suture passer 105 by retracting suture spear 116 out of window 135 of outer shaft tube 110 (FIG. 54), guiding suture S into window 135 (FIG. 55), and then advancing suture spear 116 distally through suture S (FIG. 56), whereby to secure suture S to suture passer 105. See FIG. 61.

Figure 62:
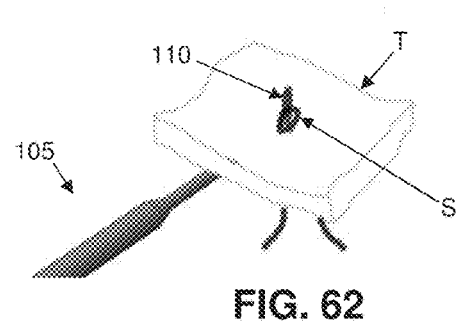
Figure 63:
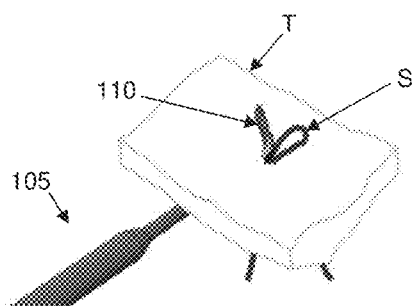
Figure 64:
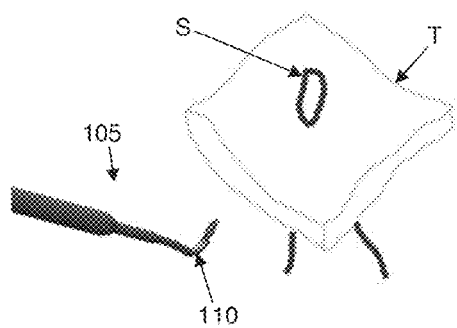

Suture passer 105 is then advanced distally so that window 135 passes through tissue T, whereby to carry suture S through the tissue (FIG. 62). With suture S extending through tissue T, and looking now at FIG. 63, suture spear 116 is retracted proximally so as to release suture S from suture passer 105, and then suture passer 105 and/or suture S are manipulated so that suture S is clear of window 135 (FIG. 63). Suture passer 105 may then be withdrawn back through tissue T, leaving suture S extending through tissue T, as shown in FIG. 64.

Using the Novel "Spear" Suture Passer to Draw Suture from the Far Side of Tissue to the Near Side of Tissue In another preferred form of the present invention, the spear suture passer 105 can be used to draw suture S from the far side of tissue T to the near side of tissue T (i.e., in a "retrograde" manner).

More particularly, in this form of the invention, the suture S is loaded into suture passer 5 on the far side of the tissue T. This is done by first passing suture passer 105 through tissue T so that window 135 resides on the far side of the tissue, and then moving suture spear 116 proximally so that suture spear 116 is withdrawn from window 135 (if the suture spear has not already been withdrawn from window 135). Suture S (disposed on the far side of tissue T) is then positioned into window 135, and suture spear 116 is advanced distally so as to spear suture S and secure the suture to suture passer 105. Outer shaft tube 110 is then retracted proximally through tissue T, carrying suture S therethrough. If desired, suture S can then be released from suture passer 105 by moving suture spear 116 distally.

Significantly, by alternating the aforementioned antegrade suture passing procedure (FIGS. 61-64) with the aforementioned retrograde suture passing procedure (discussed in the paragraph immediately preceding this paragraph), with the needle "plunges" being laterally spaced from one another in the tissue, a mattress stitch may be placed in the tissue, as will be appreciated by one skilled in the art.

If desired, the spear suture passer 105 may also be used to pass suture S around a side edge of the tissue T, rather than passing the suture S through the tissue. By way of example but not limitation, if the outer shaft tube 110 is passed around the side edge of the tissue (rather than through the tissue), the suture passer could then be used to retrieve the suture on the far side of the tissue and draw it back around the side edge of the tissue so that the suture is brought to the near side of the tissue.

As described above, the novel suture passer 105 has the ability to both pass (advance) and retrieve (draw) the suture S through and/or around the tissue in a continuous series of steps. This allows the surgeon to complete the desired suture passing without having to remove the suture passer 105 from the portal through which the suture passer 105 is being used. Significantly, this passing/retrieving process can be accomplished with a single instrument, rather than requiring one instrument for passing and a separate instrument for retrieving. This offers significant advantages in convenience and in reducing surgery time.

Figure 65:
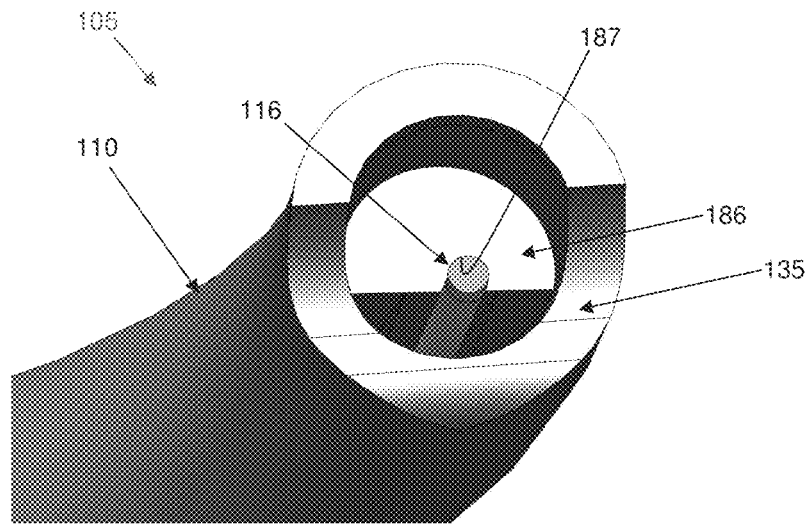
FIGS. 65-67 show variations of the novel suture passer shown in FIGS. 48-60.

If desired, the function of the inner guide tube 112 can be replaced by a rod 186 with a slot 187, as shown in FIG. 65. This rod 186 could also have other cross-sectional shapes (such as that of a ribbon, etc.) that act to constrain the suture spear 116 to the desired position relative to the window 135. This positioning scheme can also take the form of multiple wires filling the space where the suture spear is desired not to go.

Figure 66:
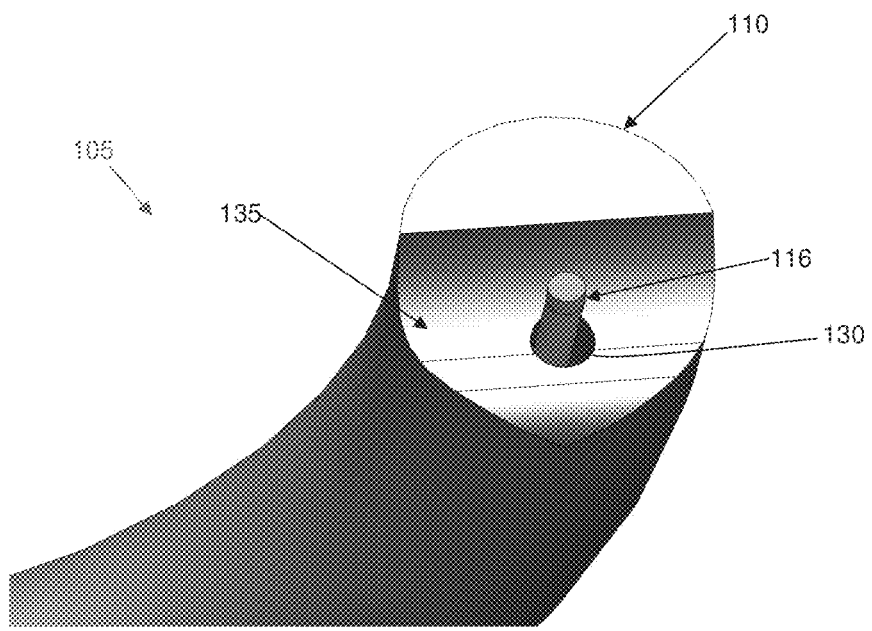

The function of inner guide tube 112 can also be incorporated into the outer shaft tube 110. For example, the outer shaft tube 110 can have a lumen 130 which is offset towards window 135, e.g., as shown in FIG. 66.

Figure 67:
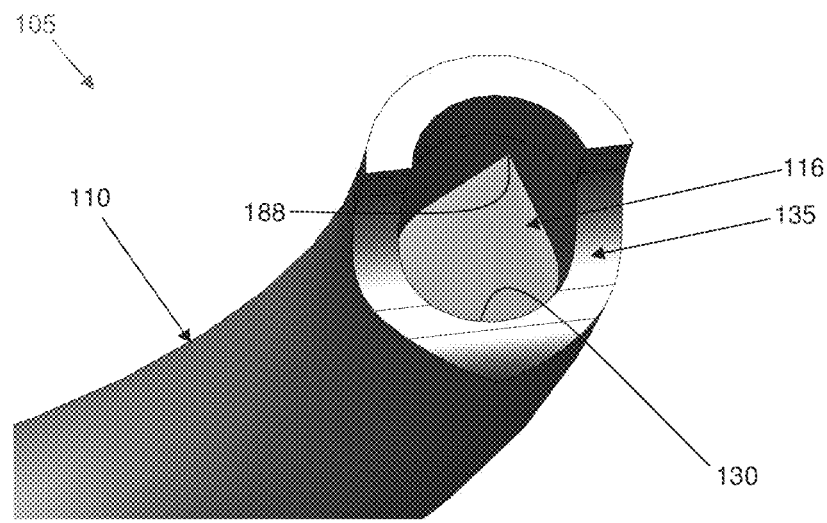
Figure 68:
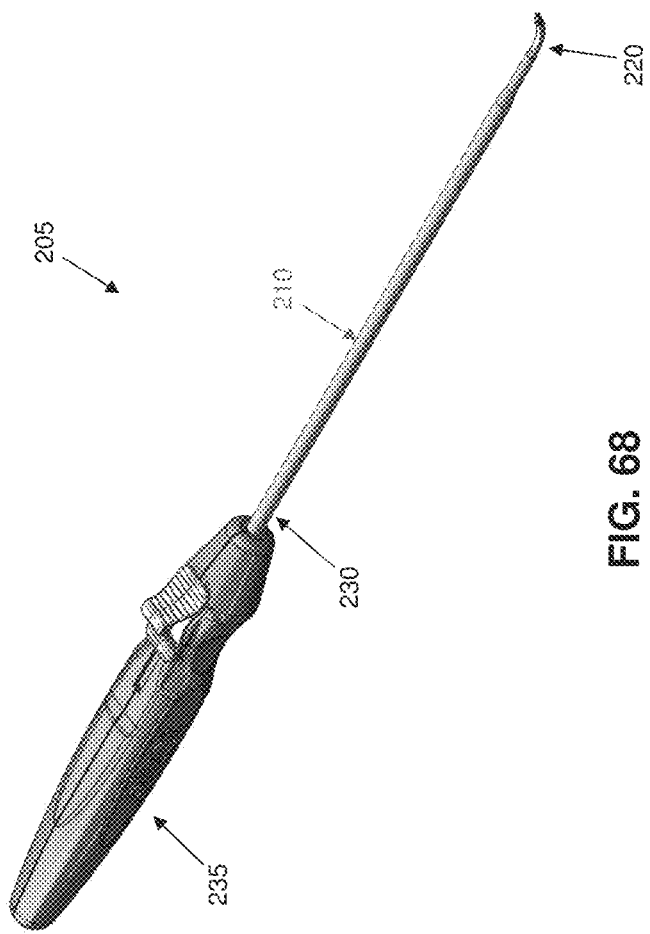
FIGS. 68-81 are schematic views showing another novel form of suture passer formed in accordance with the present invention.
Figure 69:
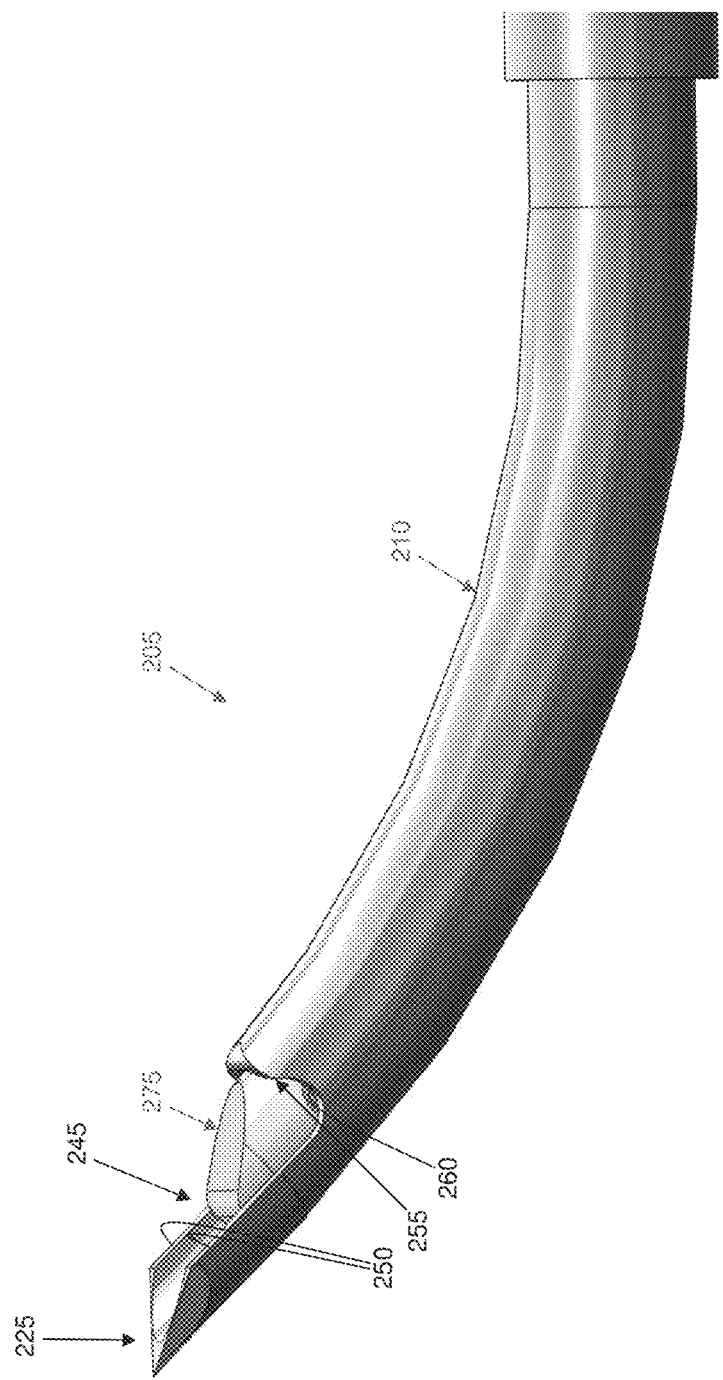

Additionally, suture spear 116 can occupy the entire internal diameter of lumen 130 of outer shaft tube 110. In this embodiment, and as shown in FIG. 67, the suture spear 116 is a rod with a sharpened feature 188 (e.g., a point) located in the window 135. In this embodiment, the inner guide tube 112 is not required.

Additional Novel Suture Passer

Looking next at FIGS. 68-81, there is shown a novel suture passer 205 formed in accordance with the present invention. Suture passer 205 generally comprises a hollow tube 210 and a clamping rod 215 slidably disposed within the lumen of hollow tube 210, as will hereinafter be discussed in further detail.

More particularly, hollow tube 210 comprises a distal end 220 preferably terminating in a sharp point 225, and a proximal end 230 preferably terminating in a handle 235, with a lumen 240 extending therebetween. It will be appreciated that the pointed hollow tube 210 essentially comprises a hollow needle adapted to pierce tissue.

Hollow tube 210 further comprises a cutaway 245 disposed just proximal to sharp point 225 and which communicates with lumen 240. Cutaway 245 preferably comprises a pair of longitudinally-extending edges 250 which terminate at their proximal ends at a circumferentially-extending edge 255. Preferably circumferentially-extending edge 255 is recessed at 260 so as to form seats for a suture grasped by suture passer 205, as will hereinafter be discussed. Alternatively, recess 260 can be omitted from circumferentially-extending edge 255 (e.g., circumferentially-extending edge 255 can be formed with a substantially "flat" profile).

Hollow tube 210 is preferably formed out of a substantially rigid material (e.g., stainless steel) so as to maintain rigidity when passing through tissue, particularly relatively tough fibrous tissue (e.g., the labrum of the hip, the capsule of the hip joint, etc.).

In one preferred form of the present invention, the distal end 220 of hollow tube 210 is curved, however, it should be appreciated that hollow tube 210 can be formed in other configurations well known in the art (e.g., straight, compound curves, etc.).

Clamping rod 215 comprises a distal end 265 and a proximal end 270. Distal end 265 of clamping rod 215 is bifurcated so as to form a first arm 275 and a second arm 280. The distal ends of first arm 275 and second arm 280 are biased laterally so that first arm 275 and second arm 280 will extend both distally and laterally when the distal ends of first arm 275 and second arm 280 are advanced distally out of the distal end of hollow tube 210, as will hereinafter be discussed in further detail. Preferably first arm 275 and second arm 280 have different degrees of lateral bias so that they will together define a funnel region therebetween when the distal ends of first arm 275 and second arm 280 are advanced distally out of the distal end of hollow tube 210, as will hereinafter be discussed in further detail.

More particularly, first arm 275 comprises a clamping surface 285, with clamping surface 285 extending radially from the longitudinal axis of clamping rod 215. Clamping surface 285 may take the form of a hook, as shown in the construction illustrated in FIGS. 68-81. This hook helps trap the suture S between clamping surface 285 of clamping rod 215 and the aforementioned recesses 260 of circumferentially-extending edge 255 of hollow tube 210, in the manner shown in FIGS. 77 and 78.

Figure 73:
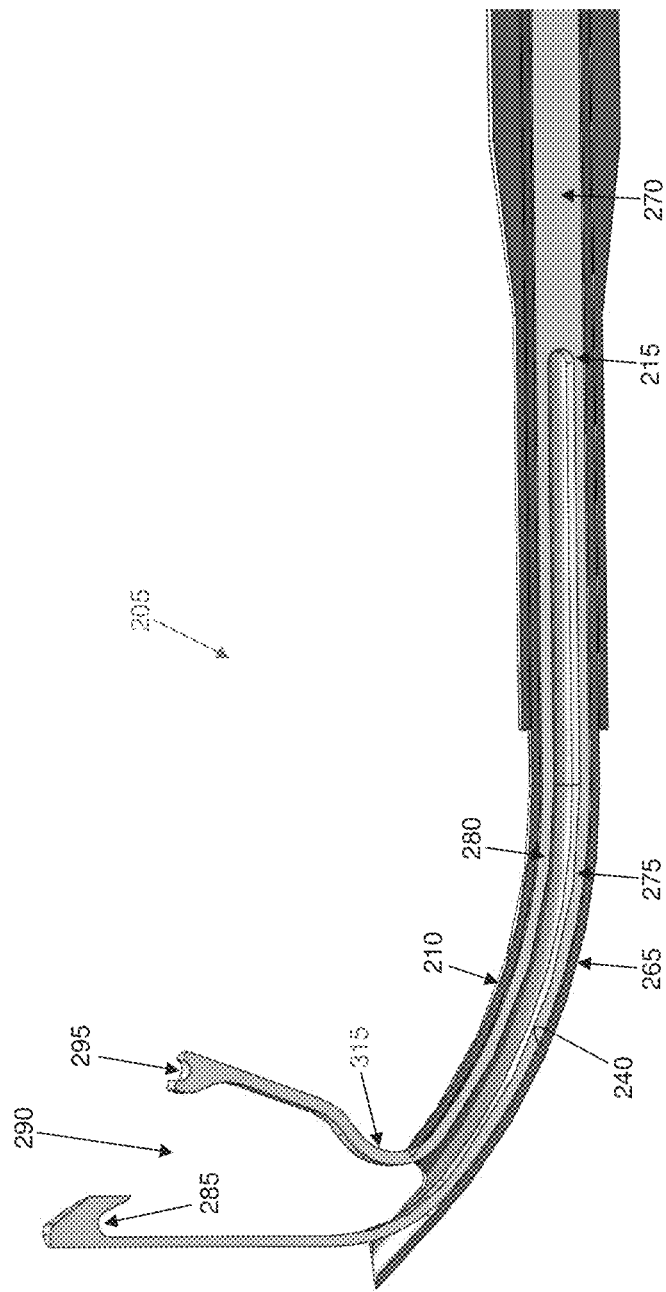
Figure 74:
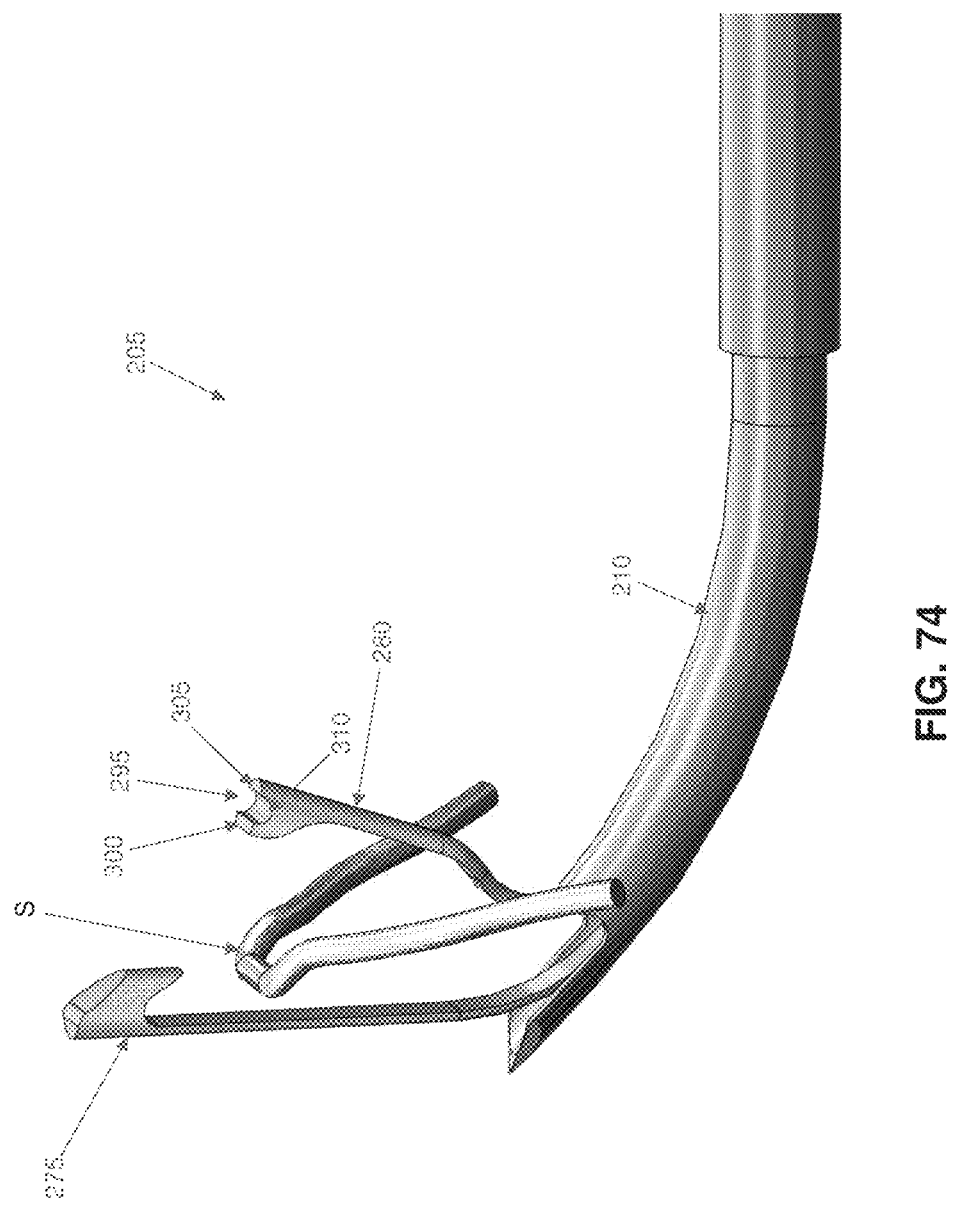
Figure 75:
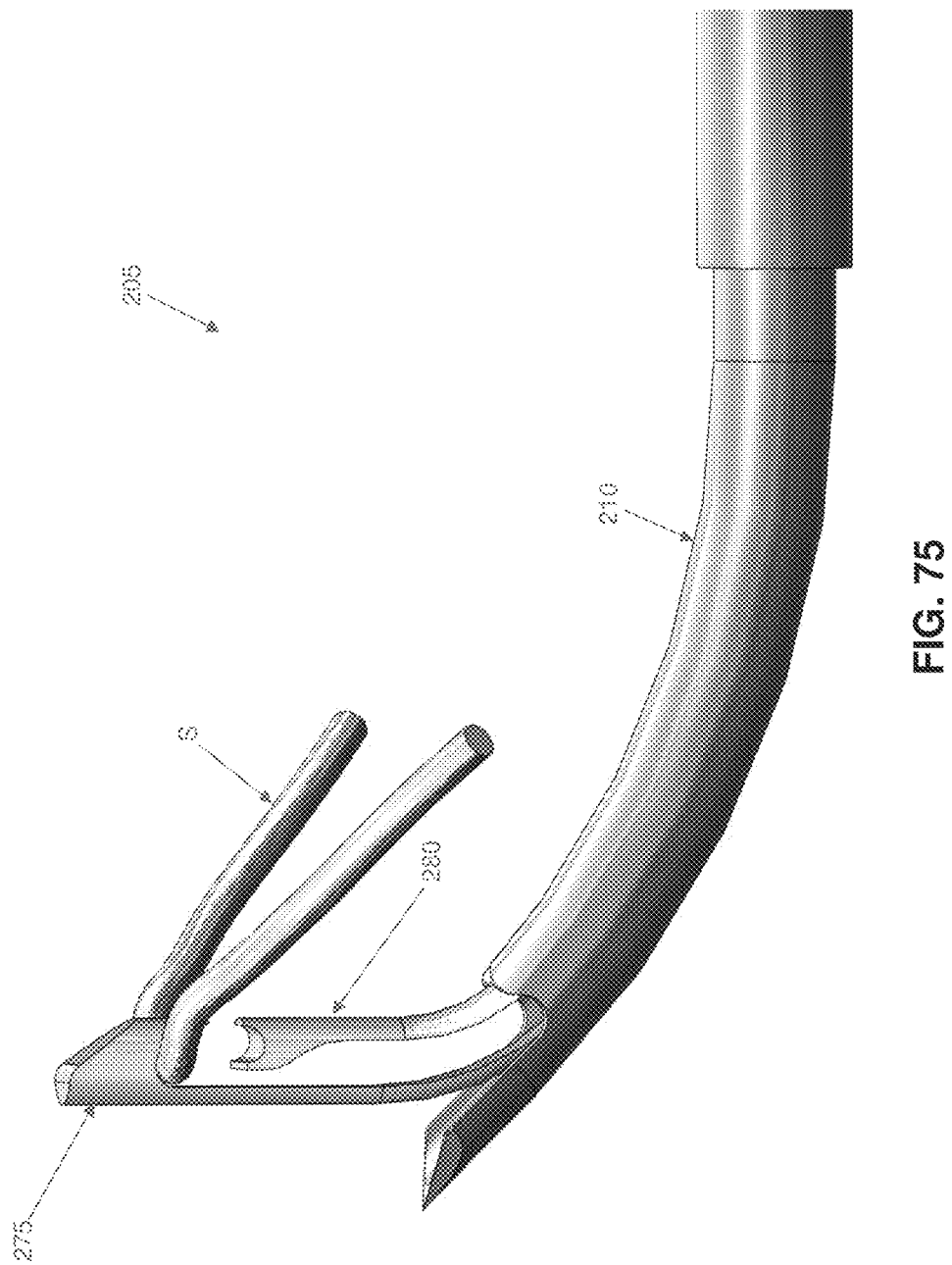
Figure 76:
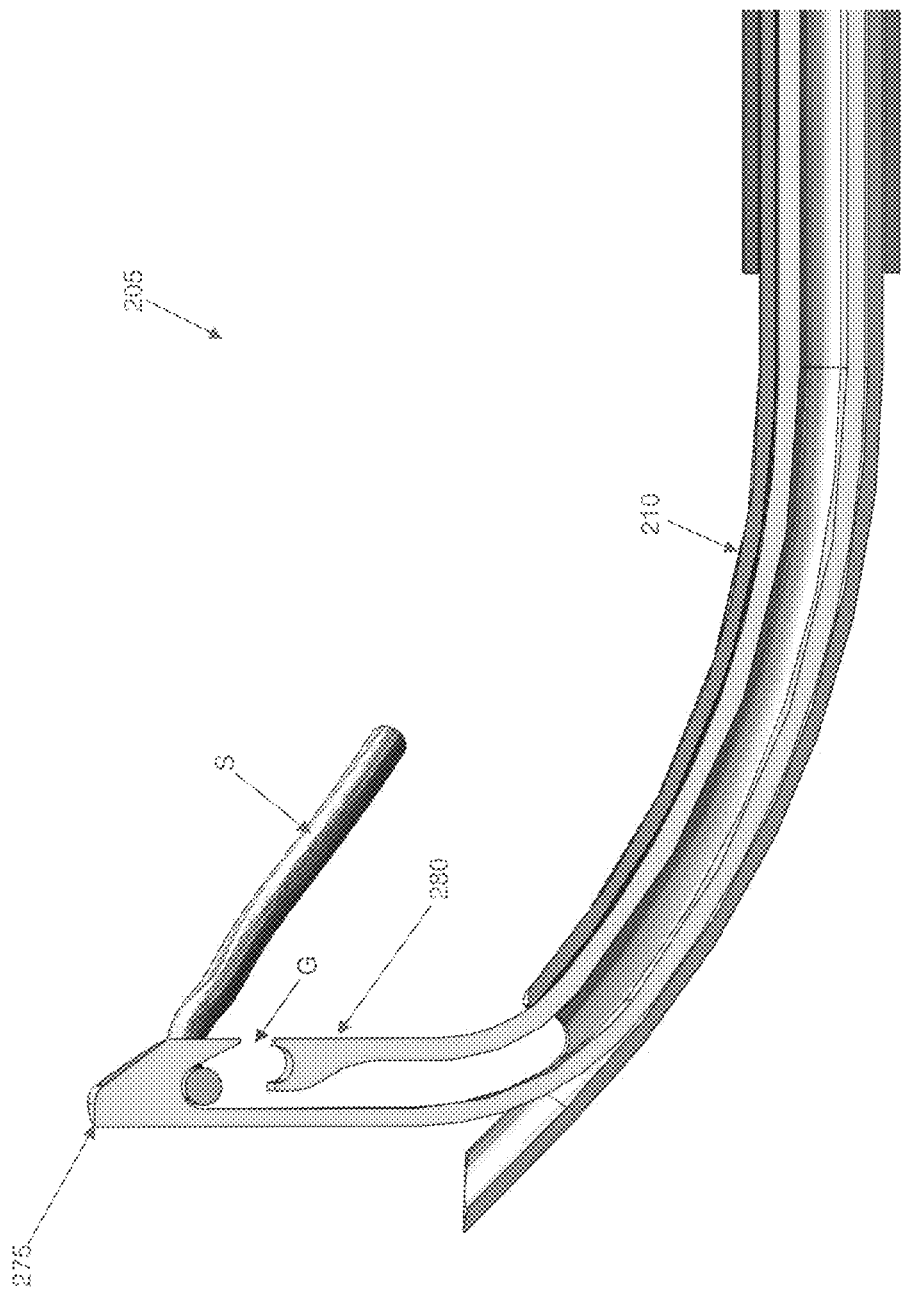

First arm 275 is outwardly biased so that when first arm 275 advances along cutaway 245, first arm 275 passes radially outwardly through the cutaway so as to project at an angle of approximately 60 degrees relative to the adjacent longitudinal axis of hollow tube 210 (i.e., the longitudinal axis of hollow tube 210 at the point adjacent to where first arm 275 advances through cutaway 245), whereby to create one half of a funnel region 290 established between first arm 275 and second arm 280 when first arm 275 and second arm 280 extend out of cutaway 245 (FIG. 73). To this end, first arm 275 is preferably formed out of a material consistent with this spring bias (e.g., a superelastic material such as Nitinol, etc.). In one preferred form of the invention, the entire clamping rod 215 is formed out of a superelastic material such as Nitinol.

Figure 70:
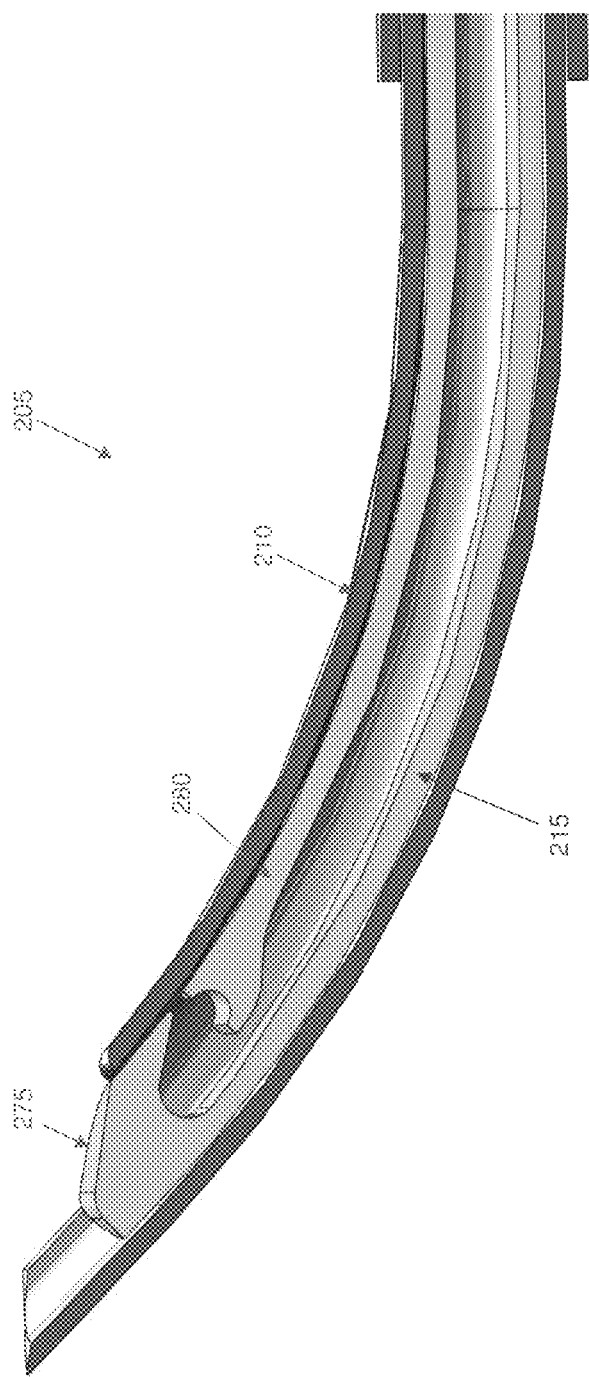
Figure 71:
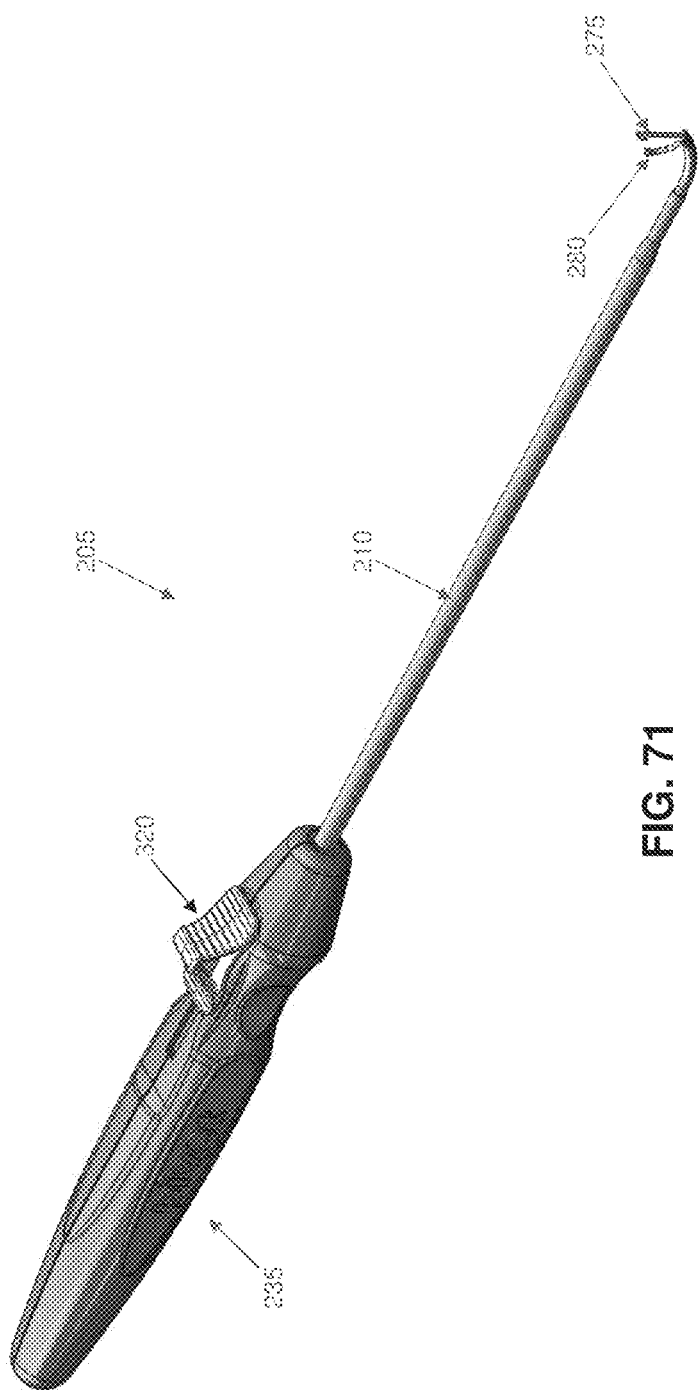

Second arm 280 extends parallel to first arm 275 when clamping rod 215 is disposed within lumen 240 of hollow tube 210, with second arm 280 terminating proximally of first arm 275, proximal of clamping surface 285 (FIG. 70). Second arm 280 comprises a recess 295 at its distal tip. Recess 295 forms a seat for suture S at the distal tip of second arm 280, such that when a suture S is seated in cutaway 245 and second arm 280 thereafter extends out of cutaway 245, recess 295 in second arm 280 will engage suture S and carry suture S away from cutaway 245, whereby to help separate suture S from suture passer 205. In one preferred form of the invention, recess 295 comprises a distal finger 300, a proximal finger 305 and a groove 310 formed therebetween. If desired, distal finger 300 and proximal finger 305 may have substantially the same length and/or width.

Second arm 280 is outwardly biased so that when second arm 280 advances along cutaway 245, second arm 280 passes radially outwardly through the cutaway 245 so as to project at an angle of approximately 90 degrees relative to the adjacent longitudinal axis of hollow tube 210 (i.e., the longitudinal axis of hollow tube 210 at the point adjacent to where second arm 280 advances through cutaway 245), whereby to create the aforementioned funnel region 290 between first arm 275 and second arm 280 when first arm 275 and second arm 280 extend out of cutaway 245. To this end, second arm 280 is preferably formed out of a material consistent with this spring bias (e.g., a superelastic material such as Nitinol, etc.). As noted above, in one preferred form of the invention, the entire clamping rod 215 is formed out of a superelastic material such as Nitinol.

The gap between first arm 275 and second arm 280 (see gap G in FIG. 76) is carefully sized, i.e., it is larger than the diameter of a suture so as to prevent a suture from being inadvertently lodged between first arm 275 and second arm 280, which could effectively jam the components, but not so large that the transfer of suture S from first arm 275 to second arm 280 is undermined. In one preferred form of the invention, the gap between first arm 275 and second arm 280 is approximately 1-3 times the diameter of the suture, and preferably about 1.5 times the diameter of the suture.

In one preferred form of the present invention, second arm 280 may comprise a compound curve 315 (FIG. 73) so as to facilitate proper disposition of second arm 280 when it is projected distally and laterally out of cutaway 245.

If desired, the degree of the outward bias of first arm 275 and second arm 280 can be varied from the angles described above, e.g., first arm 275 can extend at an angle of approximately 45 degrees relative to the adjacent longitudinal axis of hollow tube 210 when first arm 275 advances out of the distal end of hollow tube 210, and second arm 280 can extend at an angle of approximately 135 degrees relative to the adjacent longitudinal axis of hollow tube 210 when second arm 280 advances out of the distal end of hollow tube 210. In one form of the invention, first arm 275 can extend at an angle of 0-90 degrees relative to the adjacent longitudinal axis of hollow tube 210, and second arm 280 can extend at an angle of 20-160 degrees relative to the adjacent longitudinal axis of hollow tube 210 (but in any case at an angle which is greater than the angle of the first arm so that the two arms do not cross over one another). Still other appropriate constructions will be apparent to those skilled in the art in view of the present disclosure.

The proximal end 270 of clamping rod 215 extends through lumen 240 of hollow tube 210 and is connected to an actuator 320 which is movably mounted to handle 235, such that movement of actuator 320 relative to handle 235 causes movement of clamping rod 215 relative to hollow tube 210.

Figure 72:
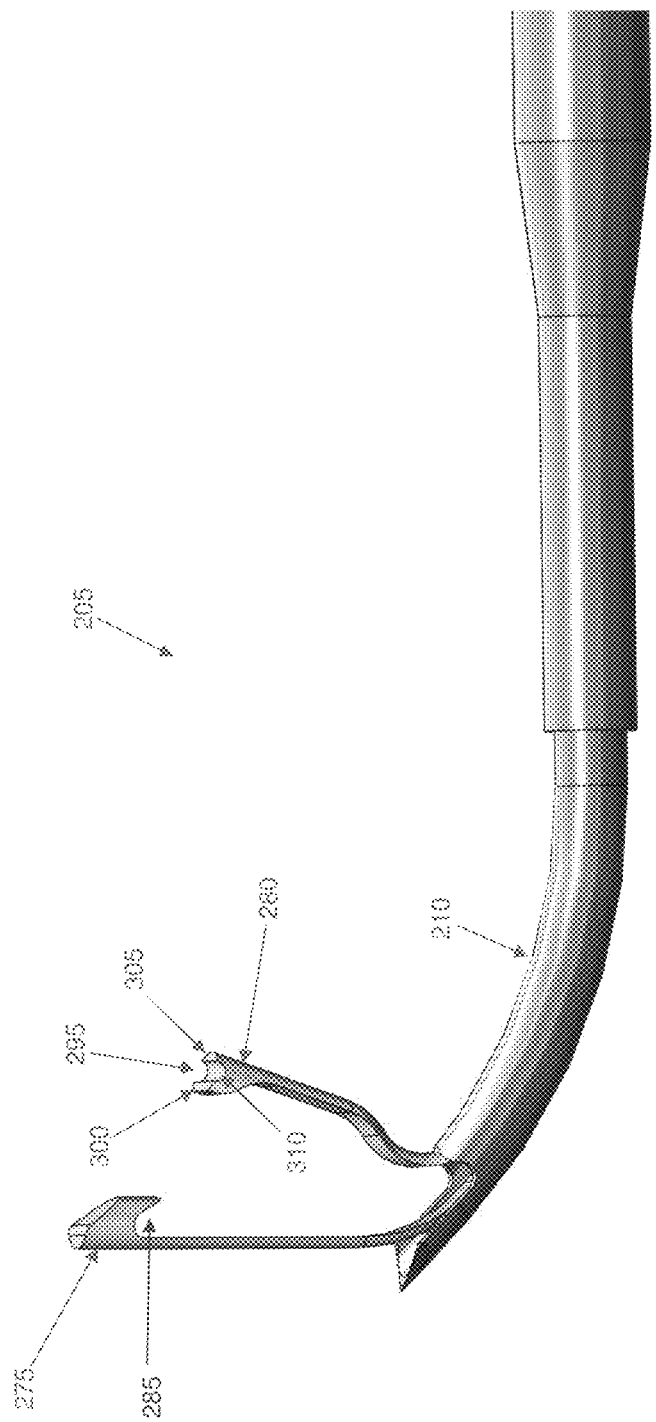
Figure 77:
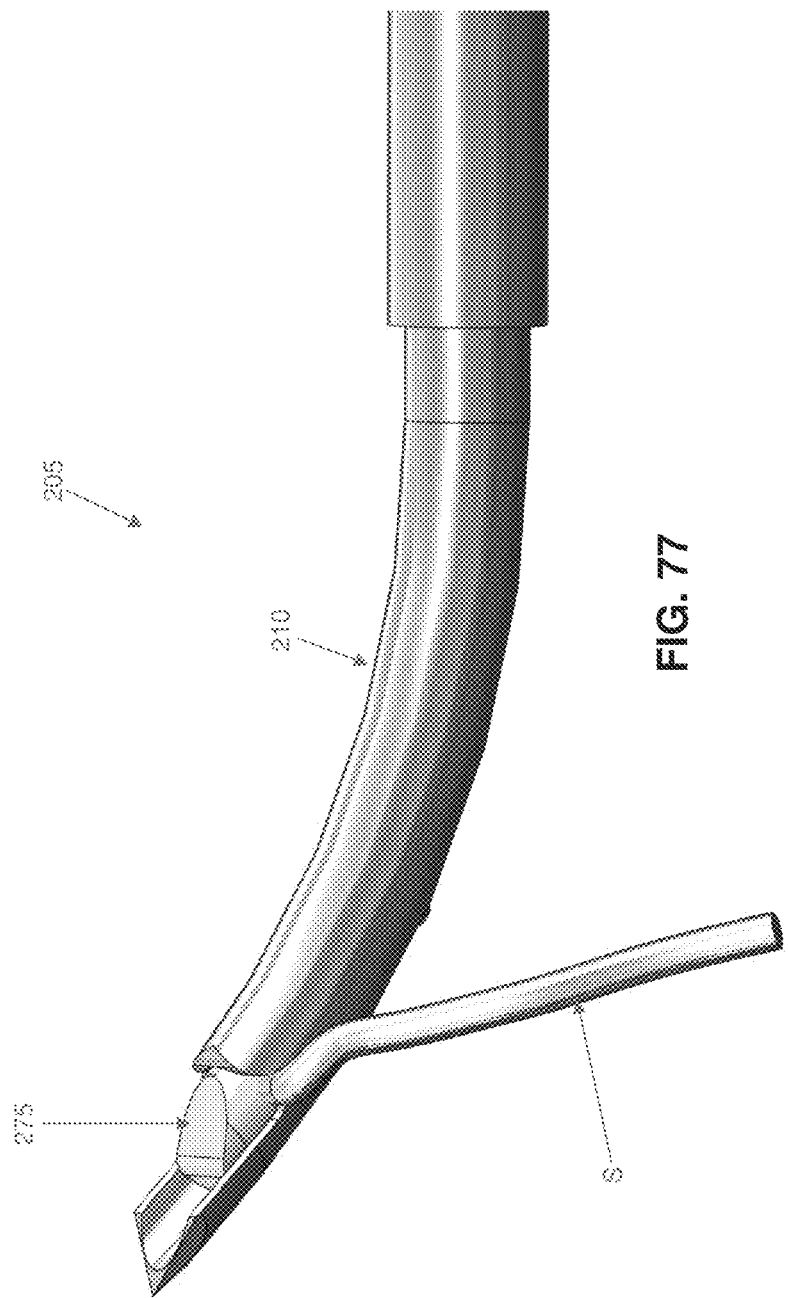
Figure 78:
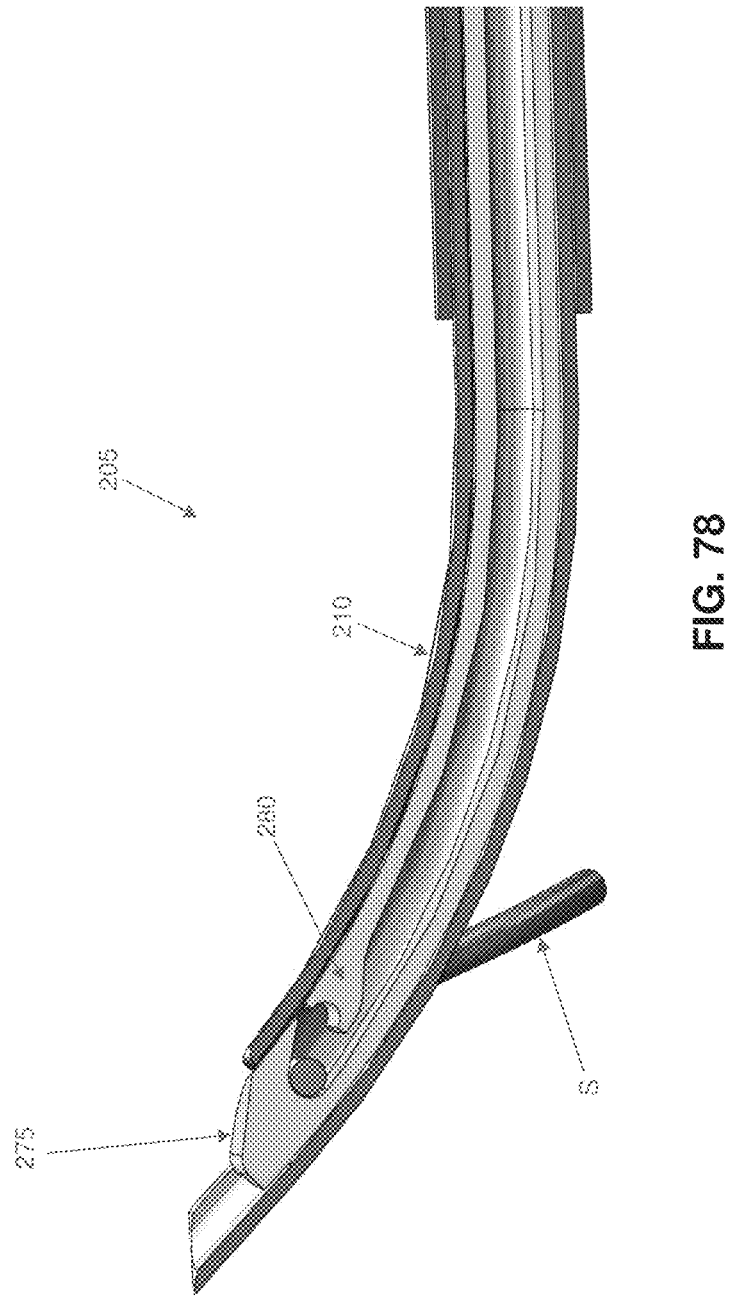
Figure 79:
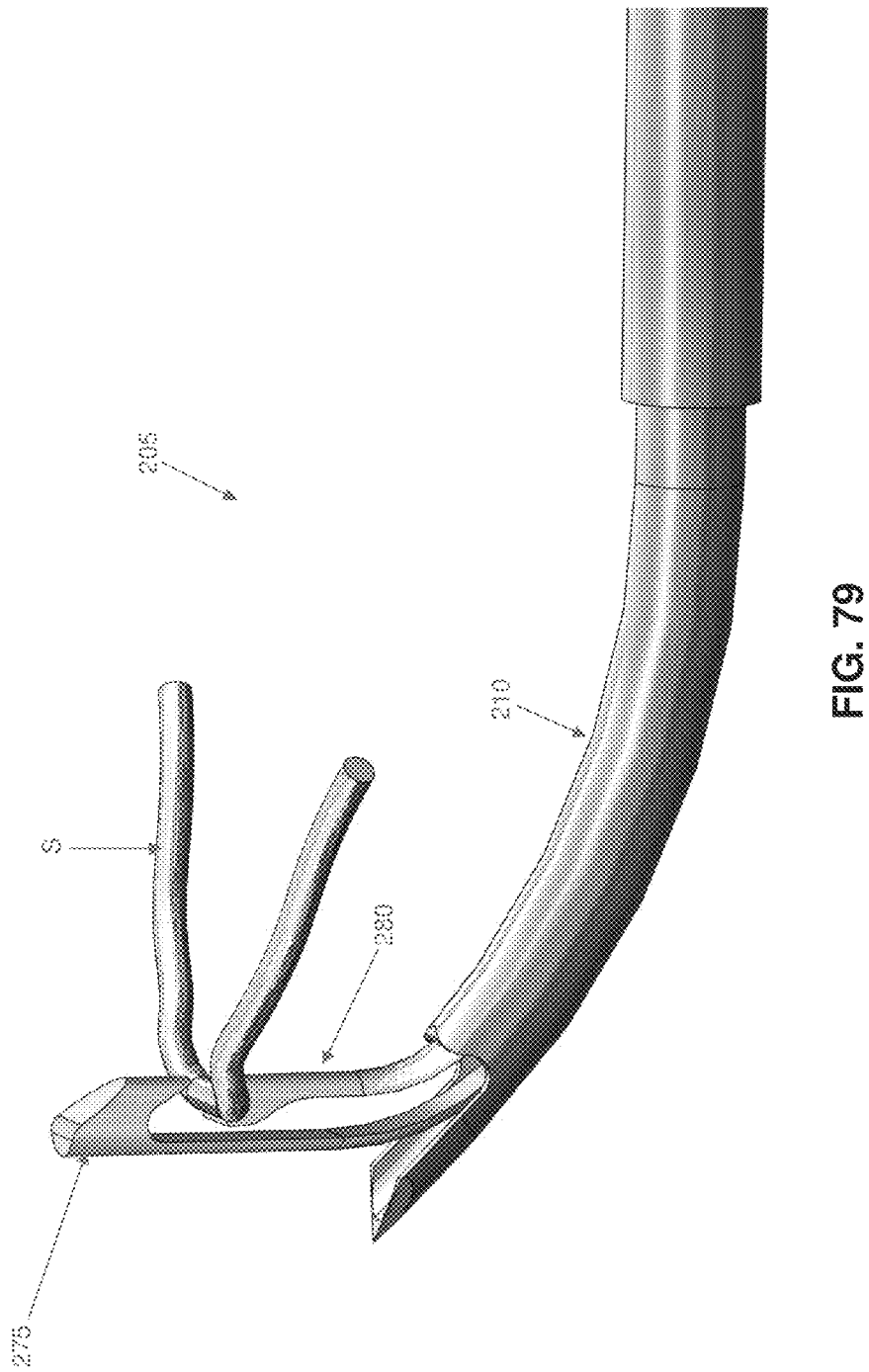
Figure 80:
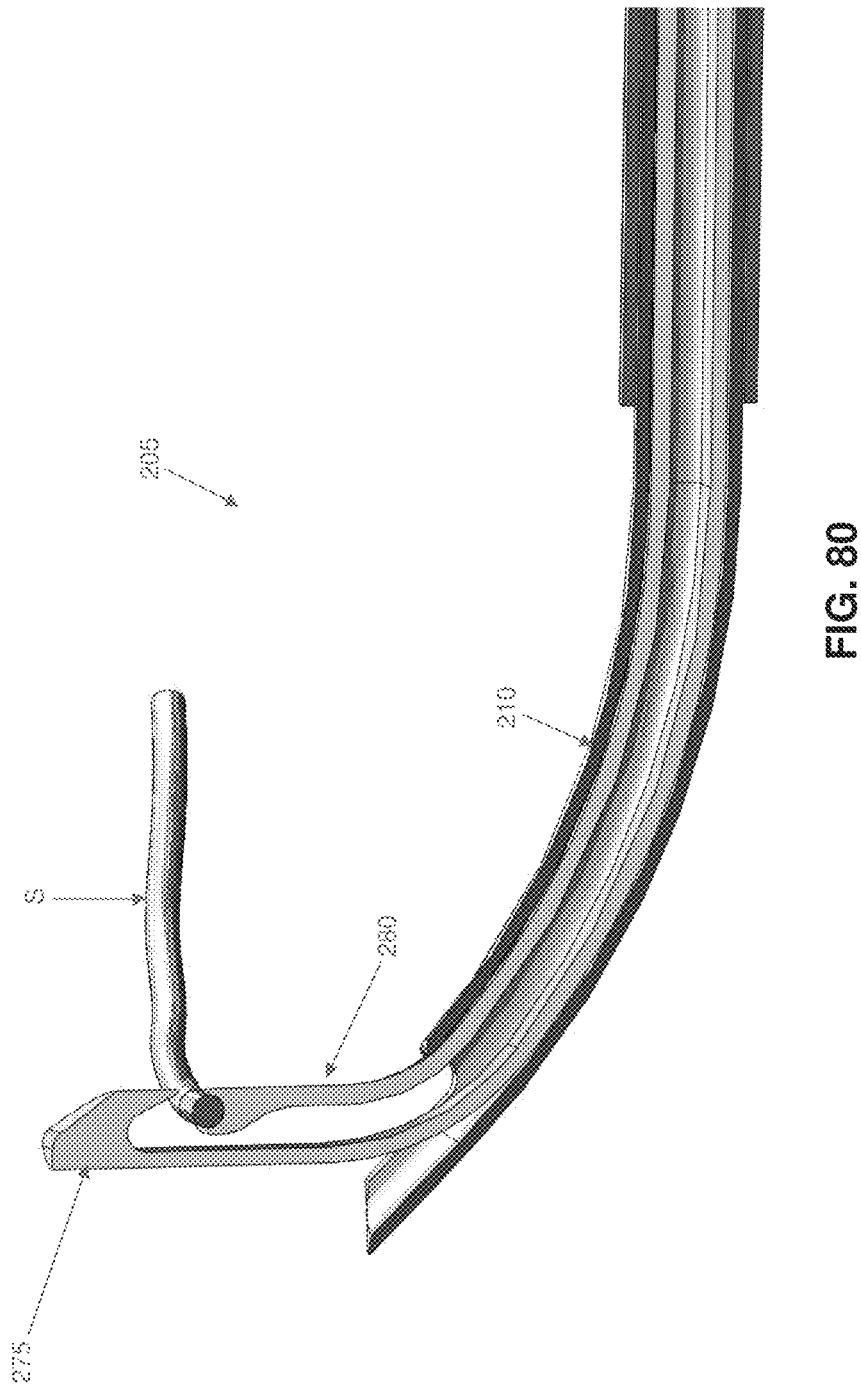
Figure 81:
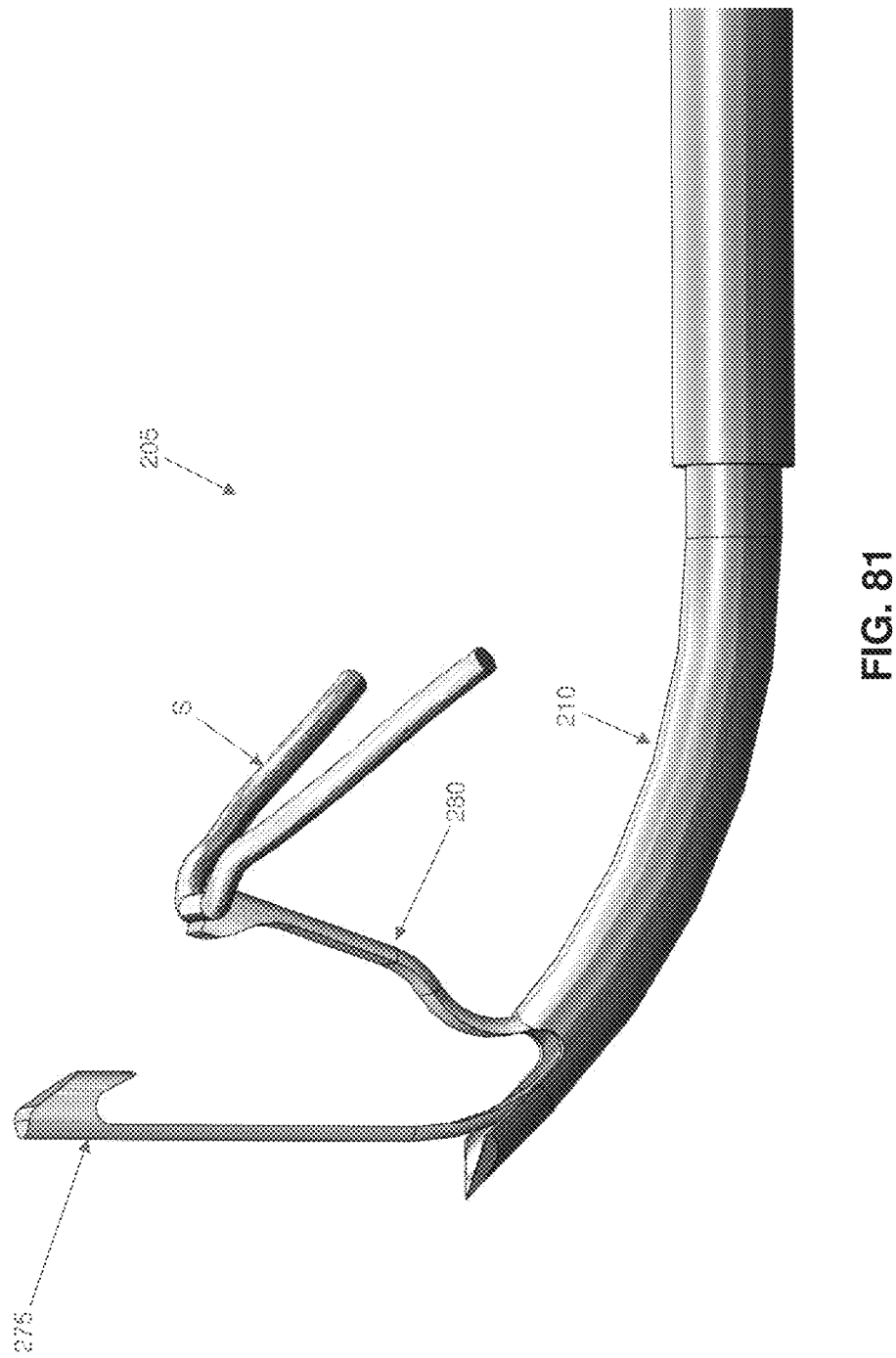

It will be appreciated that, on account of the foregoing construction, a piece of suture S may be clamped to the distal end of suture passer 205 by (i) moving clamping rod 215 to the position shown in FIGS. 72 and 73 (e.g., by moving actuator 320 distally relative to handle 235) so that first arm 275 and second arm 285 extend distally and laterally out of cutaway 245 and create the aforementioned funnel region 290; (ii) positioning the suture S in funnel region 290 (FIG. 74), preferably moving suture passer 205 and/or suture S as appropriate so as to settle the suture S deep within funnel region 290 (i.e., close to or against the pair of longitudinally-extending edges 250 and/or the circumferentially-extending edge 255, or hooking suture S with the clamping surface 285 of first arm 275; and (iii) moving clamping rod 215 proximally (e.g., by moving actuator 320 proximally relative to handle 235) so as to cause clamping surface 285 of first arm 275 to engage suture S (FIGS. 75 and 76) and retract suture S proximally, whereby to clamp suture S against recesses 260 of circumferentially-extending edge 255 of hollow tube 210, as shown in FIGS. 77 and 78. In this respect it will be appreciated that the creation of the funnel region 290 (established between the extended first arm 275 and the extended second arm 280) at the mouth of cutaway 245 facilitates guidance of suture S into clamping position, as shown in FIGS. 74-78.

It will also be appreciated that, on account of the foregoing construction, a clamped piece of suture S may thereafter be released from suture passer 205 by (a) moving clamping rod 215 distally (FIGS. 77-81) so as to space clamping surface 285 of first arm 275 away from recesses 260 of circumferentially-extending edge 255 of hollow tube 210, whereby to release suture S from its clamped condition, and with recess 295 of second arm 280 engaging suture S and driving it distally and laterally, so that suture S moves clear of cutaway 245 (FIGS. 79-81); and (b) causing suture S to be withdrawn from the suture passer, either by moving suture S relative to suture passer 205, or by moving suture passer 205 relative to suture S, or by moving both suture S and suture passer 205 relative to one another.

It should be appreciated that, in one preferred form of the invention, when clamping rod 215 is moved proximally, both first arm 275 and second arm 280 are disposed within lumen 240 of hollow tube 210, so that the distal end of suture passer 205 presents a smooth outer surface, whereby to facilitate passage of the distal end of suture passer 205 through tissue.

Using the Novel Suture Passer to Pass Suture from the Near Side of Tissue to the Far Side of Tissue In one preferred form of the present invention, the novel suture passer 205 can be used to pass suture S from the near side of tissue to the far side of tissue (i.e., in an "antegrade" manner).

More particularly, the preliminary loading of suture S into suture passer 205 may be performed away from the surgical site (e.g., outside of the patient) or it may be performed adjacent to the near side of the tissue which is to be sutured (e.g., inside of the patient). This is achieved by advancing clamping rod 215 to its distalmost position so that first arm 275 and second arm 280 advance out of cutaway 245, whereby to project the distal ends of the first and second arms out of the axis of hollow tube 210 and create the aforementioned funnel region 290. Suture S is then guided into cutaway 245 using this funnel effect, either by moving suture S relative to suture passer 205, or by moving suture passer 205 relative to suture S, or by moving both suture S and suture passer 205 relative to one another. If desired, the suture S may be tensioned so as to help draw it into cutaway 245. Or suture S may be hooked with clamping surface 285 of first arm 275. Clamping rod 215 is then retracted proximally so that clamping surface 285 of first arm 275 clamps suture S between clamping surface 285 of first arm 275 and recesses 260 of circumferentially-extending edge 255 of hollow tube 210.

Suture passer 205 is then advanced distally so that cutaway 245 passes through tissue, whereby to carry suture S through the tissue. With suture S extending through the tissue, clamping rod 215 is advanced distally so that first arm 275 and second arm 280 extend out of cutaway 245, thereby spacing clamping surface 285 from circumferentially-extending edge 255 of hollow tube 210, whereby to release suture S from suture passer 205 and with second arm 280 driving suture S before it as second arm 280 advances distally and proximally out of cutaway 245. See FIG. 79. Preferably, second arm 280 can flex proximally slightly at the end of the distal stroke, whereby to allow suture S to "slip off" the distal end of second arm 280. (see FIG. 81). In this respect it will be appreciated that second arm 280 is flexible, but also has column strength, so that second arm 280 can drive the suture S distally relative to hollow tube 210, but then, as the portion of second arm 280 projecting out of hollow tube 210 gets longer and longer, the second arm 280 eventually "flops over" under the drag of the suture S which is being pushed by second arm 280, whereby to cause suture S to fall free of second arm 280. Suture passer 205 and/or suture S are then manipulated so that suture S is clear of suture passer 205. Clamping rod 215 is then moved proximally so as to retract first arm 275 and second arm 280 back into hollow tube 210. Suture passer 205 may then be withdrawn back through the tissue, leaving suture S extending through the tissue.

Significantly, by providing second arm 280 of clamping rod 215 with a recess 295, the suture being driven forward by second arm 280 of clamping rod 215 can be "controlled" longer during the distal stroke, i.e., the suture can be retained for a longer period of time on the distally-moving second arm 280 of clamping rod 215. As a result, it is possible to advance longer lengths of suture through the tissue without driving the needle further through the tissue. This can be highly advantageous where longer lengths of suture may be required on the far side of the tissue, e.g., when suturing closed the capsule of the hip joint at the conclusion of an arthroscopic procedure but where the needle cannot be advanced further (e.g., if bone obstructs further passage of the needle, such as in a hip joint). At the same time, by forming second arm 280 out of a flexible, outwardly biased material, as the second arm 280 extends further and further out of hollow tube 210, the drag on suture S will eventually cause second arm 280 to "flop over", whereby to release the suture S from second arm 280.

Using the Novel Suture Passer to Draw Suture from the Far Side of Tissue to the Near Side of Tissue In another preferred form of the present invention, the novel suture passer 205 can be used to draw suture S from the far side of tissue to the near side of tissue (i.e., in a "retrograde" manner).

More particularly, in this form of the invention, the suture S is loaded into suture passer 205 on the far side of the tissue. This is done by first passing suture passer 205 through the tissue so that cutaway 245 resides on the far side of the tissue, and then moving clamping rod 215 distally so that first arm 275 and second arm 280 extend distally and proximally out of cutaway 245, whereby to create the aforementioned funnel region 290. This funnel effect is then used to guide a free suture (disposed on the far side of the tissue) into cutaway 245, either by moving suture S relative to suture passer 205, or by moving suture passer 205 relative to suture S, or by moving both suture S and suture passer 205 relative to one another. If desired, the suture S may be tensioned so as to help draw it into cutaway 245. Or suture S may be hooked with clamping surface 285 of first arm 275.

Next, clamping rod 215 is retracted proximally so as to releasably secure suture S between clamping surface 285 of first arm 275 and recesses 260 of circumferentially-extending edge 255 of hollow tube 210. Suture passer 205 is then retracted proximally through the tissue, carrying suture S therethrough. Suture S can then be released from suture passer 205 by moving clamping rod 215 distally, whereby to cause second arm 280 to drive suture S out of cutaway 245 and clear of suture passer 205.

Forming First Arm 275 without an Outward Bias

If desired, first arm 275 can be formed without an outward bias, so that only second arm 280 has an outward bias. In this form of the invention, the funnel region 290 is still formed between the distal ends of first arm 275 and second arm 280, however, the funnel region 290 will extend at a different angle relative to the adjacent longitudinal axis of hollow tube 210 than when both first arm 275 and second arm 280 are outwardly biased.

Forming Second Arm 280 with a Modified Construction

Figure 82:
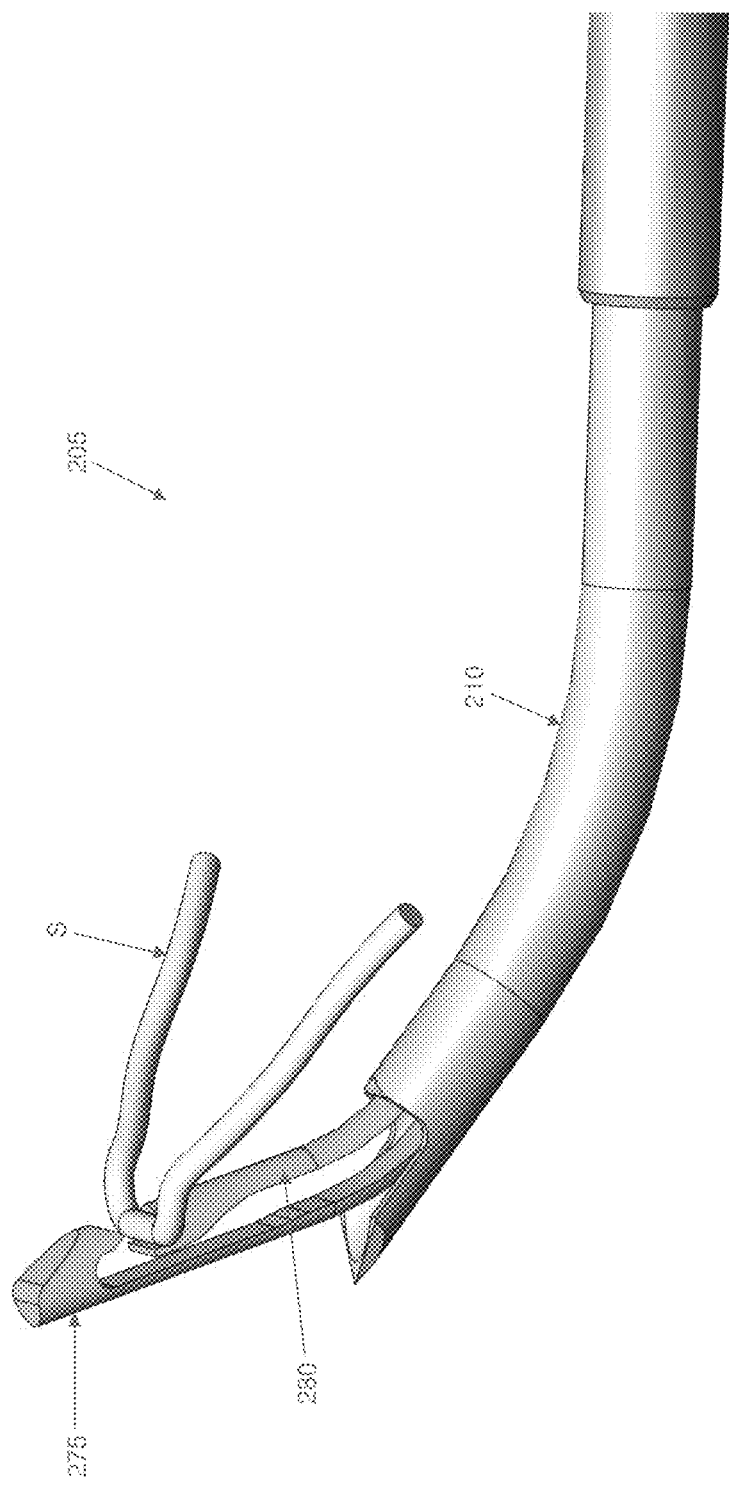
FIGS. 82-84 are schematic views showing another novel form of suture passer formed in accordance with the present invention.
Figure 83:
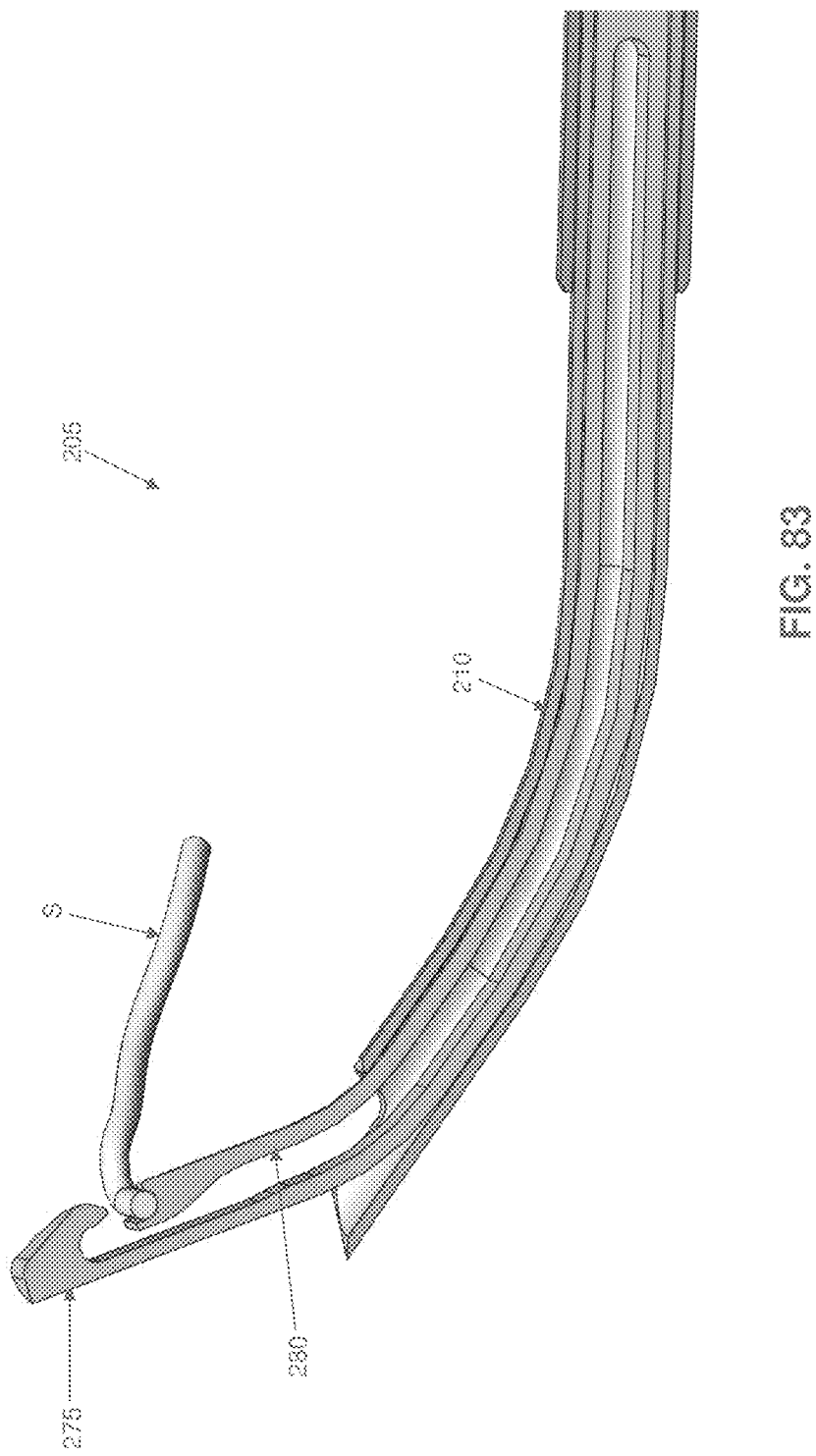
Figure 84:
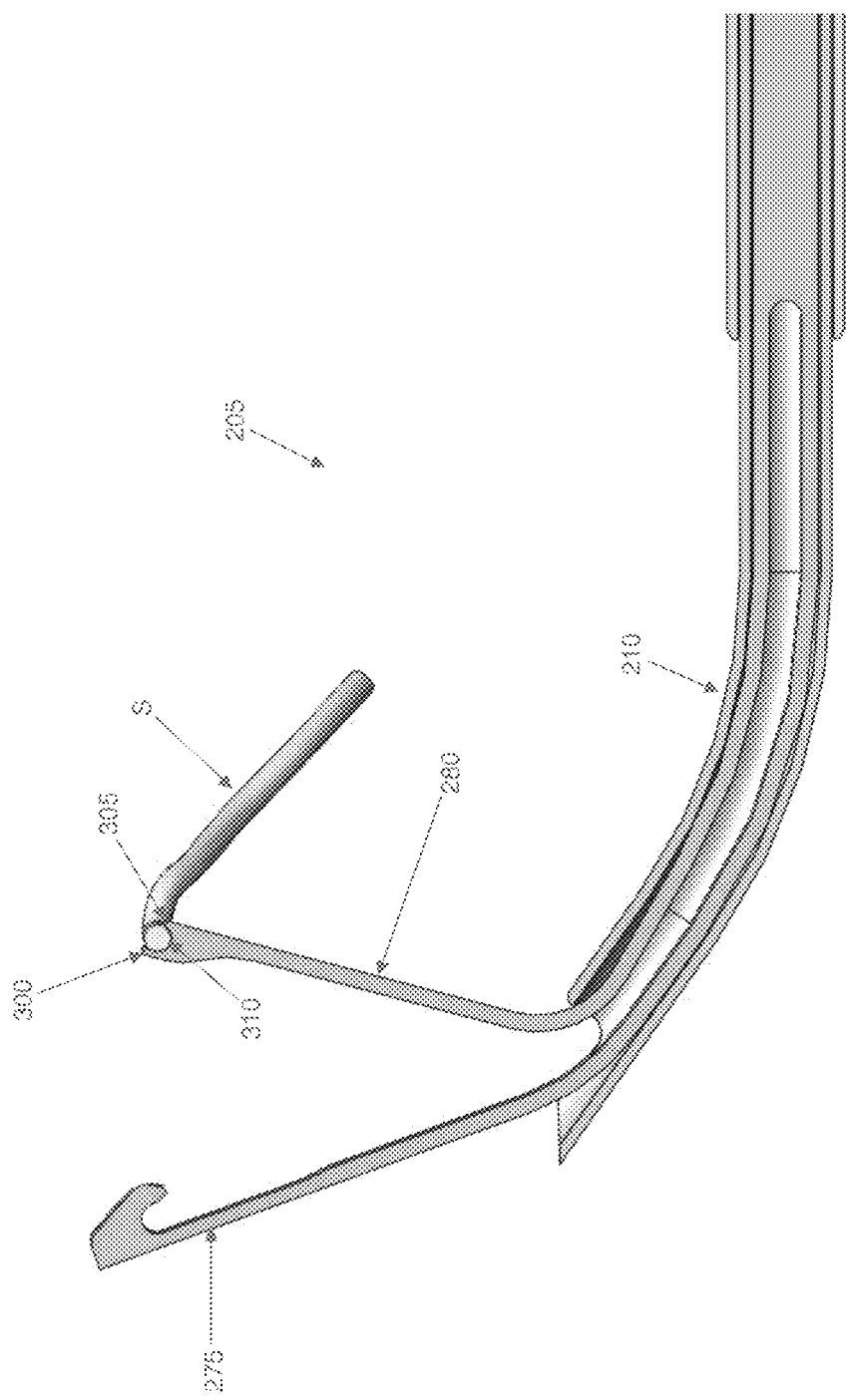

If desired, and looking now at FIGS. 82-84, second arm 280 may be formed without the aforementioned compound curve 315.

Furthermore, if desired, recess 295 at the distal tip of second arm 280 may be formed with a different geometry, e.g., so as to facilitate separation of suture S from second arm 280 at the end of the second arm's distal stroke. By way of example but not limitation, recess 295 may comprise a longer distal finger 300 and a shorter proximal finger 305, with the groove 310 being formed therebetween. As a result of this construction, when a suture S is seated in cutaway 245 and second arm 280 thereafter extends out of cutaway 245, recess 295 in second arm 280 will engage suture S and carry suture S away from cutaway 245, and the shorter proximal finger 305 will thereafter facilitate separation of suture S from suture passer 205. In effect, and as best seen in FIG. 84, as second arm 280 moves further and further out of hollow tube 210, the second arm 280 becomes progressively less supported by hollow tube 210 which, at the end of the second arm's distal stroke and in combination with the shorter proximal finger 305, allows the suture S to fall away from second arm 280 in the proximal direction. In this respect it will also be appreciated that where suture S extends through tissue proximal to second arm 280, friction between suture S and this tissue during distal movement of second arm 280 imposes a proximally-directed force on suture S, which (i) helps cause second arm 280 to bend proximally at the end of its distal stroke, thereby directing groove 310 more proximally, and (ii) helps suture S to pull off second arm 280. If desired, second arm 280 can be formed with proximal finger 305 omitted, so that second arm 280 comprises only the distal finger 300.

Figure 85:
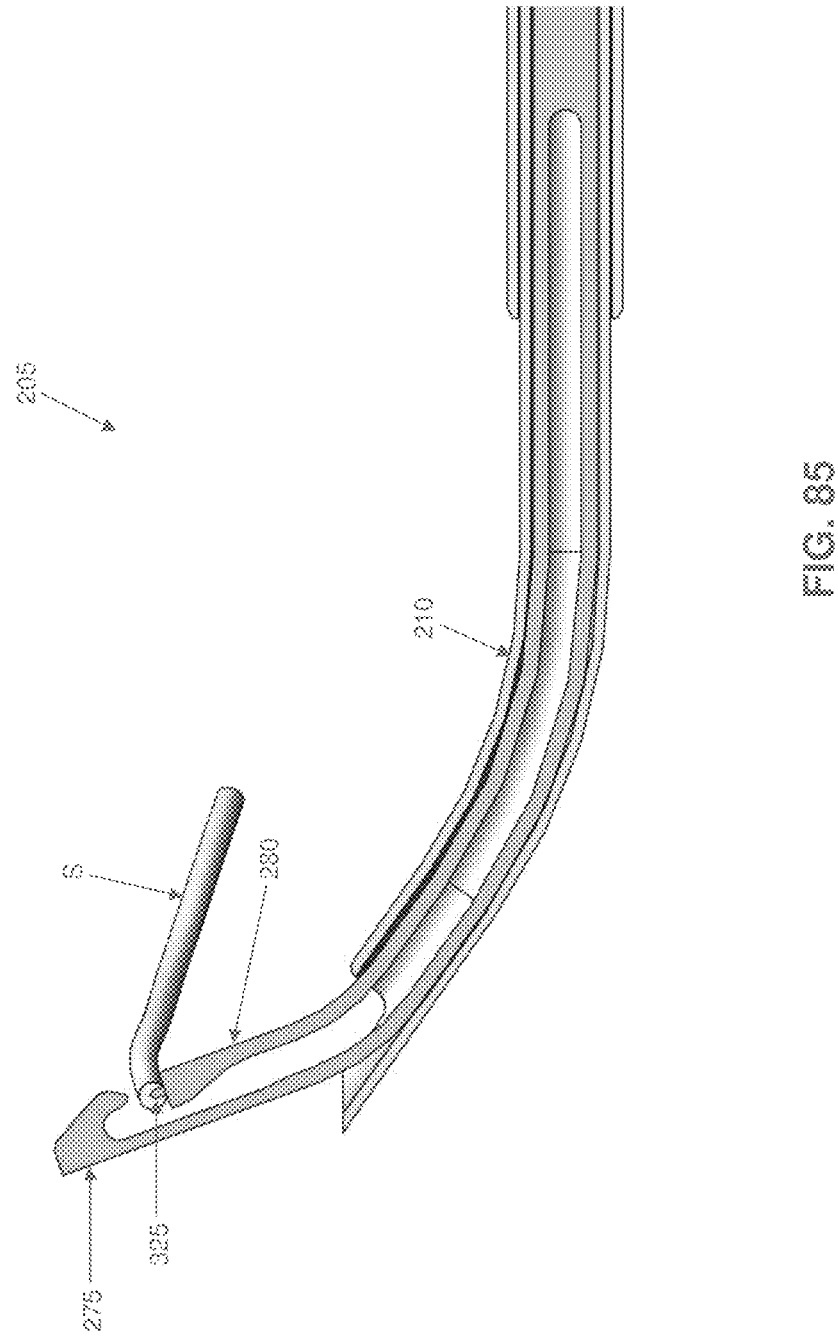
FIGS. 85 and 86 are schematic views showing still another novel form of suture passer formed in accordance with the present invention.
Figure 86:
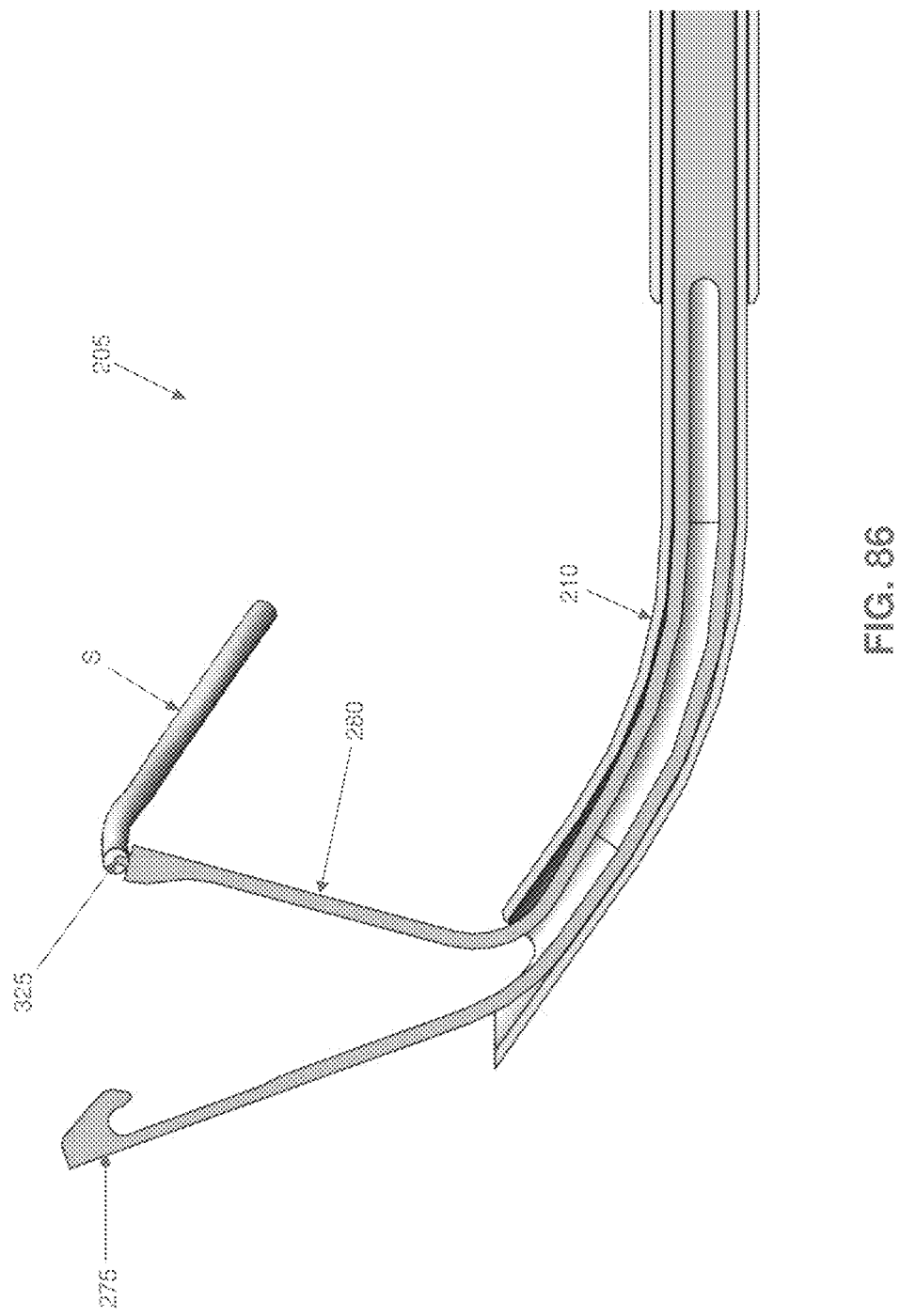

Additionally, if desired, and looking now at FIGS. 85 and 86, recess 295 at the distal end of second arm 280 may be replaced by a relatively short spike 325. In this form of the invention, when a suture S is seated in cutaway 245 and second arm 280 thereafter extends out of cutaway 245, spike 325 at the distal end of second arm 280 piercingly engages suture S and helps hold suture S on the distal end of second arm 280 as second arm 280 extends out of cutaway 245, whereafter the relatively short spike 325 allows suture S to separate from suture passer 205. More particularly, it will be appreciated that as second arm 280 moves further and further out of hollow tube 210, the second arm 280 becomes progressively less supported by hollow tube 210 which, in combination with the relatively short length of spike 325, allows the suture S to fall away from second arm 280 in the proximal direction. In this respect it will also be appreciated that where suture S extends through tissue proximal to second arm 280, friction between suture S and this tissue during distal movement of second arm 280 imposes a proximally-directed force on suture S, which (i) helps cause second arm 280 to bend proximally at the end of its distal stroke, thereby directing spike 325 more proximally, and (ii) helps suture S to pull off second arm 280.

Additional Construction Wherein the First and Second Arms Extend at Smaller Angles Relative to the Adjacent Longitudinal Axis of the Hollow Tube Looking next at FIGS. 87-91, there is shown a construction wherein first arm 275 and second arm 280 both extend at smaller angles (than those previously disclosed) relative to the adjacent longitudinal axis of hollow tube 210. More particularly, in this form of the invention, first arm 275 extends substantially parallel to the adjacent longitudinal axis of hollow tube 210, and second arm 280 extends at an angle of approximately 35 degrees relative to the adjacent longitudinal axis of hollow tube 210. It has been found that by configuring second arm 280 so that it extends at a smaller angle (than those previously disclosed) relative to the adjacent longitudinal axis of hollow tube 210, the suture is more easily released from the tool after the tool has been used to pass suture in an antegrade fashion through the tissue.

In one preferred form of the invention, second arm 280 comprises a plurality of bends (e.g., two bends 281A and 281B) which act in an "additive" fashion so as to together provide an increased opening for funnel region 290.

In addition, in this form of the invention, second arm 280 is configured so that it extends laterally (of hollow tube 210) "sooner" (i.e., when clamping rod 215 is at a more proximal position than previously disclosed) so as to open funnel region 290 closer to the distal end of hollow tube 210. This is a consequence of locating bend 281A closer to the distal end of second arm 280. As a result, the tool can be used to retrieve suture without having to fully extend first arm 275 and second arm 280, which can sometimes be difficult to do in constrained spaces.

Figure 87:
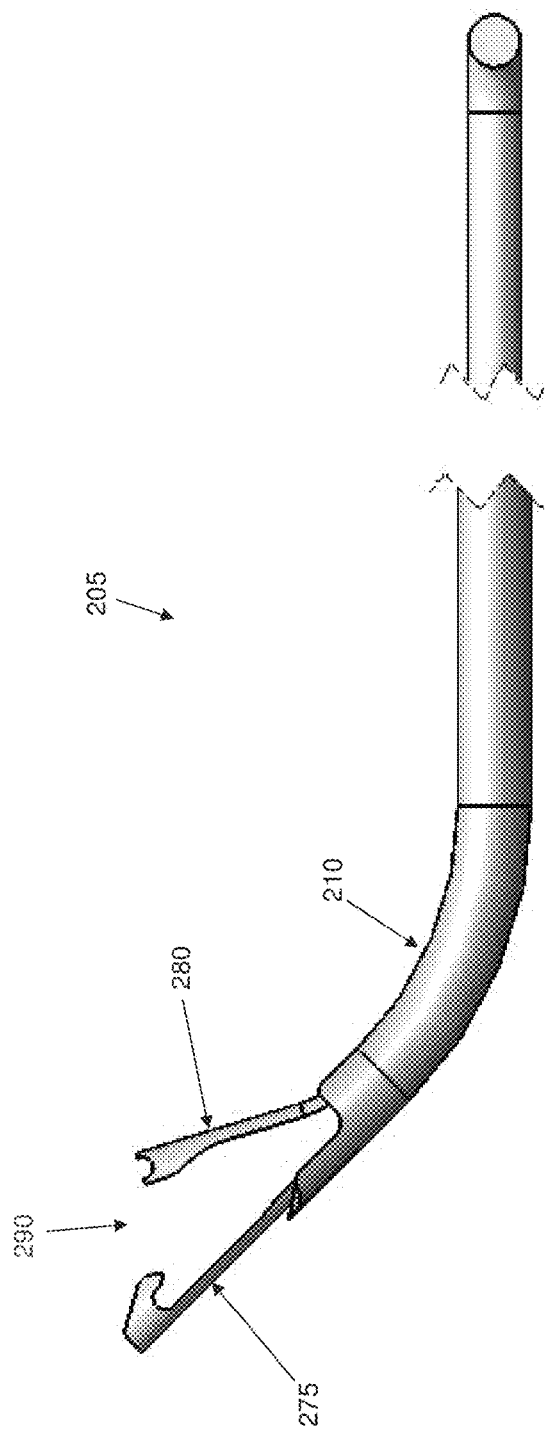
Figure 88:
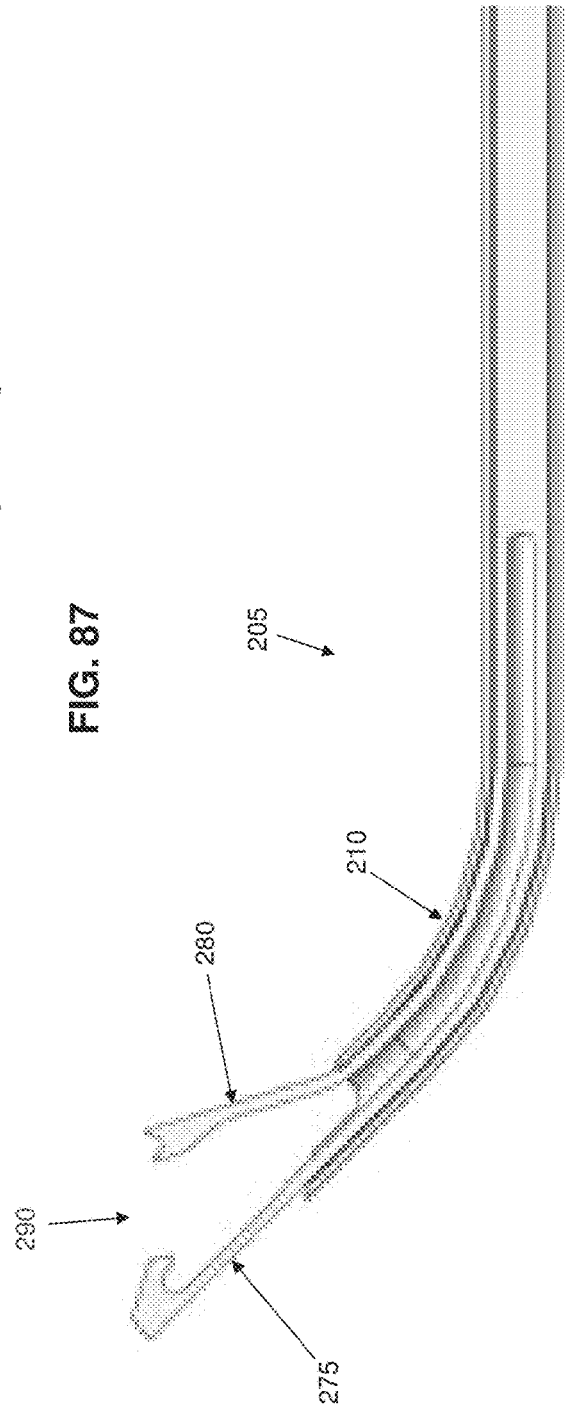
Figure 92:
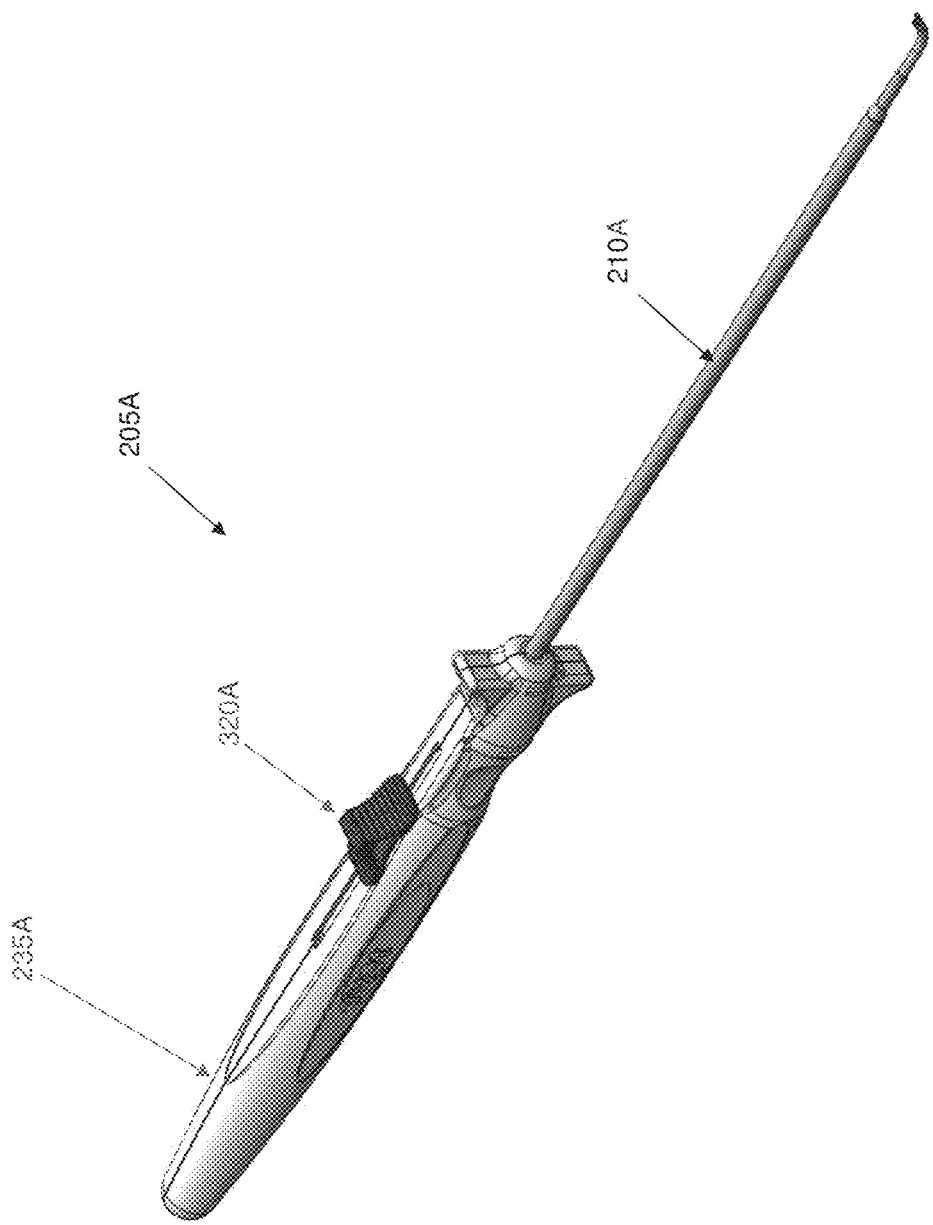
FIGS. 92-95 are schematic views showing another suture passer formed in accordance with the present invention, wherein the suture passer has its hooking rod disposed within the interior of its hollow tube.
Figure 93:
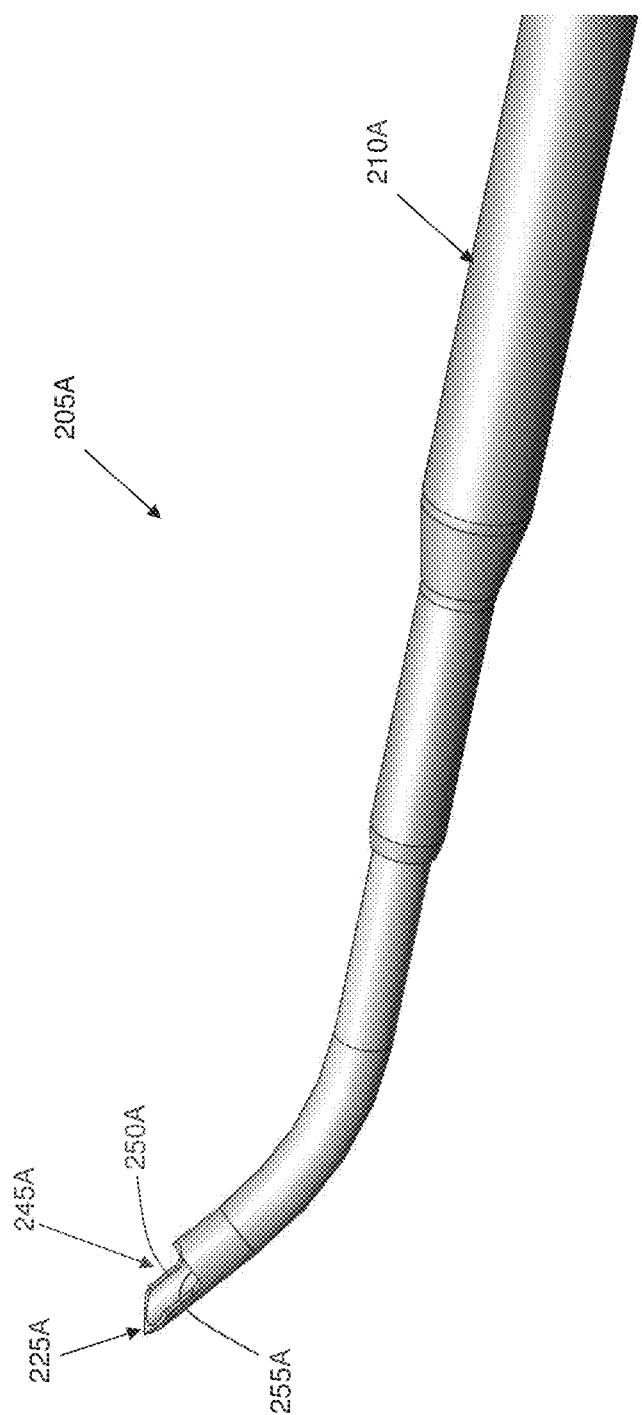
Figure 94:
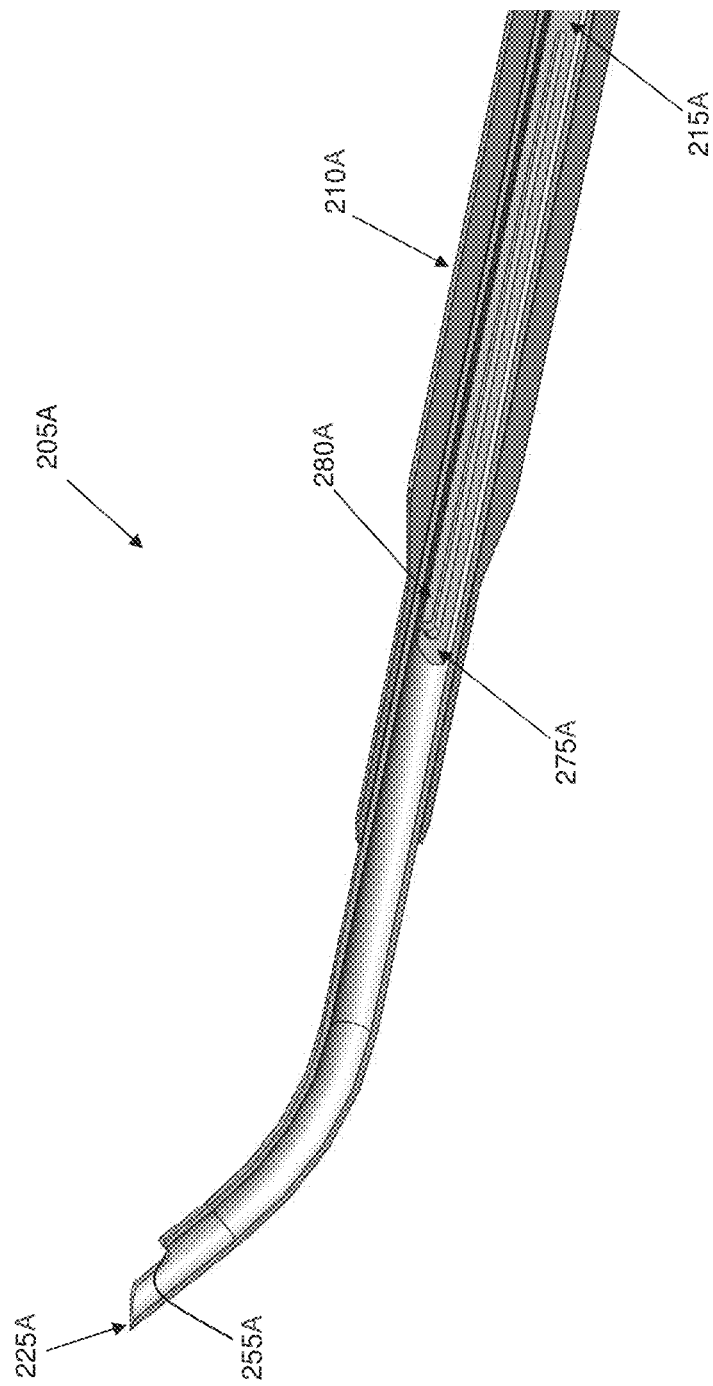

FIGS. 87-88 show first arm 275 and second arm 280 in a partially-extended position (i.e., in a position where suture can be adequately retrieved), while FIGS. 89-90 show first arm 275 and second arm 280 in a fully-extended position (i.e., in a position where suture can be fully advanced when being passed through tissue). FIG. 91 shows clamping rod 215 prior to assembly into suture passer 205.

Additional Aspects of the Invention

Significantly, by alternating the aforementioned antegrade suture passing procedure with the aforementioned retrograde suture passing procedure, with the needle "plunges" being laterally spaced from one another in the tissue, a mattress stitch may be placed in the tissue.

If desired, the novel suture passer 205 may also be used to pass suture S around a side edge of the tissue, rather than passing the suture S through the tissue. By way of example but not limitation, if the hollow tube 210 is passed around the side edge of the tissue (rather than through it), the suture passer could then be used to retrieve the suture on the far side of the tissue and draw it back around the side edge of the tissue so that the suture is brought to the near side of the tissue.

As described above, the novel suture passer 205 has the ability to both pass (advance) and retrieve (draw) the suture S through and/or around the tissue in a continuous series of steps. This allows the surgeon to complete the desired suture passing without having to remove the suture passer 205 from the portal through which the suture passer 205 is being used. Significantly, this passing/retrieving process can be accomplished with a single instrument, rather than requiring one instrument for passing and a separate instrument for retrieving. This offers significant advantages in convenience and in reducing surgery time.

Additional Suture Passer Construction

In the preceding disclosure, there are shown various novel suture passers (e.g., novel suture passer 5, novel suture passer 105, novel suture passer 205, etc.) which can be used to pass suture from one side of tissue to another side of tissue.

By way of example but not limitation, the novel suture passers can be used to pass suture from the near side of tissue to the far side of tissue (see, for example, FIGS. 12-18, where novel suture passer 5 is used to pass suture from the near side of tissue T to the far side of tissue T, in an "antegrade" manner). It will be appreciated that the suture extends alongside the exterior of the suture passer during such antegrade passing of the suture through the tissue.

By way of further example but not limitation, the novel suture passers can be used to draw suture from the far side of tissue to the near side of tissue (see, for example, FIGS. 19-25, where novel suture passer 5 is used to draw suture S from the far side of tissue T to the near side of tissue T, in a "retrograde" manner).

In some circumstances, it may be desirable to use the novel suture passers to pass suture from the near side of tissue to the far side of tissue at a first location, deposit a loop of suture on the far side of the tissue at that first location, withdraw the suture passer back through the tissue at that first location, move the suture passer laterally to a second location, advance the suture passer from the near side of the tissue to the far side of the tissue at that second location, pick up the loop of suture left on the far side of the tissue with the suture passer, and then use the suture passer to draw that loop of suture from the far side of the tissue to the near side of the tissue at that second location. In this way, a "stitch" of suture can be set through the tissue, with the suture advancing through the tissue at the first location and returning from the tissue at the second location.

However, it has been found that, in some circumstances, the tissue can form a tight fit about the suture passer. As a result, inasmuch as the suture extends alongside the exterior of the suture passer during an antegrade pass (see above), when the suture passer has dropped off the loop of suture on the far side of the tissue and the suture passer is thereafter withdrawn back through the tissue, the suture passer may unintentionally pull the suture back through the tissue with the withdrawing suture passer, which can result in, at best, a smaller loop of suture being left on the far side of the tissue (thereby making later retrieval of suture S with the suture passer more difficult) or, at worst, pulling the loop of suture completely back through the tissue with the returning suture passer (thereby making later retrieval of the suture S with the suture passer impossible).

To counteract this effect, the first and second arms of the clamping rod may be projected further out of the distal end of the hollow tube of the suture passer, so that a larger loop of suture is deposited on the far side of the tissue. Then, even if some of the suture should be pulled back through the tissue with the returning suture passer, it is likely that an adequate loop of suture will still remain on the far side of the tissue.

However, in some circumstances, there may be inadequate space on the far side of the tissue to accommodate longer first and second arms (and hence a longer projection of the first and second arms beyond the distal end of the hollow tube). By way of example but not limitation, there may be inadequate space on the far side of the tissue where the tissue is located in close proximity to an underlying structure (e.g., bone, delicate vascular and/or neurological tissue, etc.).

With this in mind, and looking now at FIGS. 92-112, there is now provided a further novel suture passer 205A which is generally similar to the novel suture passer 205 discussed above, except that hollow tube 210A and clamping rod 215A are sized so that clamping rod 215A can draw suture S within the interior of hollow tube 210A, without causing clamping surface 285A of clamping rod 215A to trap suture S against the circumferentially-extending edge 255A of hollow tube 210A (as is the case with suture passer 205 described above and shown in FIGS. 68-91). Thus, in this form of the invention, "clamping" surface 285A functions more like a "hooking" surface than a "clamping" surface, and clamping rod 215A functions more like a "hooking" rod than a "clamping" rod. For the purposes of the following discussion, surface 285A will be referred to herein as a hooking surface, and rod 215A will be referred to herein as a hooking rod. The suture that is drawn within the interior of hollow tube 210A is payed back out again when hooking rod 215A moves distally within hollow tube 210A and extends out the distal end of hollow tube 210A. In one preferred form of the invention, the suture that is drawn into the interior of hollow tube 210A is pushed back out of hollow tube 210A by (i) pushing by hooking surface 285A of first arm 275A when hooking rod 215A moves distally within hollow tube 210A and extends out the distal end of hollow tube 210A (inasmuch as the suture S releasably adheres to hooking surface 285A by a creasing or crimping action during suture capture), as hereinafter discussed below, and/or (ii) pushing by the distal end of second arm 280A when hooking rod 215A moves distally within hollow tube 210A and extends out the distal end of hollow tube 210A, as hereinafter discussed below.

As a result of this construction, suture length can effectively be "stored" within the interior of hollow tube 210A during antegrade passage of suture passer 205A through tissue T, whereby to deploy an enlarged loop of suture S on the far side of tissue T when hooking rod 215A is advanced out the distal end of hollow tube 210A. Then, even if some of the suture loop should be pulled back through the tissue with the returning suture passer, it is likely that an adequate loop of suture will still remain on the far side of the tissue, thus significantly improving the ease of subsequent suture retrieval on the far side of the tissue. This is especially true if, for example, the location at which the suture passer 205A must retrieve the suture S is located a substantial distance away from the location at which suture S was passed through the tissue. For example, if there is a gap between opposing sides of a cut tissue which is being sutured closed, when the suture passer 205A deploys an enlarged loop of suture S on the far side of tissue T, it will be easier to thereafter retrieve the loop of suture S when suture passer 205A pierces the opposite side of the cut to retrieve the suture S. It should be appreciated that the greater the distance suture S is drawn into hollow tube 210A, the larger the size of the suture loop that will be payed out on the far side of the tissue. For example, if the suture S is drawn into hollow tube 210A a distance of 1 inch, then a suture loop comprising approximately 2 inches of suture S will be delivered out the end of hollow tube 210A.

Thus, with the suture passer 205A shown in FIGS. 92-112, a larger loop of suture S can be deployed on the far side of the tissue without requiring the first and second arms 275A, 285A of hooking rod 215A to extend further out of the distal end of hollow tube 210A.

FIGS. 92-95 show suture passer 205A with its hooking rod 215A disposed within the interior of hollow tube 210A.

Figure 96:
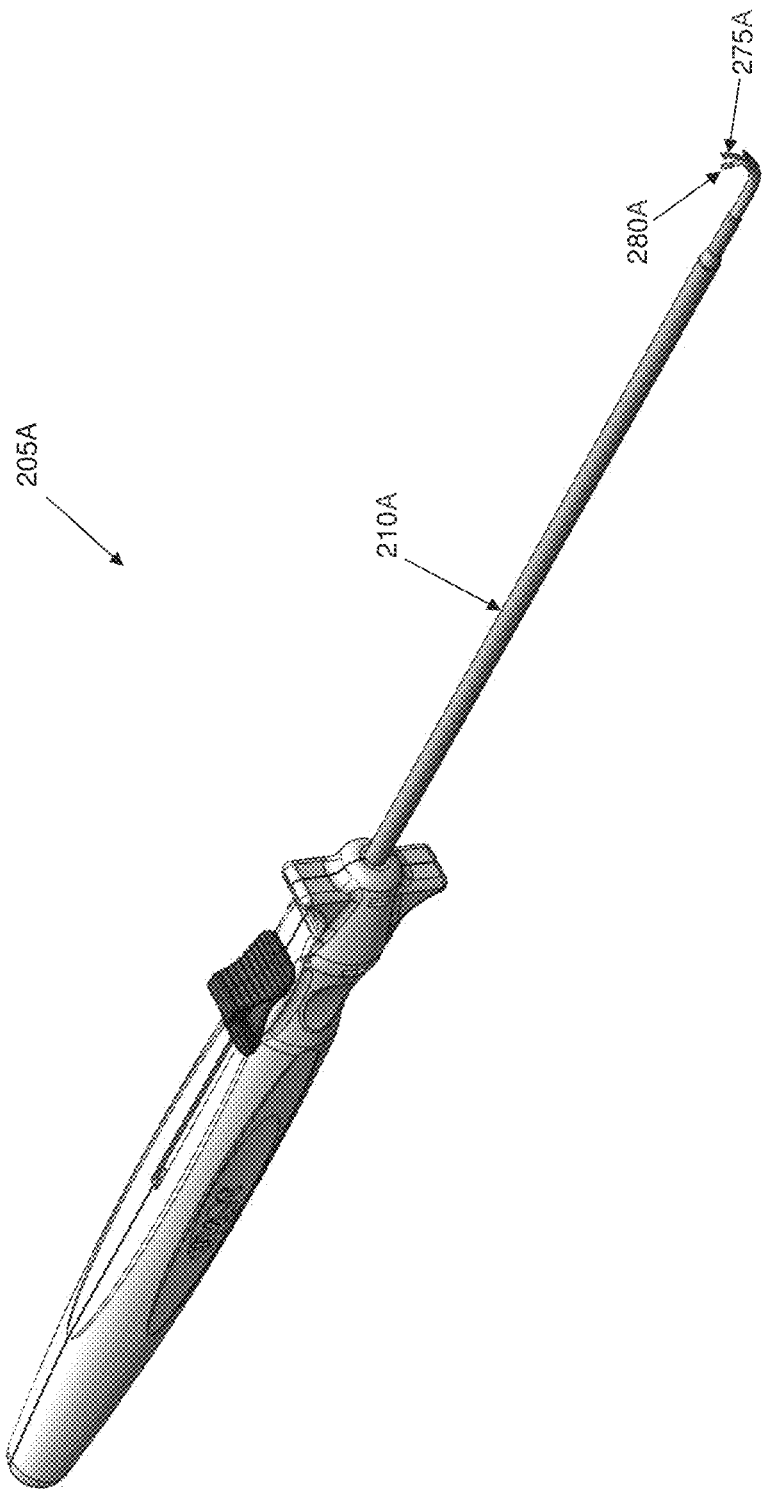
FIGS. 96-98 are schematic views showing the suture passer of FIGS. 92-95 with the distal end of its hooking rod projecting out the distal end of its hollow tube, wherein the first arm of the hooking rod is shown as extending at an angle to the local longitudinal axis of the distal end of the hollow tube when the first arm projects out of the distal end of the hollow tube.
Figure 97:
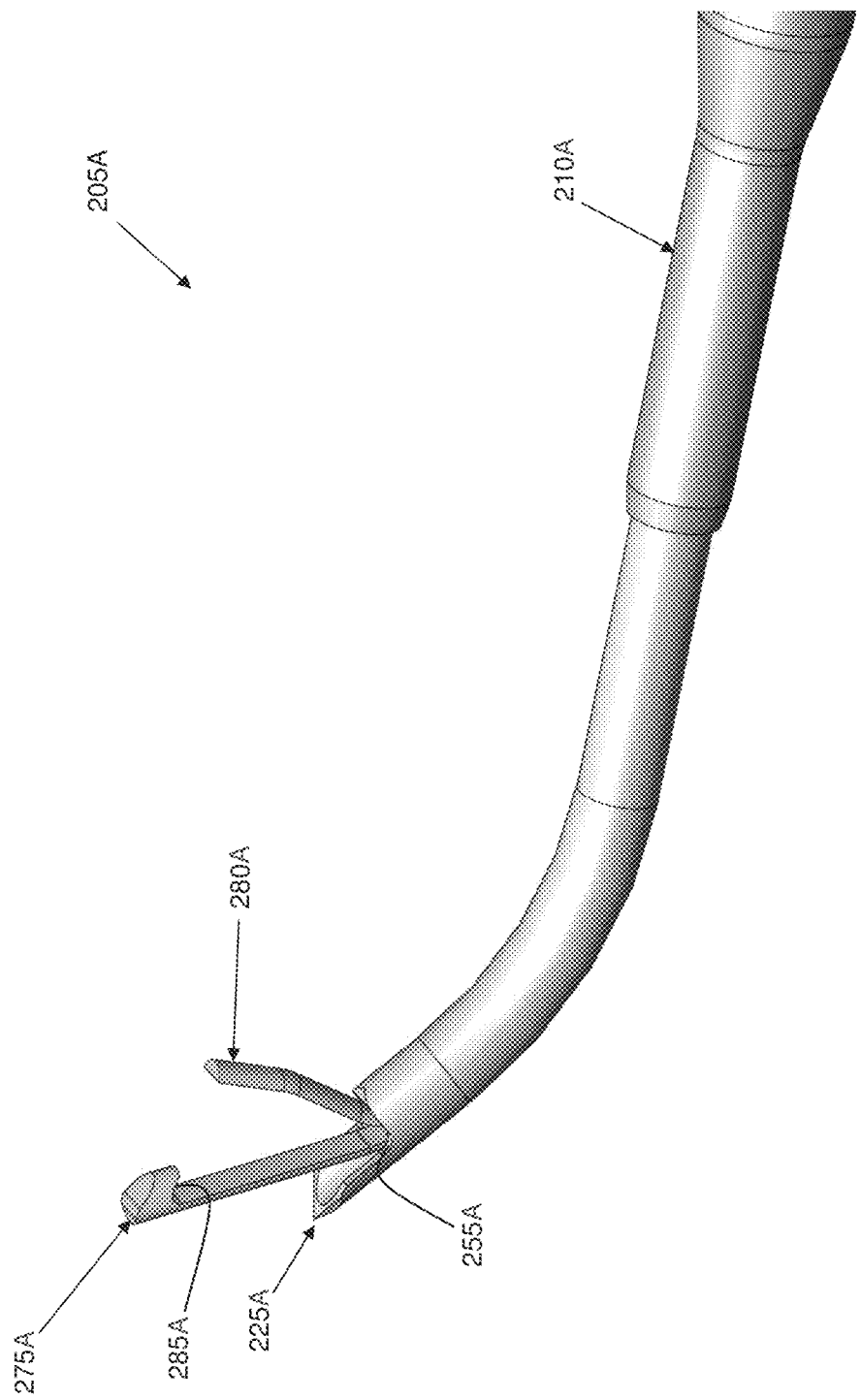
Figure 98:
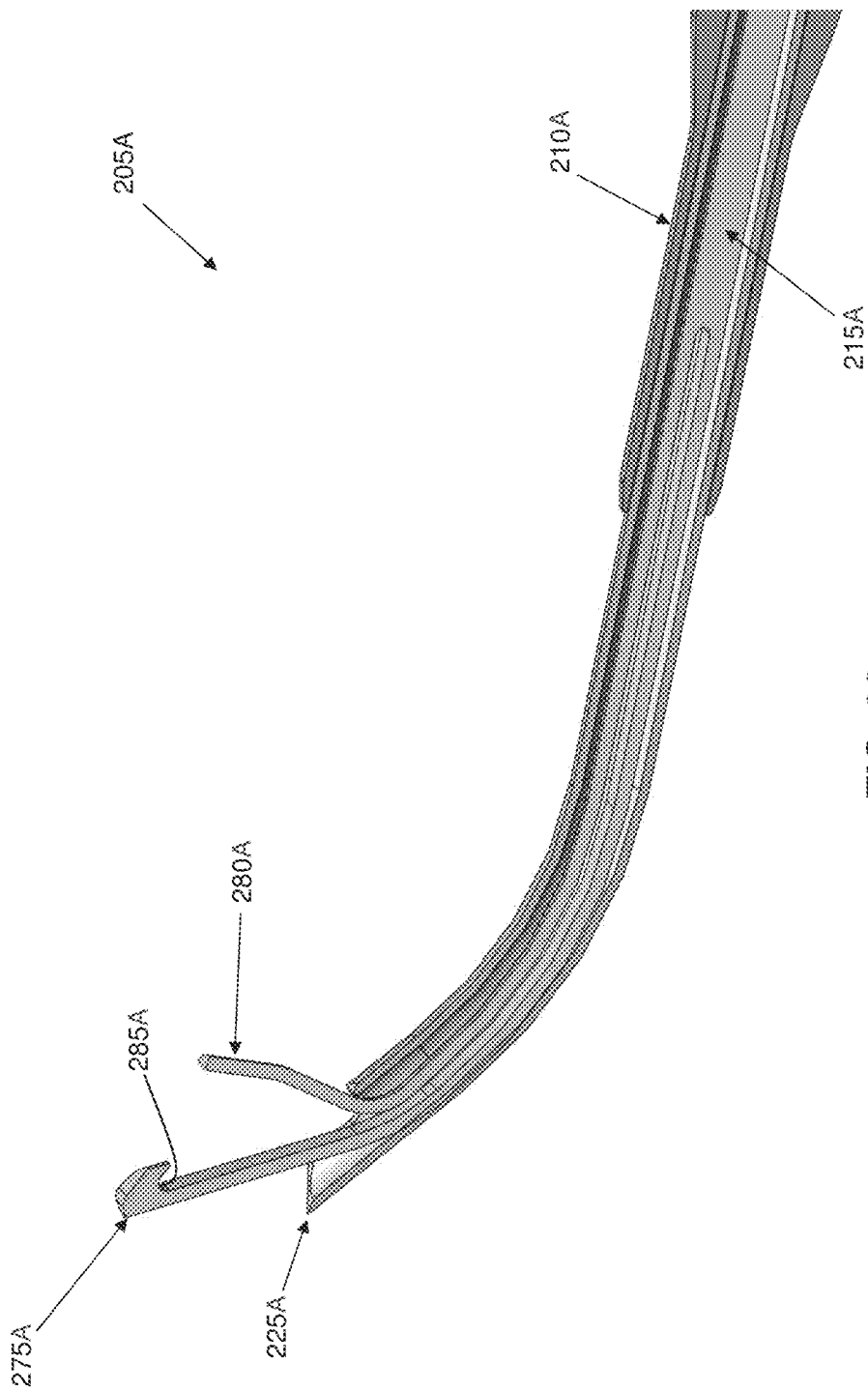

FIGS. 96-98 show suture passer 205A with the distal end of its hooking rod 215A projecting out the distal end of hollow tube 210A. Note that in FIGS. 96-98, first arm 275A of hooking rod 215A is shown as extending at an angle to the local longitudinal axis of the distal end of hollow tube 210A when first arm 275A projects out of the distal end of hollow tube 210A.

Figure 99:
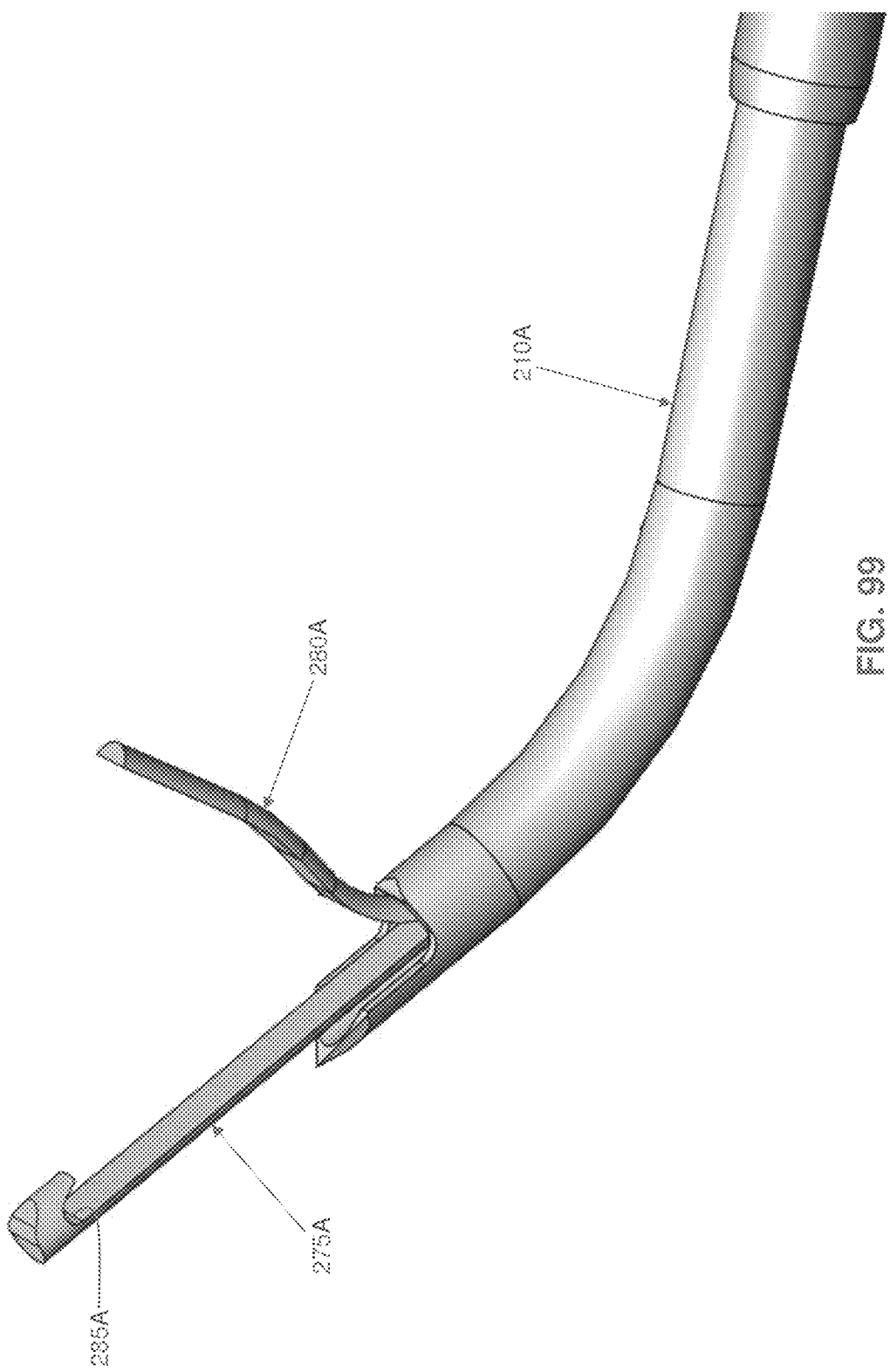
FIG. 99 is a schematic view showing the suture passer of FIGS. 92-95 and 96-98, except that the first arm of the hooking rod is configured to extend parallel to the local longitudinal axis of the distal end of the hollow tube when the first arm projects out of the distal end of the hollow tube.

More preferably, and looking now at FIG. 99, first arm 275A of hooking rod 215A is configured to extend parallel to the local longitudinal axis of the distal end of hollow tube 210A when first arm 275A projects out of the distal end of hollow tube 210A.

FIGS. 100-109 show suture passer 205A capturing a suture S by means of the interaction of first arm 275A and second arm 280A of hooking rod 215A, and drawing a portion of that suture S within the interior of hollow tube 210A by means of hooking surface 285A of first arm 275A of hooking rod 215A.

Figure 110:
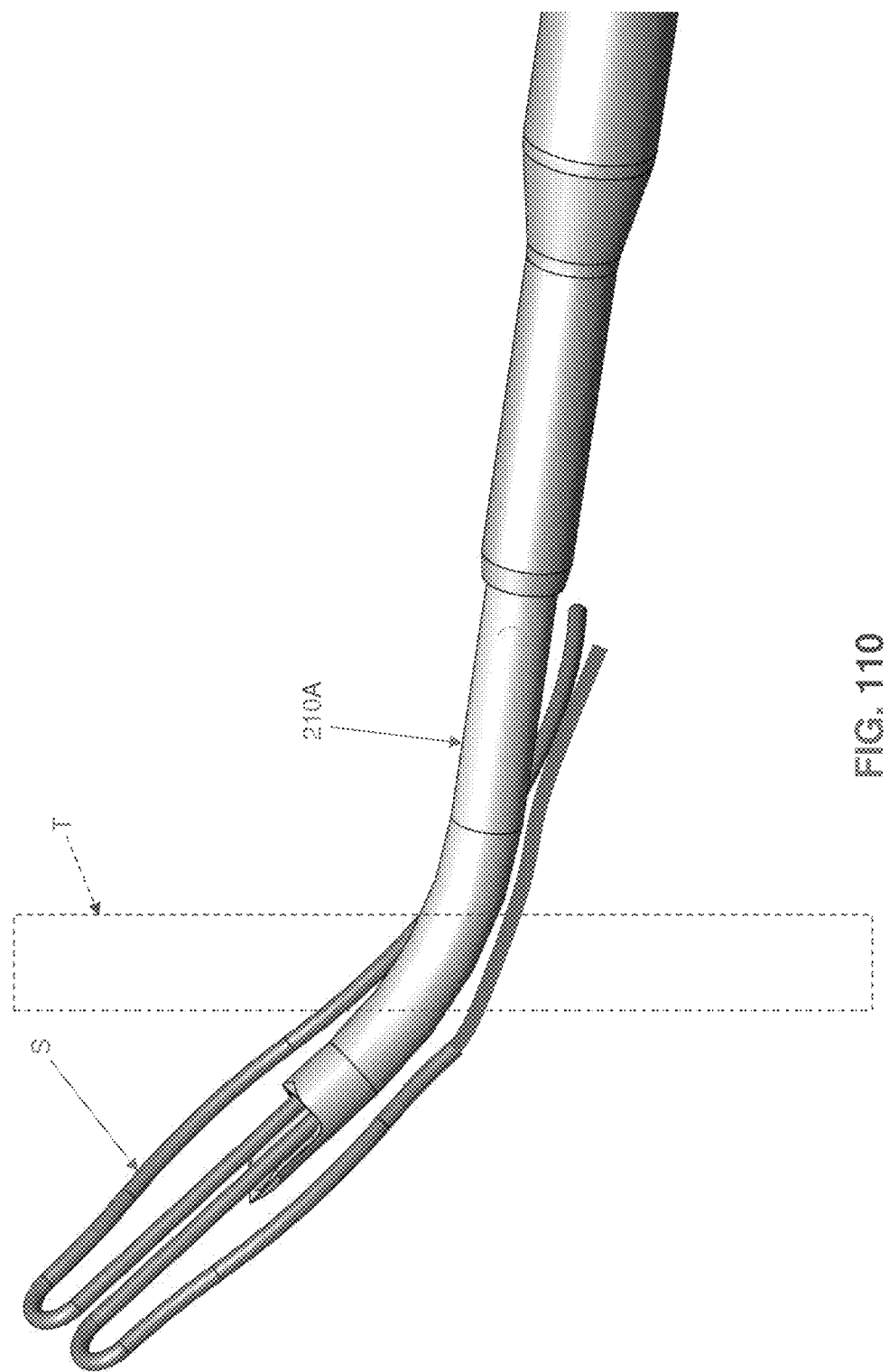
FIGS. 110-112 are schematic views showing the suture passer of FIGS. 92-109 releasing a suture which had been previously captured by the suture passer and which had a portion of that suture "stored" within the interior of hollow tube 210A, e.g., by using the distal end of the second arm of the hooking rod to push the "stored" suture back out of the hollow tube.
Figure 111:
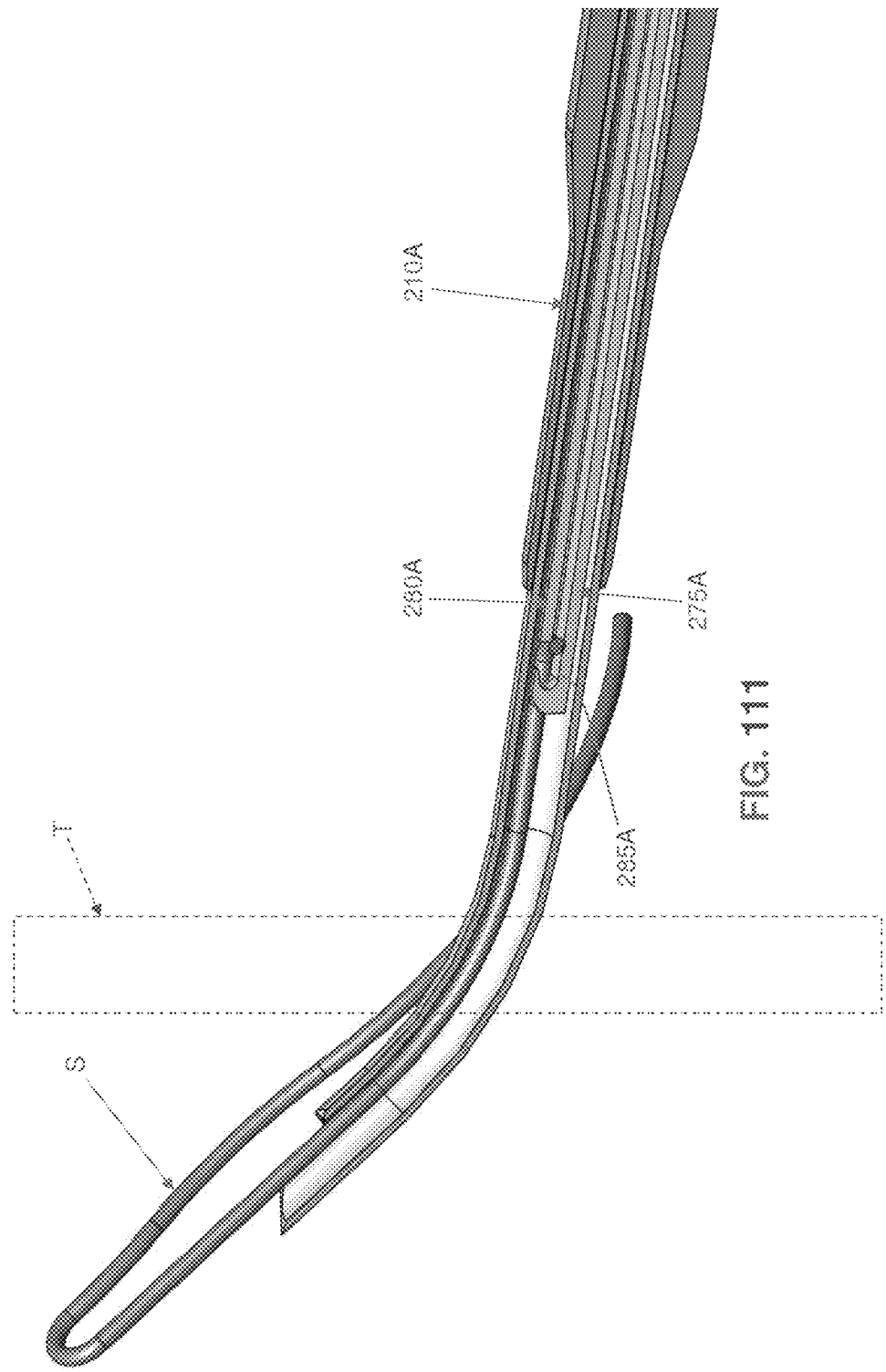
Figure 112:
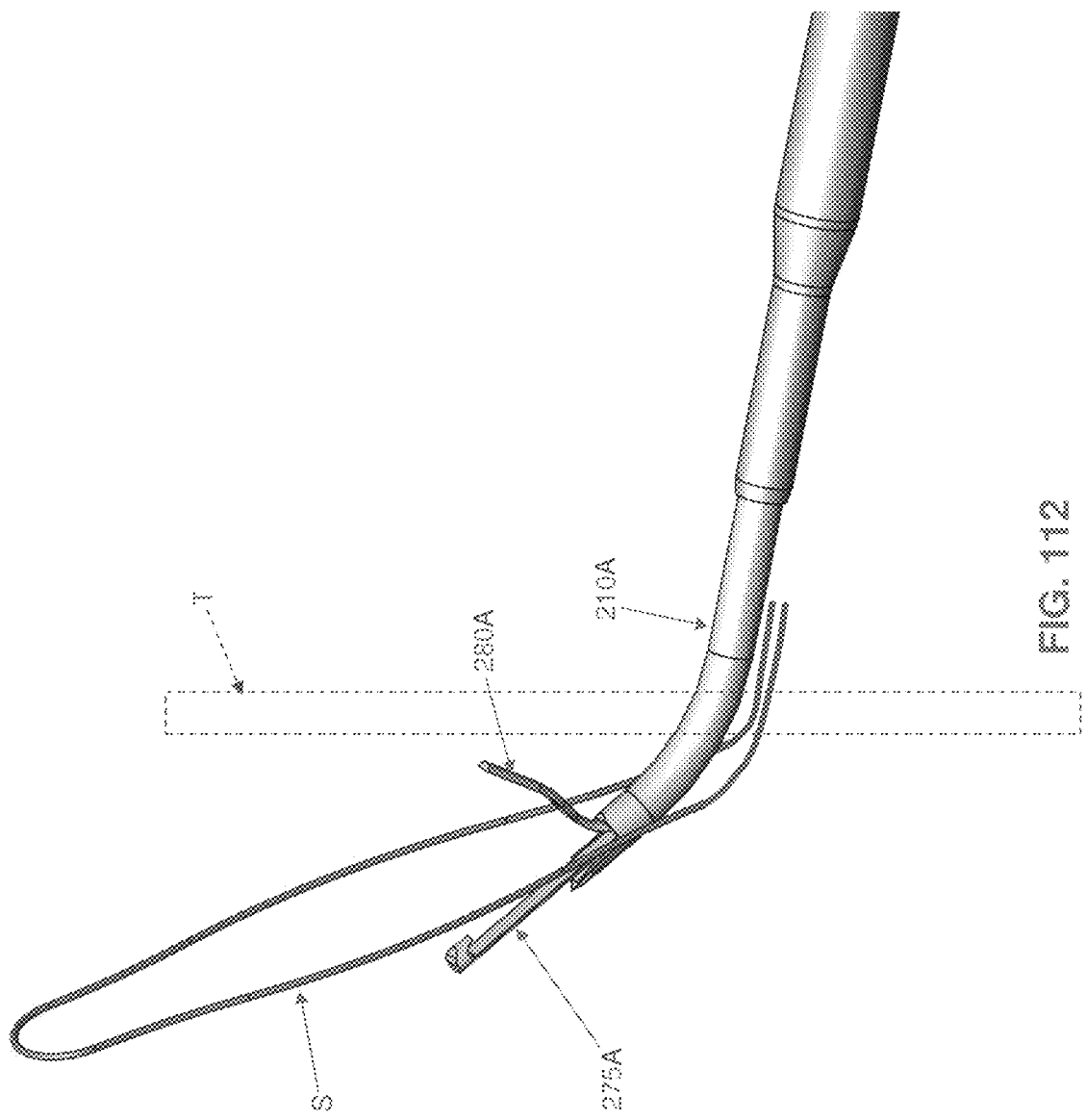

FIGS. 110-112 show suture passer 205A releasing a suture which had been previously captured by suture passer 205A and which had a portion of that suture "stored" within the interior of hollow tube 210A, e.g., by using the distal end of second arm 280A of hooking rod 215A to push the "stored" suture back out of hollow tube 210A.

As noted above, with this form of the invention, hooking surface 285A of first arm 275A functions like a hooking surface (i.e., to draw suture S into the interior of hollow tube 210A) rather than as a clamping surface to clamp suture S against circumferentially-extending edge 255A of hollow tube 210A. Hooking surface 285A of first arm 275A may also help push suture S distally as hooking rod 215A advances distally within and out of hollow tube 210A, inasmuch as suture S releasably adheres to hooking surface 285A by a creasing or crimping action during suture capture, as will hereinafter be discussed. It should be appreciated that a sufficient gap is formed between the outer surface of the distal end of first arm 275A and the inner surface of hollow tube 210A such that suture S can slide without binding as hooking rod 215A is withdrawn into, and advanced out of, hollow tube 210A, such that suture S can be drawn into hollow tube 210A and be pushed out of hollow tube 210A. It should also be appreciated that, inasmuch as there can be appreciable tension on suture S as suture S is passed and retrieved through tissue, in order for suture S to be held securely onto hooking surface 285A of hooking rod 215A once suture S is drawn into hollow tube 210A, the gap between the outer surface of the distal end of first arm 275A and the inner surface of hollow tube 210A cannot be so great as to allow suture S to prematurely slip off the hooking surface 285A of hooking rod 215A (i.e., to flip up and over the edge of the hook, then pass distally between the distal end of first arm 275A and hollow tube 210A). See FIG. 108. Thus, there is an optimally sized gap between the outer surface of the distal end of first arm 275A and the inner surface of hollow tube 210A which keeps suture S secure on hooking surface 285A of first arm 275A yet allows suture S to slide when hooking rod 215A is moved within hollow tube 210A.

By way of example but not limitation, where suture S is a size #2 orthopedic braided suture with an external diameter of 0.021 inches, the distal end of first arm 275A may have an outer diameter of approximately 0.045 inches and hollow tube 210A may have an inner diameter of 0.063 inches. As such, the inner diameter of hollow tube 210A is approximately 300% larger than the diameter of suture S. It has been discovered that best results are achieved where the inner diameter of outer tube 210A is preferably between approximately 200% to 600% larger than the diameter of suture S, and more preferably approximately 300% to 500% larger than the diameter of suture S. Also, as such, there is a 0.009 inch gap (between the outer surface of the distal end of first arm 275A and the inner surface of hollow tube 210A) for suture S to pass between the outer surface of the distal end of first arm 275A and the inner surface of hollow tube 210A.

A size #2 orthopedic braided suture has a diameter of approximately 0.021 inches; therefore, it is compressed to approximately 0.009 inches (i.e., the size of the gap between the outer surface of the distal end of first arm 275A and the inner surface of hollow tube 210A), or to approximately 43% of its original diameter (see FIG. 108) when the suture is drawn into hollow tube 210A by hooking rod 215A. It has been found that if the outer diameter of the distal end of first arm 275A is 0.048 inches (i.e., the suture compresses to 36% of its original diameter), suture S may bind to hollow tube 210A as hooking rod 215A moves within hollow tube 210A. Preferably, suture S is compressed to greater than approximately 36% of its original diameter when suture S is disposed between the outer surface of the distal end of first arm 275A and the inner diameter of hollow tube 210A.

It should be appreciated that the distance that hooking surface 285A is recessed (i.e., distance "L" in FIG. 95) within the distal end of first arm 275A also affects the holding force of suture S when suture S is held within hollow tube 210A. Increasing distance "L" increases the holding force applied to suture S, whereas decreasing distance "L" decreases the holding force applied to suture S. By way of example but not limitation, where the outer diameter of the distal end of first arm 275A is 0.045 inches and the inner diameter of hollow tube 210A is 0.063 inches and hooking surface 285A is recessed 0.027 inches, when suture S has been drawn into the interior of hollow rod 210A by hooking rod 215A and tension is thereafter applied to one limb of suture S in an approximately longitudinal direction, a #2 orthopedic suture will be held with approximately 5-9 lbs. of force before releasing from hooking rod 215A.

It should also be appreciated that the shape and size of the hooking surface 285A of first arm 275A can affect the ability of suture S to exit the recess of the hook of first arm 275A. For example, when first arm 275A is fully extended out of hollow tube 210A and second arm 280A is biased away from first arm 275A, a hooking surface 285A having a smaller radius R (FIG. 95) may tend to bind the suture and prevent it from exiting the recess of first arm 285A, and a hooking surface 285A of a larger radius R enables the suture to more freely exit the recess of first arm 285A. Conversely, a hooking surface 285A having a radius R of a large size may not sufficiently bind suture S. In a preferred embodiment, hooking surface 285A has a radius R of 0.011 inches, or a radius R approximately equal to one half the diameter of suture S when suture S is a #2 orthopedic suture. Hooking surface 285A of first arm 275A may function to help push suture S distally as hooking rod 215A advances distally within hollow tube 210A. More particularly, suture passer 205A may rely on a degree of binding between hooking surface 285A of hooking rod 215A and suture S in order to carry suture S distally. In this respect it will be appreciated that suture S may "crease" or "crimp" slightly around edges of hooking surface 285A of first arm 275A as suture S is drawn into hollow tube 210A due to tension on suture S. The "crease" or "crimp" of the suture will create a slight adhesion of the suture S to hooking surface 285A of first arm 275A, so that suture S will be carried distally with first arm 275A when hooking rod 215A moves distally within and out of hollow tube 210A.

It should also be appreciated that with this form of the invention, second arm 280A may also "push" suture S distally as hooking rod 215A advances distally within and out of hollow tube 210A.

As described above, suture S will preferably bind to hooking surface 285A of first arm 275A when suture S is drawn into hollow tube 210A. However, in some circumstances, upon distal movement of hooking rod 215A within hollow tube 210A (i.e., when suture S is payed back out of suture passer 205A) suture S may dislodge from hooking surface 285A of first arm 275A. In this event, the distal end of second arm 280A engages suture S and pushes it distally. In other words, if suture S dislodges from hooking surface 285A of first arm 275A, the distal end of second arm 280A then "pushes" suture S distally as hooking rod 215A advances distally within hollow tube 210A and extends out the distal end of hollow tube 210A (up until the point when second arm 280A biases laterally away from first arm 275A). The thickness TH of second arm 280A (FIG. 95) must be sufficiently large so as not to pierce suture S during such distal movement of hooking rod 215A. To this end, it has been found that thickness TH of second arm 280A should be minimally at least as large as 50% of the diameter of suture S, and more preferably approximately equal to the diameter of suture S.

Figure 95:
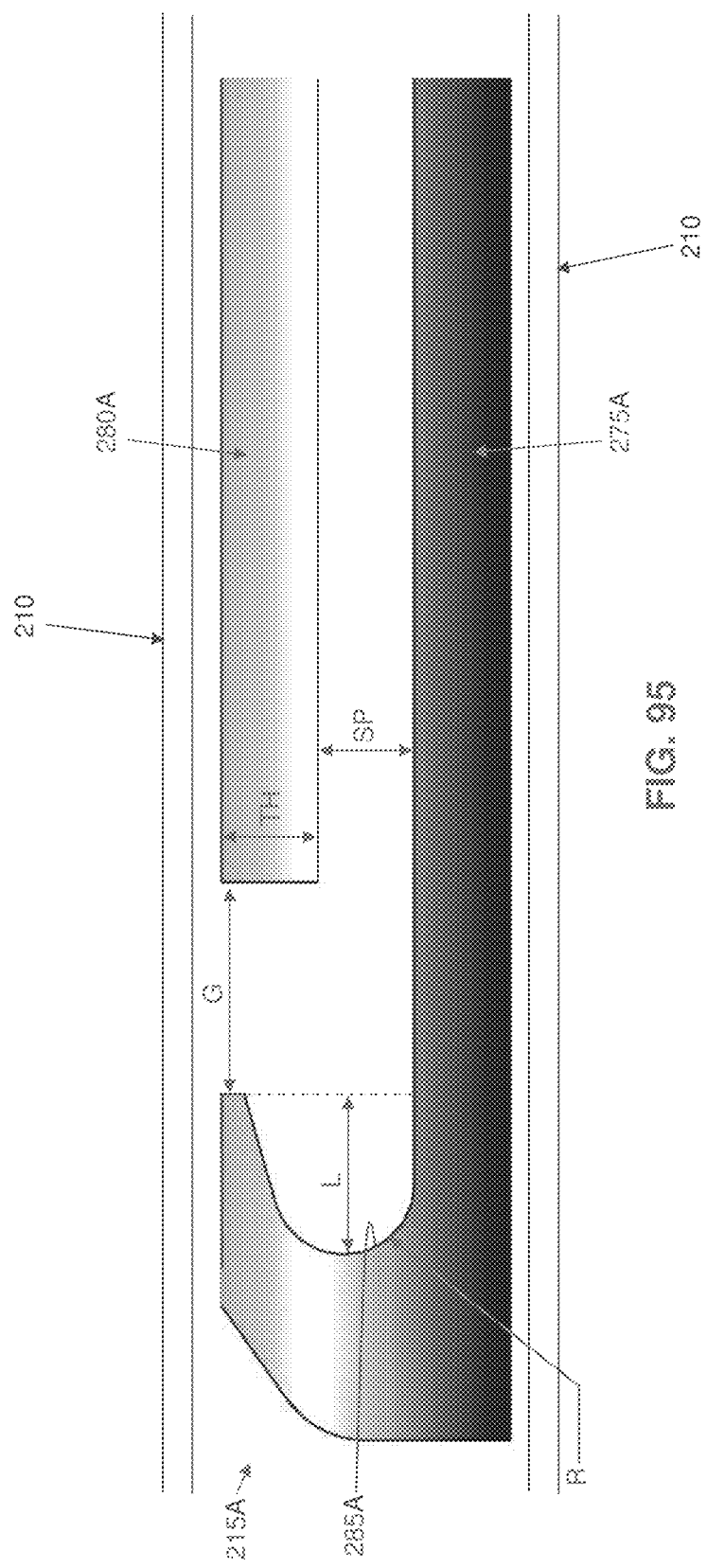
Figure 100:
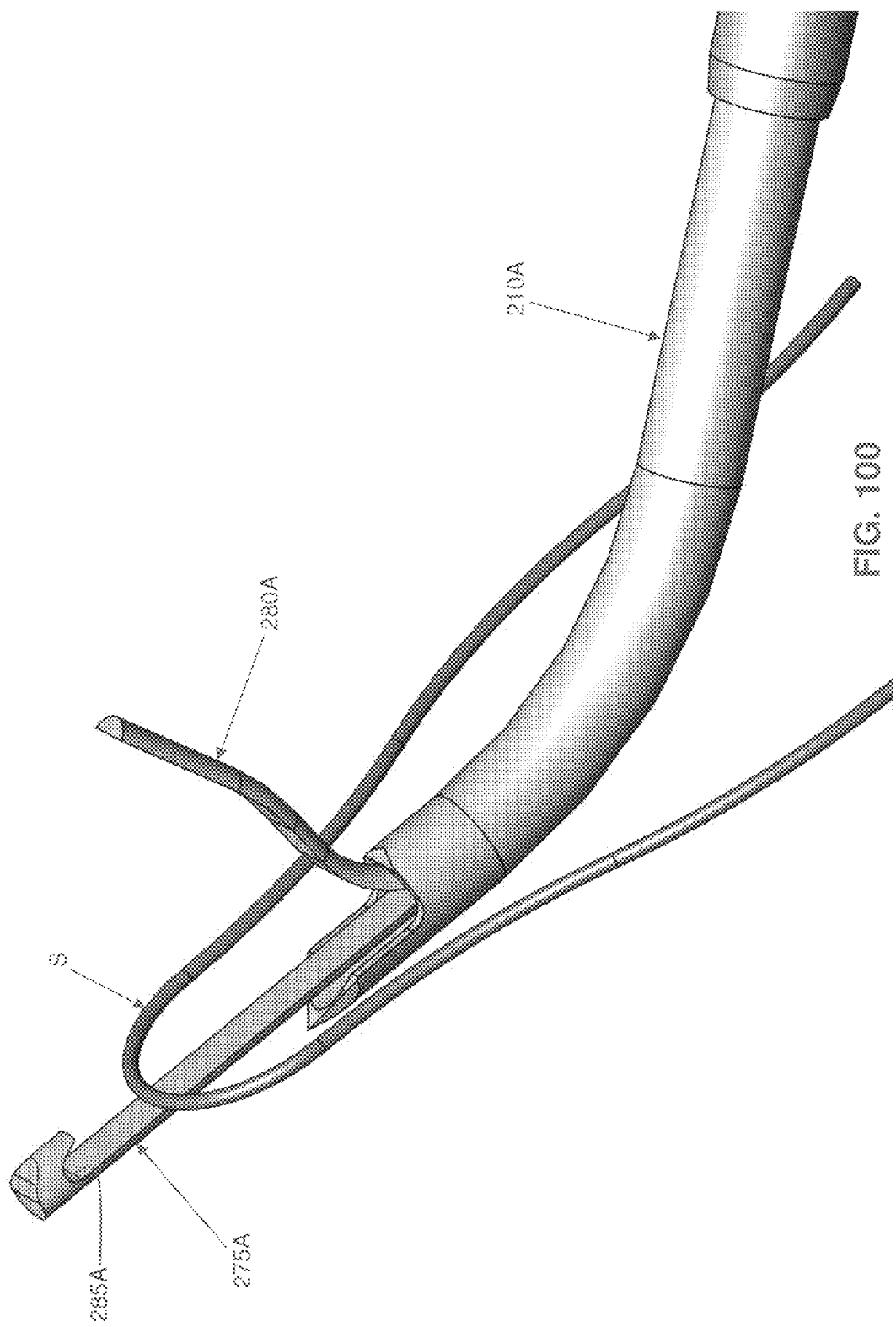
FIGS. 100-109 are schematic views showing the suture passer of FIGS. 92-99 capturing a suture by means of the interaction of the first arm and the second arm of the hooking rod, and drawing a portion of that suture within the interior of the hollow tube by means of the hooking surface of the first arm 275A of hooking rod 215A.
Figure 101:
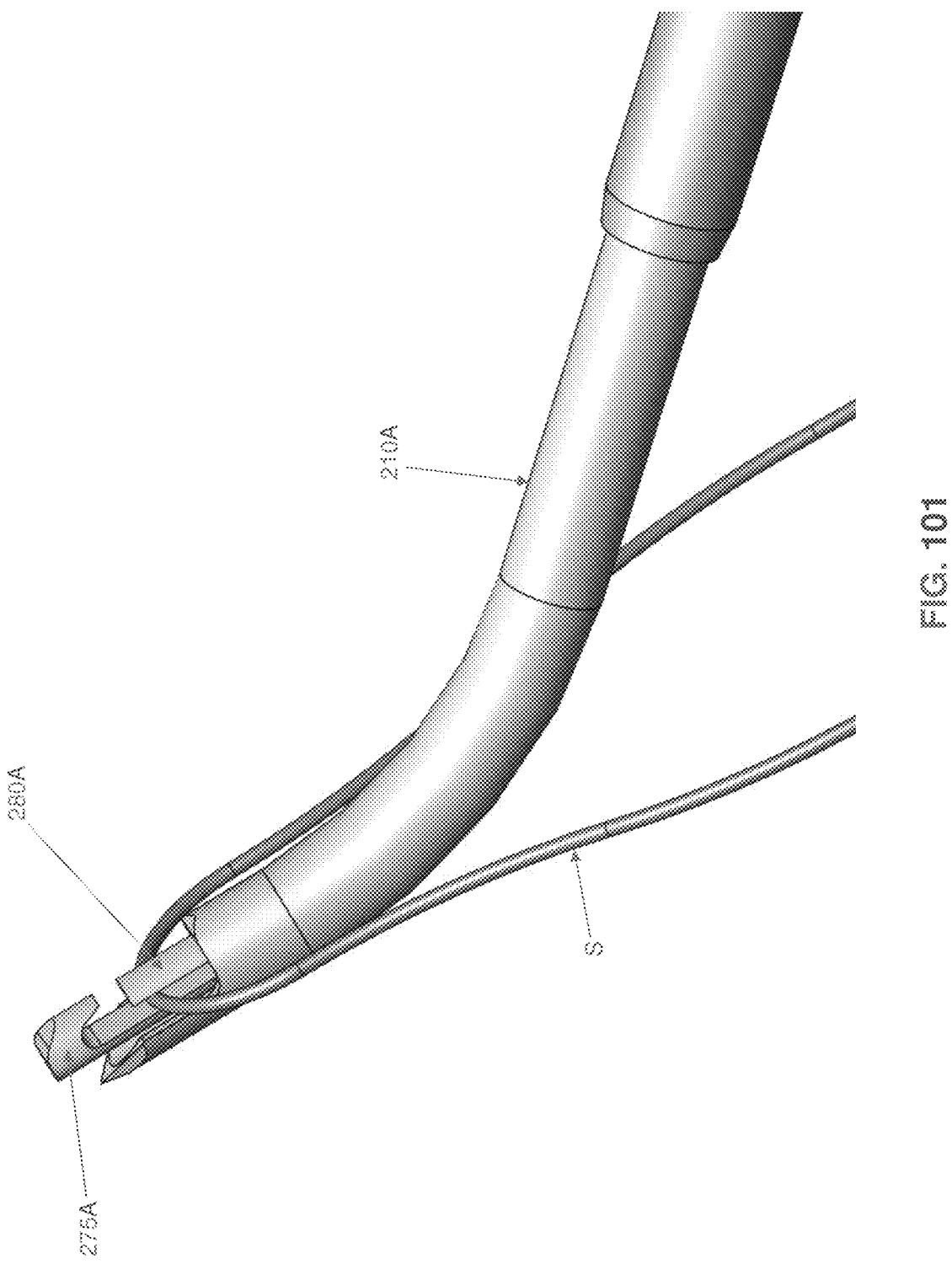
Figure 102:
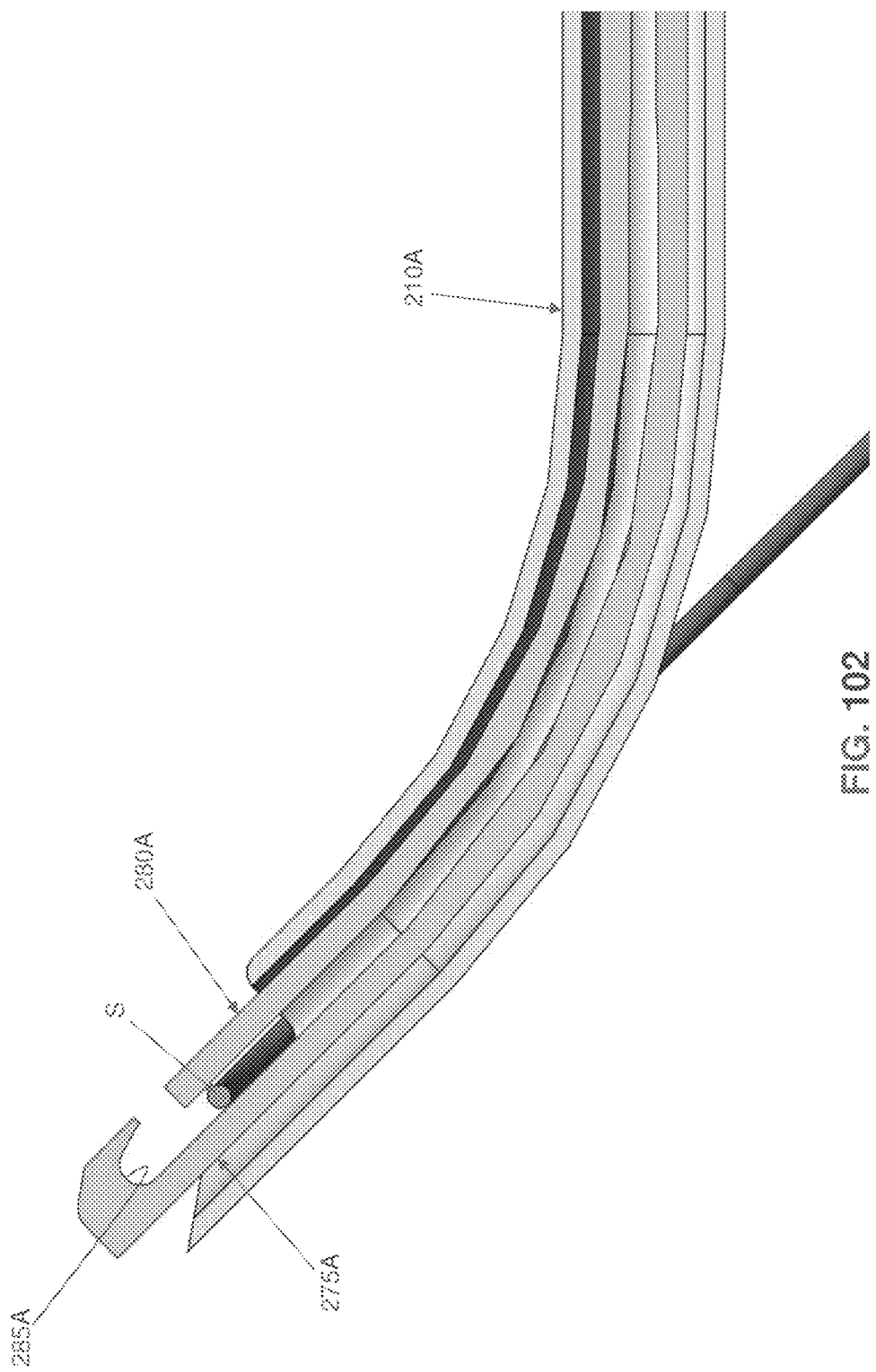
Figure 103:
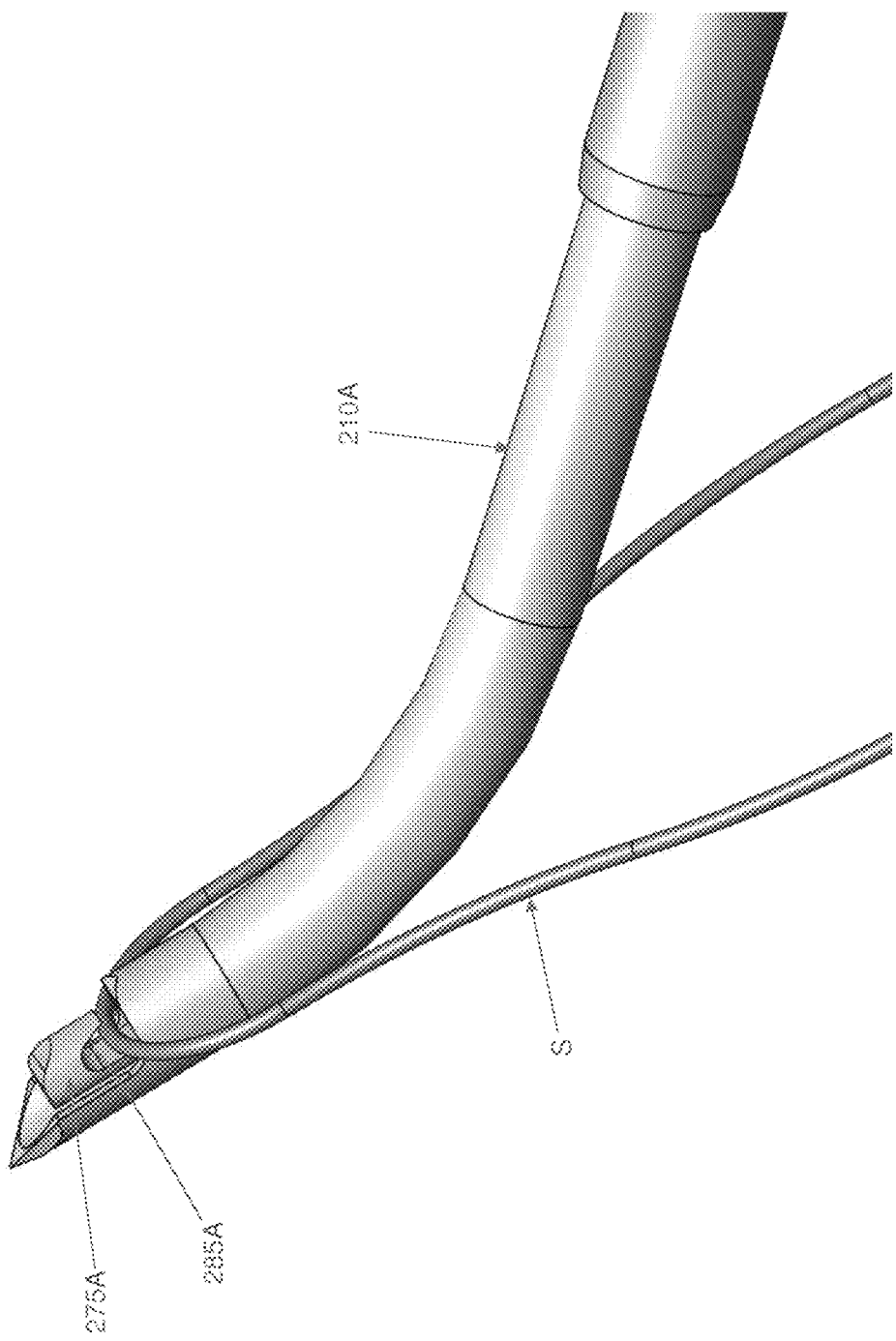
Figure 104:
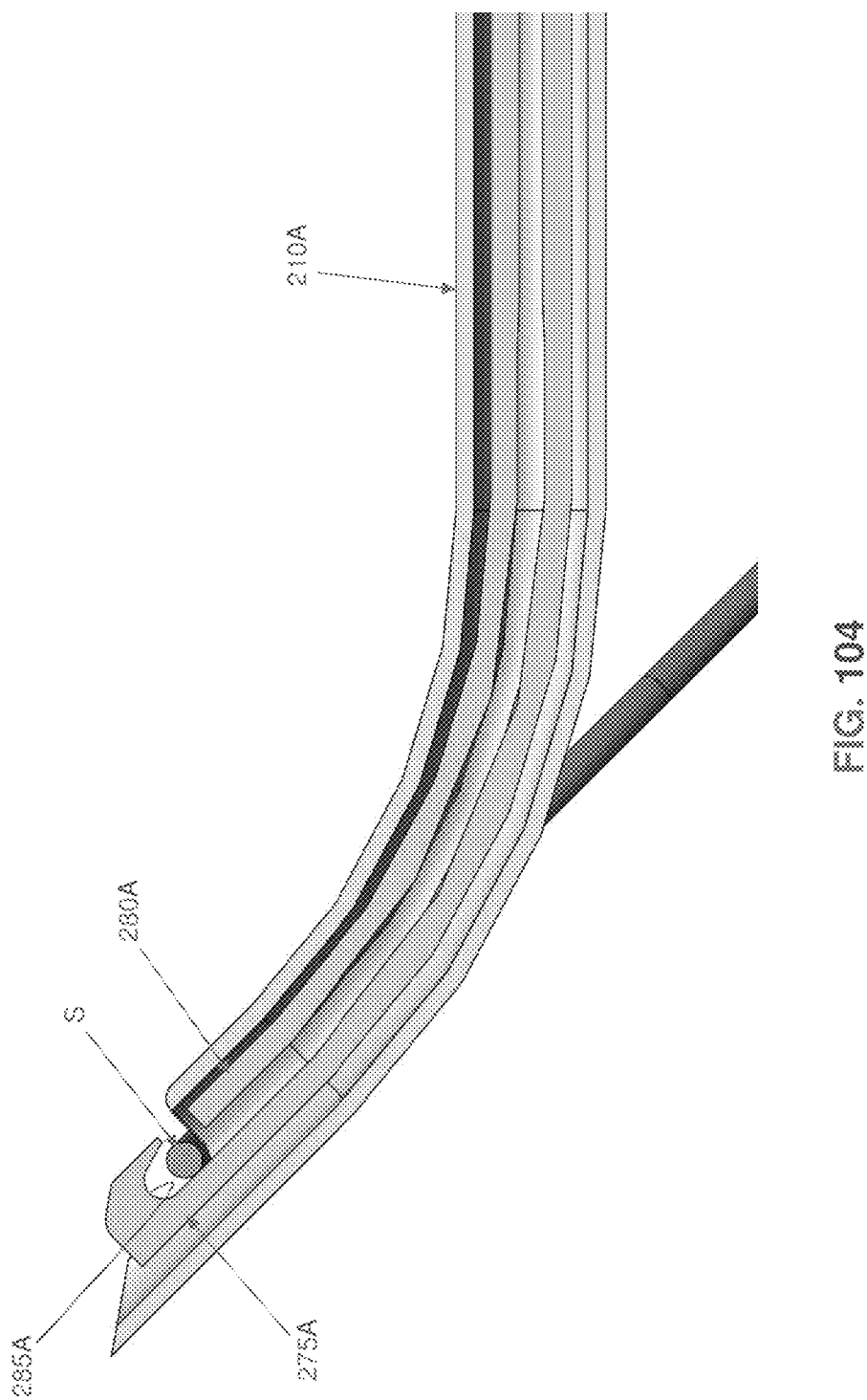
Figure 105:
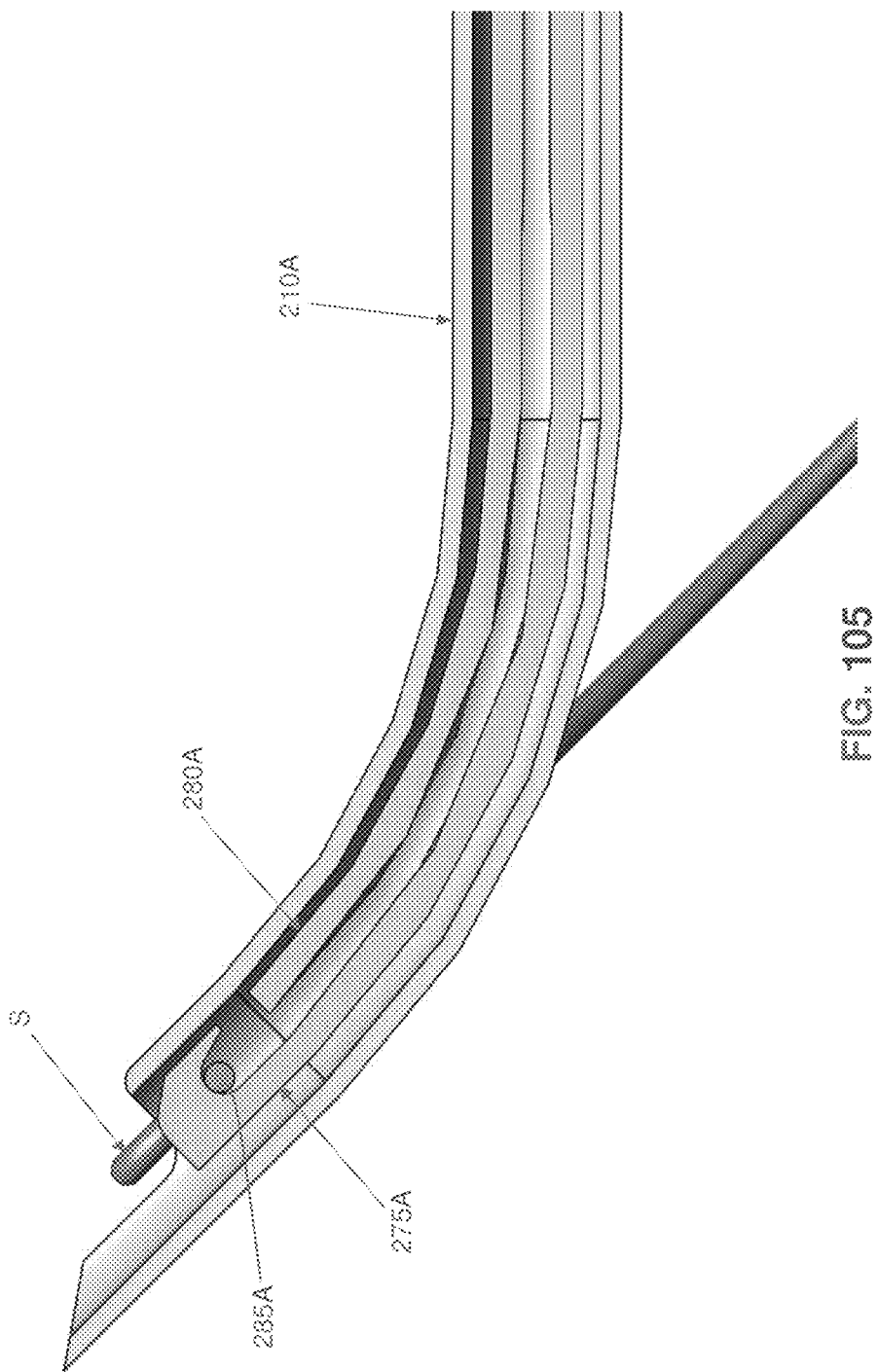
Figure 106:
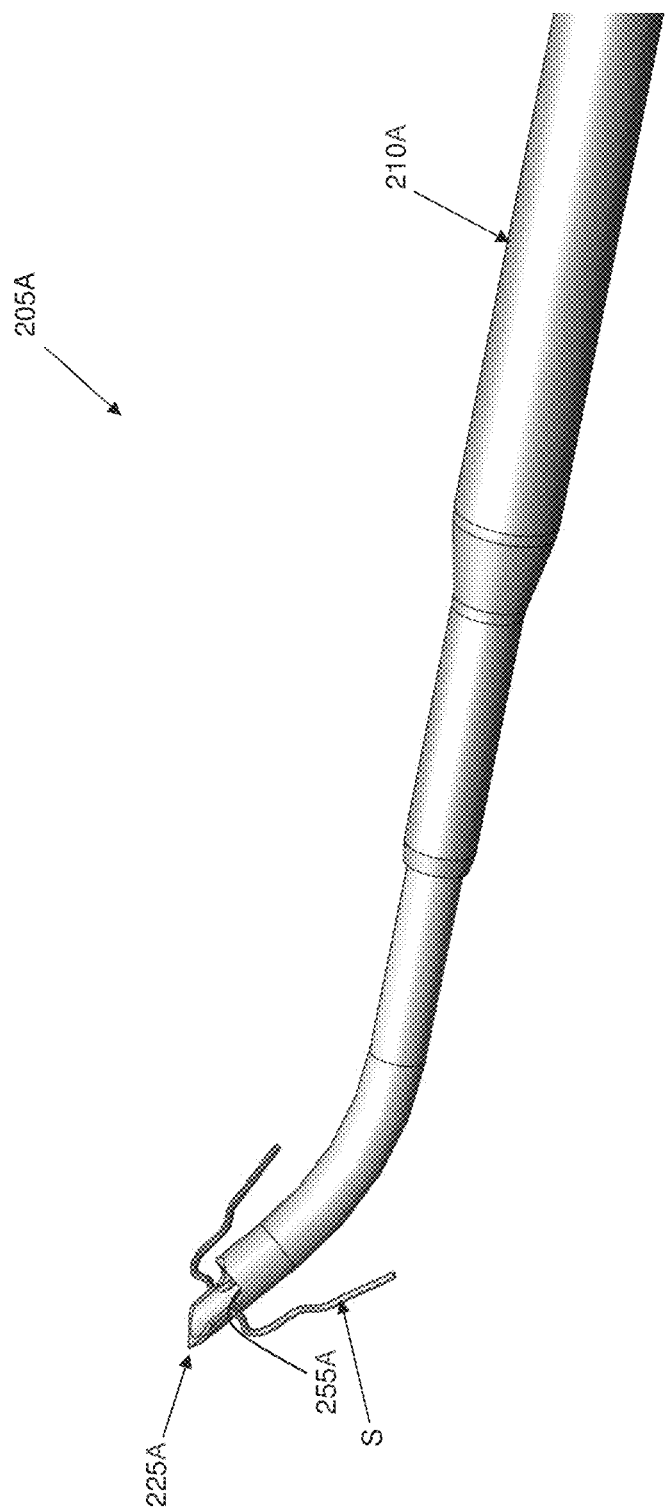
Figure 107:
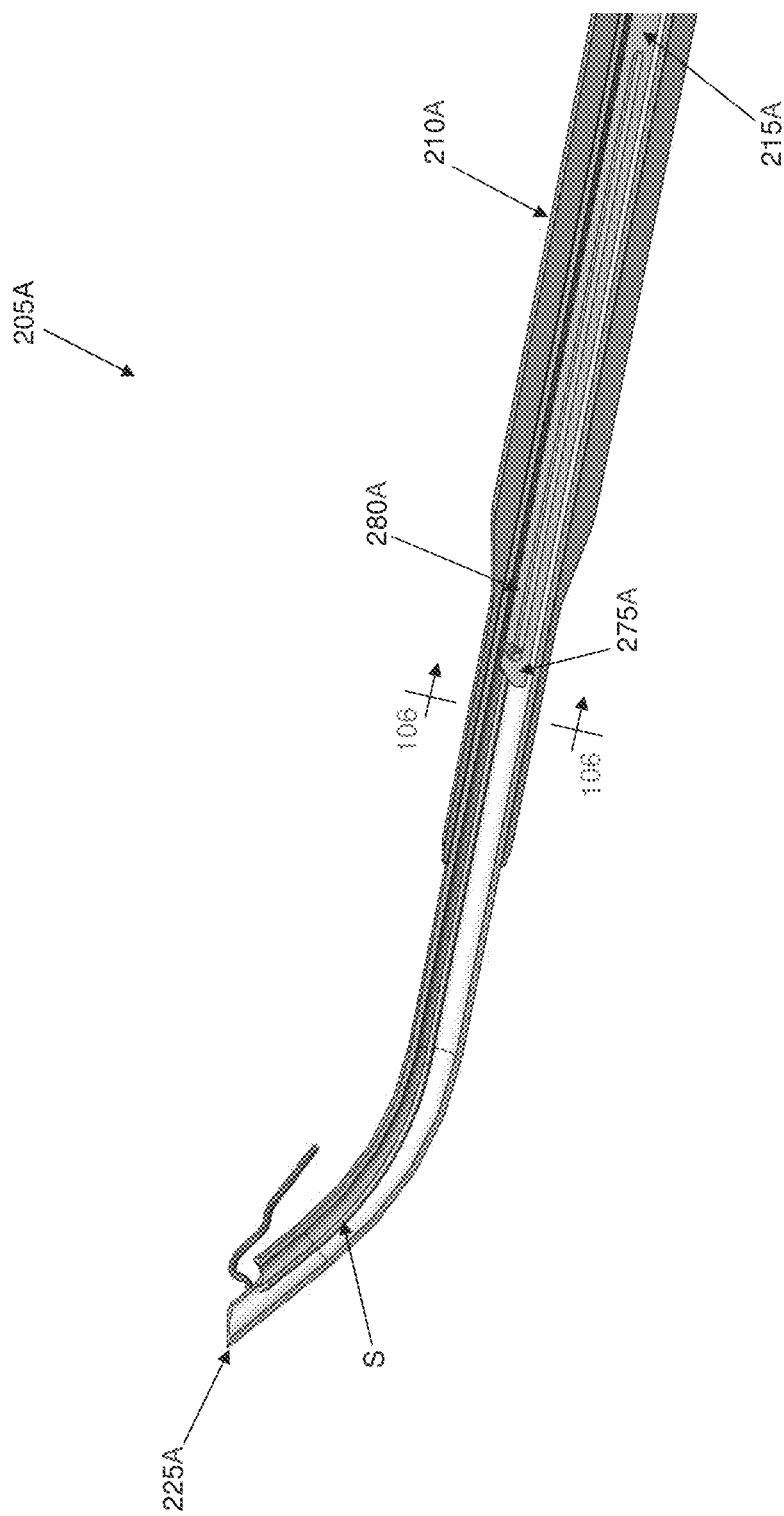

Second arm 280A may also function to help retrieve suture S, either at the initial pick-up of the suture S or after the suture has been deployed through tissue. By way of example but not limitation, once suture passer 205A has passed suture S through tissue, suture passer 205A can be used to thereafter retrieve suture S, either after suture passer 205A has been passed through tissue at another location or directly (e.g., via access from a different direction). Inasmuch as second arm 280A is biased away from first arm 275A when the distal end of hooking rod 215A extends out the distal end of hollow tube 210A, suture S can be positioned in the gap between first arm 275A and second arm 280A (FIG. 100). When hooking rod 215A is thereafter moved proximally, second arm 280A will close toward first arm 275A and capture suture S in the space SP between first arm 275A and second arm 280A (FIGS. 95, 101 and 102). Upon further proximal movement of hooking rod 215A, as suture S engages circumferentially-extending edge 255A of hollow tube 210A, suture S may be held for pick-up by hooking surface 285A of first arm 275A (FIGS. 103 and 104) as hooking surface 285A of first arm 275A passes by circumferentially-extending edge 255A of hollow tube 210A. Upon still further proximal movement of clamping rod 215, suture S is drawn into hollow tube 210A (FIGS. 105-107).

The gap G (FIG. 95) between the proximal tip of the hook of first arm 275A and the distal end of second arm 280A must be large enough that second arm 280A does not bind to the hook of first arm 275A as the distal end of hooking rod 215A passes through the curvature of hollow tube 210A. In this respect it should be appreciated that the distal end of second arm 280A will move towards the hook of first arm 275A as hooking rod 215A passes through a curvature (in the direction of second arm 280A) in hollow tube 210A. In other words, as hooking rod 215A passes through a curvature (in the direction of second arm 280A) in hollow tube 210A, the gap G between the hook tip of first arm 275A and the distal end of second arm 280A will be reduced, since both the proximal tip of the hook of first arm 275A and the distal end of second arm 280A are offset from the central axis of hooking rod 215A. Thus, the gap must be large enough to prevent binding between first arm 275A and second arm 280A as hooking rod 215A traverses a curve in hollow tube 210A. At the same time, the gap G between the hook tip of first arm 275A and the distal end of second arm 280 must also not be so great so as to insufficiently retain suture S as suture S is being pushed distally in hollow tube 210 (i.e., if the gap G is too large, the suture may shift relative to clamping rod 215 and compromise subsequent distal movement of the suture during suture release). Gap G must also not be so great so as to prevent capture of suture S between first arm 275A and second arm 280A. As described above, during retrieval of suture S, suture passer 205A may be manipulated so as to place suture S between first arm 275A and second arm 280A (FIG. 100). Once suture S is in position, hooking rod 215A is retracted proximally. As hooking rod 215A is drawn into hollow tube 210A, second arm 280A is forced to close down towards first arm 275A, trapping suture S between first arm 275A and second arm 280A (FIG. 101). If gap G is too large, second arm 280A may miss suture S (such as, for example, if suture S is located distal to the distal end of second arm 280A) and hence not capture suture S. Gap G is preferably approximately 0.040 inches in the longitudinal direction, or approximately 90% as large as the diameter of the hooking rod 215A. Gap G may be approximately 10% to 200% of the diameter of the hooking rod 215A depending on the curvature of the hollow tube 210A through which the hooking rod 215A must pass.

The space SP between first arm 275A and second arm 280A is sized to releasably capture suture S between first arm 275A and second arm 280A when hooking rod 215A is retracted into hollow tube 210A (FIGS. 105 and 106), but space SP is also sufficiently large so as to allow suture S to slide distally along first arm 275A and second arm 280A (FIGS. 103 and 104) when suture S engages circumferentially-extending edges 255A of hollow tube 210A. In other words, if suture S is not first captured directly in the hooking surface 285A of first arm 275A, when hooking rod 215A is moved proximally, at the point where second arm 280A closes, if suture S is trapped between first arm 275A and second arm 280A, circumferentially-extending edge 255A of hollow tube 210A stops suture S from moving proximally even as hooking rod 215A continues to move proximally. Once hooking surface 285A reaches circumferentially-extending edge 255A of hollow tube 210A, the space SP between first arm 275A and second arm 280A allows suture S to "slip" relative to hooking rod 215A while suture S remains against circumferentially-extending edge 255A of hollow tube 210A, until hooking surface 285A of first arm 275A engages suture S and draws suture S into hollow tube 210A (FIGS. 105-107). It has also been found that space SP is preferably at least as large as 50% of the diameter of suture S, and more preferably approximately 75-100% the diameter of suture S, so as to allow the aforementioned releasable gripping of suture S.

It should be noted that with the aforementioned suture passer 205, the distal end of hollow tube 210 preferably comprises cutaway 245, longitudinally-extending edges 250 and circumferentially-extending edge 255 as described above and shown in FIG. 69. Although with suture paser 205A suture S is no longer clamped between hooking surface 285A and cutaway 245A, it has been found that providing cutaway 245A is still beneficial in that it allows suture S to be drawn into hollow tube 210A without being dislodged from hooking surface 285A (i.e., when hooking rod 285A pulls suture S in the proximal direction). It has also been found that if the distal end of hollow tube 210A comprises a bevel cut (i.e., no cutaway 245A), suture S can be prone to dislodge from hooking surface 285A and/or the hook of first arm 275A can catch on the end of hollow tube 210A as the distal end of first arm 275A passes by the bevel cut of hollow tube 210A in a proximal direction.

Figure 109:
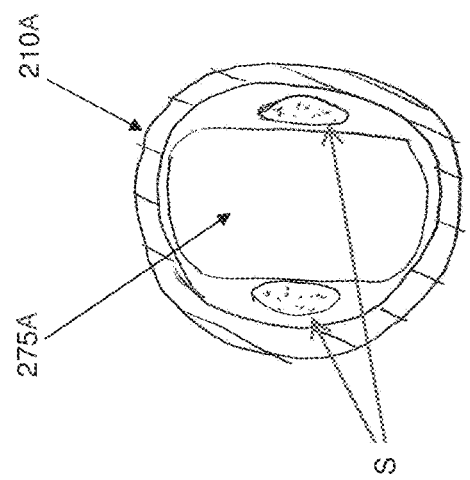
Figure 108:
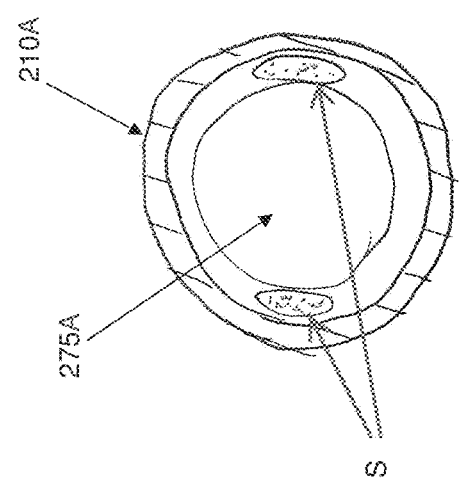

In a preferred embodiment, the distal end of hooking rod 215A has a circular cross-section (FIG. 108). In another embodiment, the distal end of first arm 275A has a smaller width as compared to its height (FIG. 109). In this latter embodiment, the gap between the top and bottom surfaces of the distal end of first arm 275A and the inner diameter of hollow tube 210A is reduced, so as to further stabilize the distal end of first arm 275A within hollow tube 210A, thus reducing any movement of first arm 285A within hollow tube 210A and hence increasing the holding force of suture S. And in this embodiment, the gap between the sides of the distal end of first arm 275A may be increased so as to enable suture S to slide more freely within hollow tube 210A. In other words, the embodiment shown in FIG. 109 may maintain or increase the holding force on suture S (as compared to the embodiment shown in FIG. 108), while improving the ability for suture S to slide freely within hollow tube 210A.

FIGS. 100-112 illustrate the suture passer 205A delivering a suture loop to the far side of tissue T. In FIG. 100, suture is loaded onto the suture passer 205A by placing the suture between first arm 275A and second arm 280A; in a preferred embodiment, suture S is placed against hooking surface 285A. In FIGS. 101-107, hooking rod 215A has been retracted proximally, carrying the suture S into the hollow tube 210A. At this point, suture passer 205A and suture S are ready to be passed through the tissue. Thereafter, in FIGS. 110-112, after suture passer 205A and suture S have been passed through the tissue, the hooking rod 215A is advanced distally and extended out of the hollow tube 210A, delivering a large suture loop (i.e., on the far side of the tissue T). To remove the suture passer from the far side of the tissue T, the suture passer 205A is moved free of the loop of suture S, hooking rod 215A is retracted back into hollow tube 210A, then the suture passer 205A is pulled back out of the tissue T (not shown).

In one form of the invention, handle 235A of suture passer 205A (FIG. 92) comprises means for enabling the user to determine how far actuator 320A has travelled. By way of example but not limitation, in one preferred form of the invention, handle 235A comprises one or more detents such that when the actuator 320A is repositioned, the user feels one or more tactile clicks, and/or hears one or more audible clicking sounds, during movement of the actuator 320A between its most distal and proximal positions on handle 235A.

Figure 113:
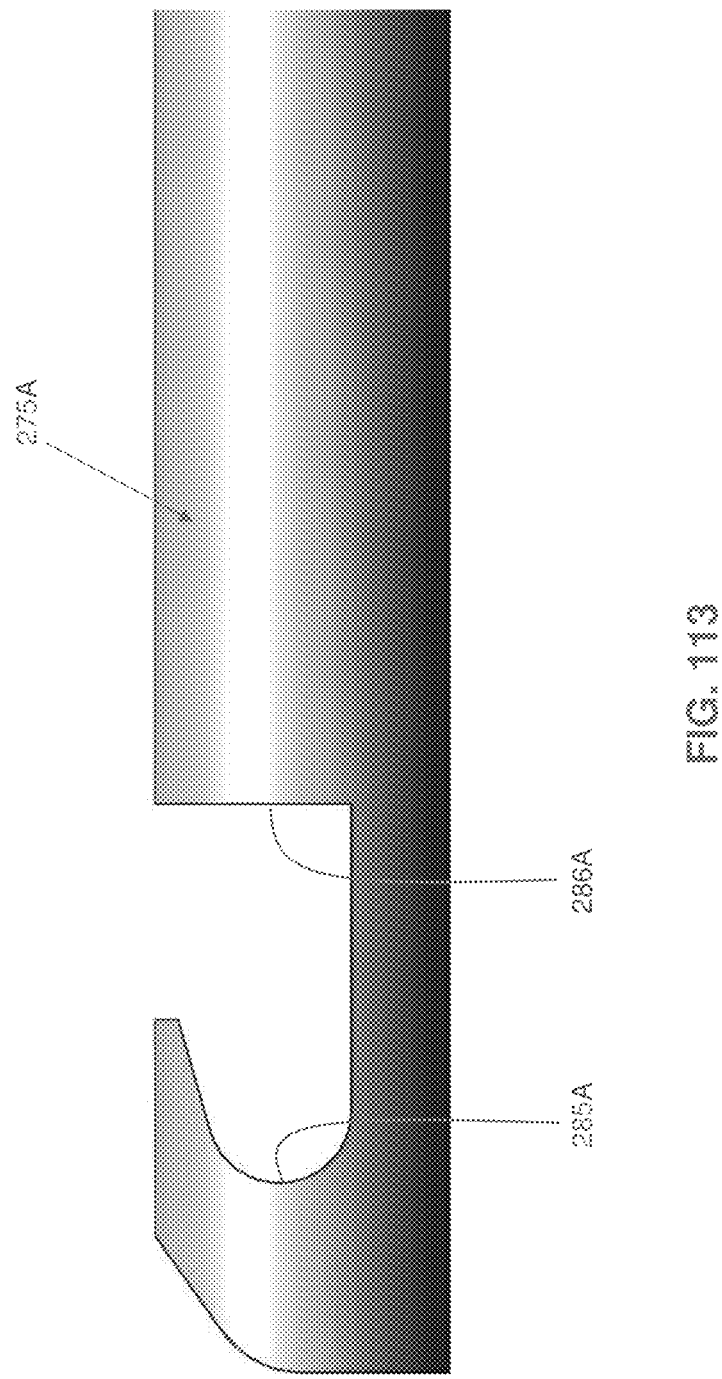
FIG. 113 is a schematic view showing an alternative form of hooking rod which may be used in accordance with the present invention shown in FIGS. 92-112.

In another form of the present invention, hooking rod 215A comprises only a first arm 275A (FIG. 113). In this embodiment, a pushing surface 286A may serve to engage and help push the suture S when suture S is being moved distally within hollow tube 210A. Pushing surface 286A is spaced from hook of first arm 275A by a gap similar to gap G as described above. In all other respects, first arm 275A and hollow tube 210A operate in the same manner as described above.

Figure 114:
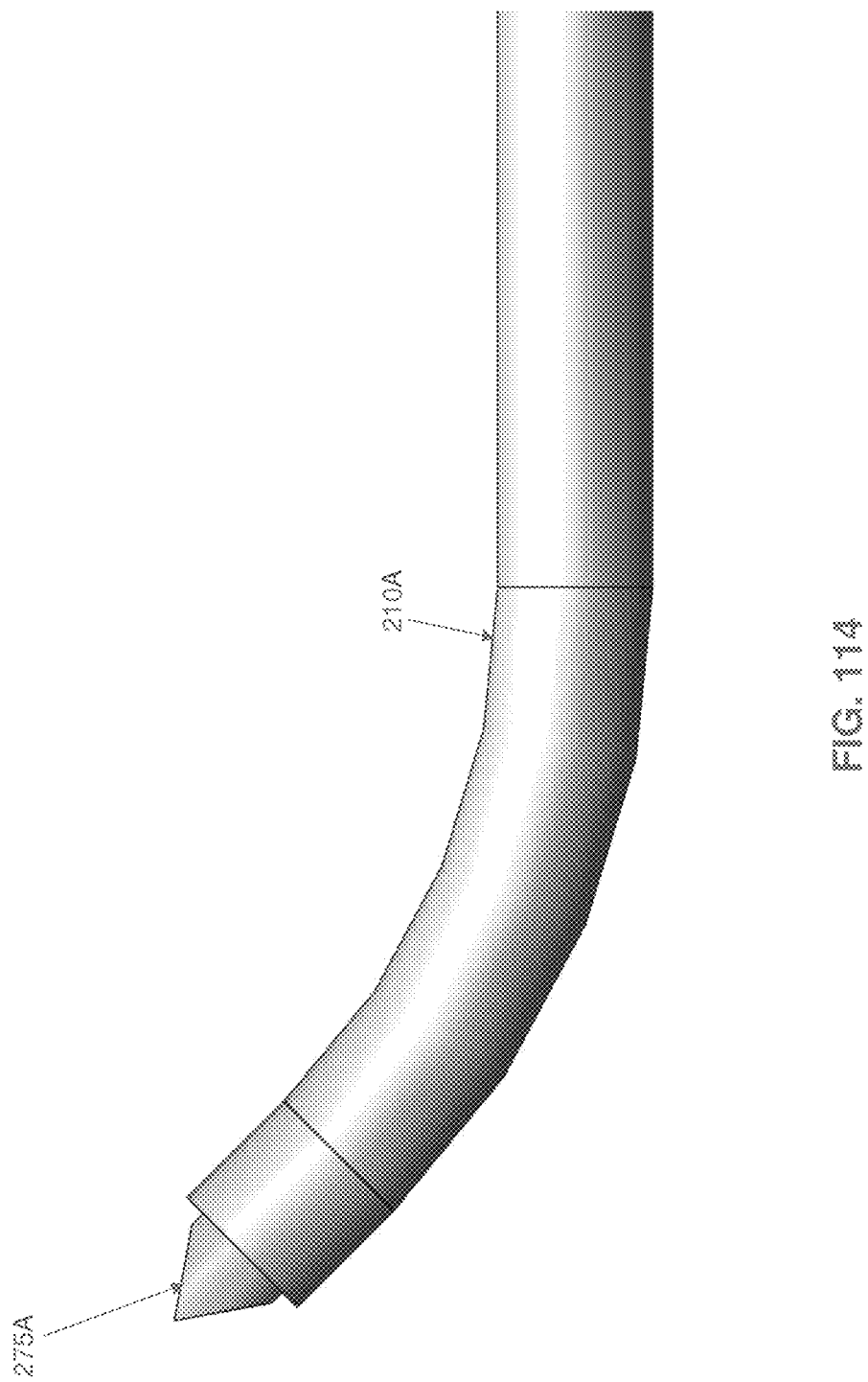

In yet another form of the present invention, first arm 275A of hooking rod 215A has a tissue-penetrating distal end (FIGS. 114 and 115). In this embodiment, hollow tube 210A does not have a tissue-penetrating distal end. In all other respects, the invention as described above and shown in FIGS. 92-112 apply (i.e., the construction and operation of first arm 275A, second arm 280A, hollow tube 210A, etc.).

MODIFICATIONS

It should also be understood that many additional changes in the details, materials, steps and arrangements of parts, which have been herein described and illustrated in order to explain the nature of the present invention, may be made by those skilled in the art while still remaining within the principles and scope of the invention.

The invention claimed is:

1. A method for passing a suture, comprising:
   extending a distal end of a suture manipulator of a suture passer from a distal portion of a hollow tube of the suture passer;
   locating a portion of a suture adjacent to a catching portion of the suture manipulator;
   retracting the distal end of the suture manipulator into the hollow tube and pulling the portion of the suture into the hollow tube so that a loop of the suture is located in the lumen and the portion of the suture is compressed by an inner surface of the hollow tube and a side surface of the catching portion; and
   sliding the suture manipulator distally relative to the hollow tube and pushing the portion of the suture with a pushing portion of the suture manipulator that is located proximally of the catching portion to expel the suture from the hollow tube, wherein a pushing surface of the pushing portion that contacts the portion of the suture for pushing the portion of the suture is located proximally of the catching portion.

2. The method of claim 1, comprising passing a distal portion of the suture passer with the portion of the suture through tissue prior to expelling the suture from the hollow tube.

3. The method of claim 2, wherein the tissue is a labrum.

4. The method of claim 2, wherein the tissue is a joint capsule.

5. The method of claim 2, wherein the tissue is located in a hip.

6. The method of claim 1, wherein the distal portion of the hollow tube is curved.

7. The method of claim 1, wherein the distal end of the hollow tube tapers to a pointed tip.

8. The method of claim 7, wherein the distal portion of the hollow tube comprises a cutaway in a side of a wall defining the distal portion of the hollow tube that is proximal of the tapered distal end.

9. The method of claim 8, wherein a first portion of the cutaway curves around a longitudinal axis of the distal portion of the hollow tube and two longitudinally extending portions of the cutaway extend distally from the first portion to the tapered distal end of the hollow tube.

10. The method of claim 9, wherein extending the distal end of the suture manipulator from the distal portion of the hollow tube comprises extending at least a portion of the suture manipulator laterally outwardly through the cutaway.

11. The method of claim 1, wherein the distal portion of the hollow tube has a longitudinal axis and at least a portion of the suture manipulator extends laterally away from the longitudinal axis.

12. The method of claim 1, wherein a width of the pushing surface is at least 50% of a diameter of the portion of the suture.

13. The method of claim 12, wherein a width of the pushing surface is at least 50% of a diameter of a size #2 orthopedic braided suture.

14. The method of claim 1, wherein the pushing portion extends along a longitudinal axis that intersects the catching portion.

15. The method of claim 1, wherein the catching portion of the suture manipulator comprises a proximally extending tip.

16. The method of claim 1, wherein the distal portion of the suture manipulator has a non-circular cross section such that the width of the distal portion of the suture manipulator is smaller than a height of the distal portion of the suture manipulator.

17. The method of claim 1, wherein the distal portion of the suture manipulator comprises two opposed flat sides and the portion of the suture is compressed between the inner surface of the hollow tube and the two opposed flat sides.

18. The method of claim 1, wherein the suture is a #2 orthopedic suture and the portion of the suture is compressed to at least 36% of an uncompressed diameter.

19. The method of claim 1, wherein the suture is a #2 orthopedic suture, and the method comprises applying a force of at least five pounds to the suture in a longitudinal direction of the distal portion of the suture manipulator while the portion of the suture is compressed within the hollow tube and the suture remaining in place.

20. A method for passing a suture, comprising:
   extending a distal end of a suture manipulator of a suture passer from a distal portion of a hollow tube of the suture passer, the distal portion of the suture manipulator forming a single arm so that only the single arm extends out of the distal end of the hollow tube when the suture manipulator is fully extended;
   locating a portion of a suture adjacent to a catching portion of the suture manipulator;
   retracting the distal end of the suture manipulator into the hollow tube and pulling the portion of the suture into the hollow tube so that a loop of the suture is located in the lumen and the portion of the suture is compressed by an inner surface of the hollow tube and a side surface of the catching portion; and
   sliding the suture manipulator distally relative to the hollow tube and pushing the portion of the suture with a pushing portion of the suture manipulator that is located proximally of the catching portion to expel the suture from the hollow tube.

* * * * *